United States Patent
Lumb et al.

(10) Patent No.: US 9,856,208 B2
(45) Date of Patent: Jan. 2, 2018

(54) METHOD FOR PRODUCING AN ARENE WITH AN AROMATIC C—N BOND ORTHO TO AN AROMATIC C—O BOND

(71) Applicant: THE ROYAL INSTITUTION FOR THE ADVANCEMENT OF LEARNING/MCGILL UNIVERSITY, Montreal (CA)

(72) Inventors: Jean-Philip Lumb, Montreal (CA); Kenneth V. N. Esguerra, Toronto (CA)

(73) Assignee: The Royal Institution for the advancement of Learning/McGill University, Montreal (CA)

( * ) Notice: Subject to any disclaimer, the term of this patent is extended or adjusted under 35 U.S.C. 154(b) by 0 days.

(21) Appl. No.: 15/255,957

(22) Filed: Sep. 2, 2016

(65) Prior Publication Data

US 2017/0066711 A1    Mar. 9, 2017

Related U.S. Application Data

(60) Provisional application No. 62/213,681, filed on Sep. 3, 2015.

(51) Int. Cl.
| | |
|---|---|
| C07C 249/02 | (2006.01) |
| C07C 213/08 | (2006.01) |
| C07C 45/29 | (2006.01) |
| C07D 265/36 | (2006.01) |
| C07D 263/56 | (2006.01) |
| C07C 46/08 | (2006.01) |
| C07F 7/00 | (2006.01) |
| C07F 7/08 | (2006.01) |

(52) U.S. Cl.
CPC ............ *C07C 249/02* (2013.01); *C07C 46/08* (2013.01); *C07C 213/08* (2013.01); *C07D 263/56* (2013.01); *C07D 265/36* (2013.01); *C07F 7/00* (2013.01); *C07F 7/0812* (2013.01); *C07C 2601/14* (2017.05); *C07C 2601/16* (2017.05); *C07C 2602/10* (2017.05)

(58) Field of Classification Search
CPC ..... C07C 249/02; C07C 213/08; C07C 45/29; C07D 265/36; C07D 265/56; C07D 263/56
See application file for complete search history.

(56) References Cited

U.S. PATENT DOCUMENTS

2008/0280891 A1   11/2008 Kelly et al.

OTHER PUBLICATIONS

Venkateswarlu, V.; Kumar, K. A. A.; Balgotra, S.; Reddy, G. L.; Srinivas, M.; Vishwakarma, R. A.; Sawant, S. D. C—H Oxygenation and N-Trifluoroacylation of Arylamines Under Metal-Free Conditions: A Convenient Approach to 2-Aminophenols and N-Trifluoroacyl-ortho-aminophenols. Chemistry European Journal 2014, 20, 6641-6645.

Vickers, C. J.; Mei, T.-S.; Yu, J.-Q. Pd(II)-Catalyzed o—C—H Acetoxylation of Phenylalanine and Ephedrine Derivatives with MeCOOOtBu/Ac2O. Organic Letters 2010, 12, 2511-2513.

Vinsova, J.; Cermakova, K.; Tomeckova, A.; Ceckova, M.; Jampilek, J.; Cermak, P.; Kunes, J.; Dolezal, M.; Staud, F. Synthesis and antimicrobial evaluation of new 2-substituted 5,7-di-tert-butylbenzoxazoles. Bioorganic & Medicinal Chemistry 2006, 14, 5850-5865.

Wang, S.; Ni, Z.; Huang, X.; Wang, J.; Pan, Y. Copper-Catalyzed Direct Amination of Heterocycles with N-Fluorobenzenesulfonimide. Org. Lett. 2014, 16, 5648-5651.

Wang, C.; Chen, L.-A.; Huo, H.; Shen, X.; Harms, K.; Gong, L.; Meggers, E. Asymmetric Lewis acid catalysis directed by octahedral rhodium centrochirality. Chemical Science 2015, 6, 1094-1100.

Wang, Y.; Wu, C.; Nie, S.; Xu, D.; Yu, M.; Yao, X. Ligand-promoted, copper nanoparticles catalyzed one-pot synthesis of substituted benzoxazoles from 2-bromoanilines and acyl chlorides. Tetrahedron Letters 2015, 56, 6827-6832.

Wasa, M.; Yu, J.-Q., Synthesis of beta- gamma-, and delta-Lactams via Pd(II)-Catalyzed C—H Activation Reactions. J. Am. Chem. Soc. 2008, 130, 14058-14059.

Weinstein, A. B.; Stahl, S. S. Palladium catalyzed aryl C—H amination with O2 via in situ formation of peroxide-based oxidant(s) from dioxane. Catalysis Science & Technology 2014, 4, 4301-4307.

Weissermel, K.; Arpe, H.-J. Benzene Derivatives. In Industrial Organic Chemistry, Wiley-VCH Verlag GmbH: 2008; pp. 337-385.

Wendlandt, A. E.; Suess, A. M.; Stahl, S. S. Copper-Catalyzed Aerobic Oxidative C—H Functionalizations: Trends and Mechanistic Insights. Angewandte Chemie International Edition 2011, 50, 11062-11087.

(Continued)

*Primary Examiner* — Kahsay Habte
(74) *Attorney, Agent, or Firm* — Isabelle Pelletier

(57) ABSTRACT

A method for producing an arene with an aromatic C—N bond ortho to an aromatic C—O bond from a hydroxy arene comprising said aromatic C—O bond is provided. This method comprising the steps a) ortho-oxygenating the hydroxy arene to produce an ortho-quinone, b) condensating the ortho-quinone with a nitrogen nucleophile to generate a compound of Formula (IVa) or (IVb), and c) allowing 1,5-hydrogen atom shift of the compound of Formula (IVa) or (IVb), thereby producing arenes with a C—N bond ortho to a C—O bond of Formula (Va) and (Vb), respectively:

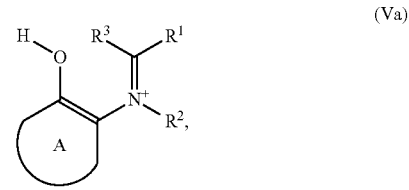

(Va)

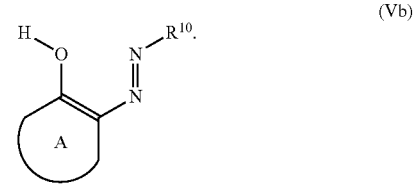

(Vb)

20 Claims, 32 Drawing Sheets

(56) References Cited

OTHER PUBLICATIONS

Wendlandt, A. E.; Stahl, S. S. Chemoselective Organocatalytic Aerobic Oxidation of Primary Amines to Secondary Imines. Organic Letters 2012, 14, 2850-2853.

Wendlandt, A. E.; Stahl, S. S. Bioinspired Aerobic Oxidation of Secondary Amines and Nitrogen Heterocycles with a Bifunctional Quinone Catalyst. Journal of the American Chemical Society 2014, 136, 506-512.

Wendlandt, A. E.; Stahl, S. S. Modular o-Quinone Catalyst System for Dehydrogenation of Tetrahydroquinolines under Ambient Conditions. Journal of the American Chemical Society 2014, 136, 11910-11913.

Woo Bae, J.; Hwan Lee, S.; Jin Cho, Y.; Min Yoon, C. A reductive amination of carbonyls with amines using decaborane in methanol. Journal of the Chemical Society, Perkin Transactions 1 2000, 145-146.

Wu, X.; See, J. W. T.; Xu, K.; Hirao, H.; Roger, J.; Hierso, J.-C.; Zhou, J. A. General Palladium-Catalyzed Method for Alkylation of Heteroarenes Using Secondary and Tertiary Alkyl Halides. Angewandte Chemie 2014, 126, 13791-13795.

Yan, X.; Yang, X.; Xi, C. Recent progress in copper-catalyzed electrophilic amination. Catalysis Science & Technology 2014, 4, 4169-4177.

Yan, S.; Ye, L.; Liu, M.; Chen, J.; Ding, J.; Gao, W.; Huang, X.; Wu, H. Unexpected TFA-catalyzed tandem reaction of benzo[d]oxazoles with 2-oxo-2-arylacetic acids: synthesis of 3-aryl-2H-benzo[b][1,4]oxazin-2-ones and cephalandole A. RSC Advances 2014, 4, 16705-16709.

Yang, X.; Shan, G.; Rao, Y. Synthesis of 2-Aminophenols and Heterocycles by Ru-Catalyzed C—H Mono- and Dihydroxylation. Organic Letters 2013, 15, 2334-2337.

Yoshida, S.; Shiokawa, S.; Kawano, K.-I.; Ito, T.; Murakami, H.; Suzuki, H.; Sato, Y. Orally Active Benzoxazole Derivative as 5-HT3 Receptor Partial Agonist for Treatment of Diarrhea-Predominant Irritable Bowel Syndrome. Journal of Medicinal Chemistry 2005, 48, 7075-7079.

Yoshino, J.; Furuta, A.; Kambe, T.; Itoi, H.; Kano, N.; Kawashima, T.; Ito, Y.; Asashima, M. Intensely Fluorescent Azobenzenes: Synthesis, Crystal Structures, Effects of Substituents, and Application to Fluorescent Vital Stain. Chemistry European Journal 2010, 16, 5026-5035.

Yuan, H.; Yoo, W.-J.; Miyamura, H.; Kobayashi, S. Discovery of a Metalloenzyme-like Cooperative Catalytic System of Metal Nanoclusters and Catechol Derivatives for the Aerobic Oxidation of Amines. Journal of the American Chemical Society 2012, 134, 13970-13973.

Zalatan, D. N.; Du Bois, J. In C—H Activation vol. 292 Topics in Current Chemistry (eds Jin-Quan Yu & Zhangjie Shi) Ch. 19, 347-378 (Springer Berlin Heidelberg, 2010).

Zhang, Z.-J.; Quan, X.-J.; Ren, Z.-H.; Wang, Y.-Y.; Guan, Z.-H. A Facile BPO-Mediated ortho-Hydroxylation and Benzoylation of N-Alkyl Anilines for Synthesis of 2-Benzamidophenols. Organic Letters 2014, 16, 3292-3295.

Zhu, D.; Yang, G.; He, J.; Chu, L.; Chen, G.; Gong, W.; Chen, K.; Eastgate, M. D.; Yu, J.-Q. Ligand-Promoted ortho-C—H Amination with Pd Catalysts. Angewandte Chemie International Edition 2015, 54, 2497-2500.

Grobler, J. A.; Dornadula, G.; Rice, M. R.; Simcoe, A. L.; Hazuda, D. J.; Miller, M. D. HIV-1 reverse transcriptase plus-strand initiation exhibits preferential sensitivity to non-nucleoside reverse transcriptase inhibitors in vitro. Journal of Biological Chemistry 2007, 282, 8005-10.

Hansen, T. V.; Skattebol, L. One-pot synthesis of substituted catechols from the corresponding phenols. Tetrahedron Letters 2005, 46, 3357-3358.

Hartwig, J. F. Carbon-heteroatom bond formation catalysed by organometallic complexes. Nature 2008, 455, 314-322.

Hernandez-Molina, R.; Mederos, A. 1.19—Acyclic and Macrocyclic Schiff Base Ligands A2—McCleverty, Jon A. In Comprehensive Coordination Chemistry II, Meyer, T. J. Ed. Pergamon: Oxford, 2003; pp. 411-446.

Herrmann, A. Dynamic mixtures and combinatorial libraries: imines as probes for molecular evolution at the interface between chemistry and biology. Organic & Biomolecular Chemistry 2009, 7, 3195-3204.

Hili, R.; Yudin, A. K. Making carbon-nitrogen bonds in biological and chemical synthesis. Nature Chemical Biology 2006, 2, 284-287.

Hong, W. P.; Iosub, A. V.; Stahl, S. S. Pd-Catalyzed Semmler-Wolff Reactions for the Conversion of Substituted Cyclohexenone Oximes to Primary Anilines. J. Am. Chem. Soc. 2013, 135, 13664.

Horton, D. A.; Bourne, G. T.; Smythe, M. L. The Combinatorial Synthesis of Bicyclic Privileged Structures or Privileged Substructures. Chemical Reviews 2003, 103, 893-930.

Huang, C.; Ghavtadze, N.; Chattopadhyay, B.; Gevorgyan, V. Synthesis of Catechols from Phenols via Pd-Catalyzed Silanol-Directed C—H Oxygenation. Journal of the American Chemical Society 2011, 133, 17630-17633.

Iida, K.; Miura, T.; Ando, J.; Saito, S., The Dual Role of Ruthenium and Alkali Base Catalysts in Enabling a Conceptually New Shortcut to N-Unsubstituted Pyrroles through Unmasked Alpha-Amino Aldehydes. Org. Lett. 2013, 15, 1436-1439.

Izawa, Y.; Pun, D.; Stahl, S. S. Palladium-Catalyzed Aerobic Dehydrogenation of Substituted Cyclohexanones to Phenols. Science 2011, 333, 209-213.

Jagadeesh, R. V., Natte, K., Junge, H. & Beller, M. Nitrogen-Doped Graphene-Activated Iron-Oxide-Based Nanocatalysts for Selective Transfer Hydrogenation of Nitroarenes. ACS Catalysis 5, 1526-1529, (2015).

Jawale, D. V.; Gravel, E.; Shah, N.; Dauvois, V.; Li, H.; Namboothiri, I. N. N.; Doris, E. Cooperative Dehydrogenation of N-Heterocycles Using a Carbon Nanotube-Rhodium Nanohybrid. Chemistry European Journal 2015, 21, 7039-7042.

Jiang, L.; Buchwald, S. L. Palladium-Catalyzed Aromatic Carbon-Nitrogen Bond Formation. In Metal-Catalyzed Cross-Coupling Reactions, Wiley-VCH Verlag GmbH: 2008; pp. 699-760.

Jiang, T.-S.; Wang, G.-W. Palladium-Catalyzed Ortho-Alkoxylation of Anilides via C—H Activation. The Journal of Organic Chemistry 2012, 77, 9504-9509.

Johnson, T. W.; Corey, E. J. Enantiospecific Synthesis of the Proposed Structure of the Antitubercular Marine Diterpenoid Pseudopteroxazole: Revision.

Jordan-Hore, J. A.; Johansson, C. C. C.; Gulias, M.; Beck, E. M.; Gaunt, M. J. Oxidative Pd(II)-Catalyzed C—H Bond Amination to Carbazole at Ambient Temperature. Journal of the American Chemical Society 2008, 130, 16184-16186.

Kim, H. J.; Kim, J.; Cho, S. H.; Chang, S. Intermolecular Oxidative C—N Bond Formation under Metal-Free Conditions: Control of Chemoselectivity between Aryl sp2 and Benzylic sp3 C—H Bond Imidation. Journal of the American Chemical Society 2011, 133, 16382-16385.

Kogan, V. A.; Lyubchenko, S. N.; Shcherbakov, I. N.; Ionov, A. M.; Tkachev, V. V.; Shilov, G. V.; Aldoshin, S. M. New Metal Chelates with Sterically Hindered Azo Ligands: Synthesis and Physicochemical.

Kremer, C. B. The Dual Role of Ruthenium and Alkali Base Catalysts in Enabling a Conceptually New Shortcut to N-Unsubstituted Pyrroles through Unmasked alpha-Amino Aldehydes. J. Am. Chem. Soc. 1939, 61, 1321-1324.

Kumar, R.; Ermolat'ev, D. S.; Van Der Eycken, E. V. Synthesis of Differentially Substituted 2-Aminoimidazolidines via a Microwave-Assisted Tandem Staudinger/Aza-Wittig Cyclization. The Journal of Organic Chemistry 2013, 78, 5737-5743.

Laliberte D.; Maris, T.; Wuest, J. D. Molecular Tectonics. Porous Hydrogen-Bonded Networks Built from Derivatives of Pentaerythrityl Tetraphenyl Ether. The Journal of Organic Chemistry 2004, 69, 1776-1787.

Largeron, M.; Chiaroni, A.; Fleury, M.-B. Environmentally Friendly Chemoselective Oxidation of Primary Aliphatic Amines by Using a Biomimetic Electrocatalytic System. Chemistry European Journal 2008, 14, 996-1003.

(56) References Cited

OTHER PUBLICATIONS

Largeron, M.; Fleury, M.-B. A Biologically Inspired CuI/Topaquinone-Like Co-Catalytic System for the Highly Atom-Economical Aerobic Oxidation of Primary Amines to Imines. Angewandte Chemie International Edition 2012, 51, 5409-5412.
Largeron M.; Fleury, M.-B. A Metalloenzyme-Like Catalytic System for the Chemoselective Oxidative Cross-Coupling of Primary Amines to Imines under Ambient Conditions. Chemistry European Journal 2015, 21, 3815-3820.
Layer, R. W. The Chemistry of Imines. Chem. Rev. 63, 489-510, (1963).
Leaver, I. H.; Milligan, B., Fluorescent Whitening Agents—A Survey (1974-82) Dyes and Pigments 1984, 5, 109-144.
Lee, D. H.; Lee, K. H.; Hong, J.-I. An Azophenol-Based Chromogenic Anion Sensor. Organic Letters 2001, 3, 5-8.
Ley, S. V.; Thomas, A. W. Modern Synthetic Methods for Copper-Mediated C(aryl)-O, C(aryl)-N, and C(aryl)-S Bond Formation. Angewandte Chemie International Edition 2003, 42, 5400-5449.
Li, C.; Zeng, Y.; Zhang, H.; Feng, J.; Zhang, Y.; Wang, J. Gold(I)-Catalyzed Cycloisomerization of Enynes Containing Cyclopropenes. Angewandte Chemie International Edition 2010, 49, 6413-6417.
Louillat, M.-L. & Patureau, F. W. Toward Polynuclear Ru—Cu Catalytic Dehydrogenative C—N Bond Formation, on the Reactivity of Carbazoles. Org. Lett. 2013, 15, 164-167.
Louillat, M.-L.; Patureau, F. W. Oxidative C—H amination reactions. Chemical Society Reviews 2014, 43, 901-910.
Louillat-Habermeyer, M.-L.; Jin, R.; Patureau, F. W. O2-mediated dehydrogenative amination of phenols. Angewandte Chemie International Edition 2015, 54, 4102-4104.
Lu, S.M.; Bolm, C. Highly Enantioselective Synthesis of Optically Active Ketones by Iridium-Catalyzed Asymmetric Hydrogenation. Angew. Chem. Int. Ed. (2008), 47, 8920-8923.
Luo, G.; Mattson, G. K.; Bruce, M. A.; Wong, H.; Murphy, B. J.; Longhi, D.; Antal-Zimanyi, I.; Poindexter, G. S. Isosteric N-arylpiperazine replacements in a series of dihydropyridine NPY1 receptor antagonists. Bioorganic & Medicinal Chemistry Letters 2004, 14, 5975-5978.
Magdziak, D., Rodriguez, A. A., Van De Water, R. W., Pettus, T. R. R. Regioselective oxidation of phenols to o-quinones with o-iodoxybenzoic acid (IBX). Org. Lett. 4, 285-288, (2002).
Majhi, B.; Kundu, D.; Ahammed, S.; Ranu, B. C. tert-Butyl Nitrite Mediated Regiospecific Nitration of (E)-Azoarenes through Palladium-Catalyzed Directed C—H Activation. Chemistry—A European Journal 2014, 20, 9862-9866.
McCoy, G.; Day, A. R. The Reaction of ortho-Quinones and ortho-Quinonimines with Primary Amines. Journal of the American Chemical Society 1943, 65, 1956-1959.
McGrath, N. A.; Brichacek, M.; Njardarson, J. T. A Graphical Journey of Innovative Organic Architectures That Have Improved Our Lives. Journal of Chemical Education 2010, 87, 1348-1349.
McLaughlin, M.; Palucki, M.; Davies, I. W. Efficient Access to Azaindoles and Indoles. Organic Letters 2006, 8, 3307-3310.
Mei, T.-S.; Wang, X.; Yu, J.-Q. Pd(II)-Catalyzed Amination of C—H Bonds Using Single-Electron or Two-electron Oxidants. Journal of the American Chemical Society 2009, 131, 10806-10807.
Mei T.-S.; Kou, L.; Ma, S.; Engle, K. M.; Yu, J.-Q. Heterocycle Formation via Palladium-Catalyzed C—H Functionalization. Synthesis 2012, 44, 1778-1791.
Mei, T.-S.; Leow, D.; Xiao, H.; Laforteza, B. N.; Yu, J.-Q. Synthesis of Indolines via Pd(II)-Catalyzed Amination of C—H Bonds Using PhI(OAc)2 as the Bystanding Oxidant. Organic Letters 2013, 15, 3058-3061.
Meyer, C. D.; Joiner, C. S.; Stoddart, J. F. Template-directed synthesis employing reversible imine bond formation. Chemical Society Reviews 2007, 36, 1705-1723.
Michlik, S.; Kempe, R. A sustainable catalytic pyrrole synthesis. Nat Chem 2013, 5, 140-144.

Mirica, L. M.; Vance, M.; Rudd, D. J.; Hedman, B.; Hodgson, K.O.; Solomon, E.I.; Stack, T.D.P. Tyrosinase reactivity in a model complex: an alternative hydroxylation mechanism. Science 308, 1890-1892, (2005).
Miyabe, H.; Yamaoka, Y.; Takemoto, Y. Reactive Ketimino Radical Acceptors: Intermolecular Alkyl Radical Addition to Imines with a Phenolic Hydroxyl Group. The Journal of Organic Chemistry 2006, 71, 2099-2106.
Montgomery, J. H. Fenamiphos. Agrochemicals desk reference. (CRC Press, 2010).
Moon, J.-K.; Kim, J.-H.; Shibamoto, T., Photodegradation Pathways and Mechanisms of the Herbicide Metamifop in a Water/Acetonitrile Solution. J. Agric. Food. Chem. 2010, 58, 12357-12365.
Moriarty, R. M.; Om, P. Oxidation of Phenolic Compounds with Organohypervalent Iodine Reagents. In Organic Reactions, John Wiley & Sons, Inc.: 2004.
Morofuji, T., Shimizu, A., Yoshida, J.-I. Electrochemical C—H Amination: Synthesis of Aromatic Primary Amines via N-Arylpyridinium Ions. J. Am. Chem. Soc. 135, 5000-5003, (2013).
Morofuji, T.; Shimizu, A.; Yoshida, J.-I. Direct C—N Coupling of Imidazoles with Aromatic and Benzylic Compounds via Electrooxidative C—H Functionalization. Journal of the American Chemical Society 2014, 136, 4496-4499.
Morofuji, T., Shimizu, A. & Yoshida, J.-I. Electrochemical Intramolecular C—H Amination: Synthesis of Benzoxazoles and Benzothiazoles. Chemistry European Journal 21, 3211-3214, (2015).
Mukaiyama, T. Explorations into New Reaction Chemistry. Angewandte Chemie International Edition 2004, 43, 5590-5614.
Murakami, Y.; Yoshimoto, N.; Fujieda, N.; Ohkubo, K.; Hasegawa, T.; Kano, K.; Fukuzumi, S.; Itoh, S. Model Studies of 6,7-Indolequinone Cofactors of Quinoprotein Amine Dehydrogenases. The Journal of Organic Chemistry 2007, 72, 3369-3380.
Mure, M.; Klinman, J. P. Model Studies of Topaquinone-Dependent Amine Oxidases. 2. Characterization of Reaction Intermediates.
Mure, M. Tyrosine-Derived Quinone Cofactors. Accounts of Chemical Research 2004, 37, 131-139.
Nakamura, M.; Hamasaki, T.; Tokitou, M.; Baba, M.; Hashimoto, Y.; Aoyama, H. Discovery of tetrahydrotetramethylnaphthalene analogs as adult T-cell leukemia cell-selective proliferation inhibitors in a small chemical library constructed based on multi-template hypothesis. Bioorganic & Medicinal Chemistry 2009, 17, 4740-4746.
Nicolaides, D. N.; Gautam, D. R.; Litinas, K. E.; Hadjipavlou-Litina, D. J.; Kontogiorgis, C. A. Synthesis and biological evaluation of benzo[7,8]chromeno[5,6-b][1,4]oxazin-3-ones. Journal of Heterocyclic Chemistry 2004, 41, 605-611.
Nun, P.; Martinez, J.; Lamaty, F. Microwave-Assisted Neat Procedure for the Petasis Reaction. Synthesis 2010, 2010, 2063-2068.
Op't Holt, B. T.; Vance, M. A.; Mirica, L. M.; Heppner, D. E.; Stack, T. D. P.; Solomon, E. I. Reaction Coordinate of a Functional Model of Tyrosinase: Spectroscopic and Computational Characterization. Journal of the American Chemical Society 2009, 131, 6421-6438.
Ostrem, J. M.; Peters, U.; Sos, M. L; Wells, J. A.; Shokat, K. M. K-Ras(G12C) inhibitors allosterically control GTP affinity and effector interactions. Nature 2013, 503 (7477), 548-551.
Ovenden, S. P. B.; Nielson, J. L.; Liptrot, C. H.; Willis, R. H.; Tapiolas, D. M.; Wright, A. D.; Motti, C. A. Sesquiterpene Benzoxazoles and Sesquiterpene Quinones from the Marine Sponge *Dactylospongia elegans*. Journal of Natural Products 2010, 74, 65-68.
Qian, J.; Yi, W.; Huang, X.; Miao, Y.; Zhang, J.; Cai, C.; Zhang W. One-Pot Synthesis of 3,5-Disubstituted and Polysubstituted Phenols from Acyclic Precursors. Org. Lett. (2015), 17, 1090-1093.
Qin, Y.; Zhang, L.; Lv, J.; Luo, S.; Cheng, J.-P. Bioinspired Organocatalytic Aerobic C—H Oxidation of Amines with an ortho-Quinone Catalyst. Organic Letters 2015, 17, 1469-1472.
Ramsden, C. A. Chapter 1—Heterocycle-Forming Reactions of 1,2-Benzoquinones. In Advances in Heterocyclic Chemistry, Alan, R. K. Ed. Academic Press: 2010; vol. vol. 100, pp. 1-51.
Rath, R. K; Nethaji, M.; Chakravarty, A. R. Synthesis, crystal structure and catalytic properties of (p-cymene) ruthenium(II)

(56) References Cited

OTHER PUBLICATIONS azophenol complexes: azophenyl to azophenol conversion by oxygen insertion to a ruthenium段 carbon bond. Journal of Organometallic Chemistry 2001, 633, 79-84.
Ren, P.; Salihu, I.; Scopelliti, R.; Hu, X. Copper-Catalyzed Alkylation of Benzoxazoles with Secondary Alkyl Halides. Organic Letters 2012, 14, 1748-1751.
Riley, P. A.; Ramsden, C. A.; Land, E. J. Biological Chemistry of o-Quinones. In Melanins and Melanosomes, Wiley-VCH Verlag GmbH & Co. KGaA: 2011; pp. 63-86.
Rodriguez, A. D.; Ramirez, C.; Rodriguez, II; Gonzalez, E., Novel Antimycobacterial Benzoxazole Alkaloids, from the West Indian Sea Whip *Pseudopterogorgia elisabethae*. Org. Lett. 1999, 1 (3), 527-30.
Rueping, M.; Antonchick, A. P.; Theissmann, T., Remarkably Low Catalyst Loading in Bronsted Acid Catalyzed Transfer Hydrogenations: Enantioselective Reduction of Benzoxazines, Benzothiazines, and Benzoxazinones. Angew. Chem. Int. Ed. 2006, 45, 6751-6755.
Ruiz-Castillo, P.; Blackmond, D. G.; Buchwald, S. L. Rational Ligand Design for the Arylation of Hindered Primary Amines Guided by Reaction Progress Kinetic Analysis. Journal of the American Chemical Society 2015, 137, 3085-3092.
Said, G.; Grippon, S.; Kirkpatrick, P. Tafamidis. Nat Rev Drug Discov 2012, 11, 185-6.
Salehzadeh, H.; Nematollahi, D.; Hesari, H. An efficient electrochemical method for the atom economical synthesis of some benzoxazole derivatives. Green Chemistry 2013, 15, 2441-2446.
Sandhu, J. S. & Sain, B. Some Recent Advances in the Chemistry of Imines, in Particular Cycloaddition Reactions. Heterocycles 26, 777-818 (1987).
Sapountzis, I.; Knochel, P. A. New General Preparation of Polyfunctional Diarylamines by the Addition of Functionalized Arylmagnesium Compounds to Nitroarenes. Journal of the American Chemical Society 2002, 124, 9390-9391.
Sato, S.; Kajiura, T.; Noguchi, M.; Takehana, K.; Kobayashi, T.; Tsuji, T., AJI9561, a New Cytotoxic Benzoxazole Derivative Produced by *Streptomyces* sp. J Antibiot (Tokyo) 2001, 54, 102-4.
Seth, K.; Garg, S. K.; Kumar, R.; Purohit, P.; Meena, V. S.; Goyal, R.; Banerjee, U. C.; Chakraborti, A. K. 2-(2-Arylphenyl)benzoxazole as a Novel Anti-Inflammatory Scaffold: Synthesis and Biological Evaluation. ACS Medicinal Chemistry Letters 2014, 5, 512-516.
Seth, K.; Purohit, P.; Chakraborti, A. K. Cooperative Catalysis by Palladium-Nickel Binary Nanocluster for Suzuki-Miyaura Reaction of Ortho-Heterocycle-Tethered Sterically Hindered Aryl Bromides. Organic Letters 2014, 16, 2334-2337.
Seth, K.; Nautiyal, M.; Purohit, P.; Parikh, N.; Chakraborti, A. K. Palladium catalyzed Csp2-H activation for direct aryl hydroxylation: the unprecedented role of 1,4-dioxane as a source of hydroxyl radicals. Chemical Communications 2015, 51, 191-194.
Shabashov, D.; Daugulis, O. Auxiliary-assisted palladium-catalyzed arylation and alkylation of sp2 and sp3 carbon-hydrogen bonds. J Am Chem Soc 2010, 132, 3965-72.
Shu, W.-M.; Zheng, K.-L.; Ma, J.-R.; Wu, A.-X. Transition-Metal-Free Multicomponent Benzannulation Reactions for the Construction of Polysubstituted Benzene Derivatives. Organic Letters 2015, 17, 5216-5219.
Smith, M.B.; March, J. March's Advanced Organic Chemistry: Reactions, Mechanisms and Structure, 5th Ed. Wiley; New York. 2001; pp. 1552-1554.
Sparling, B. A.; Moslin, R. M.; Jamison, T. F. SmI2-Promoted Reformatsky-Type Coupling Reactions in Exceptionally Hindered Contexts. Organic Letters 2008, 10, 1291-1294.
Sprott, K. T.; Corey, E. J., A New Cationic, Chiral Catalyst for Highly Enantioselective Diels-Alder Reactions. Org. Lett. 2003, 5, 2465-2467.
Srimani, D.; Ben-David, Y.; Milstein, D. Direct Synthesis of Pyrroles by Dehydrogenative Coupling of beta-Aminoalcohols with Secondary Alcohols Catalyzed by Ruthenium Pincer Complexes. Angewandte Chemie International Edition 2013, 52, 4012-4015.
Sun, K.; Li, Y.; Xiong, T.; Zhang, J.; Zhang, Q., Palladium-Catalyzed C—H Aminations of Anilides with N-fluorobenzenesulfonimide. J. Am. Chem. Soc. 2011, 133, 1694-1697.
Surry, D. S.; Buchwald, S. L. Dialkylbiaryl phosphines in Pd-catalyzed amination: a user's guide. Chemical Science 2011, 2, 27-50.
Tajbakhsh, M.; Hosseinzadeh, R.; Alinezhad, H.; Ghahari, S.; Heydari, A.; Khaksar, S. Catalyst-Free One-Pot Reductive Alkylation of Primary and Secondary Amines and N,N-Dimethylation of Amino Acids Using Sodium Borohydride in 2,2,2-Trifluoroethanol. Synthesis 2011, 3, 490-496.
Takamatsu, K.; Hirano, K.; Satoh, T.; Miura, M. Synthesis of Indolines by Copper-Mediated Intramolecular Aromatic C—H Amination. The Journal of Organic Chemistry 2015, 80, 3242-3249.
Tanaka, R.; Viehmann, P.; Hecht, S. Bis(phenoxy-azo)titanium(IV) Complexes: Synthesis, Structure, and Catalytic Activity in Styrene Polymerization. Organometallics 2012, 31, 4216-4220.
Taylor, E. C.; Katz, A. H.; Alvarado, S. I.; McKillop, A. Thallium in organic synthesis. 65. A novel synthesis of benzoxazoles from anilides. The Journal of Organic Chemistry 1986, 51, 1607-1609.
Thansandote, P.; Lautens, M. Construction of Nitrogen-Containing Heterocycles by C—H Bond Functionalization. Chemistry European Journal 2009, 15, 5874-5883.
Thirunavukkarasu, V. S.; Kozhushkov, S. I.; Ackermann, L., C—H nitrogenation and oxygenation by ruthenium catalysis. Chem. Commun. 2014, 50, 29-39.
Tsang, W. C. P.; Zheng, N.; Buchwald, S. L. Combined C—H Functionalization/ C—N Bond Formation Route to Carbazoles. Journal of the American Chemical Society 2005, 127, 14560-14561.
Tsang, W. C. P.; Munday, R. H.; Brasche, G.; Zheng, N.; Buchwald, S. L. Palladium-Catalyzed Method for the Synthesis of Carbazoles via Tandem C—H Functionalization and C—N Bond Formation. The Journal of Organic Chemistry 2008, 73, 7603-7610.
Tully, D. C.; Liu, H.; Alper, P. B.; Chatterjee, A. K.; Epple, R.; Roberts, M. J.; Williams, J. A.; Nguyen, K. T.; Woodmansee, D. H.; Tumanut, C.; Li, J.; Spraggon, G.; Chang, J.; Tuntland, T.; Harris, J. L.; Karanewsky, D. S. Synthesis and evaluation of arylaminoethyl amides as noncovalent inhibitors of cathepsin S. Part 3: Heterocyclic P3. Bioorganic & Medicinal Chemistry Letters 2006, 16, 1975-1980.
Ueda, S.; Nagasawa, H. Synthesis of 2-Arylbenzoxazoles by Copper-Catalyzed Intramolecular Oxidative C—O Coupling of Benzanilides. Angewandte Chemie 2008, 120, 6511-6513.
Ueki, M.; Ueno, K.; Miyadoh, S.; Abe, K.; Shibata, K.; Taniguchi, M.; Oi, S. UK-1, a novel cytotoxic metabolite from *Streptomyces* sp. 517-02. I. Taxonomy, fermentation, isolation, physico-chemical and biological properties. J Antibiot (Tokyo) 1993, 46, 1089-94.
Uyanik, M., Mutsuga, T. & Ishihara, K. IBS-Catalyzed Regioselective Oxidation of Phenols to 1,2-Quinones with Oxone®. Molecules 17, 8604-8616 (2012).
Abdel-Magid, A. F.; Carson, K. G.; Harris, B. D.; Maryanoff, C. A.; Shah, R. D. Reductive Amination of Aldehydes and Ketones with Sodium Triacetoxyborohydride. Studies on Direct and Indirect Reductive Amination Procedures. The Journal of Organic Chemistry 1996, 61, 3849-3862.
Alla, S. K.; Kumar, R. K.; Sadhu, P.; Punniyamurthy, T. Iodobenzene catalyzed C—H amination of N-substituted amidines using m-chloroperbenzoic acid. Org Lett 2013, 15, 1334-7.
Allen, L. J.; Cabrera, P. J.; Lee, M.; Sanford, M. S. N-Acyloxyphthalimides as nitrogen radical precursors in the visible light photocatalyzed room temperature C—H amination of arenes and heteroarenes. J Am Chem Soc 2014, 136, 5607-10.
Bafana, A.; Devi, S. S.; Chakrabarti, T. Azo dyes: past, present and the future. Environmental Reviews 2011, 19, 350-370.
Bassoli, A.; Borgonovo, G.; Busnelli, G.; Morini, G. Synthesis of a New Family of N-Aryl Lactams Active on Chemesthesis and Taste. European Journal of Organic Chemistry 2006, 1656-1663.
Bruckner, R. Substitution Reactions on Aromatic Compounds. In Advanced Organic Chemistry, Bruckner, R. Ed. Academic Press: San Diego, 2002; pp. 169-219.

(56) References Cited

OTHER PUBLICATIONS

Campbell, A. N.; Stahl, S. S. Overcoming the "Oxidant Problem": Strategies to Use O2 as the Oxidant in Organometallic C—H Oxidation Reactions Catalyzed by Pd (and Cu). Accounts of Chemical Research 2012, 45, 851-863.
Campiani, G.; Morelli, E.; Fabbrini, M.; Nacci, V.; Greco, G.; Novellino, E.; Ramunno, A.; Maga, G.; Spadari, S.; Caliendo, G.; Bergamini, A.; Faggioli, E.; Uccella, I.; Bolacchi, F.; Marini, S.; Coletta, M.; Nacca, A.; Caccia, S. Pyrrolobenzoxazepinone Derivatives as Non-Nucleoside HIV-1 RT Inhibitors: Further Structure-Activity Relationship Studies and Identification of More Potent Broad-Spectrum HIV-1 RT Inhibitors with Antiviral Activity. Journal of Medicinal Chemistry 1999, 42, 4462-4470.
Canakci, D.; Tuncel, M.; Mart, H.; Serin, S. New soluble azophenol polymers prepared by oxidative polycondensation. Polymer International 2007, 56, 1537-1543.
Chen, Q.-A.; Chen, M.-W.; Yu, C.-B.; Shi, L.; Wang, D.-S.; Yang, Y.; Zhou, Y.-G. Biomimetic Asymmetric Hydrogenation: In Situ Regenerable Hantzsch Esters for Asymmetric Hydrogenation of Benzoxazinones. Journal of the American Chemical Society 2011, 133, 16432-16435.
Chen, X.; Ji, F.; Zhao, Y.; Liu, Y.; Zhou, Y.; Chen, T.; Yin, S.-F. Copper-Catalyzed Aerobic Oxidative C(aryl)-OH Bond Functionalization of Catechols with Amines Affording Benzoxazoles. Advanced Synthesis & Catalysis 2015, 357, 2924-2930.
Chen, Z.; Zeng, H.; Girard, S. A.; Wang, F.; Chen, N.; Li, C.-J. Formal Direct Cross-Coupling of Phenols with Amines. Angew Chem Int Ed 2015, 54, 14487-91.
Cheng, Y.-F.; Rong, H.-J.; Yi, C.-B.; Yao, J.-J.; Qu, J. Redox-Triggered alpha-C—H Functionalization of Pyrrolidines: Synthesis of Unsymmetrically 2,5-Disubstituted Pyrrolidines. Org Lett 2015, 17, 4758-61.
Chintareddy, V. R.; Wadhwa, K.; Verkade, J. G. P(PhCH2NCH2CH2)3N Catalysis of Mukaiyama Aldol Reactions of Aliphatic, Aromatic, and Heterocyclic Aldehydes and Trifluoromethyl Phenyl Ketone. The Journal of Organic Chemistry 2009, 74, 8118-8132.
Chiranjeevi, B.; Vinayak, B.; Parsharamulu, T.; Phanibabu, V. S.; Jagadeesh, B.; Sridhar, B.; Chandrasekharam, M. Iron(III)-Catalyzed C—H Functionalization: ortho-Benzoyloxylation of N,N-Dialkylanilines and Its Application to 1,4-Benzoxazepines. European Journal of Organic Chemistry 2014, 2014, 7839-7849.
Cho, S. H.; Kim, J. Y.; Kwak, J.; Chang, S. Recent advances in the transition metal-catalyzed twofold oxidative C—H bound activation strategy for C—C and C—N bond formation. Chem. Soc. Rev. 2011, 40, 5068-5083.
Cho, S. H.; Yoon, J.; Chang, S. Intramolecular Oxidative C—N Bond Formation for the Synthesis of Carbazoles: Comparison of Reactivity between the Copper-Catalyzed and Metal-Free Conditions. Journal of the American Chemical Society 2011, 133, 5996-6005.
Chou, C.-C.; Hu, F.-C.; Yeh, H.-H.; Wu, H.-P.; Chi, Y.; Clifford, J. N.; Palomares, E.; Liu, S.-H.; Chou, P.-T.; Lee, G.-H. Highly Efficient Dye-Sensitized Solar Cells Based on Panchromatic Ruthenium Sensitizers with Quinolinylbipyridine Anchors. Angew Chem Int Ed 2014, 53, 178-83.
Corey, E. J.; Achiwa, K. A New Method for the Oxidation of Primary Amines to Ketones. Journal of the American Chemical Society 1969, 91, 1429-1432.
Daugulis, O.; Do, H.-Q.; Shabashov, D. Palladium- and Copper-Catalyzed Arylation of Carbon-Hydrogen Bonds. Acc. Chem. Res. 2009, 42, 1074-1086.
Davidson, J. P.; Corey, E. J. First Enantiospecific Total Synthesis of the Antitubercular Marine Natural Product Pseudopteroxazole. Revision of Assigned Stereochemistry. Journal of the American Chemical Society 2003, 125, 13486-13489.
Davies, H. M. L.; Long, M. S. Recent Advances in Catalytic Intramolecular C—H Aminations. Angewandte Chemie International Edition 2005, 44, 3518-3520.
Davies, H. M. L.; Manning, J. R. Catalytic C—H functionalization by metal carbenoid and nitrenoid insertion. Nature 2008, 451, 417-424.
Deibl, N.; Ament, K.; Kempe, R. A Sustainable Multicomponent Pyrimidine Synthesis. Journal of the American Chemical Society 2015, 137, 12804-12807.
Deligeorgiev, T.; Zaneva, D.; Kalcheva, V.; Simov, D. The preparation of 5-nitro-2-aminophenol and some derivatives. Dyes and Pigments 1993, 23, 85-90.
Dey, K. Schiff-bases and their uses. J. Sci. Ind. Res. 33, 76-100 (1974).
Dick, A. R.; Sanford, M. S. Transition metal catalyzed oxidative functionalization of carbon-hydrogen bonds. Tetrahedron 2006, 62, 2439-2463.
Don, M.-J.; Shen, C.-C.; Lin, Y.-L.; Syu, W.-J.; Ding, Y. H.; Sun, C.-M. Nitrogen-containing compounds from Salvia miltiorrhiza. J. Nat. Prod. 2005, 68, 1066-70.
Dooleweerdt, K.; Fors, B. P.; Buchwald, S. L. Pd-Catalyzed Cross-Coupling Reactions of Amides and Aryl Mesylates. Organic Letters 2010, 12, 2350-2353.
Easmon, J.; Pürstinger, G.; Thies, K.-S.; Heinisch, G.; Hofmann, J. Synthesis, Structure-Activity Relationships, and Antitumor Studies of 2-Benzoxazolyl Hydrazones Derived from Alpha-(N)-acyl Heteroaromatics. Journal of Medicinal Chemistry 2006, 49, 6343-6350.
Emerson, W. S. Preparation of Amines by Reductive Alkylation. In Organic Reactions (John Wiley & Sons, Inc., 2004).
Erkkilä, A.; Majander, I.; Pihko, P. M. Iminium Catalysis. Chemical Reviews 2007, 107, 5416-5470.
Esguerra, K. V. N.; Fall, Y.; Lumb, J.-P. A Biomimetic Catalytic Aerobic Functionalization of Phenols. Angewandte Chemie International Edition 2014, 53, 5877-5881.
Esguerra, K. V. N.; Fall, Y.; Petitjean, L.; Lumb, J.-P. Controlling the Catalytic Aerobic Oxidation of Phenols. Journal of the American Chemical Society 2014, 136, 7662-7668.
Evano, G.; Blanchard, N.; Toumi, M. Copper-Mediated Coupling Reactions and Their Applications in Natural Products and Designed Biomolecules Synthesis. Chemical Reviews 2008, 108, 3054-3131.
Fache, F.; Schulz, E.; Tommasino, M. L.; Lemaire, M. Nitrogen-Containing Ligands for Asymmetric Homogeneous and Heterogeneous Catalysis. Chemical Reviews 2000, 100, 2159-2232.
Fier, P. S.; Hartwig, J. F. Synthesis and Late-Stage Functionalization of Complex Molecules through C—H Fluorination and Nucleophilic Aromatic Substitution. Journal of the American Chemical Society 2014, 136, 10139-10147.
Finkbeiner, H.; Hay, A. S.; Blanchard, H. S.; Endres, G. F. Polymerization by Oxidative Coupling. The Function of Copper in the Oxidation of 2,6-Dimethylphenol. The Journal of Organic Chemistry 1966, 31, 549-555.
Finkbeiner, P.; Kloeckner, U. & Nachtsheim, B. J. OH-Directed Alkynylation of 2-Vinylphenols with Ethynyl Benziodoxolones: A Fast Access to Terminal 1,3-Enynes. Angew. Chem. Int. Ed., doi:10.1002/anie.201412148 (2015).
Finley, K. T. Quinones as synthones. In the Quinonoid Compounds (1988), John Wiley & Sons, Inc.: 2010; pp. 637-717.
Finley, K. T. The addition and substitution chemistry of quinones. In Quinonoid Compounds (1974), John Wiley & Sons, Ltd.: 2010; pp. 877-1144.
Fishwick, C. W. G.; Jones, D. W. ortho-Quinonoid compounds. In the Quinonoid Compounds (1988), John Wiley & Sons, Inc.: 2010; pp. 403-453.
Foo, K.; Sella, E.; Thomé, I.; Eastgate, M. D.; Baran, P. S. A Mild, Ferrocene-Catalyzed C—H Imidation of (Hetero)Arenes. Journal of the American Chemical Society 2014, 136, 5279-5282.
Gao, T.; Sun, P. Palladium-Catalyzed N-Nitroso-Directed C—H Alkoxylation of Arenes and Subsequent Formation of 2-Alkoxy-N-alkylarylamines. The Journal of Organic Chemistry 2014, 79, 9888-9893.
Garcia-Amoros, J.; Velasco, D. Recent advances towards azobenzene-based light-driven real-time information-transmitting materials. Beilstein Journal of Organic Chemistry 2012, 8, 1003-1017.

(56) References Cited

OTHER PUBLICATIONS

Garcia-Amoros, J.; Velasco, D. Tautomerizable Azophenol Dyes: Cornerstones for Advanced Light-Responsive Materials. In Tautomerism, Wiley-VCH Verlag GmbH & Co. KGaA: 2016; pp. 253-272.

Gembus, V.; Poisson, T.; Oudeyer, S.; Marsais, F.; Levacher, V. Preparation of Beta-Lactams by Mannich-Type Addition of Ethyl(trimethyl-silyl)acetate (ETSA) to N-(2-Hydroxyphenyl)aldimine Sodium Salts. Synlett 2009, 2009, 2437-2440.

Girard, S. A.; Huang, H.; Zhou, F.; Deng, G.-J.; Li, C.-J. Catalytic dehydrogenative aromatization: an alternative route to functionalized arenes. Organic Chemistry Frontiers 2015, 2, 279-287.

Govindachari, T. R.Chinnasamy, P., Rajeswari, S., Chandrasekaran, S., Premila, M. S., Natarajan, S., Nagarajan, K. & Pai, B. R. Some recent work on Schiff-Bases, imines and iminium slats in synthetic heterocyclic chemistry—a review. Heterocycles 22, 585-655 (1984).

Grimsdale, A. C.; Leok Chan, K.; Martin, R. E.; Jokisz, P. G.; Holmes, A. B. Synthesis of Light-Emitting Conjugated Polymers for Applications in Electroluminescent Devices. Chemical Reviews 2009, 109, 897-1091.

*Sub-Reaction Path A:* Multi-Component Petasis Coupling

Dehydrogenative Coupling with Pyrrolidine

*Sub-Reaction Path A:* 1,2-Shift (A) Explanation of Regiochemistry:

(B) Selective Deprotection:

(A) Classical Approaches:
(i) Diazo Coupling:

(ii) Desymmetrization of azobenzenes:

(B) Deamination Catalyzed by PPQ (C) This work:

Less Successful Hyrdazine Substrates:

METHOD FOR PRODUCING AN ARENE WITH AN AROMATIC C—N BOND ORTHO TO AN AROMATIC C—O BOND

CROSS REFERENCE TO RELATED APPLICATIONS

This application claims benefit, under 35 U.S.C. §119(e), of U.S. provisional application Ser. No. 62/213,681, filed on Sep. 3, 2015. All documents above are incorporated herein in their entirety by reference.

FIELD OF THE INVENTION

The present invention relates to a method for producing arenes with an aromatic C—N bond ortho to an aromatic C—O bond. More specifically, the present invention is concerned with a method for producing such compounds via the condensation of a nitrogen nucleophile (i.e. an amine, hydrazine, or hydrazide) with an ortho-quinone.

BACKGROUND OF THE INVENTION 1,2-Amino-oxy arenes, such as o-aminophenols, and related nitrogen-containing heterocycles with aromatic C—N bonds are ubiquitous moieties in pharmaceutical, agrochemical and materials sciences, where they impart desirable and essential properties to small molecules as well as macromolecules. Examples of 1,2-amino-oxy arenes include:

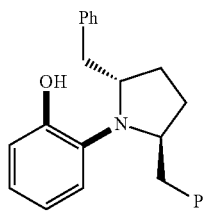
Ligand for Asymmetric Diels-Alder (E. J. Corey)

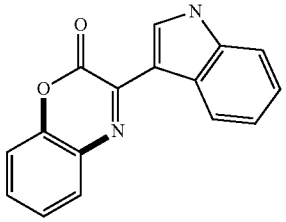
Cephalandole A (Alkaloid)

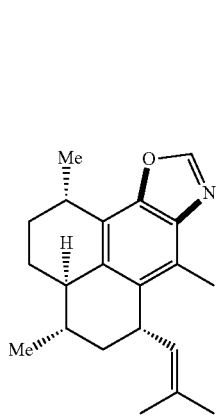
Pseudopteroxazole (antitubercular activity)

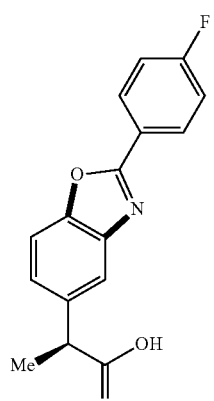
Fenoxaprop (herbicide)

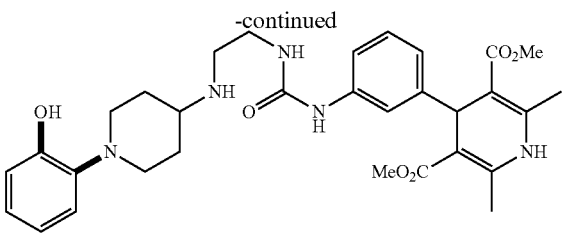
BMS-189323
NPY Receptor Agonist

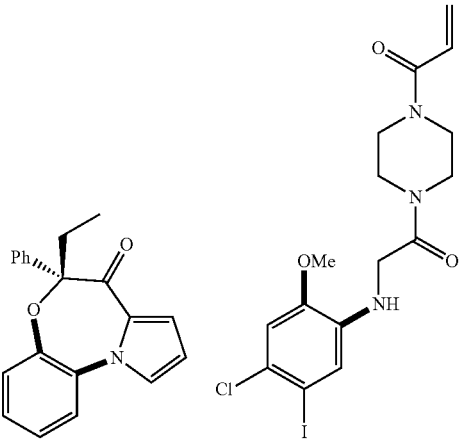
Pyrrolobenzoxazepinones
HIV-1 RT Inhibitor

YM-254850
K-Ras Inhibitor (anti-tumor)

(The aromatic C—O and C—N bonds of the arene are in bold.)

However, despite its importance to the function of organic molecules, nitrogen is not present in petrochemical building blocks. These starting materials possess high ratios of hydrogen to carbon, making the selective oxidation of C—H bonds critically important to laboratory and industrial chemical synthesis. In fact, the site-selective introduction of nitrogen, in particular, the amination of aromatic rings, is fundamentally important to the petrochemical industry, since it dictates the efficiency of feedstock valorization.

Modern technologies to introduce nitrogen are dominated by metal-catalyzed cross-coupling reactions, where the most desirable examples introduce aromatic C—N bonds directly from aromatic C—H bonds and un-functionalized amines. These so-called Crossed Dehydrogenative Coupling (CDC) reactions are efficient because they combine un-functionalized starting materials. However, their poor chemoselectivity, regioselectivity, and their poor atom economy remain persistent drawbacks.

Improving the synthesis of ortho-amino-phenols and their 1,2-oxy-amino derivatives is a fundamentally important challenge, since this motif is found in pharmacologically active compounds, chemical dyes, agrochemicals, and catalysts (see above). However, their synthesis involves a non-regioselective nitration of phenols, followed by multi-step syntheses that involves protecting group strategies for further derivatization. Fragment-coupling reactions of halogenated arenes with nitrogen or oxygen nucleophiles can be preferable, but requires pre-functionalization of the arene, and catalyst optimization for a given heteroatom nucleophile. Thus, a more direct functionalization of aromatic C—H bonds is desirable, but currently suffers from limited scope, and requires pre-functionalization of the nitrogen coupling partner or stoichiometric quantities of an oxidant.

Azophenols are also important scaffold and are present in organic dyes, ancillary ligands, molecular switches, fluorescent probes and chemosensors. Here are selected examples of azophenol derivatives:

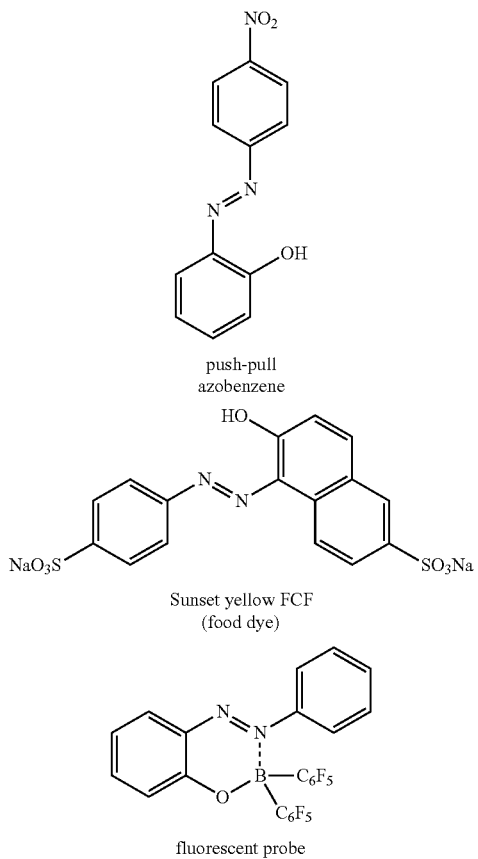

push-pull
azobenzene

Sunset yellow FCF
(food dye)

fluorescent probe

Azophenols display unusually rapid cis-to-trans thermal relaxation, and the rate of this isomerization is influenced by the electronic properties of each of the arene rings. For example, the thermal isomerization of azophenols with push-pull configuration (i.e. with an adjacent electron-deficient arene) are amongst the fastest. Despite their utility, efficient synthesis to access this core system is limited, and a catalytic aerobic method has not been reported. Traditionally, azophenol is generated from the fragment coupling of aryl diazonium salt and phenol. However, this coupling requires in situ preparation of diazonium salts, which is obtained from the oxidation of the corresponding aniline with stoichiometric amounts of toxic nitrous acid.

Transition metal catalyzed ortho-functionalization of symmetric azobenzenes have been proposed. However, these protocols provide a mixture of mono- and di-hydroxylated products, and produces azoxybenzene byproducts. Consequently, the use of these methodologies on asymmetric substrates can give rise to complex product mixtures, and predicting the site of hydroxylation can be difficult for substrates with electronically and sterically comparable arene rings. Thus, a general, regioselective and aerobic catalytic method for the synthesis of azophenol would be highly attractive.

SUMMARY OF THE INVENTION

In accordance with the present invention, there is provided:

1. A method for producing an arene with an aromatic C—N bond ortho to an aromatic C—O bond from a hydroxy arene comprising said aromatic C—O bond, the method comprising the following steps:
   a. ortho-oxygenating a hydroxy arene of Formula (I) to produce an ortho-quinone of Formula (II):

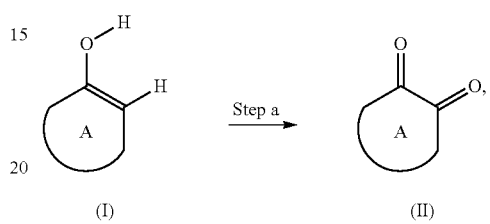

b. condensating the ortho-quinone of Formula (II) with a nitrogen nucleophile of Formula (IIIa):

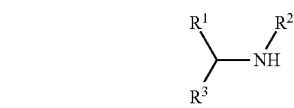

or (IIIb):

$R^{10}$
   $\diagdown$
   $NH-NH_2$ to generate a compound of Formula (IVa) or (IVb), respectively:

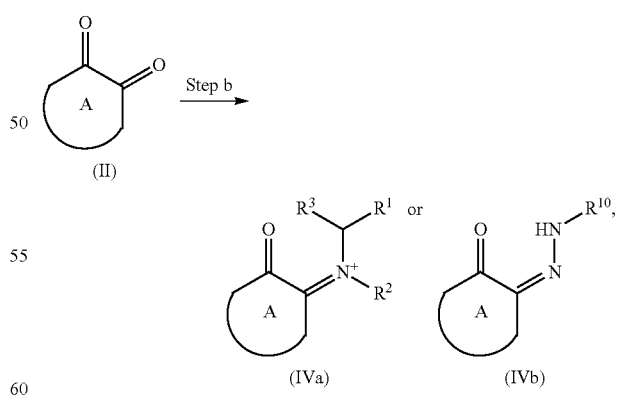

and
   c. allowing 1,5-hydrogen atom shift of the compound of Formula (IVa) or (IVb), thereby producing arenes with a C—N bond ortho to a C—O bond of Formula (Va) and (Vb), respectively:

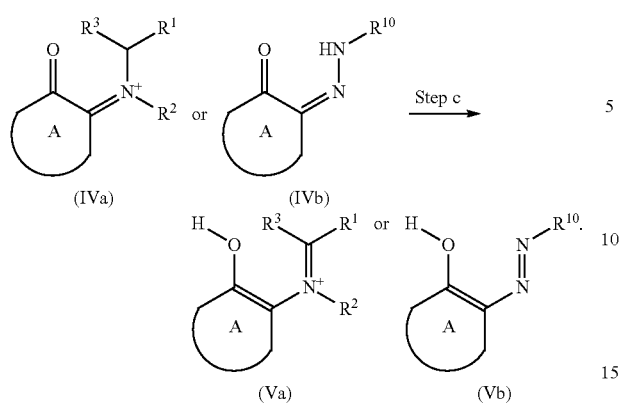

2. The method of item 1, wherein the nitrogen nucleophile is of Formula (IIIa) and wherein $R^1$, $R^2$, and $R^3$ each independently represent:
   a hydrogen atom,
   alkyl unsubstituted or substituted with one or more one or more substituents selected from the group consisting of:
      aryl unsubstituted or substituted with one or more hydroxy,
      hydroxy,
      alkoxy unsubstituted or substituted with one or more aryl,
      aminoalkyl or aminodialkyl,
      alkoxy carbonyl,
      alkylthio,
      heterocycloalkyl, and
      halogen atom,
   cycloalkyl,
   alkenyl,
   hydroxyl,
   —C(=O)—O—$R^{20}$), wherein $R^{20}$ is aliphatic or aromatic (preferably alkyl, aryl or an amino acid) unsubstituted or substituted, or
   aryl or heteroaryl unsubstituted or substituted with one or more one or more substituents selected from the group consisting of:
      alkyl unsubstituted or substituted with one or more halogen atoms,
      alkoxy,
      aryl unsubstituted or substituted with one or more alkyl, the alkyl being unsubstituted or substituted with one or more halogen atoms,
      nitro,
      sulfonamine, and
      halogen atom; or
   $R^1$ and $R^3$ together with the carbon atom to which they are attached form a ring; or
   $R^1$ and $R^2$ together with the carbon and nitrogen atoms to which they are attached form a ring, that:
      is saturated or unsaturated;
      is unsubstituted or substituted with one or more hydroxy;
      optionally comprises, in addition to the nitrogen atom to which $R^2$ is attached, one or more additional heteroatom; and
      is optionally fused with an aromatic ring that is unsubstituted or substituted with one or more alkyloxy.
3. The method of item 2, wherein $R^2$ represents a hydrogen atom.

4. The method of item 3, wherein $R^3$ represents a hydrogen atom and wherein the compound of Formula (Va) spontaneously forms an oxazole arene of Formula (VI):

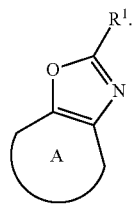

5. The method of item 3, wherein $R^3$ does not represent a hydrogen atom.
6. The method of item 5, further comprising hydrolysis to produce an ortho-amino-hydroxy arene of Formula (X):

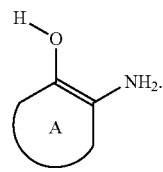

7. The method of item 5, further comprising reaction with an organometallic reagent of formula $R^4$-M to yield an α,α,α-trisubstituted compound of Formula (XI):

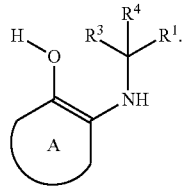

8. The method of item 5, wherein $R^3$ represents —C(=O)—O—$R^{20}$ and the method further comprises lactonization to produce an oxazinone arene of Formula (IX):

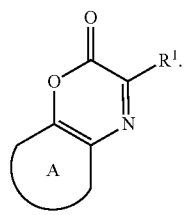

9. The method of item 8, wherein $R^1$ in the oxazinone arene of Formula (IX) comprises a hydroxy arene and steps a) to c) followed by lactonization are repeated multiple times to produce a heterocyclic polymer.
10. The method of item 2, wherein $R^3$ represents a hydrogen atom and $R^1$ and $R^2$ together with the carbon and nitrogen atoms to which they are attached form a ring.
11. The method of item 10, wherein said ring is pyrrolidine, piperazine, morpholine, indoline, iso-indoline, tetrahydroisoquinoline, piperidine, 2,5-dihydropyrrole, dihydropyrrolidine, dihydroindoline, or dihydroisoindoline or one of their substituted derivatives.

12. The method of item 10, further comprising quenching the reaction mixture to produce a dihydrooxazole arene of Formula (XII):

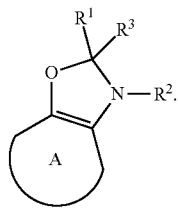

13. The method of item 12, further comprising reducing the dihydrooxazole arene of Formula (XII) to yield to yield an ortho-amino-hydroxy arene of Formula (XIII):

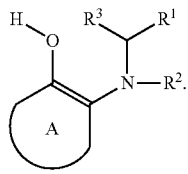

14. The method of item 13, further comprising reacting with an aryl boronic acid to yield a compound of Formula (XV):

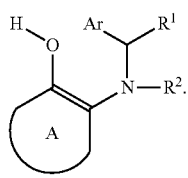

15. The method of any one of items 2 to 14, wherein arene A is benzene unsubstituted or substituted by one or more substituents selected from the group consisting of:
   alkyl unsubstituted or substituted with one or more:
      aryl,
      sulfoamidoaryl unsubstituted or substituted with one or more alkyl,
      hydroxy, and/or
      aryl carbamoyl,
   cycloalkyl,
   alkenyl, and
   aryl unsubstituted or substituted with one or more:
      alkyl,
      alkyloxy,
      halogen atom,
      trialkylsilyl, and/or
      halogen atoms.
16. The method of item 1, wherein the nitrogen nucleophile is of Formula (IIIb) and wherein $R^{10}$ represents:
   aryl substituted with one or more substituents selected from the group consisting of:
      —$NO_2$,
      —$SO_2$,
      halogen atom, and
      perfluorinated alkyl,
   heteroaryl unsubstituted or substituted with one or more:
      —$NO_2$,
      —$SO_2$,
      halogen atom, and
      perfluorinated alkyl, or
   —C(=O)—$R^{11}$, wherein $R^{11}$ represents:
      aryl or heteroaryl unsubstituted or substituted with one or more aryl, or
      alkyloxy
   with the proviso that nitrogen nucleophile is Formula (IIIb) is not

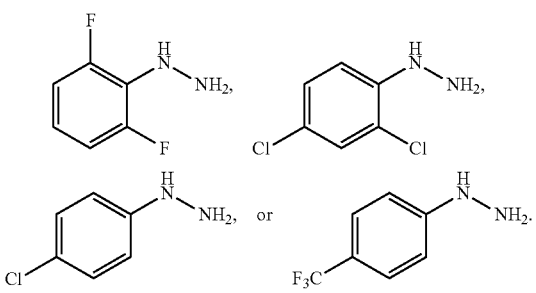

17. The method of item 16, wherein nitrogen nucleophile of Formula (IIIb) is

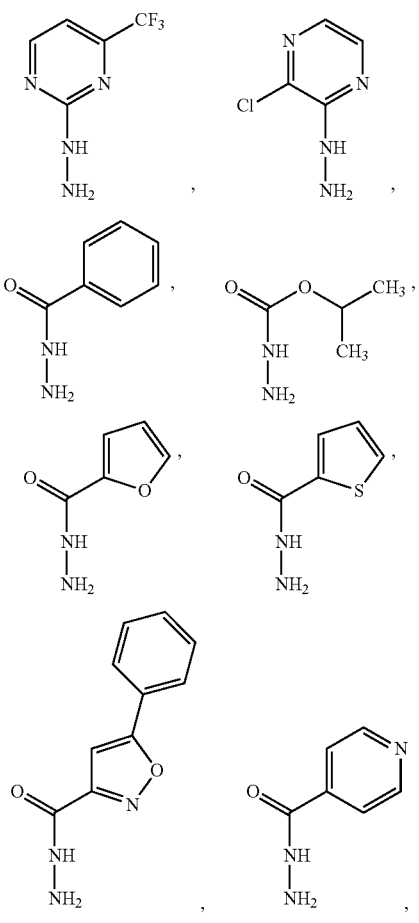

18. The method of item 16 or 17, wherein arene A is benzene unsubstituted or substituted by one or more substituents selected from the group consisting of:

$NO_2$, alkyl, trialkylsilyl, and/or aryl substituted with one or more alkyl and/or halogen atoms.

wherein arene A is optionally fused with a cycloalkyl, the cycloalkyl being optionally substituted with one or more alkyl.

19. The method of any one of items 1 to 18, wherein step a) comprises reacting the hydroxy arene of Formula (I) in a reaction mixture with a solvent with $[Cu(CH_3CN)_4]PH_6$ and N,N'-di-tert-butyl-ethylene diamine at about room temperature in the presence of $O_2$.

20. The method of any one of items 1 to 19, wherein step b) comprises mixing the nitrogen nucleophile of Formula (IIIa) or (IIIb) in the reaction mixture.

DETAILED DESCRIPTION OF THE INVENTION

Turning now to the invention in more details, there is provided a method for producing arenes with an aromatic C—N bond ortho to an aromatic C—O bond starting from a hydroxy arene comprising said aromatic C—O bond. Herein, an aromatic C—N or C—O are bonds in which the carbon atom is part of an aromatic ring. The present method is a conceptually different Crossed Dehydrogenative Coupling (CDC) reaction for the synthesis of aromatic C—N bonds. It constitutes a method distinct from traditional cross-coupling or C—H amination strategies. This method can be carried out as a 1-pot method. In embodiments, it presents levels of efficiency for the synthesis of nitrogen rich molecules that are currently not achievable with other methods.

Figure 1:
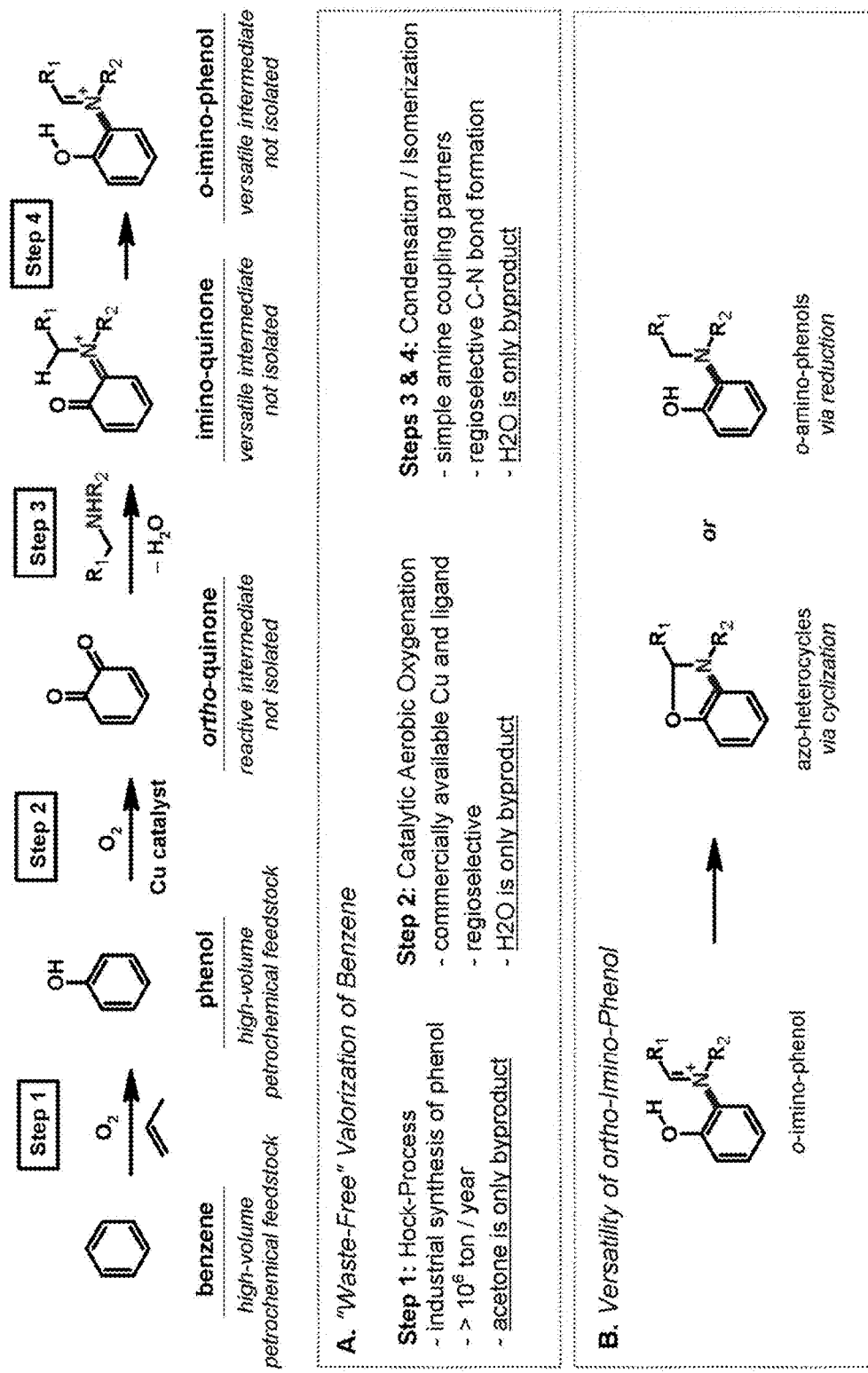
FIG. 1 shows the petrochemical valorization by dehydrogenative phenol/amine coupling.

In the present method, ortho-quinones are first produced, directly from hydroxy arenes (step a), see also a specific embodiment at FIG. 1, Step 2). Then the ortho-quinones are condensed with a nitrogen nucleophile, that can be an amine, a hydrazine or a hydrazide (step b), see also a specific embodiment at FIG. 1, Step 3), followed by spontaneous 1,5 hydrogen shift (step c), see also a specific embodiment at FIG. 1, Step 4). By passing through the ortho-quinones, this method affords predictable and selective ortho-amination. As such, this method allows the conversion of high-volume petrochemical feedstocks (phenols and, in embodiments, amines) into arenes with an aromatic C—N bond ortho to an aromatic C—O bond: ortho-azo-hydroxy arenes when hydrazines or hydrazides are used and ortho-iminium-hydroxy arenes when an amine is used. The later are versatile reactive intermediates toward high-value nitrogen containing heterocycles, including azo-heterocycles, and aminophenols, at the sole expense of reducing $O_2$ to $H_2O$ (FIG. 1, Inset A).

There is therefore provided a method for producing an arene with an aromatic C—N bond ortho to an aromatic C—O bond from a hydroxy arene comprising said aromatic C—O bond, the method comprising the steps of:

a) ortho-oxygenating a hydroxy arene of Formula (I) to produce an ortho-quinone of Formula (II):

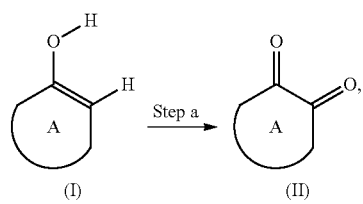

b) condensating the ortho-quinone of Formula (II) with a nitrogen nucleophile of Formula (IIIa):

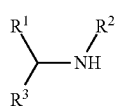

or (IIIb):

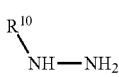

to generate a compound of Formula (IVa) or (IVb), respectively:

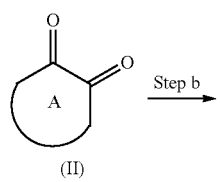

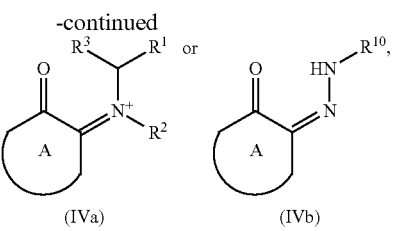

and c) allowing 1,5-hydrogen atom shift of the compound of Formula (IVa) or (IVb), thereby producing said arenes with a C—N bond ortho to a C—O bond of Formula (Va) and (Vb), respectively:

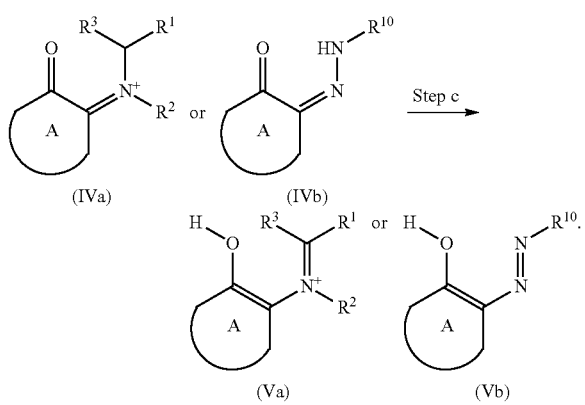

In all formulas herein, A (as in

)

denotes an unsubstituted or substituted arene. As shown herein, the above reaction is quite robust and therefore can be carried on a variety of arene compounds.

Herein, an "arene" is an aromatic hydrocarbon with its carbon atoms arranged into one or more rings, the ring(s) presenting alternating double and single bonds between the ring atoms, and wherein one or more of the carbon ring atoms may be replaced by a heteroatom, such as nitrogen or oxygen. In embodiments, the arene comprises between 1 to 3 rings. In embodiments, each of the rings of the arene comprises independently 5 or 6 ring atoms. In embodiments, all the ring atoms of the arene are carbon atoms. In other embodiments, 1 to 3 ring atoms are heteroatoms, the heteroatoms being the same or being different from one another. Preferred arenes include benzene, naphthalene or phenanthrene, more preferably benzene.

As noted above, the arene may be unsubstituted. Alternatively, the arene may be substituted by one or more, preferably 1, 2 or 3 substituents. Non-limiting examples of substituents include:

alkyl (preferably methyl, iso-propyl, n-butyl, and tert-butyl), unsubstituted or substituted with one or more:
aryl (preferably phenyl),
sulfoamidoaryl (—NH—$SO_2$-aryl), preferably —NH—$SO_2$-phenyl, unsubstituted or substituted with one or more alkyl, preferably methyl, (an example of sulfoamidoaryl is —NH-tosyl),
hydroxy, and/or
aryl carbamoyl (—C(=O)—NH-aryl), preferably phenyl carbamoyl,
cycloalkyl (preferably cyclohexyl),
alkenyl (preferably allyl),
NO₂,
trialkylsilyl (preferably —Si(CH₂CH₃)₃),
aryl (preferably phenyl), unsubstituted or substituted with one or more:
alkyl (preferably methyl),
alkyloxy (preferably methoxy),
halogen atom (preferably Cl or F),
trialkylsilyl (preferably —Si(CH₃)₃ or —Si(CH₂CH₃)₃), and/or
halogen atoms (preferably Cl or F).

Furthermore, the arene may be fused with a cycloalkyl, preferably cyclohexyl, the cyclohexyl being optionally substituted with one or more alkyl (preferably methyl).

For reaction with the compound of Formula (IVa)—primary and secondary amines—preferred arenes are unsubstituted, or substituted by one or more, preferably 1, 2 or 3 substituents. Non-limiting examples of suitable substituents include:
alkyl (preferably methyl, iso-propyl, n-butyl, and tert-butyl), unsubstituted or substituted with one or more:
aryl (preferably phenyl),
sulfoamidoaryl (—NH—SO₂-aryl), preferably —NH—SO₂-phenyl, unsubstituted or substituted with one or more alkyl, preferably methyl, (an example of sulfoamidoaryl is —NH-tosyl),
hydroxy, and/or
aryl carbamoyl (—C(=O)—NH-aryl), preferably phenyl carbamoyl),
cycloalkyl (preferably cyclohexyl),
alkenyl (preferable allyl), and
aryl (preferably phenyl), unsubstituted or substituted with one or more:
alkyl (preferably methyl),
alkyloxy (preferably methoxy),
halogen atom (preferably Cl or F),
trialkylsilyl (preferably —Si(CH₃)₃ or —Si(CH₂CH₃)₃), and/or
halogen atoms (preferably Cl or F).

For reaction with the compound of Formula (IVb)—hydrazine or hydrazide—preferred arenes are unsubstituted, or substituted by one or more, preferably 1, 2 or 3 substituents. Non-limiting examples of suitable substituents include:
NO₂,
alkyl (preferably tert-butyl),
trialkylsilyl (preferably triethylsilyl), and/or
aryl (preferably phenyl) substituted with one or more:
alkyl (preferably methyl), and/or
halogen atoms (preferably Cl or F).
Furthermore, the arene may be fused with a cycloalkyl, preferably cyclohexyl, the cyclohexyl being optionally substituted with one or more alkyl (preferably methyl).

Herein, a hydroxy arene is an arene as defined above bearing a hydroxyl group (—OH). Such compounds can also be called "phenols" or "phenol derivatives". Preferred hydroxy arenes include the phenols found in the petrochemical feedstocks. More preferred hydroxy arenes include unsubstituted phenol

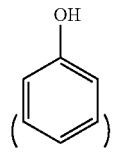

or substituted phenol such as 3,5-di-tert-butylphenol and others. In preferred embodiment, the hydroxy arene bears two substituents of different sizes on each side of the aromatic ring as this increases the regioselectivity of the ortho-oxygenation reaction in step a). In embodiments in which the arene is a benzene, these two substituents of different sizes, which may be located at positions 3 and 5 when the following numbering is used:

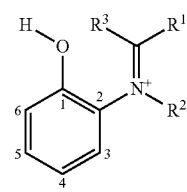

(numbering shown for Formula (Va), the same arene numbering can be used for all formulas).

As noted above, in step a), the hydroxy arene is ortho-oxygenated to produce an ortho-quinone. The ortho-oxygenation of the hydroxy arene to produce an ortho-quinone is carried out under catalytic aerobic conditions. More specifically, this reaction is carried in the presence of O₂ (1 or 2 atm or open flask, preferably 1 atm). A catalytic quantity of a Cu salt is added to a reaction mixture comprising the hydroxy arene in a solvent. Non-limiting examples of suitable solvents include CH₂Cl₂, EtOAc, THF, Me-THF, Et₂O, chlorobenzene, acetone, iPrOAc, Cl₂CH₂CH₂Cl₂, preferably CH₂Cl₂, at 0.1-2.0 M, preferably 0.1M. Preferably, the concentration of the hydroxy arene in the reaction mixture is from about 1 to about 25 mmol. Preferably, the Cu salt is [Cu(CH₃CN)₄]PF₆ (Tetrakis(acetonitrile)copper(I) hexafluorophosphate, herein often abbreviated CuPF₆). Preferably, the reaction mixture comprises about 4 to about 15 mol %, preferably 8 mol %, of the Cu salt. A catalytic quantity of N,N'-di-tert-butyl-ethylene diamine (DBED) is also added to the reaction mixture. Preferably, the reaction mixture comprises about 5 to about 20 mol %, preferably 15 mol % of DBED. The reaction takes about 4 h preferably at about room temperature (e.g. 23° C.), or if desired at a higher temperature.

In step b), the ortho-quinone is condensed with the nitrogen nucleophile to generate an ortho-iminium-quinone of Formula (IVa) or a compound of Formula (IVb). The condensation of the ortho-quinone with the nitrogen nucleophile occurs via the facile condensation of the nitrogen nucleophile (a primary or secondary amine when it is of Formula (IIIa) or a hydrazine or hydrazide when it is of Formula (IIIb)) and a carbonyl to afford an imine (—C=N—C—) or an azine (—C=N—N—), wherein the carbon atom is a ring carbon atom ortho to the aromatic C—O bond in the original hydroxy arene. For step b), following oxygenation, the nitrogen nucleophile is simply mixed in the reaction mixture and the reaction is allowed to proceed in the same conditions as previously. Preferably, the nitrogen nucleophile is added in an amount corresponding from 1.2 to 2 equivalent relative to the hydroxy arene. The reaction takes between about 2 h and about 12 h at a temperature about room temperature (e.g. 23° C.) and 50° C.

In embodiments using a nitrogen nucleophile of Formula (IIIa) (amine), the arene of the ortho-quinone preferably does not bear heteroatom substituents as these tend to react with the amine used in step b) and thus lower the yield of the reaction. A heteroatom substituent is a substituent that attaches to the arene via a heteroatom. Heteroatom substituents include halogen atoms, alkyloxy, aryloxy, and sulfoamidoaryl (—NH—SO$_2$-aryl) (NTs). The alkyloxy substituted aryl and alkyl groups provided for in the above definition of arenes are not heteroatom substituents as they attach to the arene via a carbon atom.

In all of the above, each $R^1$, $R^2$, $R^3$, and $R^{10}$ independently represent a hydrogen atom or a substituent. As is shown herein, the above reaction is quite robust and will proceed for a large variety of substituents on the nitrogen nucleophile.

In embodiments, the nitrogen nucleophile is a primary or secondary amine of Formula (IIIa):

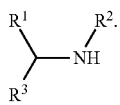

In preferred embodiments, $R^1$, $R^2$, and $R^3$ each independently represent:
a hydrogen atom,
alkyl, preferably methyl, ethyl, isopropyl, sec-butyl, or n-butyl, unsubstituted or substituted with one or more:
   aryl (preferably phenyl) unsubstituted or substituted with one or more hydroxy,
   hydroxy,
   alkoxy (preferably methoxy or isopropyloxy) unsubstituted or substituted with one or more aryl (preferably phenyl),
   aminoalkyl or aminodialkyl (preferably —CH$_2$—N(Me)$_2$),
   alkoxy carbonyl (i.e. —C(=O)—O-alkyl, preferably methoxycarbonyl),
   alkylthio (i.e. S-alkyl, preferably methylthio),
   heterocycloalkyl (preferably piperazinyl), and/or
   halogen atom (preferably Cl),
cycloalkyl (preferably cyclohexyl or cyclopropyl),
alkenyl (preferably allyl),
hydroxyl,
—C(=O)—O—R$^{20}$), wherein R$^{20}$ is aliphatic or aromatic (preferably alkyl, aryl or an amino acid) unsubstituted or substituted, or
aryl or heteroaryl (preferably phenyl, pyridine, furanyl, or thiophenyl) unsubstituted or substituted with one or more:
   alkyl (preferably C$_{1-4}$-alkyl, more preferably methyl or tert-butyl) unsubstituted or substituted with one or more halogen atoms (preferably F),
   alkoxy (preferably methoxy),
   aryl (preferably phenyl) unsubstituted or substituted with one or more alkyl (preferably methyl), the alkyl being unsubstituted or substituted with one or more halogen atoms (preferably F),
   nitro (NO$_2$),
   sulfonamine (—SO$_2$—NH$_2$), and/or
   halogen atom (preferably F, Cl, or Br); or
$R^1$ and $R^3$ together with the carbon atom to which they are attached form a ring, preferably a saturated ring, more preferably a cycloalkyl, yet more preferably cyclohexyl; or
$R^1$ and $R^2$ together with the carbon and nitrogen atoms to which they are attached form a ring, preferably a 5- or 6-membered ring, that:
   is saturated or unsaturated, preferably saturated or comprising one unsaturation;
   is unsubstituted or substituted with one or more substituents, preferably one substituent;
      Non-limiting examples of substituents for the ring include hydroxy.
   optionally comprises, in addition to the nitrogen atom to which $R^2$ is attached, one or more additional heteroatom, preferably one additional heteroatom, preferably oxygen, preferably in position para to the nitrogen atom to which $R^2$ is attached; and
   is optionally fused with an aromatic ring (preferably phenyl) that is unsubstituted or substituted with one or more substituents, preferably two substituents.
      Non-limiting examples of substituents for the aromatic ring include alkyloxy, preferably methoxy.

Preferred examples of rings formed by $R^1$ and $R^2$ together with the carbon and nitrogen atoms to which they are attached include pyrrolidine, piperazine, morpholine, indoline, iso-indoline, tetrahydroisoquinoline, piperidine, 2,5-dihydropyrrole, dihydropyrrolidine, dihydroindoline, and dihydroisoindoline as well as their substituted derivatives.

Of note, when the amine of Formula (IIIa) is a primary amine, $R^2$ represents a hydrogen atom. Primary amines are thus of Formula (IIIa'):

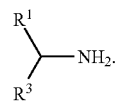

In preferred embodiments of such primary amines, $R^3$ represents a hydrogen atom.

In other preferred embodiments of such primary amines, both $R^1$ and $R^3$ do not represent hydrogen atoms. In other words, the primary amine is α-branched. In preferred such embodiments, $R^3$ is an alkoxycarbonyl (—C(=O)—O-alkyl), preferably ethoxycarbonyl.

In other preferred embodiments of such primary amines, $R^1$ and $R^3$ together with the carbon atom to which they are attached form a ring.

Preferred $R^1$ and $R^3$ combinations for primary amines include the following:

| $R^1$ | $R^3$ | Corresponding amines |
|---|---|---|
| 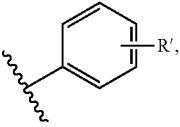 | H | 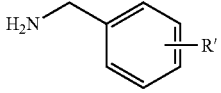 |

R' = hydrogen atom

-continued

| R¹ | R³ | Corresponding amines |
|---|---|---|
| 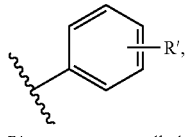<br>R' = one or more alkyl,<br>preferably 1, 2 or 3 alkyl groups<br>preferably $C_{1-4}$-alkyl,<br>more preferably methyl or tert-butyl, | H | |
| 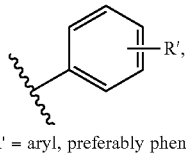<br>R' = aryl, preferably phenyl,<br>R' is preferably at position 2 | H | |
| 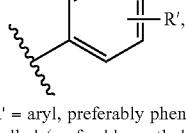<br>R' = aryl, preferably phenyl,<br>substituted with alkyl (preferably methyl) unsubstituted or<br>substituted with one or more halogen atom, preferably F,<br>preferably —$CF_3$,<br>preferably at position 4 on the aryl.<br>Preferably R' is at position 2 | H | |
| 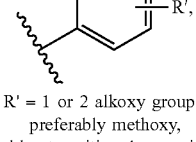<br>R' = 1 or 2 alkoxy groups,<br>preferably methoxy,<br>R' is preferably at position 4 or positions 2 and 4 | H | |
| 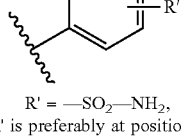<br>R' = —$SO_2$—$NH_2$,<br>R' is preferably at position 4 | H | 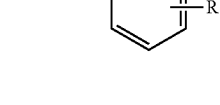 |
| 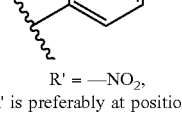<br>R' = —$NO_2$,<br>R' is preferably at position 2 | H | |
| 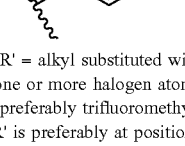<br>R' = alkyl substituted with<br>one or more halogen atoms,<br>preferably trifluoromethyl.<br>R' is preferably at position 3 | H | |

-continued

| R¹ | R³ | Corresponding amines |
|---|---|---|
| 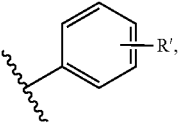<br>R' = one or more halogen atom, preferably F, Cl, or Br, preferably one F, Cl, Br, or two F. R' is preferably at positions 2, 3, or 4, or at position 2 and 6 | H | |
| Alkenyl, preferably C₂  | H | H₂N—R¹ |
| —OH | H | |
| Alkyl, preferably ethyl | H | |
| Cycloalkyl, preferably cyclohexyl | H | |
| Alkyl, preferably methyl, substituted with one or more aryl, preferably one or two aryl, preferably phenyl preferably —CH₂-phenyl or —CH(phenyl)₂ | H | |
| Alkyl, preferably C₁₋₄, substituted with hydroxyl, preferably —CH₂OH or —(CH₂)₄OH | H | H₂N—R¹ |
| Alkyl, preferably ethyl, substituted with alkoxy, preferably isopropyloxy, preferably —(CH₂)₂—O—iPr | H | |
| Alkyl, preferably methyl, substituted with aminoalkyl (—NH-alkyl) or aminodialkyl (—N(alkyl)₂), preferably —CH₂—N(Me)₂ | H | |
| Alkyl substituted with a halogen atom, preferably chloro, preferably —CH₂Cl | H | |
| H | H | H₂N—CH₃ |
| Allyl (—CH₂—CH=CH₂) | H | NH₂—CH—CH₂—CH=CH₂ |
| 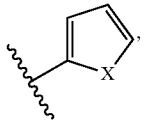<br>X = O (furanyl) or S (thiofuranyl), optionally substituted with alkyl (preferably methyl) | H | 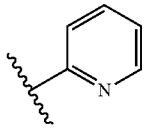 [SMILES: *c1ccccn1] |
| 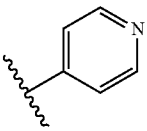 [SMILES: *c1ccncc1]<br>(o-pyridinyl) | H | H₂N—[2-pyridyl] |
| 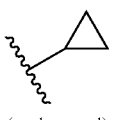<br>(p-pyridynyl) | H | H₂N—[4-pyridyl] |
| [cyclopropyl group]<br>(cyclopropyl) | H | H₂N—[cyclopropyl] |

-continued

| R¹ | R³ | Corresponding amines |
|---|---|---|
| 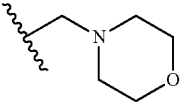 [SMILES: *CN1CCOCC1]<br>(morpholinyl) | H | 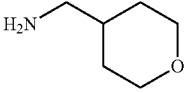 |
| Alkyl,<br>preferably methyl, isopropyl, sec-butyl, | Alkoxycarbonyl,<br>preferably<br>ethoxycarbonyl | 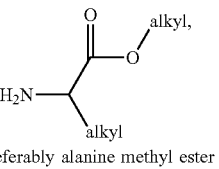<br>preferably alanine methyl ester |
| Aryl, preferably phenyl | Alkoxycarbonyl,<br>preferably<br>ethoxycarbonyl | 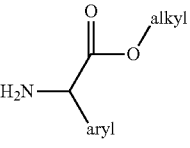 |
| Alkyl (preferably methyl)<br>substituted with alkyloxy (preferably methoxy),<br>the alkyloxy being substituted with aryl<br>(preferably phenyl)<br>More preferably —CH₂—O-benzyl | Alkoxycarbonyl,<br>preferably<br>ethoxycarbonyl | 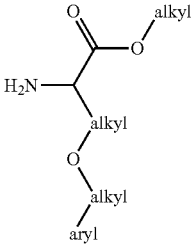 |
| Alkyl (preferably ethyl)<br>substituted with alkylthio (preferably methylthio)<br>More preferably —CH₂—CH₂—S—CH₃ | Alkoxycarbonyl,<br>preferably<br>ethoxycarbonyl | 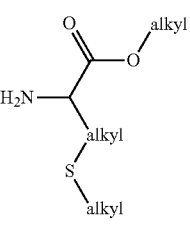 |
| Alkyl (preferably ethyl)<br>substituted with alkoxycarbonyl (—C(=O)—O-alkyl),<br>preferably methoxycarbonyl<br>More preferably —CH₂—CH₂—C(=O)—O—CH₃ | Alkoxycarbonyl,<br>preferably<br>ethoxycarbonyl | 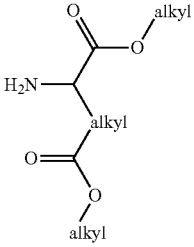 |
| Alkyl (preferably methyl)<br>substituted with aryl (preferably phenyl),<br>the aryl being substituted with hydroxy,<br>preferably at the 4 position<br>More preferably —CH₂—(C₆H₄-4-OH) | Alkoxycarbonyl,<br>preferably<br>ethoxycarbonyl | 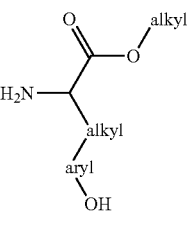 |
| Alkyl, preferably methyl | Alkyl,<br>preferably methyl | 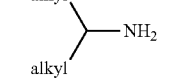 |

| R¹ | R³ | Corresponding amines |
|---|---|---|
| R¹ and R₃ together form a ring, preferably cyclohexyl | | 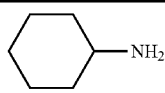 |

When the amine of formula (IIIa) is a secondary amine, $R^2$ does not represent a hydrogen atom. In preferred secondary amines, $R^3$ represents a hydrogen atom. In preferred secondary amines, $R^1$ together with $R^2$ form a ring. Preferred $R^1$, $R^2$ and $R^3$ combinations forming secondary amines include the following:

| R¹ and R² together form | R³ | Corresponding amines |
|---|---|---|
| A pyrrolidine ring, optionally substituted with a hydroxy group, preferably at position 3 | H | 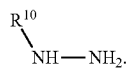 |
| A morpholine ring | H | |
| A 1,2,3,4-tetrahydroisoquinoline ring, preferably substituted by alkoxy, preferably two methoxy groups, preferably at position 6 and 7 | H | |
| A piperidine ring | H | |
| A 2,5-dihydropyrrole ring | H | |
| A dihydroindole ring | H | |
| A dihydroisoindole ring | H | |

In embodiments, the nitrogen nucleophile is Formula (IIIb):

$$R^{10}\!-\!NH\!-\!NH_2.$$

In preferred embodiments, $R^{10}$ represents:
  aryl (preferably phenyl) substituted with one or more:
    —NO₂,
    —SO₂,
    halogen atom (preferably F or Cl), and/or
    perfluorinated alkyl (preferably —CF₃),
  heteroaryl (preferably pyridinyl or diazinyl) unsubstituted or substituted with one or more:
    —NO₂,
    —SO₂,
    halogen atom (preferably F or Cl), and/or
    perfluorinated alkyl (preferably —CH), or
  —C(=O)—$R^{11}$, wherein $R^{11}$ represents:
    aryl or heteroaryl (preferably phenyl, furanyl, oxazolyl, or pyridynyl) unsubstituted or substituted with one or more aryl (preferably phenyl), or
    alkyloxy (preferably isopropyloxy),
with the proviso that nitrogen nucleophile is Formula (IIIb) is not

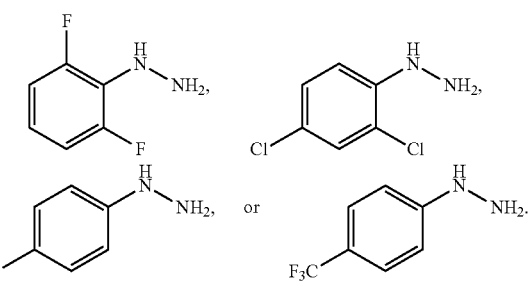

Of note, when $R_{10}$ is —C(=O)—$R^{11}$, the compound of Formula (IIIb) represents a hydrazide. Otherwise, it is a hydrazine.

Preferred nitrogen nucleophile of Formula (IIIb) include

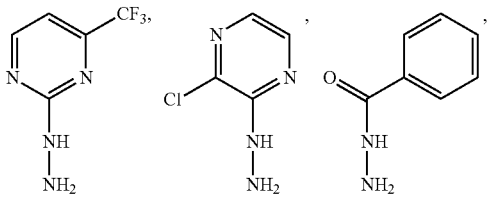

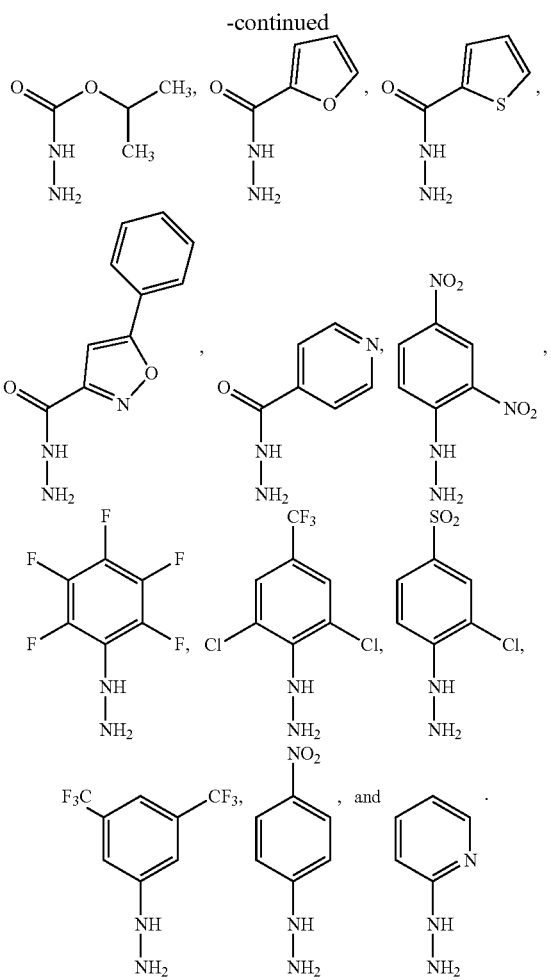

Finally, in step c), the condensation is followed by a spontaneous 1,5-hydrogen atom shift of the compound of Formula (IVa) or (IVb), thereby producing arenes with a C—N bond ortho to a C—O bond. These compounds are of Formula (Va), which is an ortho-iminium-hydroxy arene, and Formula (Vb), which is an ortho-azo-hydroxy arene, respectively. Indeed, the condensation in step b), triggers a redox-isomerization (i.e. in this case a 1,5-hydrogen atom shift) that installs the desired aromatic C—N bond on the arene.

It should be noted that the compounds of Formula (IVa) and (Va) bear a positive charge. This charge is counterbalanced by an anion present in the reaction mixture. The nature of the anion is not crucial.

Ortho-Iminium-Hydroxy Arenes of Formula (IVa)

Of note, the ortho-iminium-hydroxy arene of Formula (Va) is not typically isolated. However, the ortho-iminium-hydroxy arenes obtained above (aromatic Schiff-bases) are versatile reagents with myriad applications in synthesis and coordination chemistry. For example, these ortho-imino-hydroxy arenes can be converted into a diverse array of benz-azo heterocyclic compounds and 1,2-amino phenols (FIG. 1, Inset B).

The exact fate of the ortho-iminium-hydroxy arenes will depend on the nature of the amine used in the above condensation reaction (step b)). Indeed, various reaction paths are possible. These will be described below.

Primary Amines
Primary Amines in which Both $R^2$ and $R^3$ Represent Hydrogen Atoms When the amine is a primary amine (i.e. $R^2$ represents a hydrogen atom) and wherein $R^3$ also represents a hydrogen atom, in the above reaction conditions, the ortho-iminium-hydroxy arene of Formula (Va) spontaneously cyclizes to form an oxazole arene of Formula (VI):

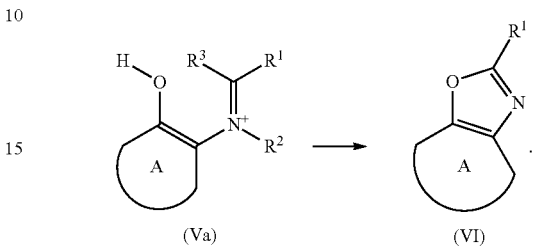

Preferred amines for this reaction are not limited (except by the fact that both $R_2$ and $R_3$ represent hydrogen atoms) and include for example aliphatic and aryl amines. A preferred amine for this reaction is benzylamine.

Primary α-Branched Amines

When the amine is a primary amine (i.e. $R^2$ is a hydrogen atom) and $R^1$ and $R^3$ do not represent hydrogen atoms, an equilibrium between the ortho-imino-hydroxy arene of Formula (VII) and its cyclized form: dihydrooxazole arene of Formula (VIII) is obtained:

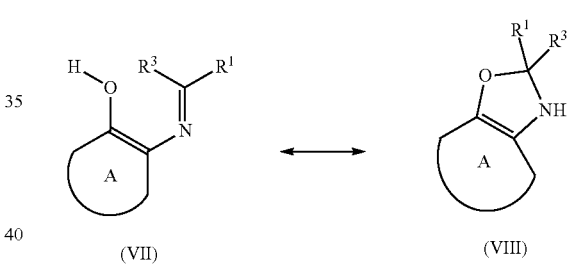

In embodiments in which $R^3$ is —C(=O)—O—$R^{20}$, the ortho-imino-hydroxy arene of Formula (VII) can be represented by Formula (VII') and the method can comprise, as a further step, the lactonization of the ortho-imino-hydroxy arene of Formula (VII) to produce an oxazinone arene of Formula (IX):

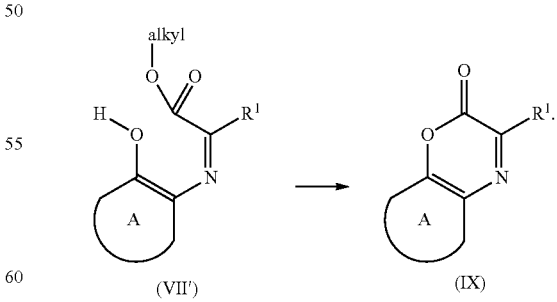

Lactonization can be effected preferably by heating the reaction mixture, for example at about 50° C., which increases yield compared to room temperature, for example in methanol, for about 4 h. Preferred amines for this reaction include amines wherein $R^{20}$ is an aliphatic or aromatic group. Particularly preferred amines include amines wherein $R^{20}$ is an alkyl, such as ethyl or an amino acid, preferably the amine is alanine methyl ester.

Figure 13:
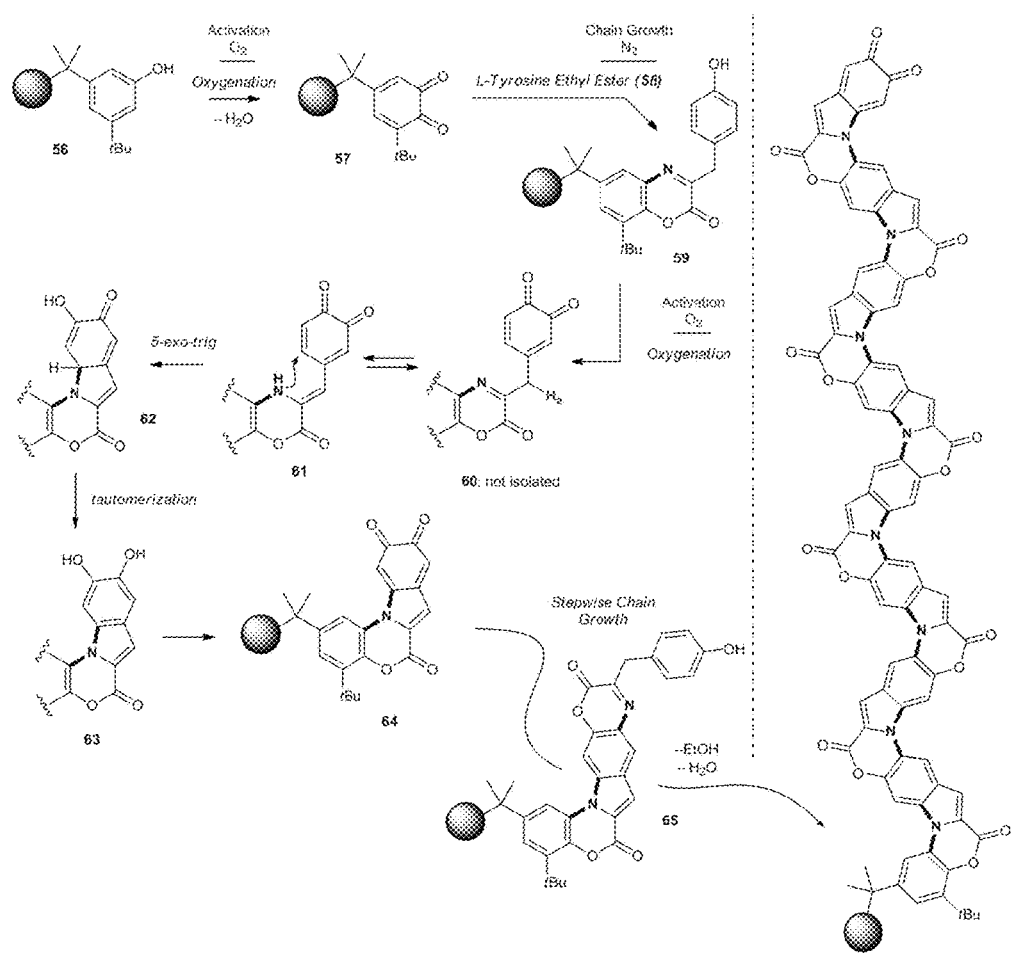
FIG. 13 shows the synthesis of polymeric benzoxazoles.

When the $R^1$ substituent of the oxazole arene of Formula (IX) comprises a hydroxy arene, preferably phenol, this compound can further be repeatedly subjected to the above steps a) to c) followed by lactonization to build an heterocyclic polymer. This concept is outlined in FIGS. 13 and 14. A preferred amine for this reaction is L-tyrosine ethyl ester.

Alternatively, the method can comprise as a further step the hydrolysis of the ortho-imino-hydroxy arene of Formula (VII) to produce an ortho-amino-hydroxy arene of Formula (X):

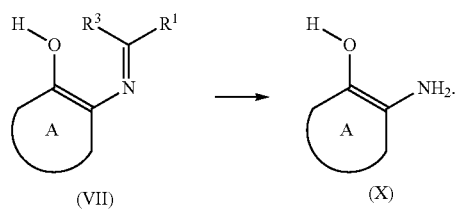

(VII)    (X)

Hydrolysis can be effected by adding an acid to the reaction mixture. Non-limiting examples of acids include $NaHSO_4$.

In alternative embodiments, the ortho-imino-hydroxy arene arene of Formula (VII) can be reacted with an organometallic reagent ($R^4$-M) to yield an $\alpha,\alpha,\alpha$-trisubstituted compound of Formula (XI):

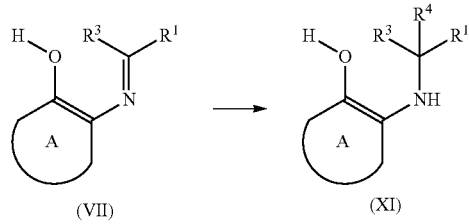

(VII)    (XI)

wherein $R^4$ is alkyl, alkenyl, aryl, O—$R^{30}$, or N($R^{30}$)$_2$, wherein is $R^{30}$ is H, or aliphatic or aromatic group. Preferred organometallic reagents ($R^4$-M) include Grigrand reagents: n-butyl-MgBr and phenyl-MgBr, as well as $CH_2$=CH—$CH_2$-TMS, boronic acids and boronic esters.

Secondary Amines

For secondary amines, the ortho-iminium-hydroxy arene of Formula (Va) is generally obtained in equilibrium with its cyclized form: dihydrooxazole arene of Formula (XII):

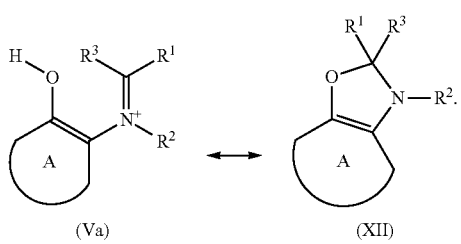

(Va)    (XII)

In embodiments, the method can further comprise the step of quenching the reaction mixture, for example by adding $NaHSO_4$ (for example 10% aqueous). This yields the above dihydrooxazole arene of Formula (XII). Preferred secondary amines for this reaction include pyrrolidine, piperidine, piperazine, dihydropyrrolidine, indoline, iso-indoline, morpholine, tetrahydroxisoquinoline as well as their derivatives and include acyclic amines, such N-benzylmethylamine, as well.

In alternative embodiments, the method can further comprise the step of reducing the dihydrooxazole arene of Formula (XII) to yield to yield an ortho-amino-hydroxy arene of Formula (XIII):

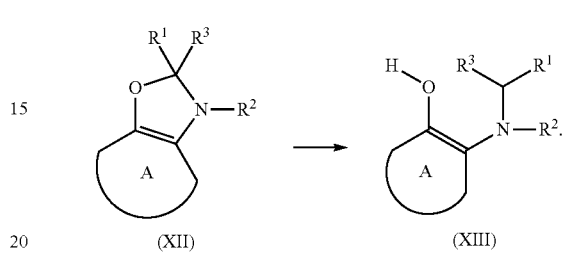

(XII)    (XIII)

This can be achieved by adding a reducing agent (for example a hydride such as $NaBH_4$ in MeOH), to the reaction mixture. Preferred secondary amines for this reaction include pyrrolidine, piperidine, morpholine, tetrahydroisoquinoline, dihydropyrrolidine, indoline, iso-indoline, piperazine as well as their derivatives. Also, this reaction can be carried with $\alpha$-branched primary amines, such as cyclohexylamine and isopropylamine, and acyclic amines, such a N-benzylmethylamine. When this reaction is carried out with pyrrolidine, a further treatment with sodium periodate ($NaIO_4$) oxidizes the $C_5$ of 2-substituted N-aryl pyrrolidine to provide the corresponding lactams.

In further embodiments, a carbon nucleophile is also added to this reaction mixture to yield a substituted ortho-amino-hydroxy arene of Formula (XIV):

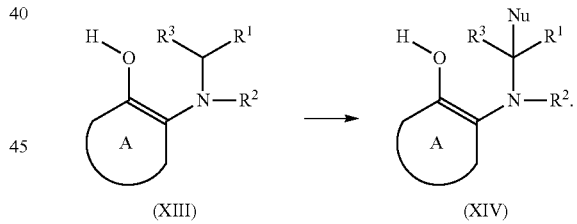

(XIII)    (XIV)

Non-limiting examples of carbon nuclophiles include Grignard reagents of formula Nu-MgBr, wherein Nu is alkyl or alkenyl, preferably methyl, ethyl, n-butyl or allyl ($CH_2$=CH—$CH_2$—). Preferred secondary amines for this reaction include pyrrolidine, dihydropyrrolidine, indoline, iso-indoline, morpholino as well as tetrahydroxisoquinoline. This reaction takes about 2 h at room temperature In further embodiments, the dihydrooxazole arene of Formula (XII), wherein $R^3$=H, can be reacted with an aryl boronic acid (Aryl-B(OH)$_2$), in a modified Petasis reaction, to yield a compound of Formula (XV). This transformation functionalizes the C—H bond adjacent to the nitrogen in what is formally a Chan-Lam coupling between an aryl boronic acid and a C—H bond. Reintroduction of $O_2$ at the end of the transformation will trigger oxidative cleavage (or deprotection) to release a functionalized amine of Formula (XVI) with concomitant recovery of the ortho-quinone of Formula (II).

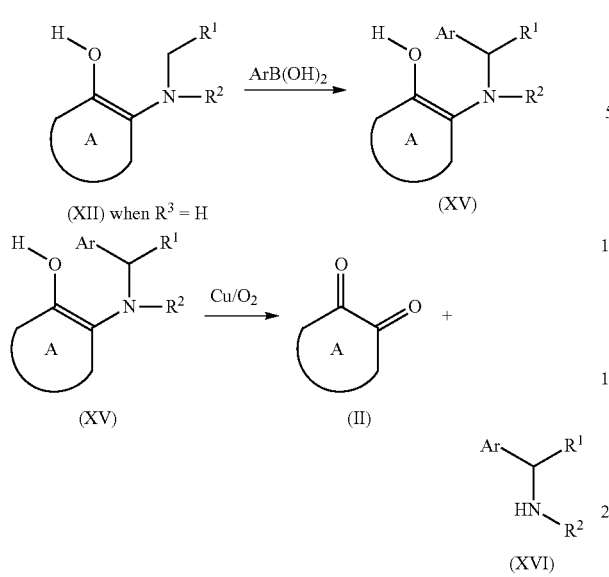

(XII) when R³ = H → (XV)

(XV) —Cu/O₂→ (II) +

(XVI)

A preferred amine for this reaction is

For secondary amines where R¹ and R² form a cycle that is substituted with a hydroxyl group (preferably located in meta to the nitrogen atom), the ortho-iminium-hydroxy arene of Formula (Va) can be represented by Formula (XVI), which rearranges through a hydrogen shift (specifically a 1,2 hydrogen shift when the hydroxyl group is located in meta to the nitrogen atom) to yield a compound of Formula (XVII):

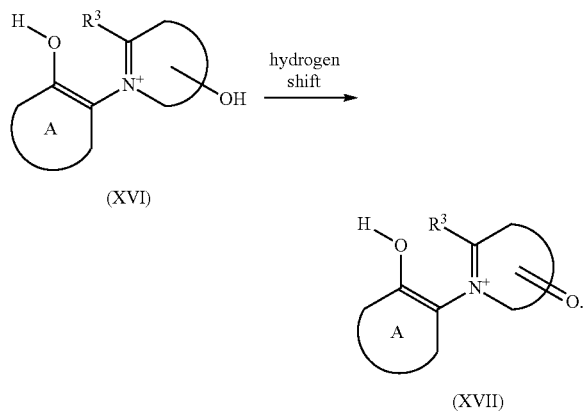

Preferred amines undergoing such shift include

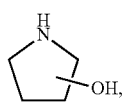

especially

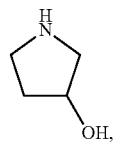

as well as their derivatives bearing additional substituents.

Furthermore, for secondary amine 2,5-dihydro-1H-pyrrole

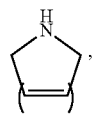

the ortho-iminium-hydroxy arene of Formula (V) can be represented by Formula (XVIII), which undergoes aromatization to yield a compound of Formula (XIX).

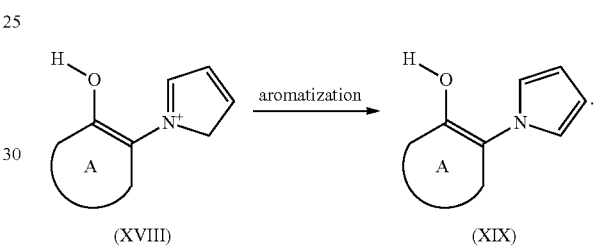

Figure 12:
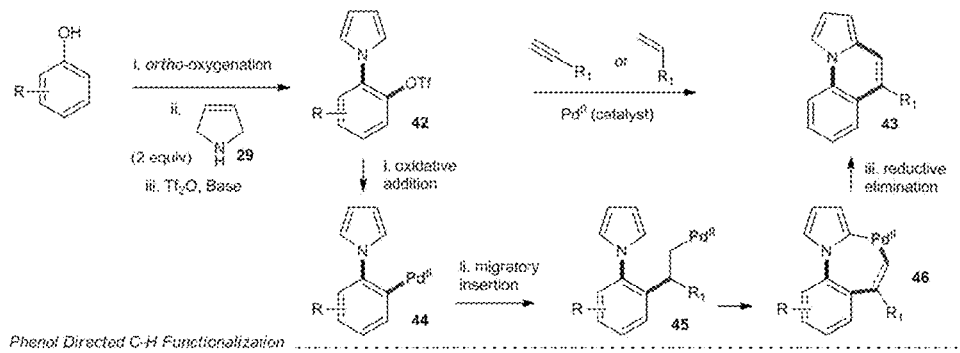
FIG. 12 shows the diversification of N-arylated pyrroles and extension to indoline and iso-indoline coupling partners.
Figure 12:
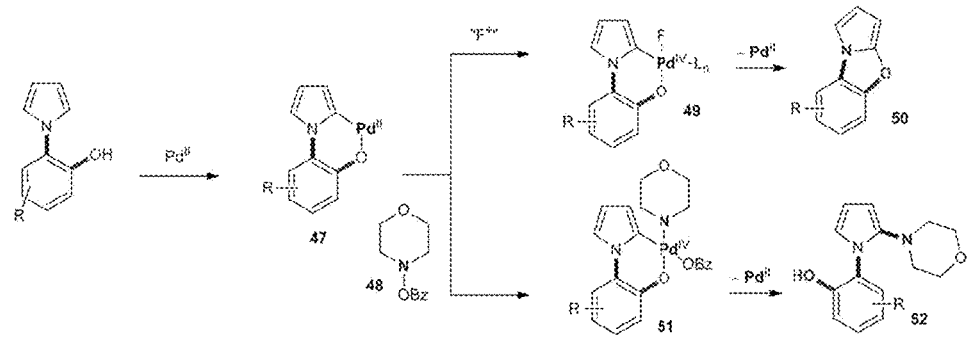
Figure 12:
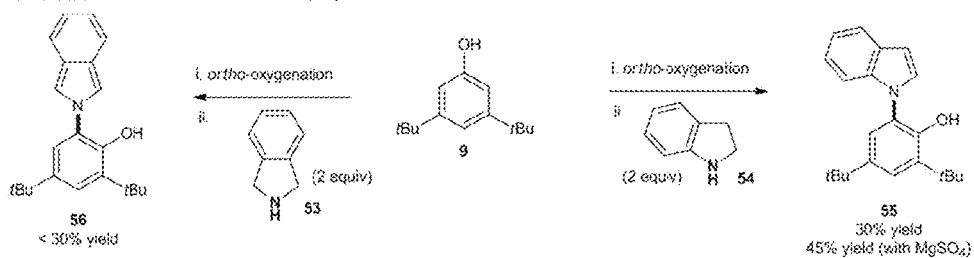

Different reaction schemes to for C—H functionalization at the 2-position of the pyrrole of compound of Formula (XIX) are shown in FIG. 12, Sub-Reaction Path B. This also applies for secondary amines dihydroindole and dihydroisoindole.

Specific Embodiments of the Reactions with Primary and Secondary Amines

Figure 2:
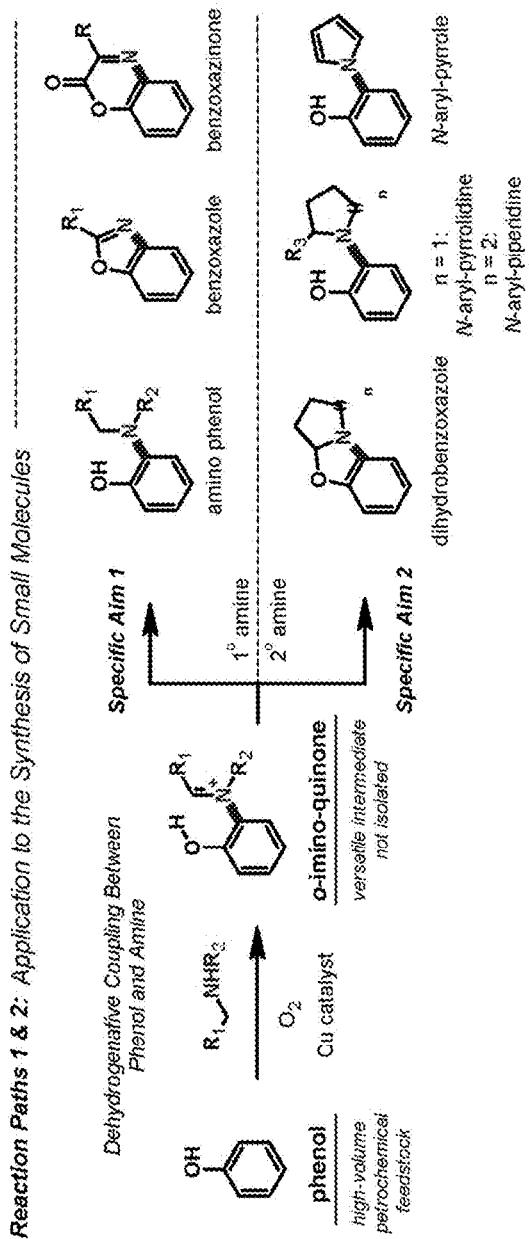
FIG. 2 shows the synthesis of azo-heterocycles and amino-phenols by direct, dehydrogenative coupling of phenols with 1° amines (Reaction Path 1) and 2° amines (Reaction Path 2)

Reaction Path 1 (FIG. 2) involves the coupling of 1° (primary) amines with phenol (as an example of an hydroxy arenol) and their direct conversion into ortho-amino phenols, benzoxazoles or benzoxazinones.

Reaction Path 2 (FIG. 2) involves 2° (secondary) amines with phenol and their direct conversion into dihydrobenzoxazoles, N-arylated pyrrolidines or piperidines, and N-arylated pyrroles. As shown above, these dihydrobenzoxazoles can be used for creating newly functionalized secondary amines.

Through Reaction Paths 1 and 2, the method of the invention represents an efficient synthesis of high-value azo-heterocycles and ortho-amino-phenols, which are of fundamental importance to the pharmaceutical and agrochemical industries.

Figure 3:
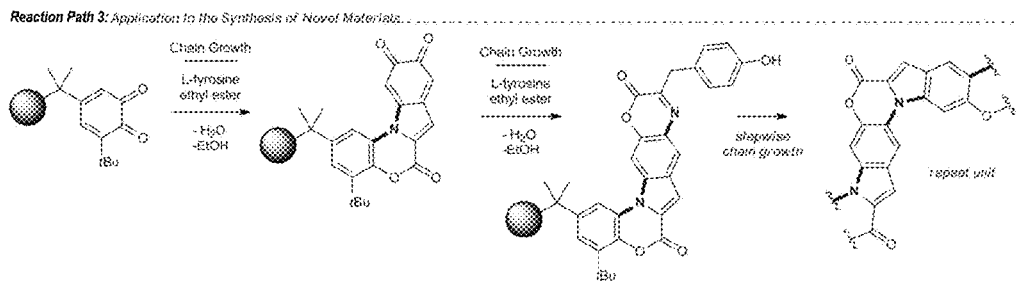
FIG. 3 shows the synthesis of extended p-systems (Reaction Path 3) by iterative chain growth.

Reaction Path 3 (FIG. 3) is a stepwise, aerobic process for the synthesis of extended nitrogen and oxygen rich π-systems. Through this reaction path, the method of the invention represents a versatile and efficient methodology for the synthesis of poly-heteroaromatic conjugated materials, including polymers. The present invention also relates to these conjugated materials, which can find application, for example, as charge carriers in electronic devices.

Reaction Paths 1 to 3 address a pressing challenge that afflicts a broad range of disciplines. The prevalence of aromatic C—N bonds in nearly all types of functional molecules and materials mandates improved efficiency for their synthesis, since more than 90% of commercial chemicals are derived from petroleum, and since petroleum is almost entirely devoid of nitrogen. While amination reactions have been a topic of extensive investigation, available methodologies, which are tailored to pharmaceutical sciences, are plagued by poor synthetic efficiency. In addition, they are not applicable to the challenges of materials science and macromolecular synthesis. This present invention demonstrates how a single methodology can accomplish this task directly from bulk petrochemicals under environmentally benign conditions.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. It is to be noted that, unless otherwise specified, the hydrocarbon chains of these groups can be linear or branched. Further, unless otherwise specified, these groups can contain between 1 and 12 carbon atoms, between 1 and 6 carbon atoms, between 1 and 3 carbon atoms, or contain 1 or 2 carbon atoms.

For more certainty, an alkyl is a monovalent saturated aliphatic hydrocarbon radical of general formula $C_nH_{2n+1}$.

For more certainty, an alkenyl is a monovalent aliphatic hydrocarbon radical comprising at least one double bond.

An alkyloxy or alkoxy is a monovalent radical of formula —O-alkyl.

Herein, the terms "cycloalkyl", "aryl", "heterocycloalkyl", and "heteroaryl", and "methylene" have their ordinary meaning in the art. For more certainty, herein, a "cycloalkyl" is a monovalent saturated aliphatic hydrocarbon radical of general formula —$C_nH_{2n-1}$, wherein the carbon atoms are arranged in ring (also called cycle). An "aryl" is a monovalent arene radical. A "heterocycloalkyl" is a cycloalkyl wherein at least one of the carbon atoms is replaced by a heteroatom, such as nitrogen or oxygen. Similarly, a "heteroaryl" is an aryl wherein at least one of the carbon atoms is replaced by a heteroatom, such as nitrogen or oxygen.

Herein, a "group substituted with one or more A, B, and/or C" means that one or more hydrogen atoms of the groups may be replaced with groups selected from A, B, and C. Of note, the groups do not need to be identical; one hydrogen atom may be replaced by A, while another may be replaced by B.

Of note, herein a general chemical structure, with various substituents ($R^1$, $R^2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—Synthesis of Nitrogen Rich Heterocycles and Amino Phenols

Figure 4:
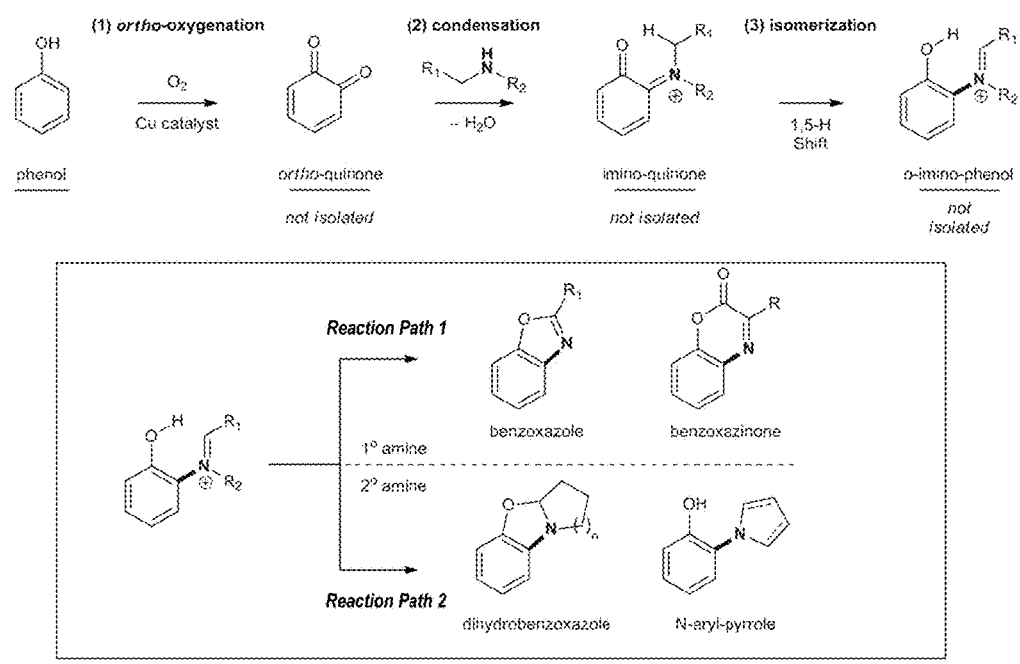
FIG. 4 shows the strategy for aromatic C—N bond formation.

We describe below the dehydrogenative coupling of phenols and amines to create nitrogen rich heterocycles and amino phenols (FIG. 4). Mechanistically, the process is composed of (1) ortho-oxygenation, (2) condensation with an amine to generate an ortho-imino-quinone, and (3) 1,5-hydrogen atom shift to obtain an ortho-imino-phenol. This is followed by various reactions to produce an array of compounds.

Reaction Path 1—Coupling of Phenols and 1° Amines

We first provide a dehydrogenative coupling between 1° amines and phenols that provides ortho-aminated benz-azo heterocycles or 1,2-amino phenols.

Figure 5:
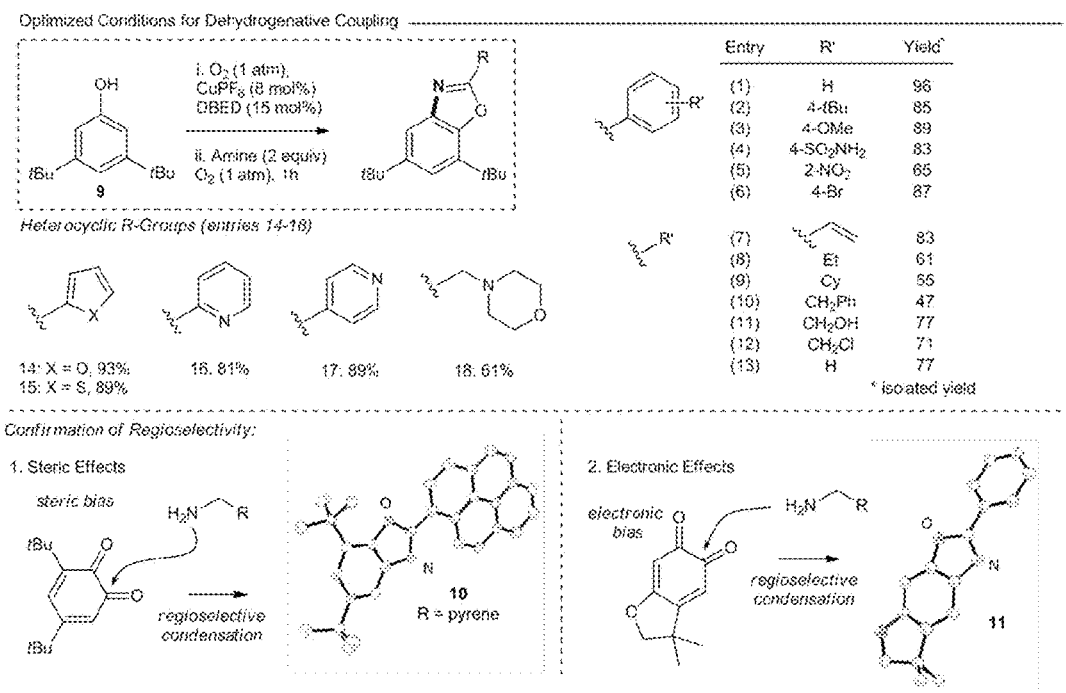
FIG. 5 shows the regioselective synthesis of benzoxazole heterocycles.
Figure 6:
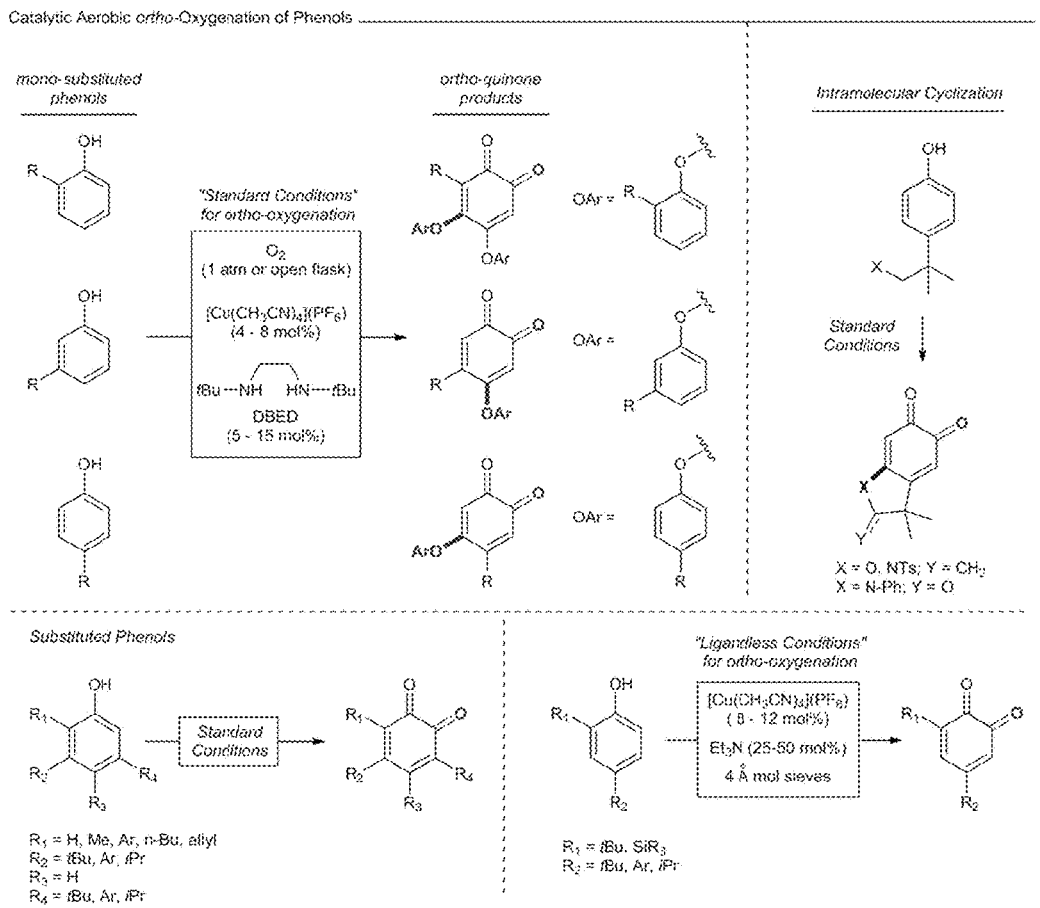
FIG. 6. shows the catalytic aerobic ortho-oxygenation of phenol.

We developed conditions for the dehydrogenative coupling of 3,5-di-tert-butylphenol (1) and 1° amines to provide benzoxazoles (FIG. 5, entries 1-18). This is a 1-pot, catalytic aerobic process that uses readily accessible phenols, and previous methods with a catalytic aerobic alternative. The reaction was conducted by oxygenation of the starting phenol under our standard conditions—which are defined in FIG. 6 (In particular, the conditions are composed of catalytic quantities of a Cu salt, along with catalytic quantities of N,N'-di-tert-butyl-ethylene diamine (DBED). The reaction can be run in a range of solvents.). Once complete (~4 h), the 1° amine was added directly to the reaction vessel, the mixture was stirred for 10 min, and oxygenation was continued for an additional 1-2 h. The x-ray crystal structures of pyrene-benzoxazole 10 and furan 11 confirmed the regioselectivity of amine condensation at the less sterically encumbered or more electrophilic of the ortho-quinone's two carbonyls.

Figure 7:
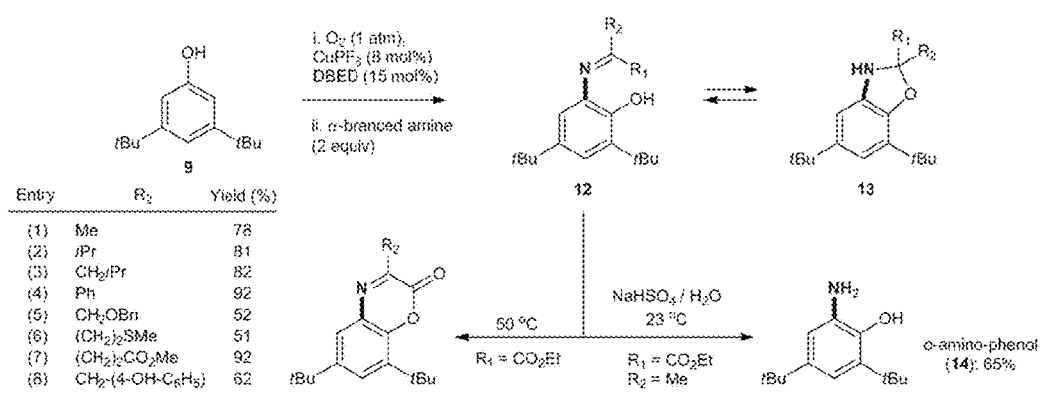
FIG. 7 shows the regioselective synthesis of benzoxazinone heterocycles and ortho-amino phenols.

When primary-α-branched amines were used in the dehydrogenative coupling, oxidation of dihydrobenzoxazole 13 was not possible, and an equilibrium with ortho-imino-phenol 12 was established (FIG. 7). If $R_1$=$CO_2Et$, 12 underwent lactonization when the reaction was warmed to 50° C. to provide benzoxazinone heterocycles (entries 1-8). Alternatively, addition of an aqueous acid to 12 at room temperature afforded ortho-amino-phenol 14 following hydrolysis. This is an attractive synthesis of 1,2-amino-phenols that employs alanine as a source of nitrogen. This is an environmentally friendly alternative to $HNO_3$, which is currently used for the synthesis of amino phenols by nitration/reduction of the corresponding phenols.

The above results demonstrate that phenols and 1° amines undergo a sequential 1-pot dehydrogenative coupling to provide benzoxazole and benzoxazinone heterocycles or ortho-amino phenols. Sub-Reaction Path A develops these preliminary results into a general heterocycle synthesis by evaluating the scope of the phenol. Sub-Reaction Path B represents a 1-pot sequential synthesis of sterically hindered aryl amines by trapping the ortho-imino-phenol with carbon nucleophiles and Sub-Reaction Path C develops aza-Wittig reagents as alternative nitrogen coupling partners for currently inaccessible substrates.

Sub-Reaction Path A—Scope of Phenol

The factors that influence regioselectivity during ortho-oxygenation (FIG. 8—Sub-Reaction Path A) were investigated. We observed complete selectivity for ortho-oxygenation of 15 at position b when $R_1$=tert-butyl or mesityl and $R_2$=Ph (c.f. quinones 16 and 17). Selectivity decreases in less biased cases (entry 1), but is sensitive to remote substituent effects (compare entries 1-3). From these results, we propose transition state model 18, which rationalizes the observed substituent effects by placing the smaller $R_2$ substituent in close proximity to the tBu-groups of the DBED ligand.

Sub-Reaction Path B—Synthesis of Hindered Aryl-Amines

Figure 8:
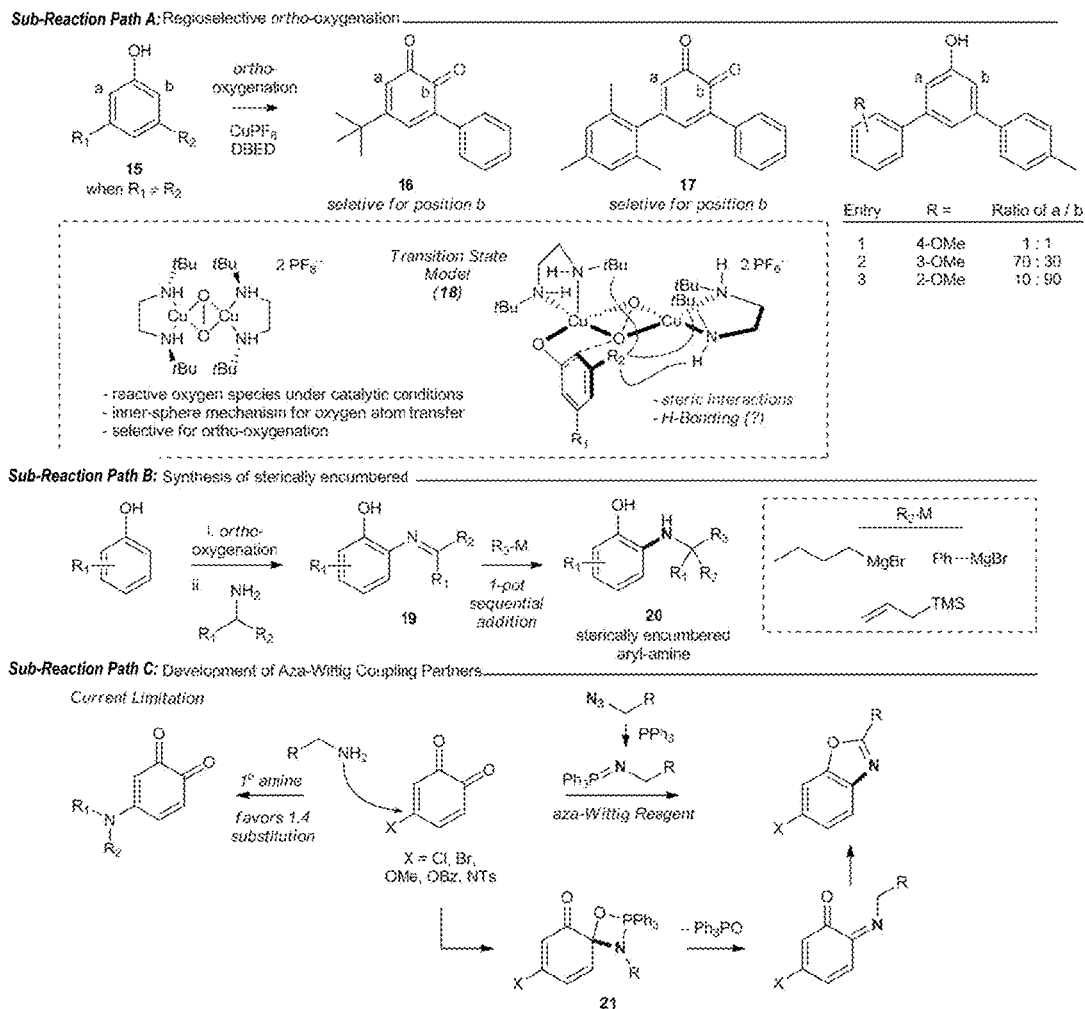
FIG. 8 shows the articulation of Sub-Reaction Paths A-C.

The challenge of coupling sterically encumbered α,α,α-trisubstituted amines was recently discussed. Here we propose an alternative approach to this class of aryl amine that alkylates ortho-imino-phenol 19 with an organometallic reagent (FIG. 8—Sub-Reaction Path B). (see below for proof of concept with 2° amines)

This would establish a 3-component coupling between a phenol, an α-branched 1° amine and readily available carbon nucleophiles to synthesize sterically demanding, 1,2-amino phenols. Imines related to 19 are widely employed electrophiles, and related coupling reactions with boronic acids have been reported (see below for additional discussion).

Sub-Reaction Path C—Aza-Wittig Reagents as Alternative Nitrogen Coupling Partners ortho-Quinones that bear heteroatom substituents are incompatible with the above described reaction conditions due to competitive substitution by 1,4-conjugate addition/elimination (FIG. 8—Sub-Reaction Path C). To improve selectivity for 1,2-addition, we investigate the aza-Wittig reagents, which is accessible from the azide and triphenyl-phosphine. These reagents react smoothly with a range of carbonyl compounds to return the corresponding imine.[68] We anticipate that a more concerted and less reversible mechanism via 4-membered intermediate 21 will improve selectivity for 1,2-addition.

Reaction Path 2: Coupling of Phenols and 2° Amines

We now describe the dehydrogenative coupling between cyclic 2° amines and phenols that provides substituted pyrroles, pyrrolidines and piperidines.

Figure 9:
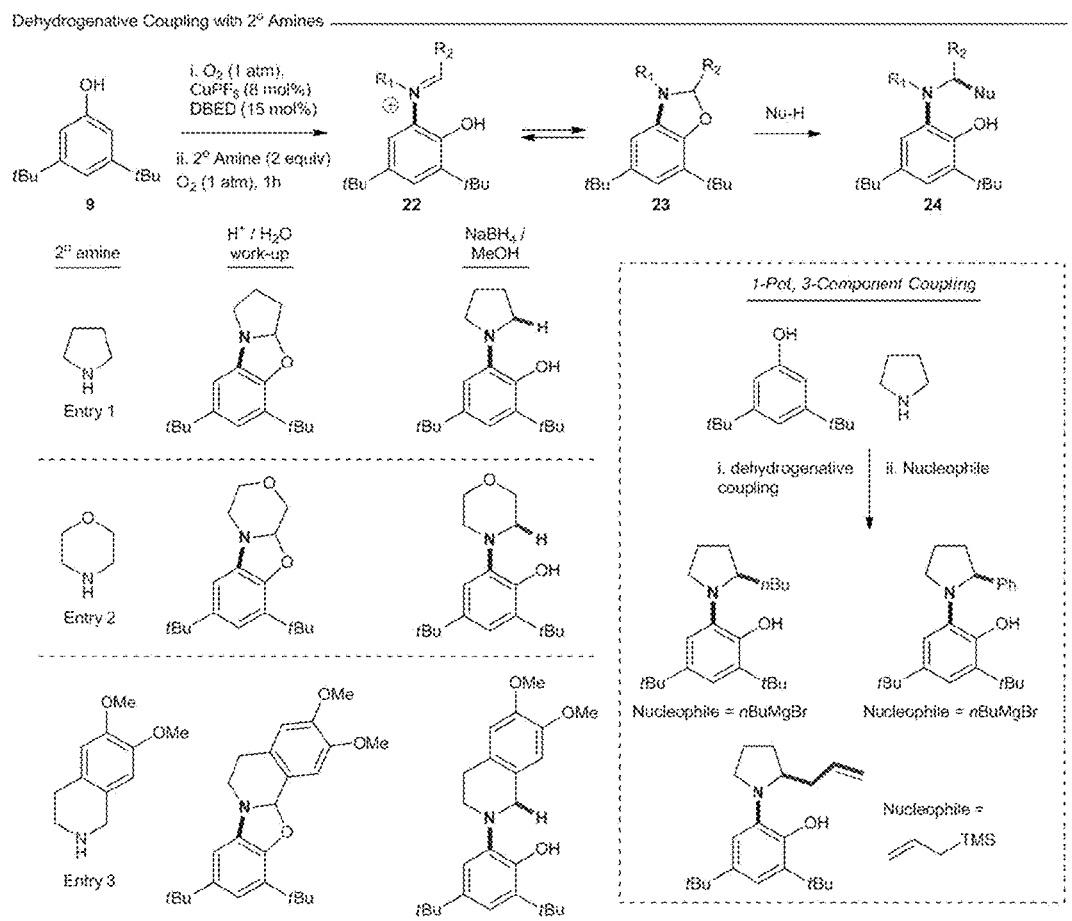
FIG. 9 shows the dehydrogenative coupling of phenols and 2° amines.

We extended the conditions for dehydrogenative coupling of 3,5-di-tert-butylphenol (9) and 1° amines to cyclic 2° amines (FIG. 9). Oxygenation, condensation and 1,5-H shift afforded iminium ion 22, which was in equilibrium with dihydrobenzoxazole 23.

If the reaction mixture was quenched by the addition of $NaHSO_4$ (10% aqueous), dihydrobenzoxales (entries 1-3) were isolated in good yields (70-90%).

Alternatively, addition of $NaBH_4$ in MeOH to the crude reaction mixture reduced 23 to amino-phenol 24, which was the product of a formal Buchwald/Hartwig coupling between an aryl halide and pyrrolidine, morpholine or isoquinoline (entries 1-3 respectively).

In addition to hydride, carbon nucleophiles were added directly to 22/23, to provide 2-functionalized pyrrolidines (FIG. 9, inset). This provided a divergent, 3-component coupling that created aromatic C—N and C—C bonds in a 1-pot, sequential process.

Figure 10:
FIG. 10 shows the dehydrogenative coupling with pyrrolidines.

More highly oxidized pyrrolidine coupling partners afforded alternative pathways for product diversification (FIG. 10). Thus, 3-hydroxy pyrrolidine (25) underwent dehydrogenative coupling with 9 to provide 3-keto-pyrrolidine 27 following 1,2-H shift of 26.

Alternatively, N-arylated pyrrole 31 was the product of a dehydrogenative coupling between 9 and 3,4-dehydropyrrolidine (29), which underwent aromatization at the stage of 30. This provides an attractive entry into $sp^2$-hybridized N-aryl bonds, which remain difficult to install by dehydrogenative coupling.

The above results demonstrate that 2°-cylic-amines undergo dehydrogenative coupling under our standard catalytic aerobic conditions (see FIG. 6) to provide dihydrobenzoxazole, N-aryl-pyrrolidine and N-aryl-pyrrole products. The expansion of scope relative to phenol has previously been discussed in Reaction Path 1, and will not be repeated here. Here, the Sub-Reaction Paths discussed focus on expanding the chemistry of the ortho-phenoxy-N-aryl iminium ion (intermediate 22 in FIG. 9). In Sub-Reaction Path A, we explore alternative mechanisms to trap the ortho-imino-phenol. In Sub-Reaction Path B, we generalize the di-hydro-pyrrolidine coupling partner to provide additional classes of $sp^2$-hybridized nitrogen heterocycles, and investigate late stage, C—H functionalization of the N-arylated pyrrole products.

Sub-Reaction Path A—Trapping the N-Aryl-Iminium Ion

Figure 11:
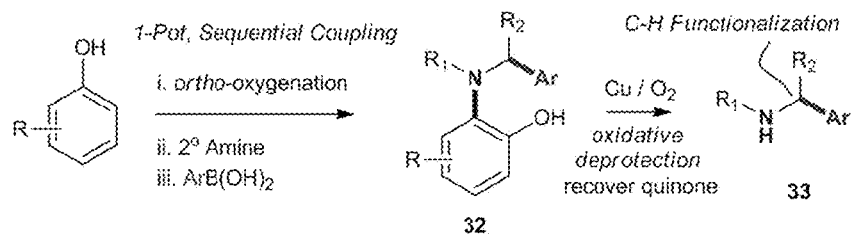
FIG. 11 shows the modified Petassis Reaction and Dehydrogenative Alkyl Group Migration.
Figure 11:
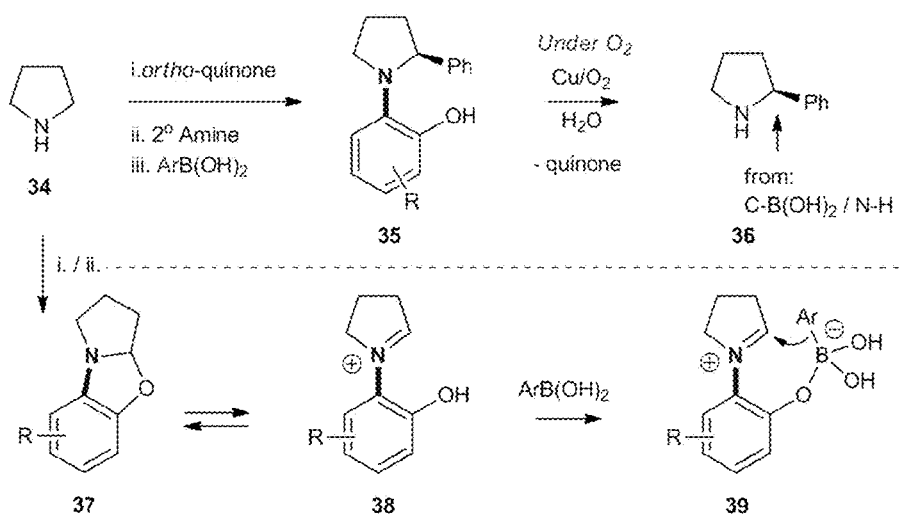
Figure 11:
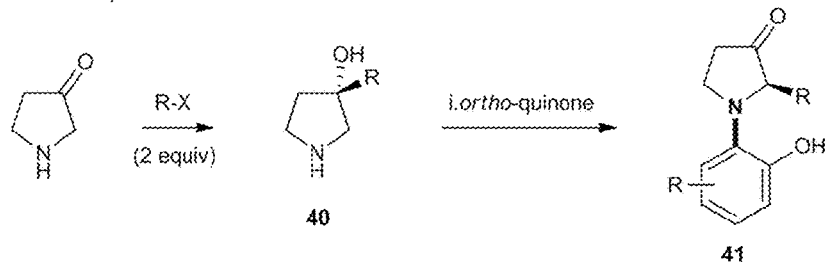

We propose a modified Petasis reaction to create an efficient 3-component coupling between phenols, 2° amines and aryl boronic acids to afford 1,2-amino phenols 32 (FIG. 11). A related reaction has been reported between salicaldehyde, amines and aryl boronic acids.[70] Our proposed reaction is illustrated for pyrrolidine (34), whose condensation with an ortho-quinone affords dihydrobenzoxazole 37. Addition of an aryl-boronic acid at this stage of the reaction would afford amino-phenol 35 following aryl transfer via 39. This transformation functionalizes the C—H bond adjacent to the nitrogen of pyrrolidine in what is formally a Chan-Lam coupling between an aryl boronic acid and a C—H bond. Reintroduction of $O_2$ at the end of the transformation will trigger oxidative cleavage (or deprotection) of 35 to release functionalized pyrrolidine 36, with concomitant recovery of the ortho-quinone. In principal, this could provide a catalytic, aerobic process for the functionalization of C—H bonds adjacent to 2° amines under mild conditions.
Sub-Reaction Path B—Diversification of N-Aryl Pyrroles and Related Heterocycles:

Dehydrogenative coupling of phenol and dihydropyrrolidine afforded N-arylated 1,2-phenoxy pyrroles in excellent yield (e.g. 31 in FIG. 10).

In Sub-Reaction Path B, we investigate two strategies for C—H functionalization at the 2-position of the pyrrole.

In the first, triflation of the phenol to provide 42 directs oxidative addition. Following migratory insertion, $Pd^{II}$ intermediate 45 undergoes substitution with pyrrole at its 2-position, and the resulting metallacycle 46 affords 43 following reductive elimination. Alternatively, phenol-directed C—H insertion[71] at the 2-position of the pyrrole provides metallacycle 47, from which C—N bond formation is triggered with oxidized morpholine coupling partner 48. Alternatively, oxidation of 47 with a cationic fluorine reagent[73] promotes C—O reductive elimination from 49 to provide 50.

We recently investigated the dehydrogenative coupling of 3,5-di-tert-butyl phenol (9) with indoline (54) or iso-indoline (55), which underwent dehydrogenative coupling to provide N-arylated indole 55 and indoline 56, respectively (FIG. 12). The low yields of this process reflect a competitive oxidation of the nitrogen coupling partner, which is consistent with Stahl's recent development of a quinone catalyzed oxidation of 2° cyclic amines.[74,75] For reasons that remain unclear, the addition of $MgSO_4$ prior to the addition of the amine but following ortho-oxygenation improved the yield of 55. From these preliminary results, we investigate the effects of Lewis acid catalysis and desiccants to improve selectivity.

Reaction Path 3: Bio-Inspired Synthesis of Aromatic Materials

The condensation between an ortho-quinone and L-tyrosine ethyl ester creates an opportunity to build extended p-networks by a stepwise construction process composed of alternating Activation (ortho-oxygenation) and Chain Growth (condensation) phases. This concept is outlined in FIG. 13, where phenol starter unit 56 is loaded onto a polystyrene bead. ortho-Oxygenation under our standard conditions (see FIG. 6) provides ortho-quinone 57, at which point $O_2$ is removed from the reaction mixture by sparging with an inert gas ($N_2$ or Ar). Addition of L-tyrosine ethylester (58) and warming to 50° C. then triggers condensation and lactonization to afford benzoxazinone 59 (see FIG. 7 for mechanism). When conversion to 59 is complete, the reaction mixture is cooled to room temperature, and $O_2$ is reintroduced to trigger ortho-oxygenation to 60. We anticipate that 60 will undergo additional dehydrogenative C—N bond formation via 61 and 62, in which conjugate addition of nitrogen onto the newly formed ortho-quinone leads to indoloquinone 64. Repetition of this process gradually builds a condensed, heterocyclic polymer composed of discrete amino phenol extender units that are added in a sequential and controlled fashion. This is reminiscent of DNA or peptide biosynthesis, in which discrete building blocks are added individually to a growing macromolecule. To our knowledge, there exist no examples of a step-wise synthesis of extended p-networks.

Figure 14:
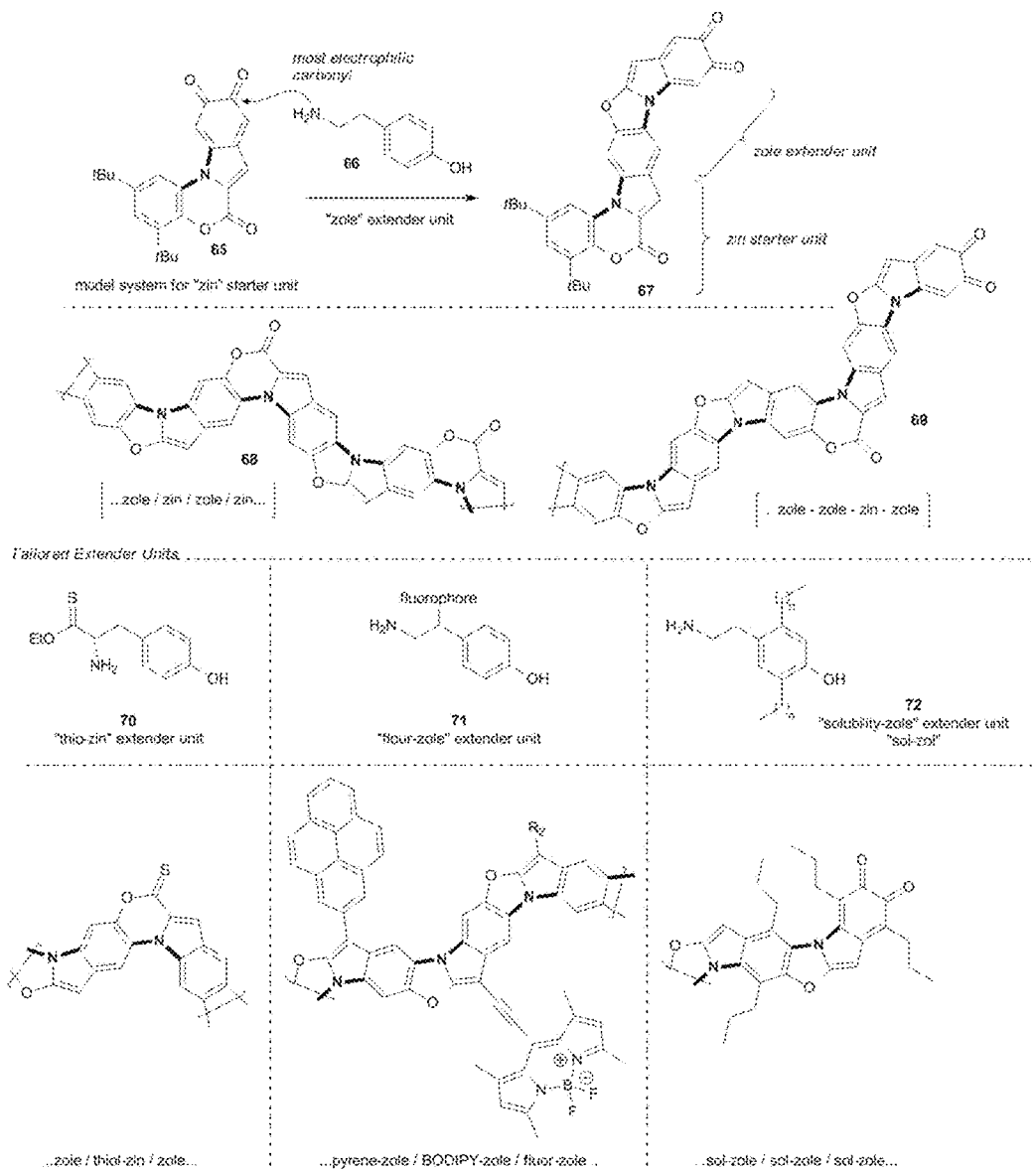
FIG. 14 shows the synthesis of polymeric benzoxazoles.
Figure 15:
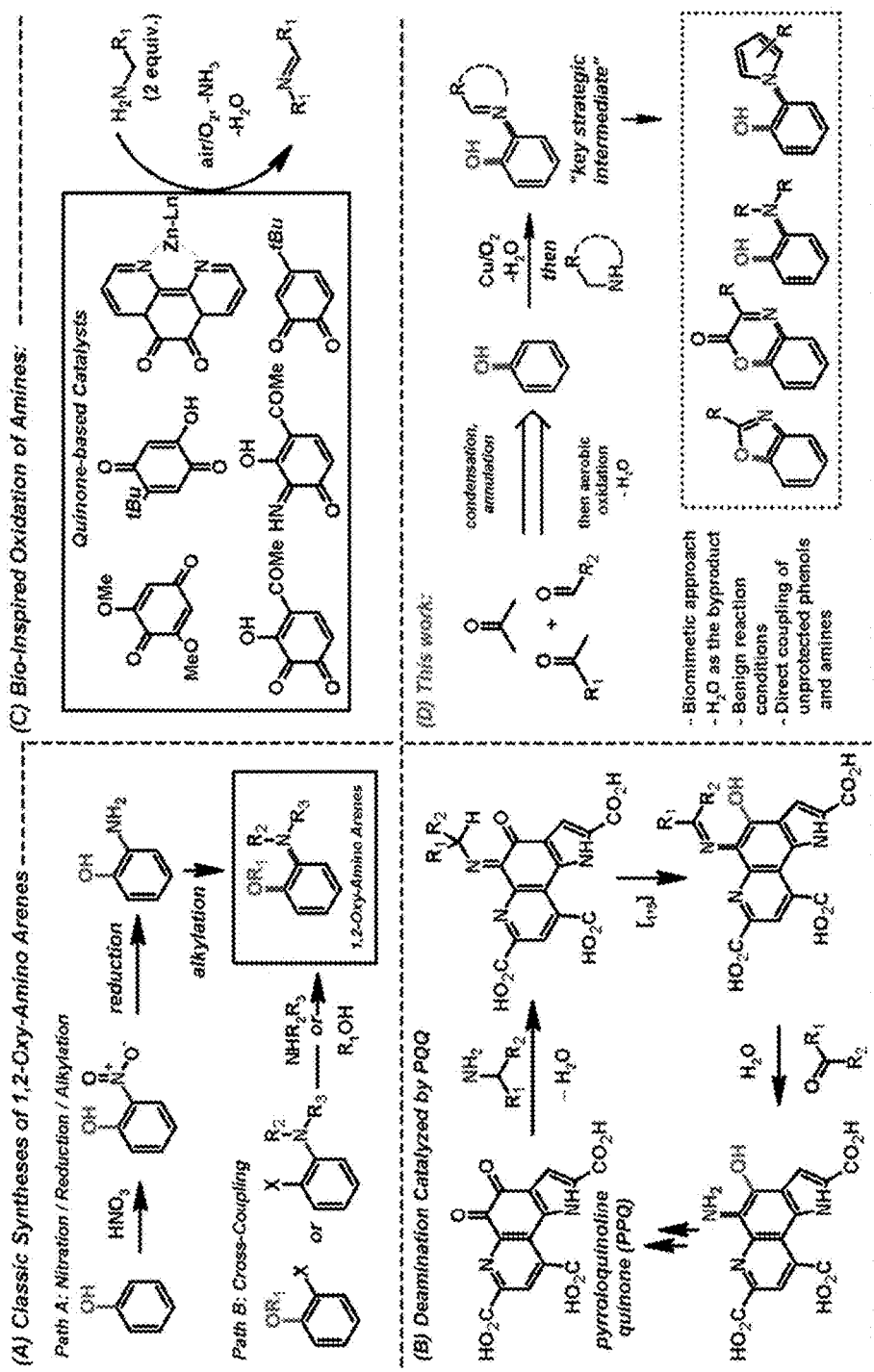
FIG. 15 shows (A) the classical syntheses by nitration/reduction and cross coupling strategies; (B) the mechanism of de-amination catalyzed by PQQ; (C) examples of quinone-mediated aerobic oxidation of amines; and a general reaction scheme according to the invention.

Chain growth should tolerate modified amino-phenols for the purposes of fine-tuning material properties (FIG. 14). For example, substitution of tyrosine ethyl ester 58, which is a benzoxazinone or "Zin"-unit, with tyramine (66) gives rise to a benzoxazole or "zole" extender unit following the mechanism discussed in FIG. 4. A polymeric sequence of zole/zin/zole/zin . . . (68) is constructed by the iterative addition of L-tyrosine ethyl ester/tyramine/L-tyrosine ethyl ester/tyramine . . . . Alternatively, amino phenols modified to incorporate sulfur (70), fluorophores (71) or solubilizing groups (72) are envisioned.

Example 2—Synthesis of 1,2-Amino-Oxy Arenes

Herein, we disclose a biomimetic approach for the synthesis of 1,2-amino-oxy arenes through the direct aerobic dehydrogenation of both unprotected phenols and amines that relies on the intermediacy of ortho-quinones, and generates water as the stoichiometric waste. Further investigation establishes guidelines for predicting regioselectivity on the nascent C—N bond formation. This 1-pot method relies on the facile condensation between ortho-quinones and amines which triggers a redox-isomerization to install the key aromatic C—N bond, a method distinct from traditional cross-coupling or C—H amination strategies.

When viewed as a fragment coupling, the condensation/redox-isomerization of amines and ortho-quinones provides a unique approach to the synthesis of 1,2-oxy-amino arenes that exploits the facile condensation of amines and carbonyls to introduce the aromatic C—N bond.

The prior art teaches that ortho-quinones are not attractive C6-building blocks since they can be reactive and thus difficult to store, and only a handful are commercially available. Their most common synthesis is by oxidation of the corresponding catechol, but catechols are themselves difficult to prepare and manipulate. Phenols are considered more attractive starting materials for ortho-quinones, but their ortho-oxygenation requires either a multi-step sequence or a stoichiometric oxidant that is not regioselective, and which can be difficult to employ in 1-pot, sequential transformations. Here, we address these challenges by describing a dehydrogenative coupling of phenols and amines that gives rise to a divergent synthesis of 1,2-aminooxy arenes. Our method exploits recently developed conditions for the catalytic aerobic oxygenation of phenols, which then enables fragment coupling with either 1° or 2° amines in a 1-pot sequential process. The transformation occurs at room temperature, uses a commercially available Cu-catalyst, generates $H_2O$ as the only stoichiometric by-product, and gives rise to no less than 4-distinct classes of nitrogen containing heterocycles. To the inventor's knowledge, comparatively mild and efficient conditions for the formation of aromatic C—N bonds have not been reported.

Outline

The course of the dehydrogenative coupling is influenced by the substitution pattern of the phenol as well as the nature of the amine. As our point of departure for reaction optimization, we chose 3,5-di-tert-butyl phenol (1) because it is symmetric, and its ortho-oxygenation results in the relatively well-behaved 3,5-di-tert-butyl ortho-quinone (2). We begin by presenting results according to the nitrogen nucleophile, so that in Part A we describe the dehydrogenative coupling of 1 with 1°-amines, in Part B with 1°-α-branched amines and in Part C with cyclic 2° amines. We then present the scope of the phenol in Part D, and conclude with a description of the rules that govern regiochemistry in Part E.

Part (A)

Reaction Optimization and Coupling with 1° Amines

We began by investigating the dehydrogenative coupling of 3,5-di-tert-butyl phenol (1) and benzyl amine (3) to provide benzoxazole (4) in a 1-pot, sequential process:

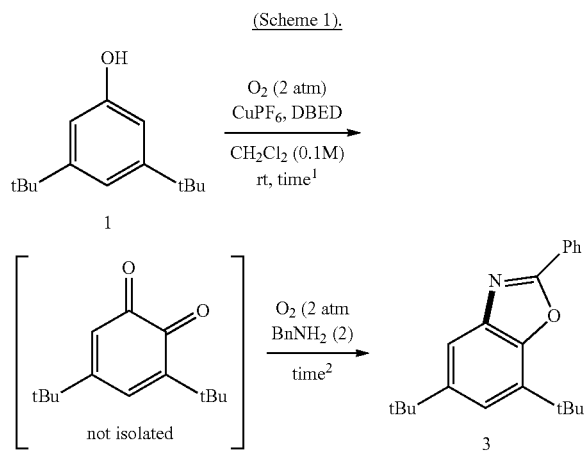

(Scheme 1).

The benzoxazole heterocycle is a privileged structure that is present in natural products, pharmaceuticals and agrochemicals. It is most commonly synthesized by condensation of a 1,2-aminophenol and a carboxylic acid, which suffers from the atom- and step-inefficiencies of introducing nitrogen that are discussed above.

In the present work, 1 was synthesized from simple carbonyl and ketones via an adaptation of Stahl's oxidative cyclo-condensation as shown in the following scheme:

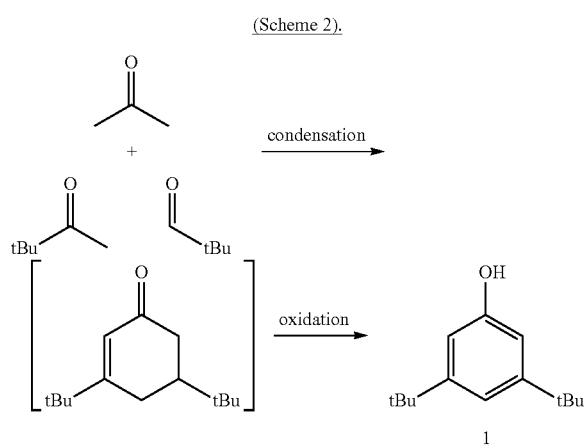

(Scheme 2).

When used in sequence with our dehydrogenative coupling, this process generates valuable benzoxazole heterocycles from simple, non-aromatic building blocks, while creating $H_2O$ as the only stoichiometric by-product.

Our previously optimized conditions for the ortho-oxygenation of phenols employs 4 mol % [Cu(CH3CN)$_4$](PF$_6$) (abbreviated CuPF$_6$), 5 mol % di-tert-butyl-ethylenediamine (DBED) and $O_2$ (1 atm overpressure).

These conditions lead to a 40% NMR yield of benzoxazole 3 after a 1-pot sequential process (entry 1). Prolonging the reaction time for the amine/quinone condensation did not improve the yield of 3 (entry 2), and control experiments revealed that unreacted 2 negatively affects the oxidative condensation of 1 and benzyl amine (see the Supporting Information). This prompted us to raise the catalyst loading, so as to ensure complete consumption of 2 within 4 h reaction time, prior to the addition of the amine. Increasing the loading of DBED to 10 mol % returns a 76% NMR yield of 3 (entry 3), which improves to 81% if the loading of Cu is also increased (entry 4). Increasing Cu loadings above 8 mol % has a negative impact on the reaction (entry 5) due to competitive formation of N-benzylidenebenzylamine (c.f. Scheme 2C). As a result, the Cu-loading was kept at 8 mol %, and optimal conditions were found by raising the DBED loading to 15 mol %, and using 2 equivalents of benzyl amine (entry 7). These conditions provide benzoxazole 3 in near quantitative yield, and remain efficient when using 25 mmols of 2 (entry 8).

TABLE 1

Initial Studies Towards Dehydrogenative Coupling of Primary Amines and Phenols[a]

| Entry | CuPF$_6$ (mol %) | DBED$_6$ (mol %) | time[1] (h) | BnNH$_2$ (2) (equiv) | time[2] (h) | Conversion of 1[b] (%) | Yield of 3[b] (%) |
|---|---|---|---|---|---|---|---|
| 1 | 4 | 5 | 4 | 1.2 | 1 | 76 | 40 |
| 2 | 4 | 5 | 4 | 1.2 | 2 | 99 | 45 |
| 3 | 4 | 10 | 4 | 1.2 | 2 | 81 | 76 |
| 4 | 8 | 10 | 4 | 1.2 | 2 | 99 | 81 |
| 5 | 15 | 20 | 4 | 1.2 | 2 | 99 | 71 |
| 6 | 8 | 15 | 4 | 2.0 | 2 | 99 | >95 |
| 7 | 8 | 15 | 4 | 2.0 | 2 | 99 | 93[e] |

[a]Conducted with 1.0 mmol of 1.
[b]Product yield and conversion are determined by $^1$H NMR using hexa-methylbenzene as an internal standard, and calculated based on 1.
[c]Benzylamine was added at the start of the reaction.
[d]Isolated yield following chromatography
[e]Isolated yield following chromatography on 25 mmol scale.

Confirmation of Regiochemistry when Using Phenol 1.

Figure 16:
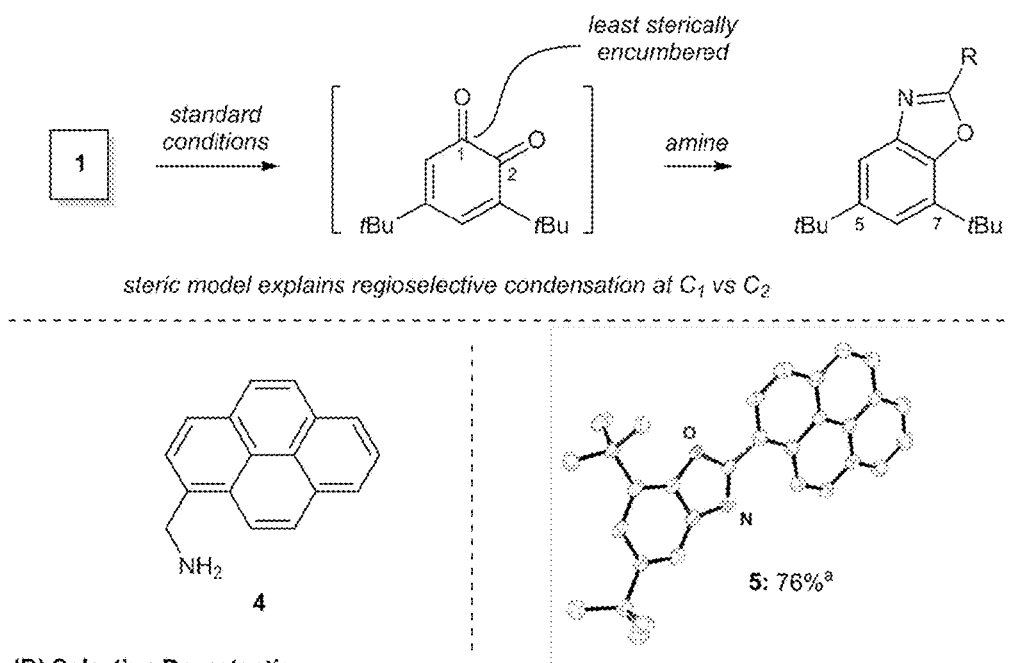
FIG. 16 summarizes the confirmation of regiochemistry.
Figure 16:
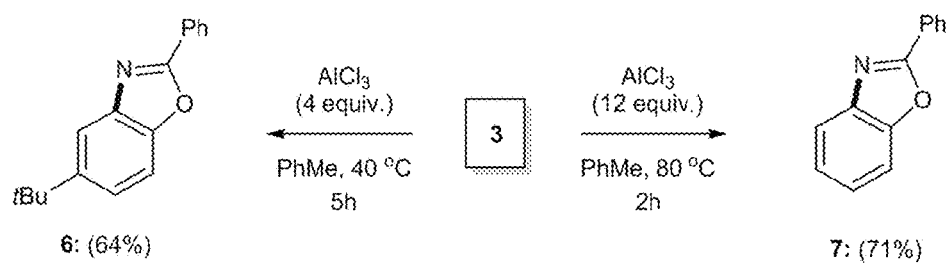

The regiochemistry of condensation was confirmed by single crystal x-ray analysis of benzoxazole 5, which results from dehydrogenative coupling with amino-pyrene 4. See FIG. 16 summarizing the confirmation of regiochemistry[a]: [a] reaction conditions: 1.0 mmol of 1, CuPF$_6$ (8 mol %), DBED (15 mol %), $O_2$ (1 atm), $CH_2Cl_2$ (0.1 M), 4 h, 23° C.; then 73 (2.0 equiv.), $O_2$ (1 atm), 2 h, 23° C.

The observed selectivity is consistent with condensation at the more sterically accessible $C_1$-carbonyl of the ortho-quinone, and replaces the oxygen atom of the starting phenol with nitrogen by a formal ipso substitution. The oxygen atom of the benzoxazole is derived from $O_2$ during the aerobic ortho-oxygenation, and is positioned ortho to the tert-butyl substituent at C7 (benzoxazole numbering), and para to the tert-butyl substituent at C5. This differentiates the two tert-butyl substituents, so that selective removal of the C7 substituent is accomplished by exposing 3 to 4 equivalent of aluminum trichloride (AlCl$_3$) at 40° C. (c.f. 6), while increased quantities of the Lewis acid and elevated temperatures removes both tert-butyl groups, and provides 2-phenylbenzoxazole (7). We use this model to assign the regiochemistry of heterocycles resulting from dehydrogenative coupling with phenol 1 in Parts A-C. More complex cases with a less explicit steric bias are presented in Part D, and rules governing their regiochemistry are discussed in Part E.

Scope of 1° Amines

Our optimized conditions remain efficient across a broad range of substituted benzyl amines (FIG. 17), including those bearing a sulfonamide (entry 4), trifluoromethyl (entry 8), halogens (entries 6, 7, 9-12) and a nitro group (entry 13). Aryl ethers are also tolerated (entry 3), however oxidative demethylation is observed for 2,4-di-methoxy-substitution, accounting for the low isolated yield in entry 5. Benzoxazoles possessing a bi-phenyl substituent at C1 (c.f. entries 14 and 15) is noteworthy, since related heterocycles display COX-$_2$ inhibitory activity, but remain difficult to synthesize by traditional cross-coupling reactions.21b Likewise, introduction of alkyl substituents at C2 of the benzoxazole through Csp$^2$-Csp$^3$ cross-coupling can be difficult due to competitive β-H elimination. However, this is not the case un-der our conditions, which tolerate aliphatic amines (entry 19, 28, and 32), and those possessing free alcohols (entries 20-22), 1° alkyl chloride (entry 23), 3o amine (entry 26), aryls (entry 16-18) and aliphatic ethers (entry 24). Some issues of selectivity are observed for products that possess activated hydrogen atoms adjacent to aryl or hetero-atoms (entries 16 and 20); however, shortened reaction times can improve product yields, and accommodates easily oxidized C—H bonds, as illustrated by the diphenylmethine in entry 25. No reaction is observed for amines bearing acidic β-protons (entry 27)—see the next section for the reaction of such amines. Allyl amine and methylamine can be employed for the synthesis of benzoxazoles possessing H- or a vinyl substituent at C$_2$, but yields are diminished (entries 31 and 37). Finally, heteroaromatic substituents frequently encountered in the pharmaceutical industry are readily installed, including morpholine (entry 33), substituted pyridines (entries 35 and 36), pyrazine (entry 34), furan (entry 29) and thiophene (entry 30) (entry 33), substituted pyridines (entries 35 and 36), pyrazine (entry 34), furan (entry 29) and thiophene (entry 30).

Figure 17:
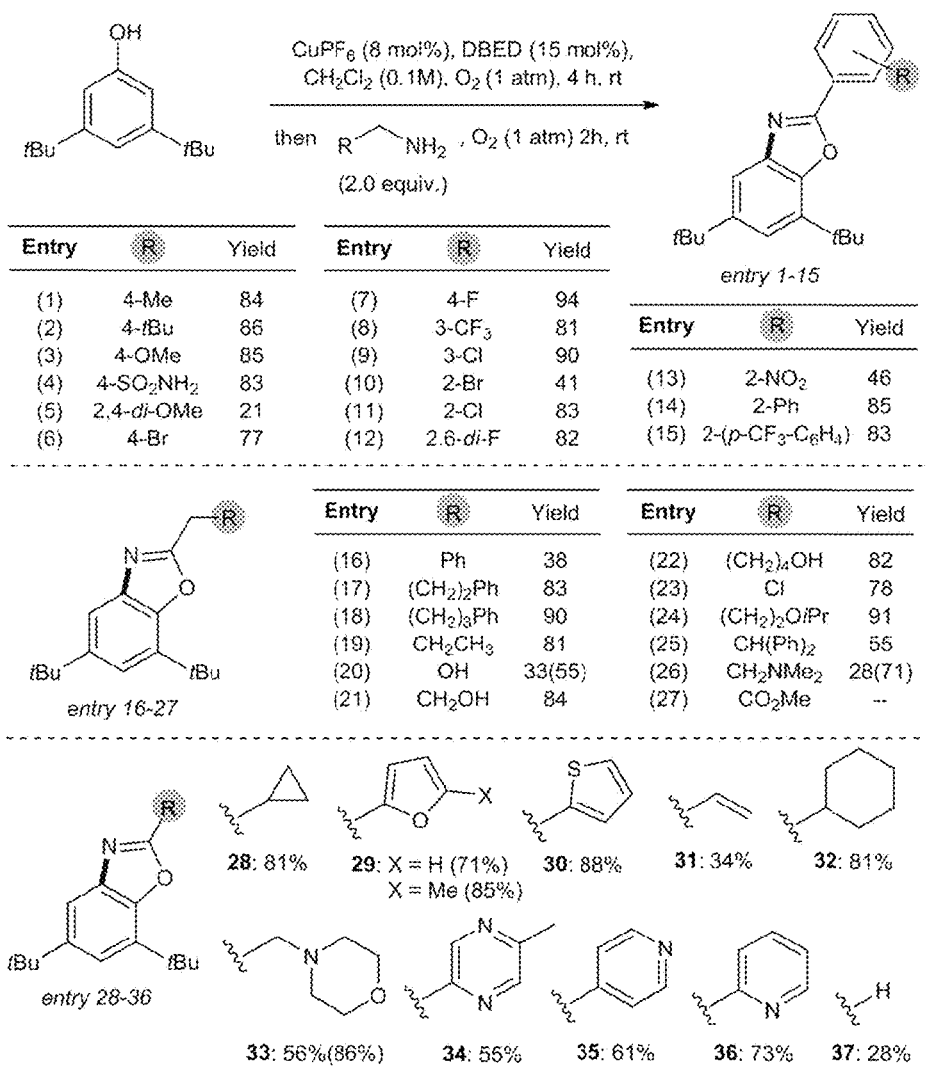
FIG. 17 summarizes the scope of primary amines.

See FIG. 17 summarizing the scope of primary amines[a]: [a] Reaction conditions: 1.0 mmol of 1, CuPF$_6$ (8 mol %), DBED (15 mol %), O$_2$ (1 atm), CH$_2$Cl$_2$ (0.1 M), 4 h, 23° C.; then amine (2.0 equiv.), O$_2$ (1 atm), 2 h, 23° C. Isolated yields are reported for each entry. Numbers in parenthesis in entries 20, 26 and 33 denotes isolated yields of 1 h oxidation following amine addition.

Part (B): Coupling with α-Branched Amino Esters.

Dihydro-benzoxazole 8 arising from α-branched 1°-amines cannot undergo further oxidation, following redox-isomerization from the imino-ortho-quinone (see FIG. 7). This provides alternative ways of diversifying the ortho-imino phenol, as illustrated by dehydrogenative coupling of glycine methyl-ester and 1. For example, hydrolysis returns ortho-amino phenol 10, and highlights a regioselective alternative to the classical amination of phenols by nitration/reduction that replaces nitric acid with an amino acid as the source of nitrogen. Alternatively, benzoxazinone 11 can be isolated in high yield if alanine methyl ester is added as a solution in MeOH at 50° C., which promotes lactonization of ortho-imino phenol 9. See FIG. 18 summarizing the initial studies on the coupling of 1 and alanine methyl ester[a]: [a] Reaction conditions: 1.0 mmol of 1, CuPF$_6$ (8 mol %), DBED (15 mol %), O$_2$ (1 atm), CH$_2$Cl$_2$ (0.1 M), 4 h, 23° C.; then amine (2.0 equiv.) 24 h, 23° C.

Figure 19:
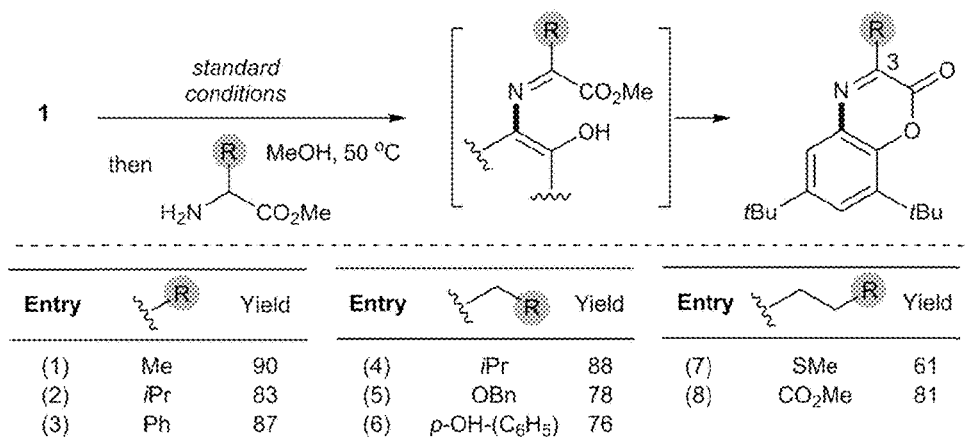
FIG. 19 summarizes the scope of primary α-branched amino asters.

Benzoxazinones are an important class of heterocycles that are present in biologically active molecules. They are also substrates for asymmetric hydrogenations that are used for the synthesis of non-natural amino-acids. Under our conditions, benzoxazinones with a variety of C$_3$-substituents (benzoxazinone numbering, see FIG. 19) can be synthesized in good yield, including those bearing alkyl (entries 1, 2 and 4) or aryl substituents (entry 3), a benzylic ether (entry 5), a thioether (entry 7), a free phenol (entry 6) or a methyl-ester (entry 8). See FIG. 19 summarizing the scope of primary α-branched amino asters[a]: [a] Reaction conditions: 1.0 mmol of 1, CuPF$_6$ (8 mol %), DBED (15 mol %), O$_2$ (1 atm), CH$_2$Cl$_2$ (0.1 M), 4 h, 23° C.; then amine (2.0 equiv.) in MeOH (5 mL), 4 h, 50° C. Isolated yields are reported for each entry.

Part (C): Dehydrogenative Coupling with Cyclic 2° and α-Branched Amines.

Figure 20:
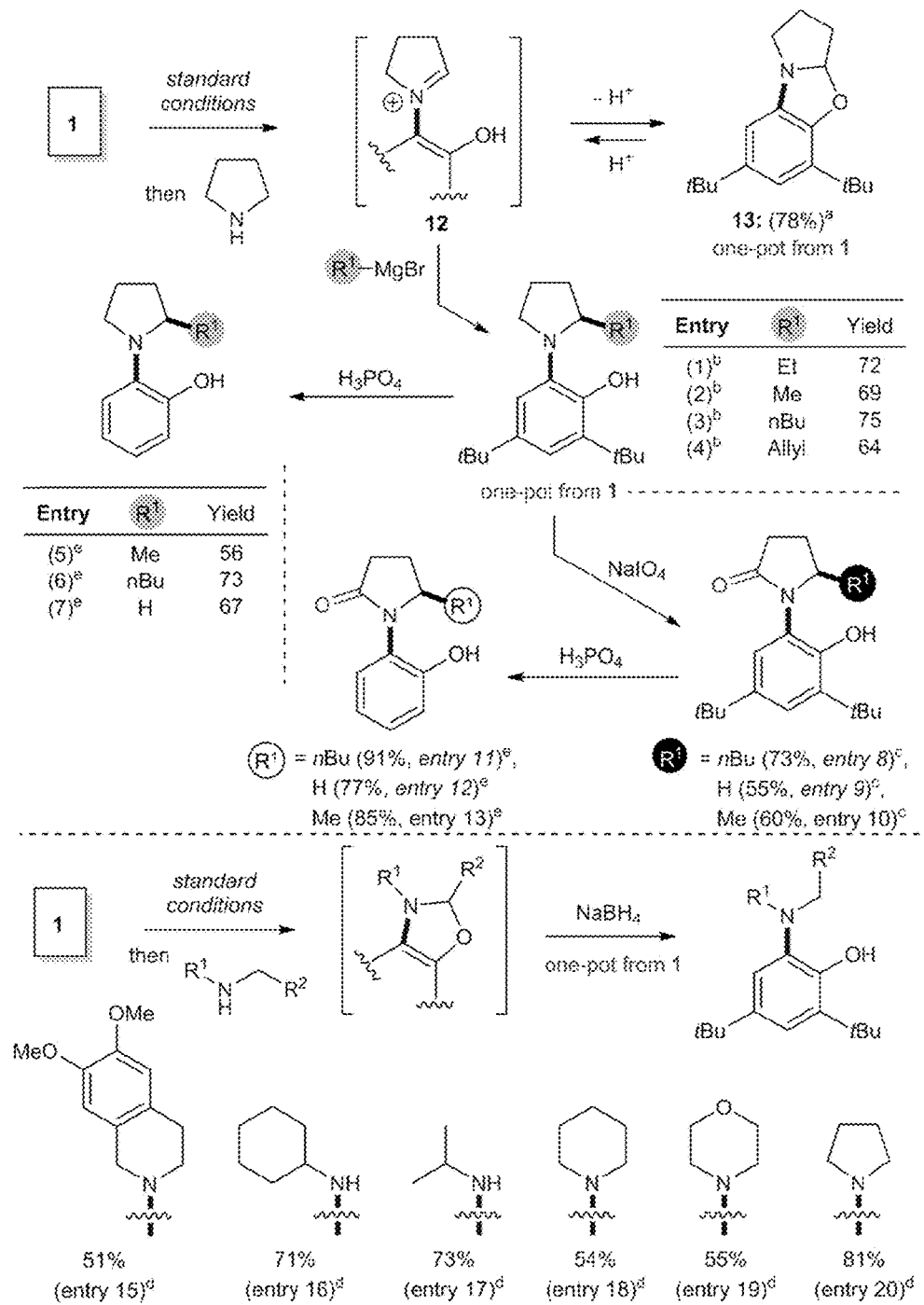
FIG. 20 summarizes the scope of secondary amines and further diversification.

Coupling of secondary amine such as pyrrolidine affords a putative positively charged iminium ion 12, which undergo ring closure to afford 13 in 78% isolated yield (see FIG. 20). Interestingly, addition of a nucleophile prior to work-up enables the synthesis of 2-substituted N-aryl-pyrrolidine in high yields, thus permits a 1-pot, 3-component coupling of reagents (i.e. phenols, amines and carbanions) all possessing nucleophilic character. Our optimized condition allows for the synthesis of N-aryl-pyrrolidine bearing alkyl (entry 1-3) or allyl (entry 4) substituent at C$_2$. Hydride is also a suitable nucleophile, and the un-substituted amino-phenol is isolated when sodium borohydride is used in a reductive work-up (entry 20). Likewise, secondary amines such as piperidine (entry 18), morpholine (entry 19) and tetrahydroisoquinoline (entry 15), and α-branched amines such as cyclohexylamine (entry 16) and isopropylamine (entry 17) afford aminophenols in modest to good yields.

Interestingly, treatment with sodium periodate (NaIO$_4$) oxidizes the C$_5$ of 2-substituted N-aryl pyrrolidine to provide the corresponding lactams (entry 8-10). Related heterocycles are widely employed as starting materials for the synthesis of biologically active small molecules. Removal of the tert-butyl groups (entry 5-7 and 11-13) is readily accomplished under previously reported conditions to provide a family of amino phenols.

See FIG. 20 summarizing the scope of secondary amines and further diversification[a]: [a] Synthesis of 13: 1.0 mmol of 1, CuPF$_6$ (8 mol %), DBED (15 mol %), O$_2$ (1 atm), CH$_2$Cl$_2$ (0.1 M), 4 h, 23° C.; then amine (2.0 equiv.), 2 h, 23° C. [b] Synthesis of 2-substituted N-aryl pyrrolidines (entries 1-4): (i) 1.0 mmol of 1, CuPF$_6$ (8 mol %), DBED (15 mol %), O$_2$ (1 atm), CH$_2$Cl$_2$ (0.1 M), 4 h, 23° C.; (ii) pyrrolidine (2.0 equiv.), 2 h, 23° C.; (iii) Grignard reagent (3.0 equiv.), 2 h, 0-23° C. Isolated yields are reported for each entry. [c] Synthesis of N-aryl lactams (entry 5): (i) N-aryl pyrrolidine (1.0 equiv.), NaIO$_4$ (3.0 equiv.), CH$_2$Cl$_2$: H$_2$O (1:1, v:v), 4 h, 23° C. [d] Synthesis of amino-phenols (entries 15-20): (i) 1.0 mmol of 1, CuPF$_6$ (8 mol %), DBED (15 mol %), O$_2$ (1 atm), CH$_2$Cl$_2$ (0.1 M), 4 h, 23° C.; (ii) amine (2.0 equiv.), 12 h, 50° C.; (iii) NaBH4 (2.0 equiv.) in MeOH (2 mL), 2 h, 0-23° C. Isolated yields are reported for each entry. [e] Removal of tBu groups: Substrate (0.01-1.0 mmol), H$_3$PO$_4$ (2 mL), 220° C.

Figure 21:
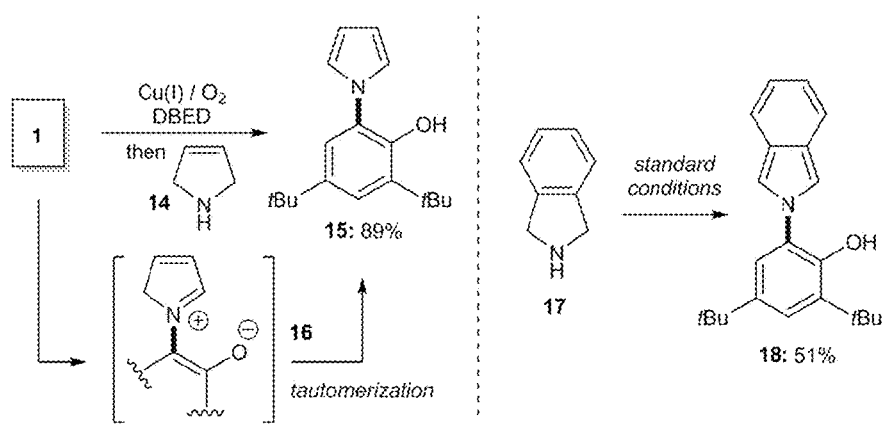
FIG. 21 also summarizes the scope of secondary amines and further diversification.

Moreover, inferences from the putative intermediate following the condensation of pyrrolidine led us to develop a unique strategy for the creation of Csp$^2$-Nsp$^2$ linkages. For instance, coupling with dihydro-pyrrole (14) provides N-arylated pyrrole 16 in near quantitative yields (FIG. 21, lower panel), highlighting a mild ortho-pyrrolation of phenols. In this case, condensation and 1,5-hydride shift lead to an iminium ion 16, which aromatizes by tautomerization. A similar strategy can be applied to the synthesis of N-arylated indole 18 via dehydrogenative coupling of 1 and dihydroisoindole 17, respectively. Notably, this approach bypasses the challenges of regioselectivity that can complicate more traditional methodologies, which typically require electron-withdrawing groups on the pyrrole and elevated reaction temperatures. See FIG. 21 summarizing the scope of secondary amines and further diversification: [a] Reaction conditions: (i) 1.0 mmol of 1, $CuPF_6$ (8 mol %), DBED (15 mol %), $O_2$ (1 atm), $CH_2Cl_2$ (0.1 M), 4 h, 23° C.; (ii) amine (2.0 equiv.), 2 h, 23° C.

Summary of Scope Relative to the Amine.

Figure 22:
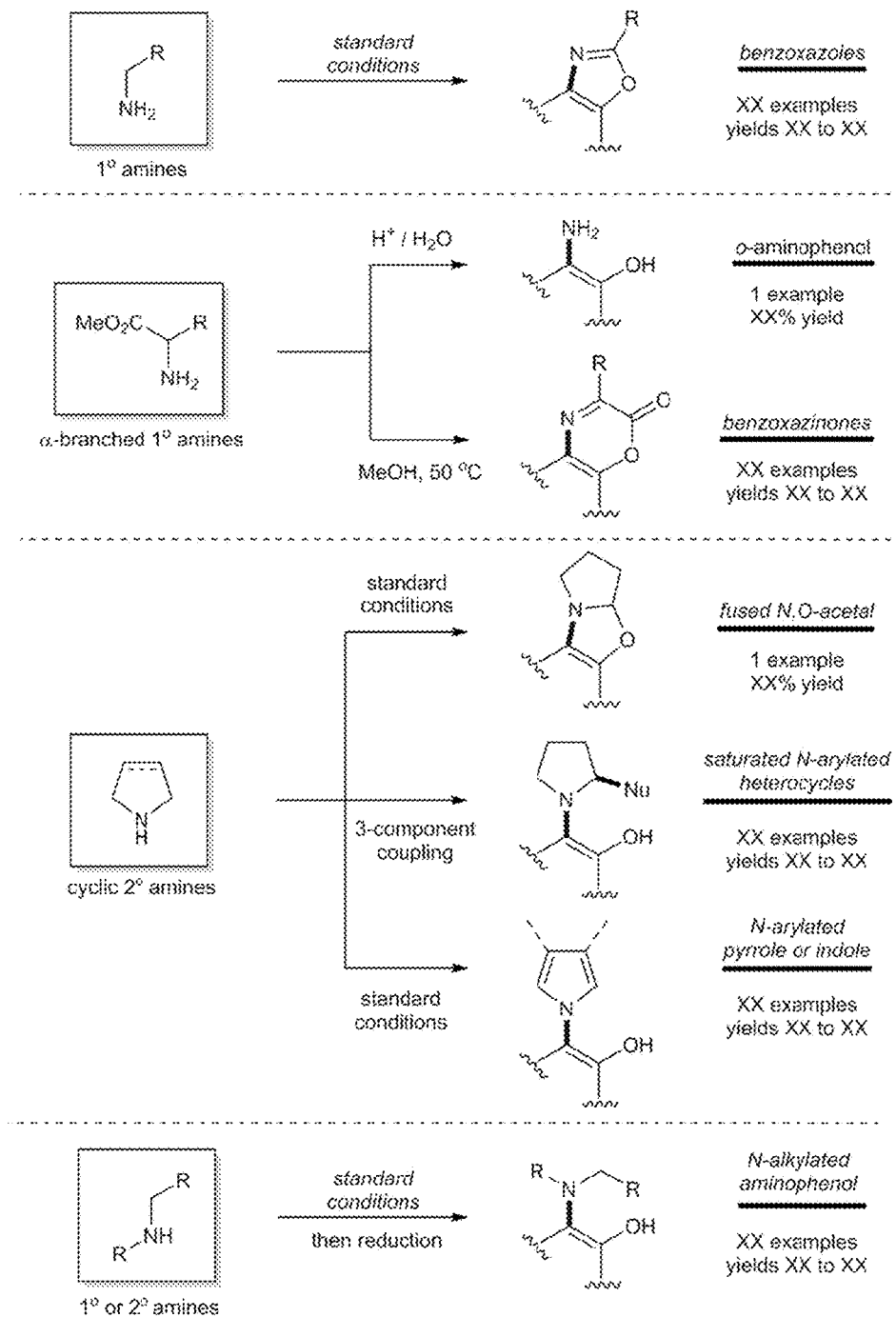
FIG. 22 summarizes the scope relative to the amine and product class.

In FIG. 22, we provide a summary of the 1,2-oxy-amino-arenes that are available by our dehydrogenative coupling methodology, as defined by the nitrogen coupling partner. It includes 5 distinct heterocyclic scaffolds, as well as 1,2-amino-phenols, which are all available using the same catalyst system under mild reaction conditions. See FIG. 22 summarizing the scope relative to the amine and product class.

Part (D): Scope of Phenols.
Di-Substituted Phenols.

Figure 23:
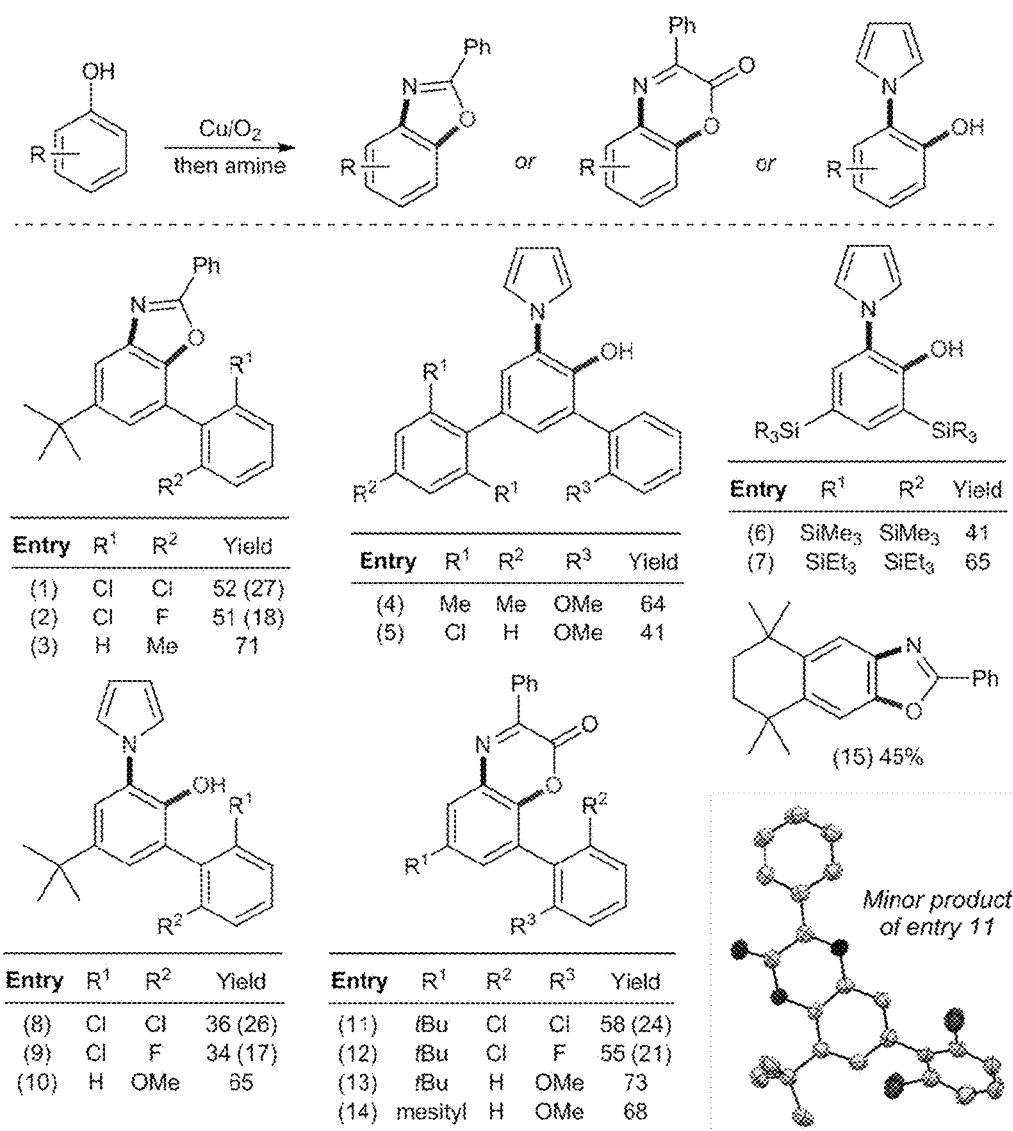
FIG. 23 summarizes the scope of the scope of di-substituted phenols

The scope of the phenol was evaluated in the dehydrogenative coupling with benzyl amine, phenylglycine methyl ester, or dihydropyrrole. Phenols with akyl and/or aryl groups are easily converted into the corresponding 1,2-oxyamino arenes (FIG. 23, entry 1-5 and 8-14). Silicon groups are tolerated at the 3- and 5-positions of the phenol (entry 6 and 7), providing valuable heterocycles with synthetic handles for further elaboration. See FIG. 23 summarizing the scope of the scope of di-substituted phenols[a]: [a] Benzoxazole synthesis: phenol (1 mmol), $CuPF_6$ (8 mol %), DBED (15 mol %), $O_2$ (1 atm), $CH_2Cl_2$ (0.1 M), 4 h, 23° C.; then benzylamine (2.0 equiv.), $O_2$ (1 atm), 2 h, 23° C. [b] Benzoxazinone synthesis: phenol (1 mmol), $CuPF_6$ (8 mol %), DBED (15 mol %), $O_2$ (1 atm), $CH_2Cl_2$ (0.1 M), 4 h, 23° C.; then phenylglycine methyl ester (2.0 equiv.) in MeOH (5 mL), 4 h, 50° C. [c] N-Aryl pyrrole synthesis: (i) phenol (1.0 mmol), $CuPF_6$ (8 mol %), DBED (15 mol %), $O_2$ (1 atm), $CH_2Cl_2$ (0.1 M), 4 h, 23° C.; (ii) 3-pyrroline (2.0 equiv.), 2 h, 23° C. Isolated yields are reported for each entry. Numbers in parenthesis denote the yield of the minor isomer.
Confirmation of Regiochemistry for 3,5-Di-Substituted Phenols.

Figure 24:
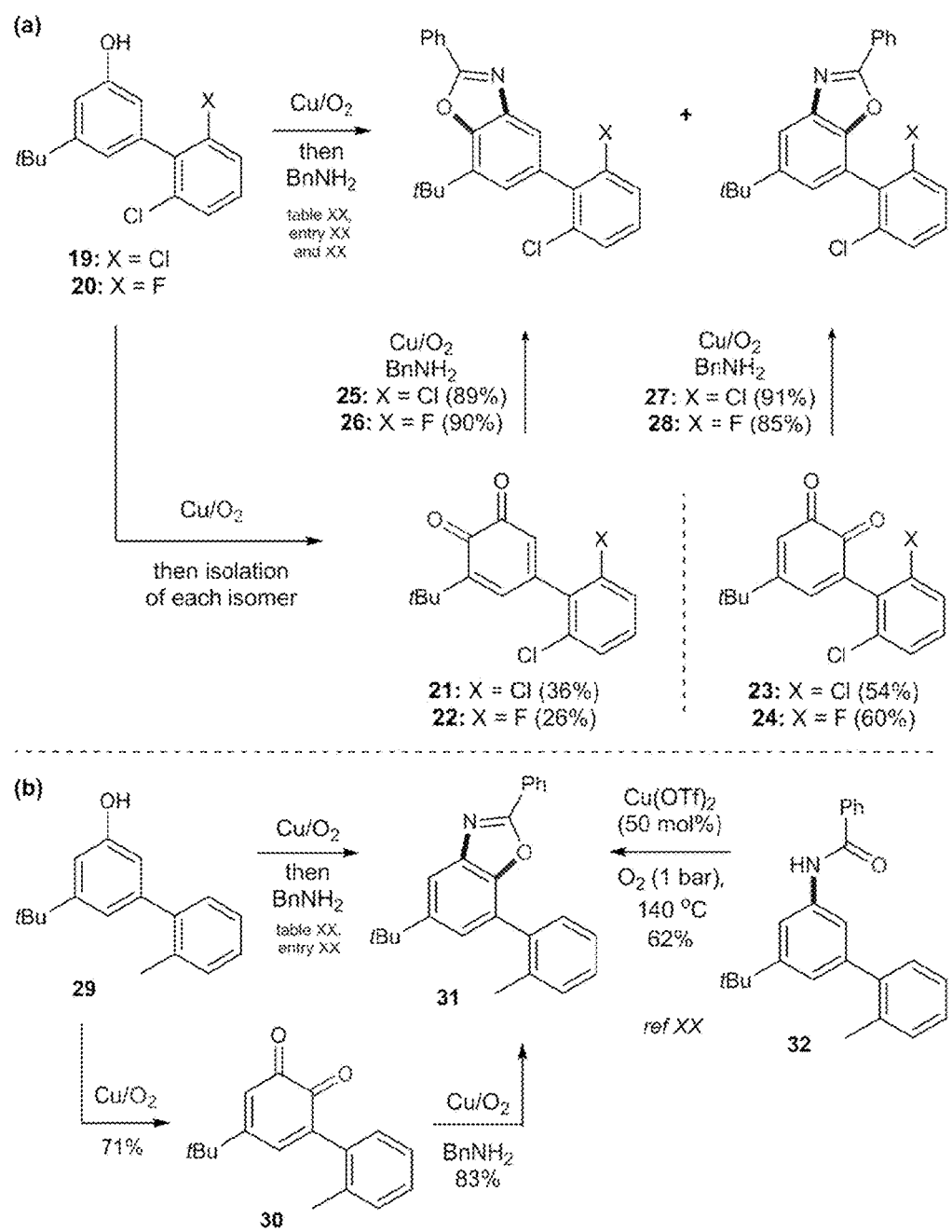
FIG. 24 summarizes the confirmation of regiochemistry for 3,5-di-substituted phenols.

When the groups at the 3- and 5-positions of the phenol are different, oxygenation is favored towards the less sterically demanding substituent. For example, ortho-oxygenation of 29 affords a single quinone regioisomer 30. However, when there is less steric bias between the 3- and 5-position, oxygenation occurs at either 2- or 6-position, resulting in a mixture of regioisomeric quinones (FIG. 24a). For example, ortho-oxygenation of 19 affords two regioisomeric quinones 21 and 23, while 20 affords or 22 and 24. This concomitantly affords a mixture of two 1,2-oxy-amino arene isomers (FIG. 24, entry 1, 2, 8, 9, 11, and 12) with a combined yield of 55% to 82%. Using single crystal x-ray analysis of the minor benzoxazinone adduct in entry 11 (FIG. 23), the observed structure is consistent with non-selective oxygenation and regioselective C—N bond formation (i.e. condensation at the least hindered carbonyl). The observed ratio between 1,2-oxy-amino arene regioisomers in the one-pot process reflect the ratio of the quinone intermediates (see FIG. 24). Moreover, isolation of each quinone intermediate 21 or 22 affords a single benzoxazole product 25 or 26, respectively. Likewise, 23 or 24 affords 27 or 28, respectively.

Using previously reported method by Ueda and coworkers (Ueda, S.; Nagasawa, H., Angew. Chem. 2008, 120 (34), 6511-6513), cyclization of amide 32, wherein the C—N bond is pre-installed, affords benzoxazole 31 (FIG. 24b) identical to the one-pot process. The rules governing regioselectivity are described in detail in Part E.

See FIG. 24 summarizing the confirmation of regiochemistry for 3,5-di-substituted phenols: [a] Oxygenation: 1.0 mmol of phenol, $CuPF_6$ (8 mol %), DBED (15 mol %), $O_2$ (1 atm), $CH_2Cl_2$ (0.1 M), 4 h, 23° C.; [b] Quinone-Amine Coupling: 1.0 mmol of phenol, $CuPF_6$ (8 mol %), DBED (15 mol %), $O_2$ (1 atm), benzylamine (2.0 equiv.), $CH_2Cl_2$ (0.1 M), 2 h, 23° C.; [c] Amide cyclization: $Cu(OTf)_2$ (50 mol %), o-xylene, 140° C. Isolated yields are reported for each entry.
Scope of 3,5-Di-Substituted Phenols with meta-(ortho-OMe-Phenyl) Substituent.

Analogous to phenol 29, oxygenation of 33 results in the formation of one quinone intermediate (see FIG. 25, see supporting information below for details), but forms mixture of benzoxazoles 34 and 35 following coupling with benzylamine. In this case, regioisomers arise from amine condensation from either one of the carbonyl moieties. Although C—N bond formation is still favored at the least encumbered carbonyl, condensation at the sterically hindered site also occurs, possibly directed by the ortho-methoxy phenyl substituent. Cyclization of amide 36 affords benzoxazole 34, while amide 37 provides benzoxazole 35, further confirming the regiochemistry of the resulting products.

Figure 25:
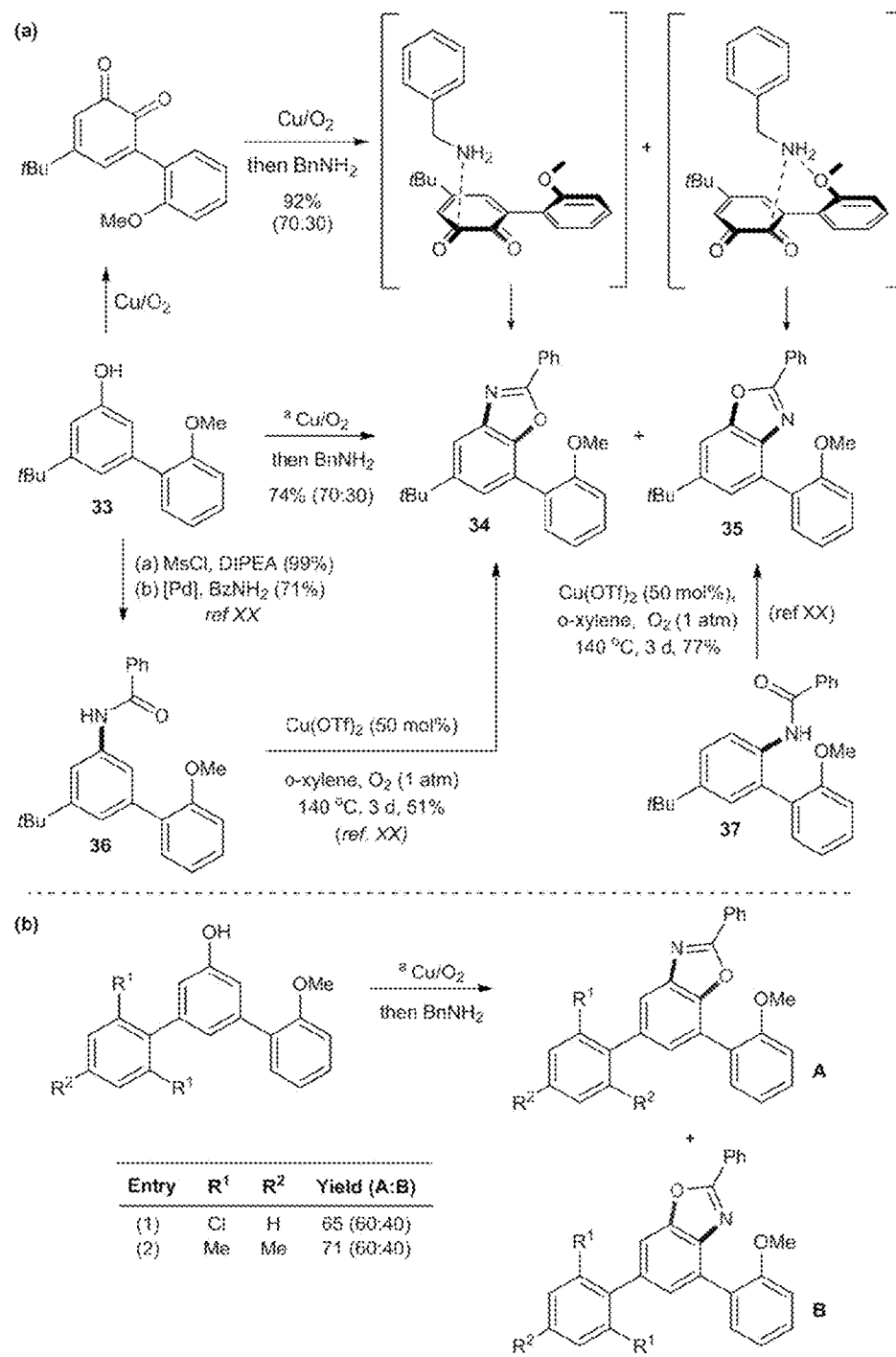
FIG. 25 summarizes the regioselectivity of phenols with meta-(ortho-oMe-phenyl) substituent.

Likewise, phenols with meta-(ortho-OMe-phenyl) substituent paired with other similar sterically encumbered substituents, such as mesityl and 2,6-dichlorophenyl, afford a mixture of two benzoxazoles (FIG. 25, entry 1 and 2).

See FIG. 25 which summarizes the regioselectivity of phenols with meta-(ortho-oMe-phenyl) substituent: [a] Benzoxazole synthesis: phenol (1.0 mmol), $CuPF_6$ (8 mol %), DBED (15 mol %), $O_2$ (1 atm), $CH_2Cl_2$ (0.1 M), 4 h, 23° C.; then benzylamine (2.0 equiv.), $O_2$ (1 atm), 2 h, 23° C. [b] Oxygenation: phenol (1.0 mmol), $CuPF_6$ (8 mol %), DBED (15 mol %), $O_2$ (1 atm), $CH_2Cl_2$ (0.1 M), 4 h, 23° C.; [c] Quinone-Amine Coupling: 1.0 mmol of phenol, $CuPF_6$ (8 mol %), DBED (15 mol %), $O_2$ (1 atm), benzylamine (2.0 equiv.), $CH_2Cl_2$ (0.1 M), 2 h, 23° C.; [d] Amide cyclization: $Cu(OTf)_2$ (50 mol %), o-xylene, 140° C. Isolated yields are reported for each entry.
Scope of Mono-Substituted Phenols.

Figure 26:
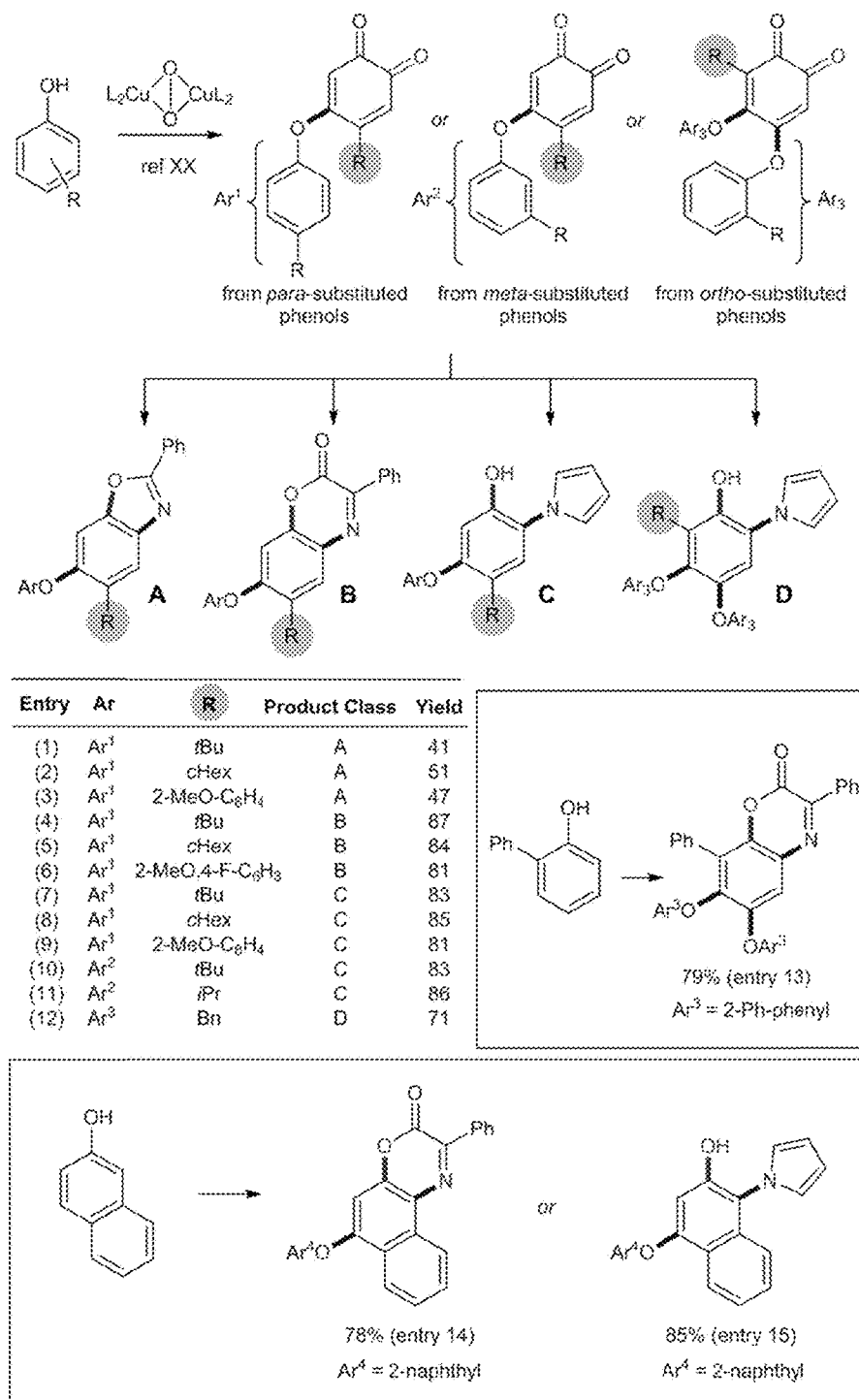
FIG. 26 summarizes the scope of mono-substituted phenols.

Mono-substituted phenols afford phenoxy-substituted quinones under catalytic aerobic conditions, and are readily converted to the analogous 1,2-oxy-amino arene products (FIG. 26). Phenols with alkyl and functionalized arene substituents are tolerated. Notably, phenols with enolizable proton at ortho- (benzyl: entry 13), meta- (isopropyl: entry 11) or para-position (cyclohexyl: entries 2, 5 and 8), as well as 2-naphthol (entry 15 and 16) undergo facile coupling with amines. We note that the synthesis of these heterocycles occurs between 23 and 50° C., uses a commercially available Cu(I) salt and amine ligand, and creates aromatic C—O and C—N bonds directly from C—H bonds, wherein $H_2O$ is generated as the sole stoichiometric by-products. See FIG. 26 summarizing the scope of mono-substituted phenols: [a] Benzoxazole synthesis: 1.0 mmol of 1, $CuPF_6$ (8 mol %), DBED (15 mol %), $O_2$ (1 atm), $CH_2Cl_2$ (0.1 M), 4 h, 23° C.; then benzylamine (2.0 equiv.), $O_2$ (1 atm), 2 h, 23° C. [b] Benzoxazinone synthesis: 1.0 mmol of 1, $CuPF_6$ (8 mol %), DBED (15 mol %), $O_2$ (1 atm), $CH_2Cl_2$ (0.1 M), 4 h, 23° C.; then phenylglycine methyl ester (2.0 equiv.) in MeOH (5 mL), 4 h, 50° C. [c] N-Aryl pyrrole synthesis: (i) 1.0 mmol of 1, $CuPF_6$ (8 mol %), DBED (15 mol %), $O_2$ (1 atm), $CH_2Cl_2$ (0.1 M), 4 h, 23° C.; (ii) 3-pyrroline (2.0 equiv.), 2 h, 23° C. Isolated yields are reported for each entry.

Interestingly, amine coupling with the resultant 4,5-di-substituted ortho-quinone intermediate bearing an oxygen heteroatom substituent at the 4-position showed preference for the carbonyl at the 1-position (entry 1-10). This aforementioned site is the most electrophilic carbonyl, thus concomitantly provides 1,2-oxy-amino arenes whereby the nitrogen incorporation occurs para to the oxygen atom substituent (i.e. phenoxy group). ortho-Substituted phenols produce 3,4,5-tri-substituted ortho-quinones bearing two phenoxy substituents (entry 12-14). In this case, the carbonyl moieties are electronically comparable, but sterically differentiated. In this case, amine condensation occurred at the least hindered site.

Synthetic Utility.

Figure 27:
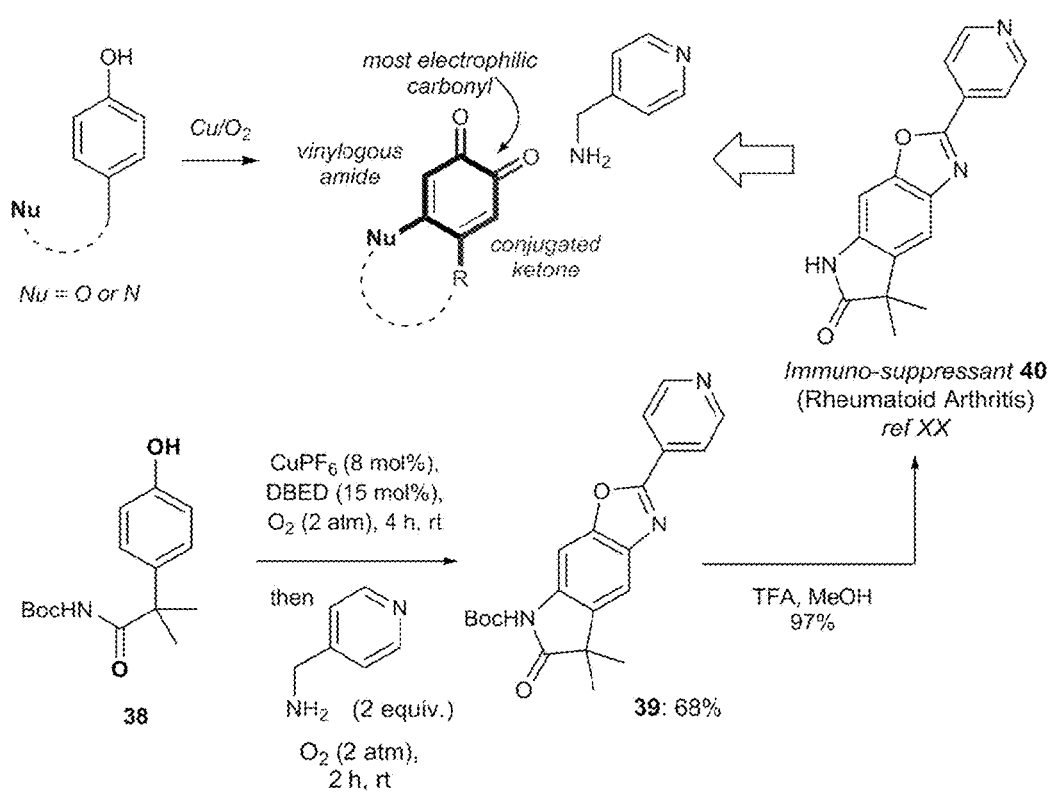
FIG. 27 shows the synthesis of an oxindole immunosuppressant.

Since ortho-oxygenation is accompanied by oxidative coupling for mono-substituted phenols, the use of phenols bearing a tethered nucleophile can be used to create complex heterocycles. For example, immuno-suppressant 40 can be envisioned to arise from analogous 4,5-di-substituted ortho-quinones (FIG. 27), resulting from ortho-oxygenation of a phenol precursor with an amide tether. Coupling of phenol 38 with 4-(aminomethyl)pyridine afford a boc-protected intermediate 39, which is easily removed by treatment with trifluoroacetic acid to provide 40. See FIG. 27 showing the synthesis of immuno-suppressant 40.

Figure 28:
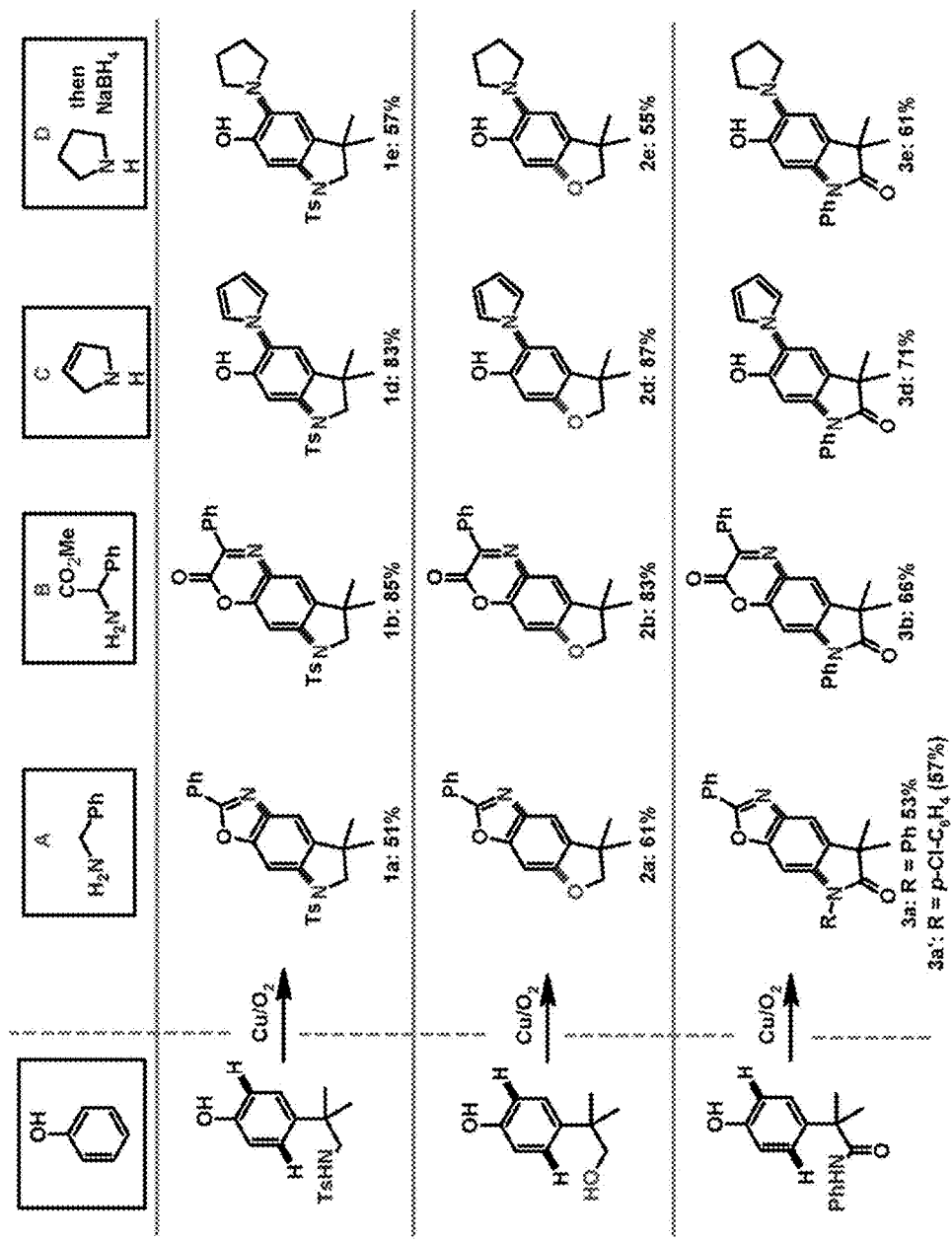
FIG. 28 shows the one-pot syntheses of immuno-suppressant derivatives via phenol and amine coupling.

Likewise, phenols with tethered oxygen and nitrogen nucleophiles are readily converted to complex benzoxazoles (FIGS. 28, 1a, 2a and 3a) by a formal two C—H bond to C—O and/or C—N bond functionalization. A simple switch of the amine coupling partner and a slight modification of the reaction conditions allow for the regioselective synthesis of a different product class (entries 1-3), thus a library of complex 1,2-oxy-amino arenes can easily be generated. See FIG. 28 showing the one-pot syntheses of immuno-suppressant derivatives via phenol and amine coupling: $^a$ Benzoxazole synthesis: 1.0 mmol of 1, CuPF$_6$ (8 mol %), DBED (15 mol %), O$_2$ (1 atm), CH$_2$Cl$_2$ (0.1 M), 4 h, 23° C.; then benzylamine (2.0 equiv.), O$_2$ (1 atm), 2 h, 23° C. $^b$ Benzoxazinone synthesis: 1.0 mmol of 1, CuPF$_6$ (8 mol %), DBED (15 mol %), O$_2$ (1 atm), CH$_2$Cl$_2$ (0.1 M), 4 h, 23° C.; then phenylglycine methyl ester (2.0 equiv.) in MeOH (5 mL), 4 h, 50° C. $^c$ N-Aryl pyrrole synthesis: (i) 1.0 mmol of 1, CuPF$_6$ (8 mol %), DBED (15 mol %), O$_2$ (1 atm), CH$_2$Cl$_2$ (0.1 M), 4 h, 23° C.; (ii) 3-pyrroline (2.0 equiv.), 2 h, 23° C. $^d$ Synthesis of amino-phenols: (i) 1.0 mmol of 1, CuPF$_6$ (8 mol %), DBED (15 mol %), O$_2$ (1 atm), CH$_2$Cl$_2$ (0.1 M), 4 h, 23° C.; (ii) amine (2.0 equiv.), 12 h, 50° C.; (iii) NaBH4 (2.0 equiv.) in MeOH (2 mL), 2 h, 0-23° C. Isolated yields are reported for each entry.

Figure 29:
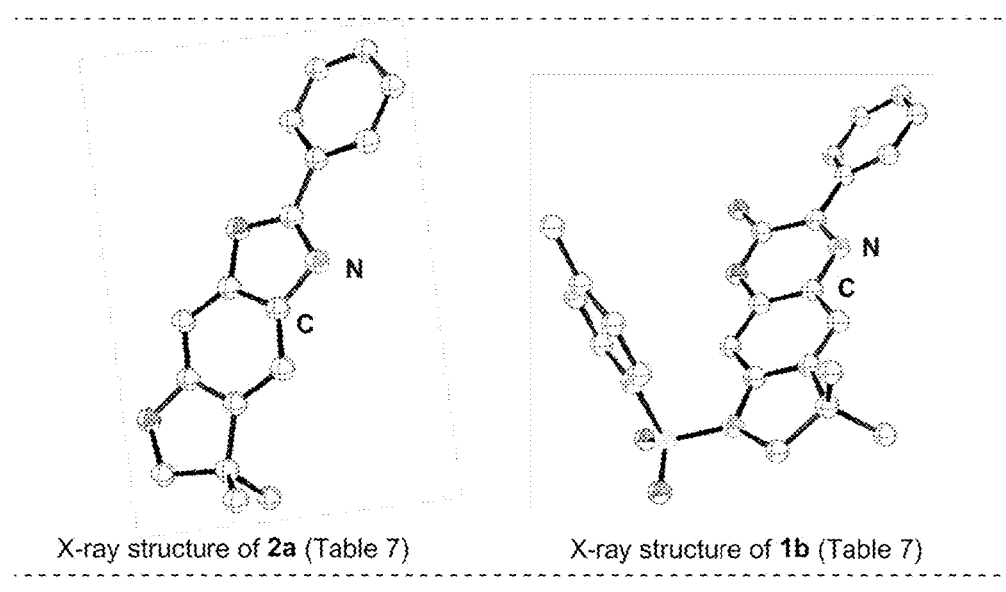
FIG. 29 shows single X-ray structures depicting the regiochemistry of amine coupling.

Single crystal x-ray analysis of two examples from two product class (FIG. 29) indicate that the two newly formed C—N and/or C—O bonds always occur para to each other, consistent previously observed 1,2-oxy-amino arene syntheses from meta- and para-substituted phenols. See FIG. 29 showing single X-ray structures depicting the regiochemistry of amine coupling Part (E): Predicting the Site of Nitrogen Incorporation.

Due to the presence of a di-keto functionality in the quinone intermediate, nitrogen coupling can occur at two possible positions. Thus, determining the site of nitrogen coupling allows for a practical guideline for both prediction, and tunability of regioselectivity.

Oxygenation of symmetric 3,5-di-substituted phenols provides a single ortho-quinone intermediate, and the resulting 1,2-oxy-amino arene reflects nitrogen incorporation at the least sterically encumbered carbonyl moiety.

For asymmetric 3,5-di-substituted phenols, a total of 4-possible isomers can result if high levels regiocontrol are not maintained during the oxygenation and condensation step. Previous mechanistic work from our group and from the group of Stack have shown that ortho-oxygenation mediated by Cu/DBED occurs by electrophilic aromatic substitution within a dinuclear Cu(III)-μ-oxo phenolate. This enforces a close contact between the meta-substituent of the phenol and the sterically demanding tert-butyl substituents of the di-amine ligand, favoring oxygenation from an intermediate that directs the least sterically encumbered substituent towards the ligand/metal complex. Since the amine condensation follows the steric model discussed above, C—N bond formation occurs regioselectivity. Thus providing two isomers wherein the product ratio is determined by relative amounts of each ortho-quinone intermediates. However, the inherent bias in the amine condensation can be over-ridden in 3,5-di-substituted phenols bearing directing groups at the meta-position such as an ortho-methoxyphenyl substituent. Thus, two isomers can arise from a single ortho-quinone intermediate.

4,5-Disubstituted ortho-quinone intermediates wherein one of the substituent is either an oxygen or nitrogen heteroatom, possesses two carbonyl moieties that are significantly differentiated electronically. These intermediates arise from meta- and para-substituted phenols. In this case, the amine condensation occurs at the most electrophilic carbonyl (i.e. the carbonyl which bears the least electron donating β-substituent), thus the newly formed C—N bond to occur para to the heteroatom substituent. In cases where both carbonyl moieties are electronically similar, C—N bond formation occurs at the sterically least encumbered site.

Example 3—Synthesis of Ortho-Azophenols

Figure 30:
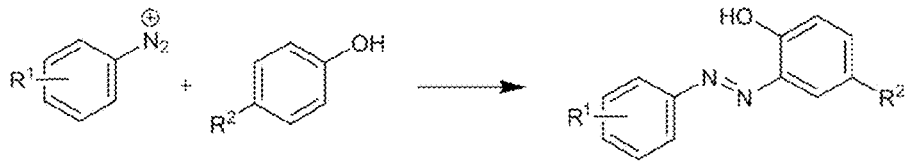
FIG. 30 shows (A) Classical syntheses by diazo coupling, and transition metal catalyzed hydroxylation; (B) PPQ-mediated deamination of amines; and (C) Dehydrogenative coupling between phenol and hydrazine/hydrazide.
Figure 30:
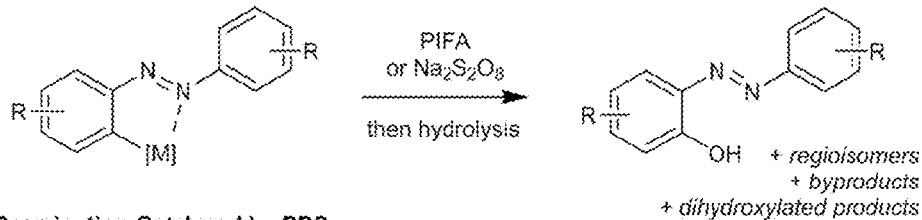
Figure 30:
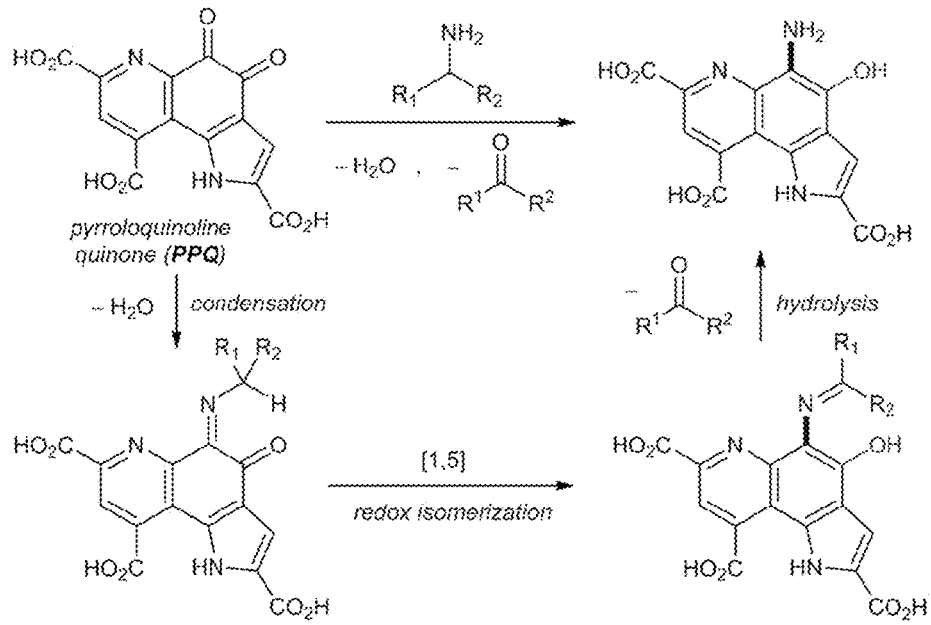
Figure 30:
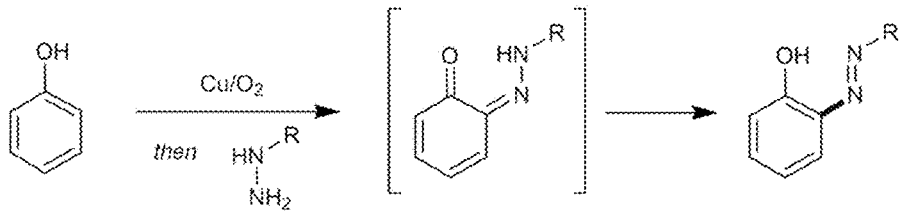

Our group has developed a bio-inspired copper-catalyzed aerobic method to generate ortho-quinones from simple phenols. Above, we have applied this methodology for the synthesis of 1,2-oxy-amino arenes through a formal dehydrogenative coupling of amines and phenols. Here, we envisaged that the redox-isomerization following hydrazine condensation affords an N=N moiety (FIG. 30C), giving rise to azophenols. The realization of this approach constitutes the first fragment coupling approach of phenols and hydrazine/hydrazides under aerobic conditions.

Having previously established a protocol for the ortho-amination of phenols, we applied this reaction condition for the transformation of 1 to 3:

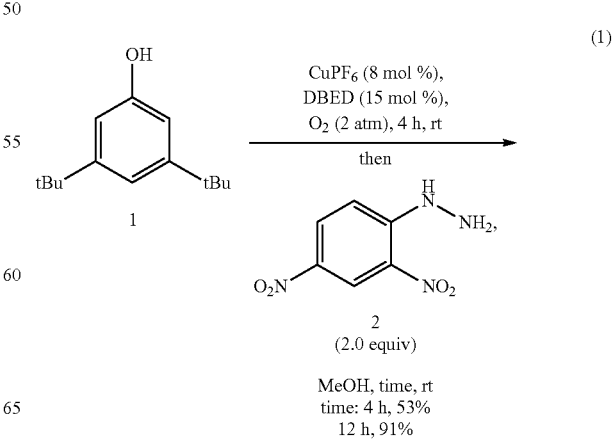

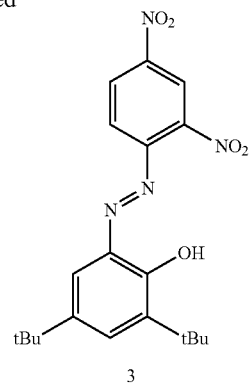

Our standard conditions for the ortho-oxygenation of 1 employ 8 mol % [Cu(CH$_3$CN)$_4$](PF$_6$) (abbreviated CuPF$_6$), 15 mol % N,N'-di-tert-butyl-ethylenediamine (DBED) and O$_2$ (1 atm overpressure). This is then followed by condensation reaction with 2.0 equivalent of hydrazine 2 for 4 h. These conditions lead to 53% of 3, but prolonged reaction time results in 91% yield. These conditions were successfully implemented on a large scale (87%, 20 mmol scale).

Figure 31:
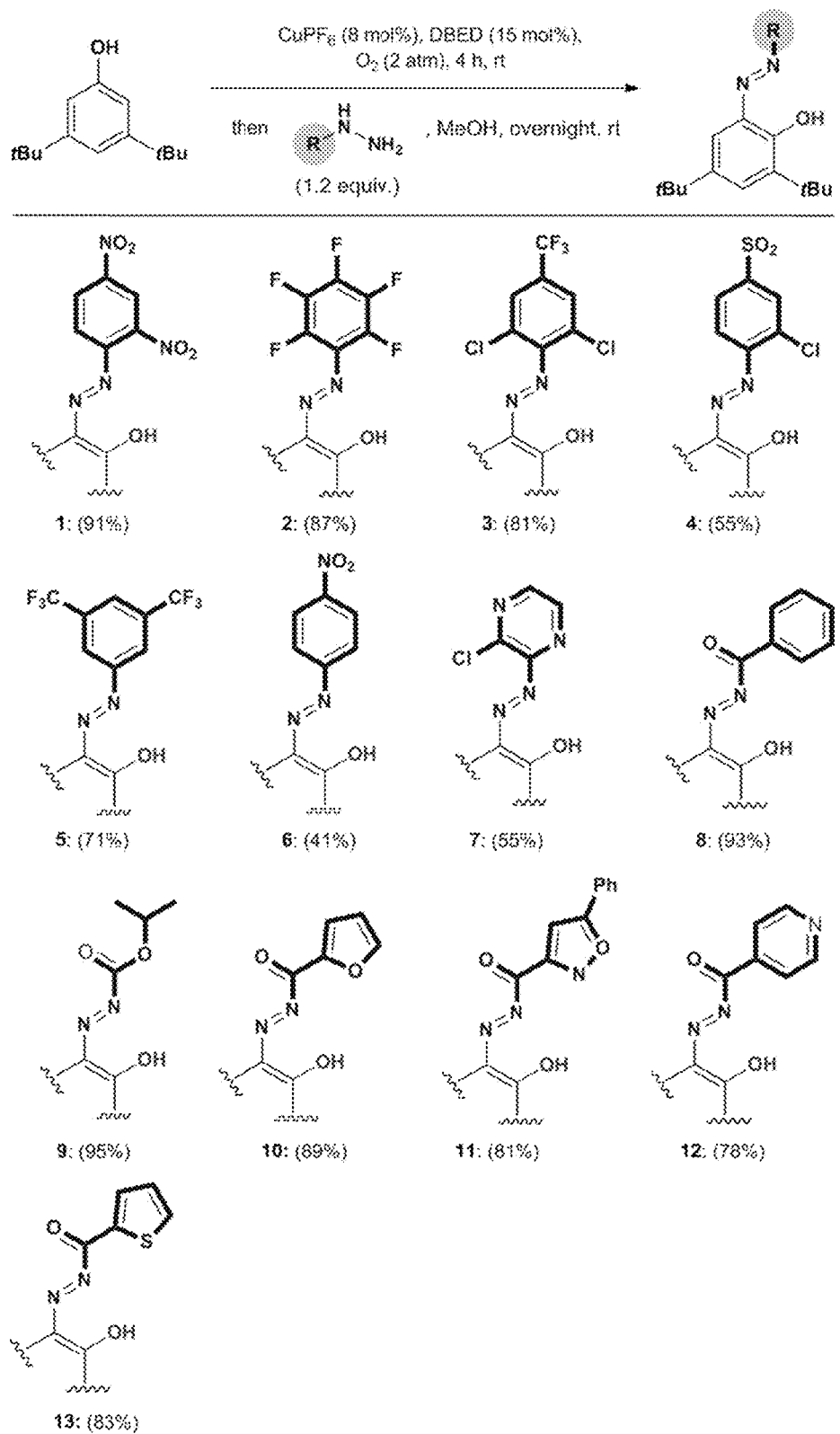
FIG. 31 summarizes the scope of hydrazines and hydrazides.

With optimized conditions in hand, we next studied the coupling of 1 with various hydrazines and hydrazides. See FIG. 31 showing the scope of hydrazines and hydrazides[a]: [a] Conducted with 1.0 mmol of 1. Isolated yields are reported for each entry. Azophenols with push-pull configuration can be easily prepared from the coupling of aryl hydrazines bearing electron-withdrawing substituents such as nitro, halogens, or trifluoromethyl groups (entries 1-6). Likewise, hydrazides bearing aryl (entry 8) and boc-group (entry 9) afforded the corresponding azo com-pound in excellent yields. Heteroaromatic substituents which are frequently encountered in the pharmaceutical and material sciences are easily installed, including pyrazine (entry 7), furan (entry 10), isoxazole (entry 11), pyridine (entry 12), and thiophene (entry 13).

Figure 32:
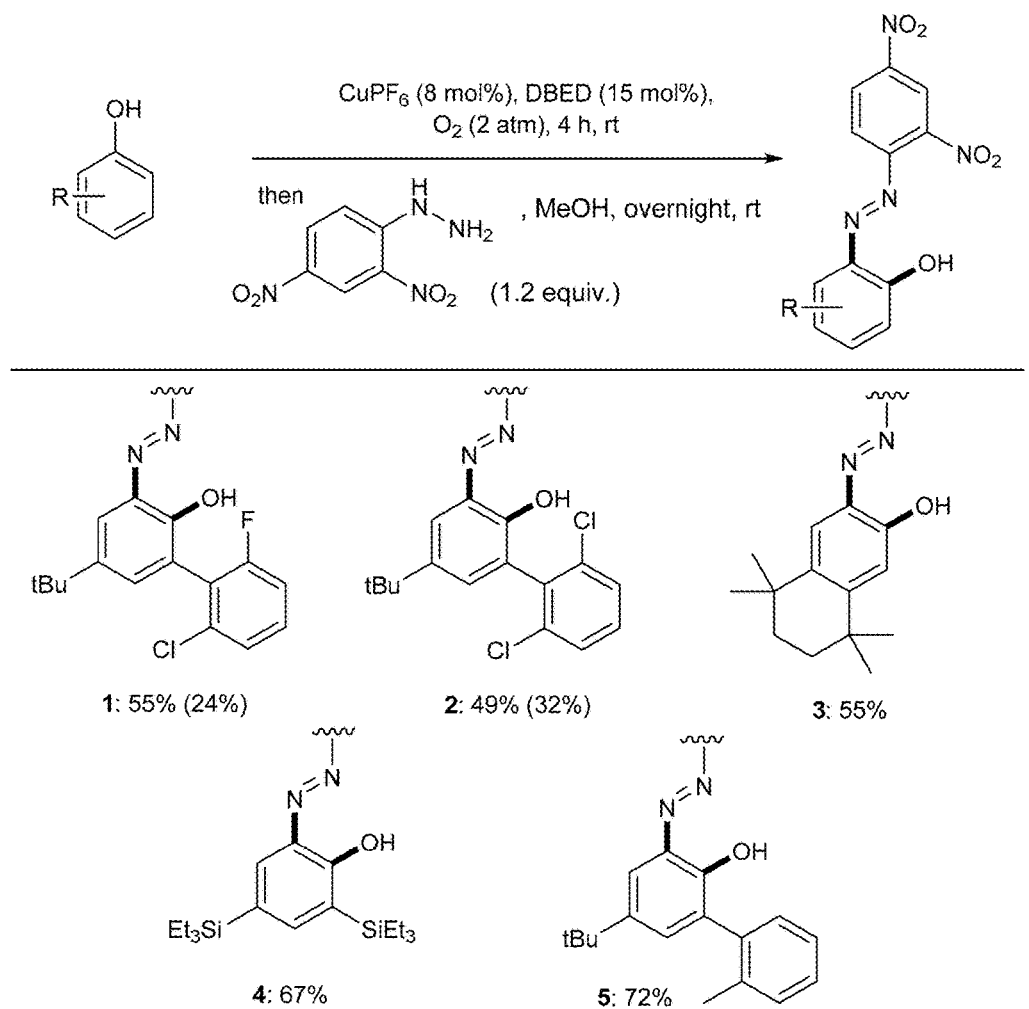
FIG. 32 summarizes the scope of disubstituted phenols.

Next, we investigated the scope of disubstituted phenols using 2 as the hydrazine coupling partner. See FIG. 32 showing the scope of disubstituted phenols[a]: [a] Conducted with 1.0 mmol of 1. Isolated yields are reported for each entry. Phenols with alkyl and/or aryl groups are easily converted the corresponding azophenol (entry 1-3 and 5). Silicon groups are tolerated at the 2- and 5-positions of the phenol (entry 4), providing azophenols with synthetic handles for further elaboration.

Figure 33:
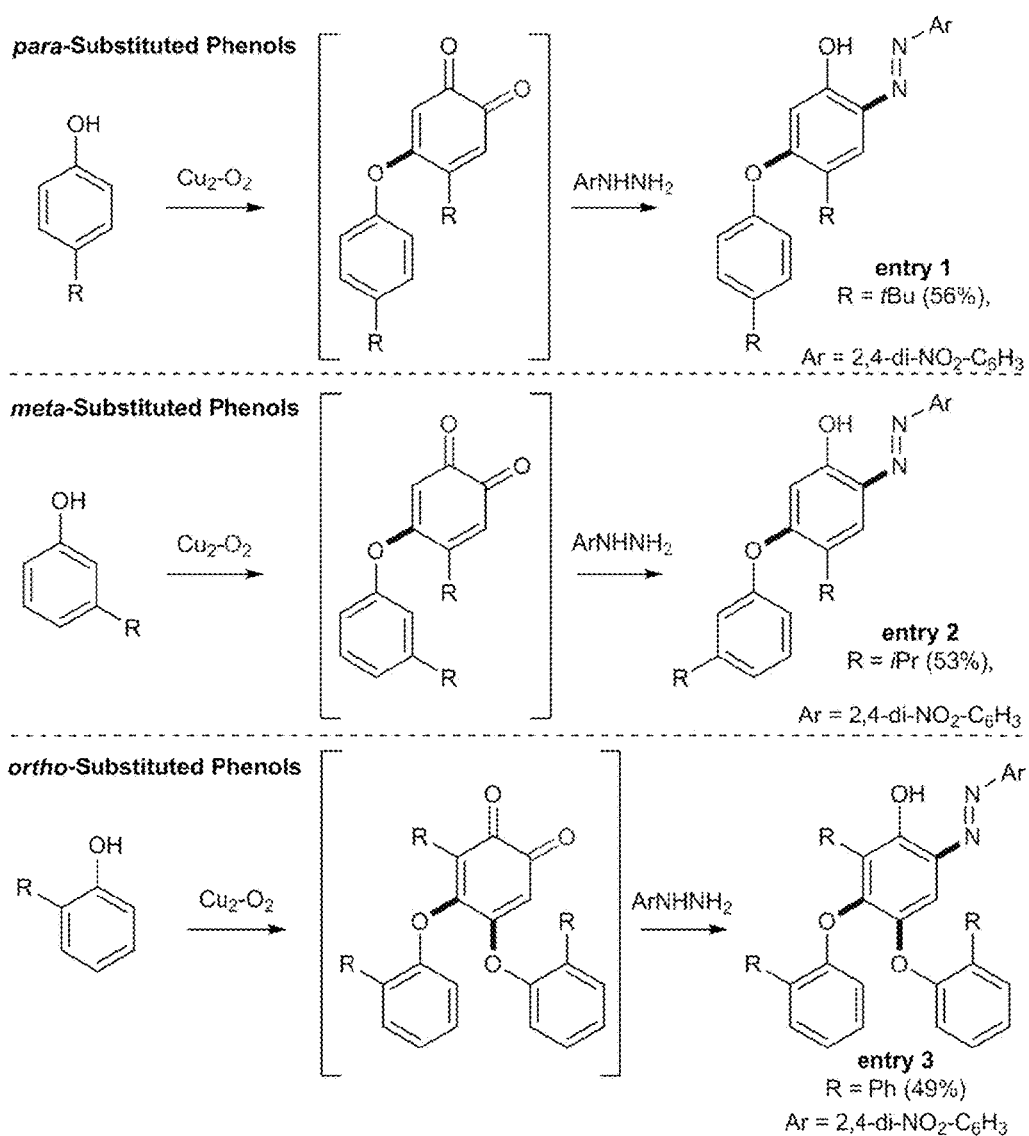
FIG. 33 summarizes the scope of disubstituted phenols.

Our above studies on the oxygenation of mono-substituted phenols show that they afford phenoxy-substituted quinones. Using our 1-pot aerobic coupling of hydrazine and phenol, azophenols bearing phenoxy-substituted arenes are easily generated, wherein two aryl C—H bonds are converted to aryl C—N and C—O bonds. See FIG. 33 showing the scope of disubstituted phenols[a]: [a] Conducted with 1.0 mmol phenol, CuPF$_6$ (8 mol %), DBED (15 mol %), O$_2$ (1 atm), CH$_2$Cl$_2$ (0.1 M), 4 h, 23° C.; then 2,4-dinitrophenylhydrazine (2.0 equiv.), 12 h, 23° C. We note that this transformation occurs at room temperature, uses a commercially available Cu$^I$ salt and amine ligands, and generates H$_2$O as the sole stoichiometric by-product.

Figure 34:
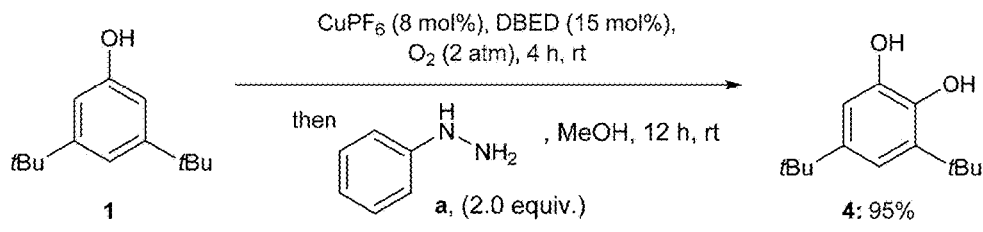
FIG. 34 shows a list of unsuccessful substrates.
Figure 34:
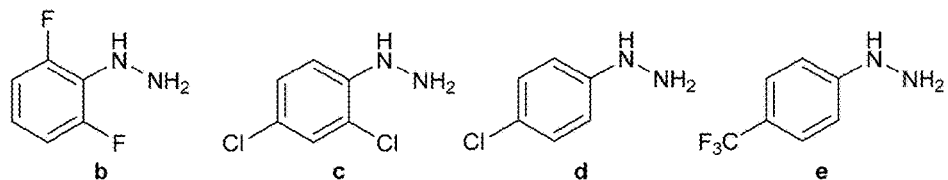

Although hydrazines with electron-deficient arene are easily tolerated, substrates bearing more electron-rich arenes (FIG. 34, a-e) are incompatible with the reaction. See FIG. 34 listing unsuccessful substrates. In this case, the hydrazine reduces the ortho-quinone intermediate and affords the corresponding catechol 4 in high yields. Attempts to favor quinone-hydrazine condensation via addition of desiccants and/or Lewis acids were unsuccessful, and studies on the effect of solvents, pH and/or temperature failed to provide the desired product (see supporting information below for details).

Figure 35:
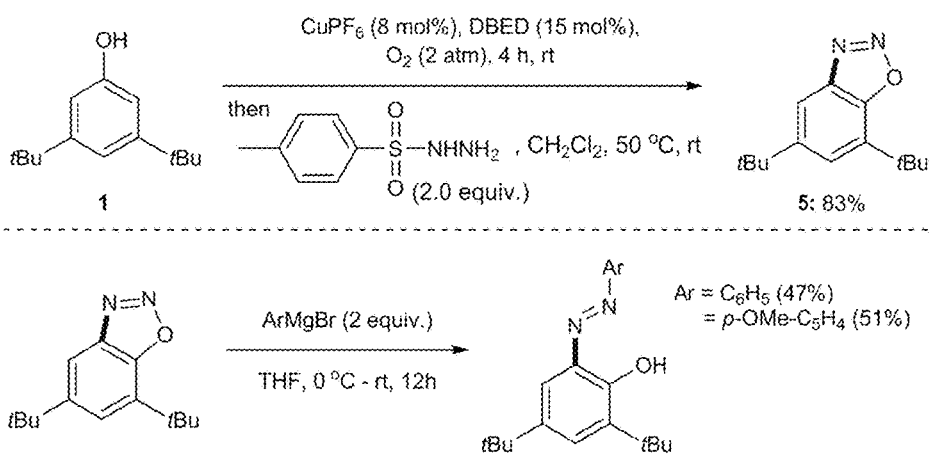
FIG. 35 shows the synthesis of diazobenzoquinone and electron-rich azophenols.

In an effort to solve this problem, we developed a two-step procedure to synthesize azophenols with more electron-rich arenes. Serendipitously, reaction of 1 with p-toluenesulfonyl hydrazide did not produced the desired azo compound, but affords diazobenzoquinone 5—see FIG. 35. Interestingly, addition of carbanion nucleophiles to 5 such as aryl Grignard reagents afford azophenols possessing electron-rich arene groups.

Supporting Information Regarding Example 2

Experimental Section

General Experimental

Chemicals and solvents were purchased from Sigma Aldrich, Alfa Aesar, Strem Chemicals or TCI. Solvents were dried and purified using a PureSolv MD 7 (from Innovative Technology) or MB SPS 800 (from MBraun). All phenol and amine substrates were purified prior to use: liquids were distilled using a Hickman apparatus immediately prior to use and solids were recrystallized. N,N'-di-tert-butylethylenediamine (DBED) were distilled over CaH$_2$ under N$_2$. [Cu(MeCN)$_4$](PF$_6$) was purchased from Sigma Aldrich or Strem. Unless otherwise noted, reactions were performed in flame-dried glassware under a positive pressure of N$_2$ using standard synthetic organic, inert atmosphere techniques. All oxidation reactions were set-up in flame-dried, 25-mL Radley tubes with a Teflon-coated stir bar under a nitrogen atmosphere (Praxair, N$_2$ pre-purified). The reaction vessels were then connected to a cylinder of O$_2$ (Praxair), purged three times with O$_2$ and then pressurized to +1.0 atm (see experimental section for details).

Proton and carbon nuclear magnetic resonance ($^1$H NMR and $^{13}$C NMR) spectra were acquired using Varian Inova 400 MHz, Varian Mercury 300 MHz spectrometers, Bruker 400 MHz, and Bruker 500 MHz. Chemical shifts (δ) are reported in parts per million (ppm) and are calibrated to the residual solvent peak. Coupling constants (J) are reported in Hz. Multiplicities are reported using the following abbreviations: s=singlet; d=doublet; t=triplet; q=quartet; m=multiplet (range of multiplet was given). Carbon nuclear magnetic resonance ($^{13}$C NMR) spectra were acquired using Varian Inova 100 MHz and Varian Mercury 75 MHz spectrometers. Chemical shifts (δ) are reported in parts per million (ppm) and are calibrated to the residual solvent peak. High resolution mass spectra (HRMS) were recorded using a Bruker maXis Impact TOF mass spectrometer. Fourier-transform infrared (FT-IR) spectra were recorded on a Perkin-Elmer FT-IR ATR spectrometer.

Analytical thin-layer chromatography was performed on pre-coated 250 μm layer thickness silica gel 60 F$_{254}$ plates (EMD Chemicals Inc.). Visualization was performed by ultraviolet light and/or by staining with potassium permanganate or iodine. Purifications by column chromatography were performed using either a Biotage Isolera™ One (Snap Ultra, particle size 25 μm, 230-400 mesh), or standard column chromatography using silica gel (40-63 μm, 230-400 mesh).

Synthesis of Phenolic Substrates:

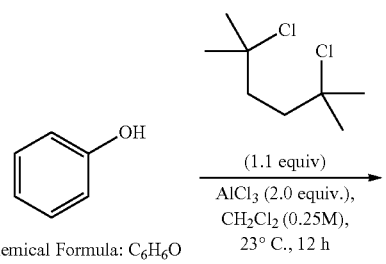

Chemical Formula: C₆H₆O
Molecular Weight: 94.11
S0

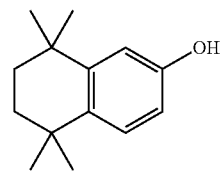

Chemical Formula: C₁₄H₂₀O
Molecular weight: 204.31
S1

A flame-dried 50-mL pressure vessel, equipped with a Teflon stir bar, was charged with phenol S0 (2 g, 21.25 mmol, 1 equiv.), 2,5-dichloro-2,5-dimethylhexane (4.28 g, 23.38 mmol, 1.1 equiv.) and CH₂Cl₂ (20 mL). Aluminum trichloride (2.83 g, 21.25 mmol, 1 equiv.) was added to this reaction mixture and the reaction was stirred at 50° C. for 12 h. The reaction mixture was quenched by the addition of distilled H₂O (20 mL), and the phases were separated. The aqueous phase was washed with CH₂Cl₂ (3×20 mL). The combined organic fractions were dried over MgSO₄, filtered and concentrated in vacuo to afford a crude residue, which was purified using flash column chromatography (silica gel with 15% EtOAc in hexanes as eluant) to afford S1 as white powder in 70% isolated yield.

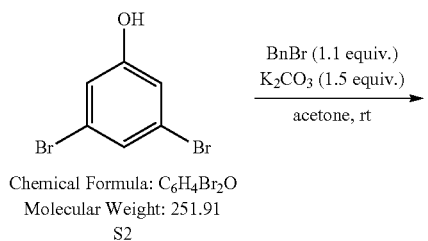

Chemical Formula: C₆H₄Br₂O
Molecular Weight: 251.91
S2

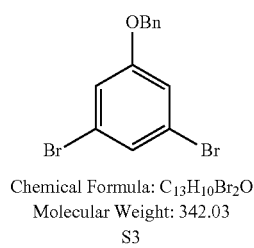

Chemical Formula: C₁₃H₁₀Br₂O
Molecular Weight: 342.03
S3

3,5-di-bromophenol S2 was synthesized according to literature procedure: Laliberte, D.; Maris, T.; Wuest, J. D. *J. Org. Chem.* (2004), 69, 1776-1787.

A flame-dried 100-mL round-bottomed flask, equipped with a Teflon stir bar, was charged with 3,5-di-bromophenol S2 (10 g, 39.70 mmol, 1 equiv.), benzyl bromide (4.68 g, 43.67 mmol, 1.1 equiv.), K₂CO₃ (8.23 g, 59.55 mmol, 1.5 equiv.) and anhydrous acetone (50-mL). The reaction mixture was stirred at room temperature for 12 h. Then, the reaction mixture was quenched by the addition of distilled H₂O (10 mL), volatiles were evaporated in vacuo, and diluted with EtOAc (100-mL). Then, the phases were separated and the organic phase was washed with brine (3×50-mL). The organic fraction was dried over MgSO₄, filtered and concentrated in vacuo to afford a crude residue, which was purified using flash column chromatography (silica gel with 5% EtOAc in hexanes as eluant) to afford S3 as white powder in 95% isolated yield.

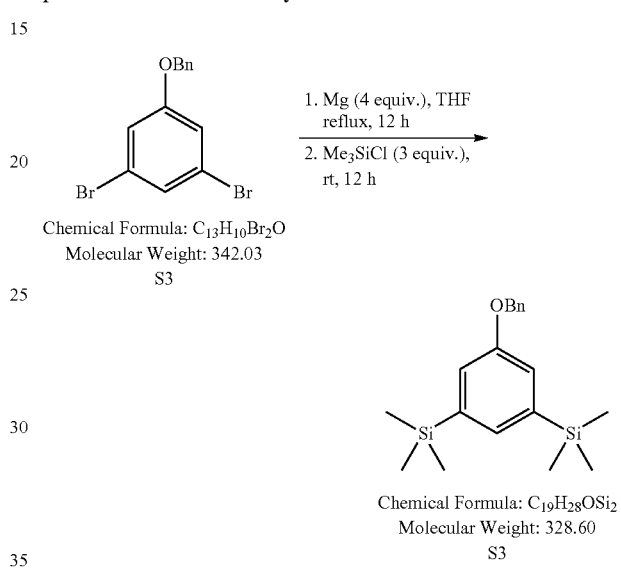

A flame-dried 100-mL round-bottomed flask, equipped with a Teflon stir bar, was charged with S3 (2.0 g, 5.85 mmol, 1.0 equiv.), magnesium turnings (0.57 g, 23.39 mmol, 4.0 equiv.), one small crystal of I₂ and degassed anhydrous THF (40 mL). The reaction mixture was stirred at 60° C. for 12 h. Then, the reaction mixture was cooled to 0° C., and Me₃SiCl (1.91 g, 2.22 mL, 17.54 mmol, 3.0 equiv.) was added dropwise via a syringe. The reaction was allowed to warm to room temperature and stirred overnight. Afterwards, the reaction was quenched by the addition of aqueous saturated NH₄Cl (50-mL), and diluted with EtOAc (100-mL). Then, the phases were separated and the organic phase was washed with brine (3×50-mL). The organic fraction was dried over MgSO₄, filtered and concentrated in vacuo to afford a crude residue, which was purified using flash column chromatography (silica gel with 10% EtOAc in hexanes as eluant) to afford S4 as white powder in 80% isolated yield.

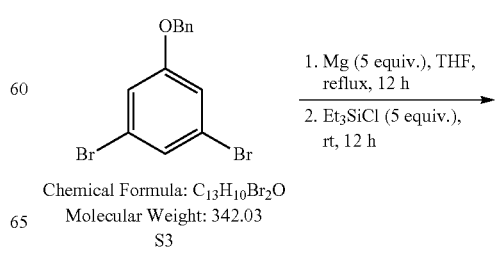

Chemical Formula: C₁₃H₁₀Br₂O
Molecular Weight: 342.03
S3

-continued

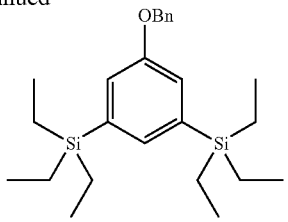

Chemical Formula: C$_{25}$H$_{40}$OSi$_2$
Molecular Weight: 412.76
S3

A flame-dried 100-mL round-bottomed flask, equipped with a Teflon stir bar, was charged with S3 (2.0 g, 5.85 mmol, 1.0 equiv.), magnesium turnings (0.71 g, 29.24 mmol, 5.0 equiv.), one small crystal of I$_2$ and dry, degassed THF (50-mL). The reaction mixture was stirred at 60° C. for 2 h. Then, the reaction mixture was cooled to 0° C., and Et$_3$SiCl (4.41 g, 4.91 mL, 29.23 mmol, 3.0 equiv.) was added dropwise via a syringe. The reaction was allowed to warm to room temperature and stirred overnight. The reaction was then quenched by the addition of aqueous saturated NH$_4$Cl (20 mL), and diluted with EtOAc (100 mL). Then, the phases were separated and the organic phase was washed with brine (3×100 mL). The organic fraction was dried over MgSO$_4$, filtered and concentrated in vacuo to afford a crude residue, which was purified using flash column chromatography (silica gel with 10% EtOAc in hexanes as eluant) to afford S5 as white powder in 75% isolated yield.

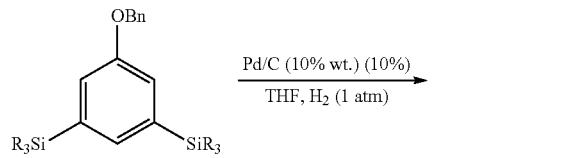

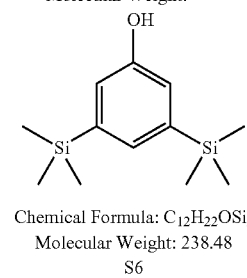 or 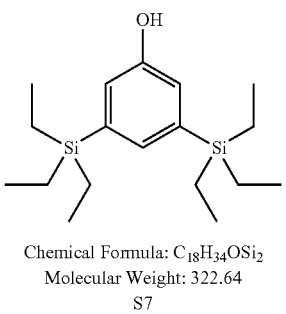

Chemical Formula: C$_{12}$H$_{22}$OSi$_2$
Molecular Weight: 238.48
S6

Chemical Formula: C$_{18}$H$_{34}$OSi$_2$
Molecular Weight: 322.64
S7

General Procedure for O-Benzyl Deprotection.

A flame-dried 50-mL round-bottomed flask, equipped with a Teflon stir bar, was charged with S4 or S5 (1.0 equiv.), Pd/C (10% wt., 10%) and dry THF (25 mL). The reaction mixture was stirred at room temperature for 12 h under an atmosphere of H$_2$ (1 atm). Afterwards, the reaction was quenched by the addition of distilled H$_2$O (50 mL), and diluted with EtOAc (50-mL). Then, the phases were separated and the organic phase was washed with brine (3×50 mL). The organic fraction was dried over MgSO$_4$, filtered and concentrated in vacuo to afford a crude residue, which was purified using flash column chromatography (silica gel with 10% EtOAc in hexanes as eluant) to afford the pure product.

3,5-di-trimethyiphenol (S6): 81% isolated yield;
3,5-di-triethylsilyiphenol (S7): 85% isolated yield

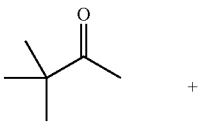

Chemical Formula: C$_6$H$_{12}$O
Molecular Weight: 100.16
S8

+

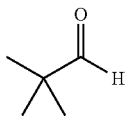

Chemical Formula: C$_5$H$_{10}$O
Molecular Weight: 86.13
S9

(i) NaOH (2 equiv.), EtOH:H$_2$O (9:1), reflux, 12 h
(ii) NaOMe (2.0 equiv.), acetone, 90° C., 3 d
(iii) [Pd] (25 mol %), O$_2$ (1 bar) 120° C., 3 d

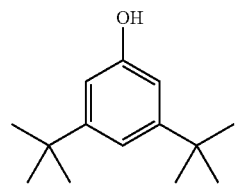

Chemical Formula: C$_{14}$H$_{22}$O
Molecular Weight: 206.33
1

Compound 1 was synthesized using a modified procedure reported by Stahl et al.: Izawa, Y.; Pun, D.; Stahl, S. S. Science. (2011), 333, 201-213. A 100-mL round-bottom flask, equipped with a Teflon coated stir bar was charged with the appropriate tert-butyl methyl ketone S8 (4.0 g, 39.94 mmol, 1.0 equiv.), pivaldehyde S9 (4.12 g, 47.92 mmol, 1.2 equiv.), and degassed ethanol/water (9:1 v:v, 40 mL). NaOH (3.19 g, 79.87 mmol, 2.0 equiv,) was then added and the reaction mixture was refluxed for 12 h. The reaction mixture was quenched by the addition of NaHSO$_4$ (40 mL, 10% by weight aqueous solution), and diluted with CH$_2$Cl$_2$ (20 mL). Then, the phases are separated and the aqueous phase was extracted with CH$_2$Cl$_2$ (3×20 mL). The combined organic fractions are dried over MgSO$_4$, filtered and concentrated in vacuo to afford a crude residue. The crude residue was washed with hexanes (50-mL) and analyzed by $^1$H NMR.

Analytical data matches that reported in the literature: Sparling B. A.; Moslin, R. M.; Jamwason, T. F. Org. Lett. (2008), 10, 1291-1294.

A 250-mL round-bottom flask, equipped with a Teflon coated stir bar was charged with the crude residue and dry acetone (50-mL). NaOMe (4.31 g, 79.87 mmol, 2.0 equiv.) was added, warmed to 50° C., and was vigorously stirred for 4 h. The reaction mixture was cooled to room temperature, quenched by the addition of NaHSO$_4$ (10 mL, 20% by weight aqueous solution), and concentrated in vacuo. The reaction mixture was diluted with CH$_2$Cl$_2$ (50 mL), and the phases were then separated and the aqueous phase was extracted with CH$_2$Cl$_2$ (3×50 mL). The combined organic fractions were then dried over MgSO$_4$, filtered and concentrated in vacuo to afford a solid crude residue.

The resulting solid was placed in a flame-dried 25-mL Radley tube, equipped with a Teflon coated stir bar. Then, Pd(TFA)$_2$ (3.32 g, 9.98 mmol, 25 mol %), p-TsOH (3.43 g, 20 mmol, 50 mol %), 2-(N,N-dimethylamino)pyridine (1.22 g, 10 mmol, 25 mol %), DMSO (6 mL) were added. The reaction vessel was capped, pressurized with O$_2$ (1 atm) and heated to 120° C. whilst stirring for 3 days. The reaction mixture was depressurized, cooled to room temperature and diluted with distilled H$_2$O (30 mL) and CH$_2$Cl$_2$ (50 mL). The phases were then separated and the aqueous phase was extracted with CH$_2$Cl$_2$ (3×50 mL). The combined organic fractions were then dried over MgSO$_4$, filtered and concentrated in vacuo to afford a crude residue, which was purified using flash column chromatography (15% EtOAc in hexanes) to afford 1 in 38% isolated yield.

3,5-Di-Substituted Phenolic Substrates were Synthesized Using Either of the One of the Two Protocols, Method 1 or 2

Method 1:

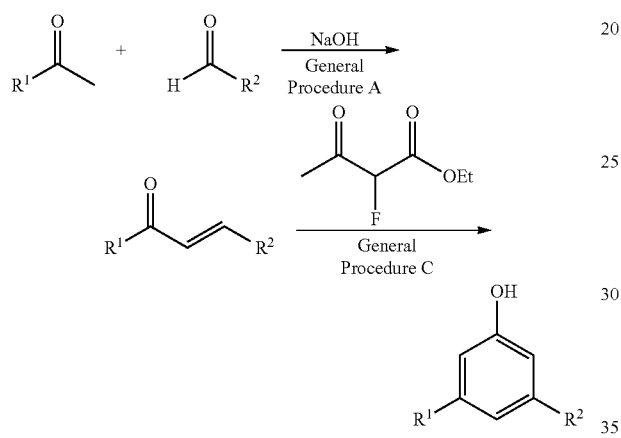

Method 2:

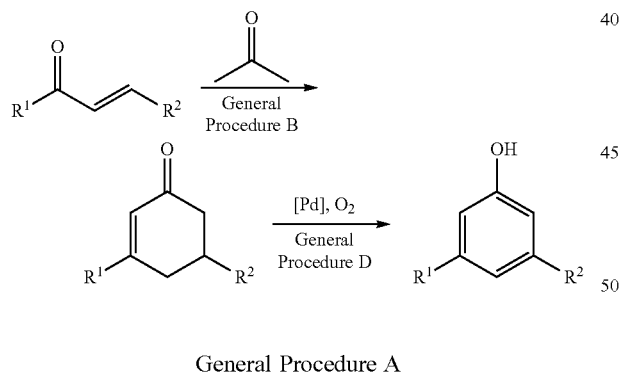

General Procedure A

Synthesis of 3,5-Di-Substituted Cyclohexenone

A 100-mL round-bottom flask, equipped with a Teflon coated stir bar was charged with the appropriate ketone (1 equiv.), aldehyde (1.2 equiv.) and degassed ethanol/water (9:1, 0.25 M with respect to the ketone). Sodium hydroxide (2 equiv.) was then added and the reaction mixture was stirred at room temperature for 12 h. The reaction mixture was quenched by the addition of NaHSO$_4$ (40 mL, 10% by weight aqueous solution), and diluted with CH$_2$Cl$_2$ (20 mL). Then, the phases are separated and the aqueous phase was extracted with CH$_2$Cl$_2$ (3×20 mL). The combined organic fractions were dried over MgSO$_4$, filtered and concentrated in vacuo to afford a crude residue, which was purified using flash column chromatography (silica gel with 20% EtOAc in hexanes as eluant) to afford a pure compound.

The following compounds were produced using general procedure A:

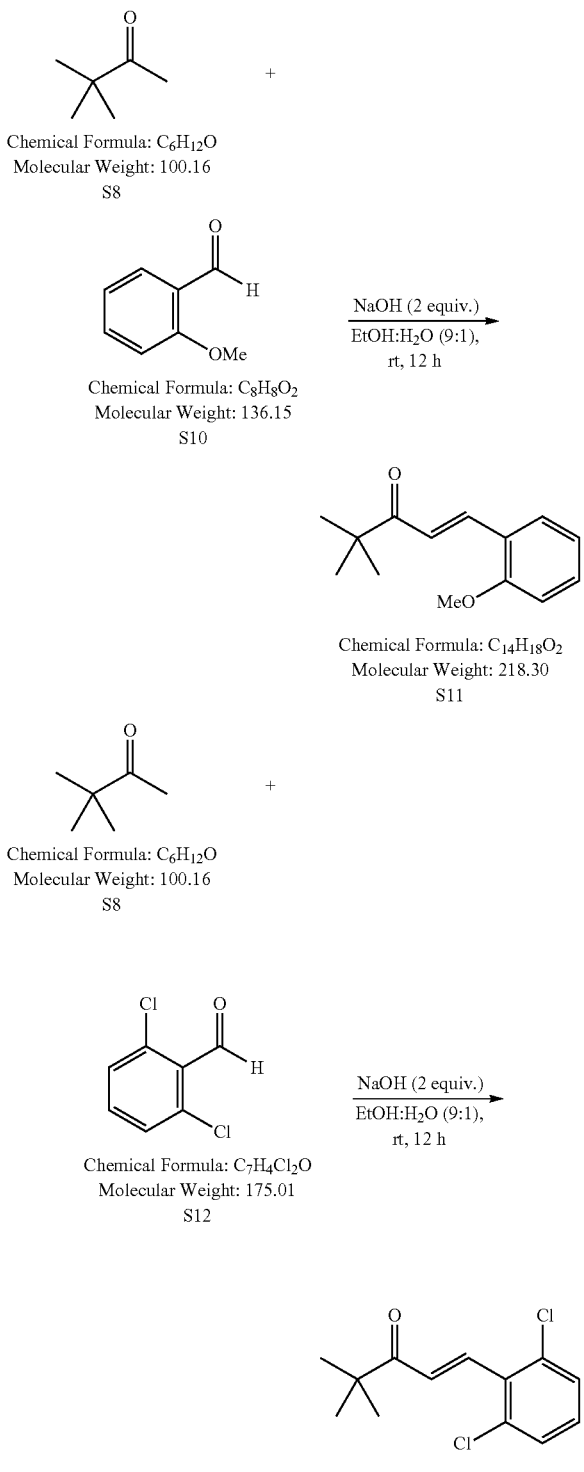

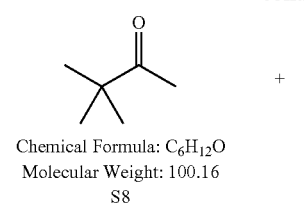

Chemical Formula: C₆H₁₂O
Molecular Weight: 100.16
S8

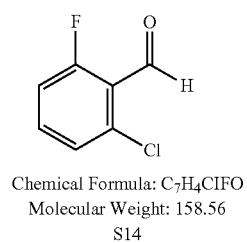

Chemical Formula: C₇H₄ClFO
Molecular Weight: 158.56
S14

NaOH (2 equiv.)
EtOH:H₂O (9:1), rt, 12 h
→

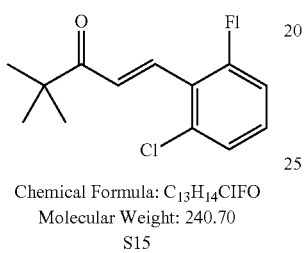

Chemical Formula: C₁₃H₁₄ClFO
Molecular Weight: 240.70
S15

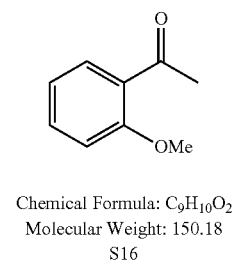

Chemical Formula: C₉H₁₀O₂
Molecular Weight: 150.18
S16

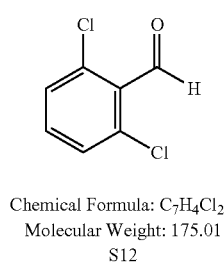

Chemical Formula: C₇H₄Cl₂O
Molecular Weight: 175.01
S12

NaOH (2 equiv.)
EtOH:H₂O (9:1), rt, 12 h
→

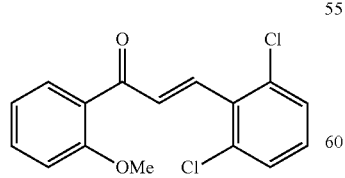

Chemical Formula: C₁₆H₁₂Cl₂O
Molecular Weight: 307.17
S17

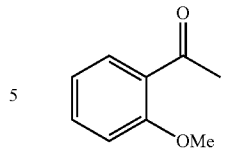

Chemical Formula: C₉H₁₀O₂
Molecular Weight: 150.18
S16

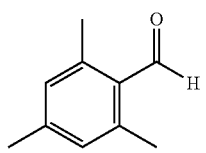

Chemical Formula: C₁₀H₁₂O
Molecular Weight: 148.21
S18

NaOH (2 equiv.)
EtOH:H₂O (9:1), rt, 12 h
→

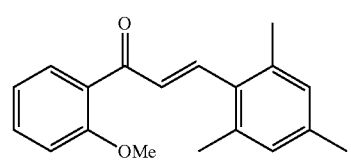

Chemical Formula: C₁₉H₂₀O₂
Molecular Weight: 280.37
S19

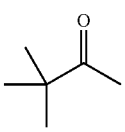

Chemical Formula: C₆H₁₂O
Molecular Weight: 100.16
S8

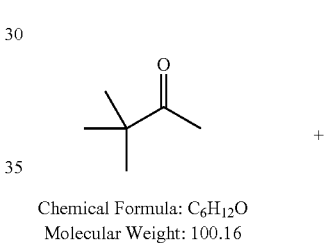

Chemical Formula: C₈H₈O
Molecular Weight: 120.15
S20

NaOH (2 equiv.)
EtOH:H₂O (9:1), rt, 12 h
→

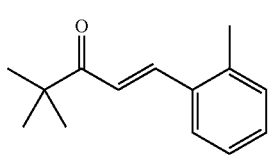

Chemical Formula: C₁₄H₁₈O
Molecular Weight: 202.30
S21

General Procedure B

Synthesis of 3,5-Di-Substituted Cyclohexenone

A 50-mL round-bottom flask, equipped with a Teflon coated stir bar was charged with the appropriate chalcone (1 equiv.) and dry acetone (25-mL). NaOMe (2 equiv.) was added, warmed to 50° C., and was vigorously stirred for 4 h. The reaction mixture was cooled to room temperature, quenched by the addition of NaHSO$_4$ (10 mL, 10% by weight aqueous solution), and concentrated in vacuo. The reaction mixture was diluted with CH$_2$Cl$_2$ (10 mL), and the phases were then separated and the aqueous phase was extracted with CH$_2$Cl$_2$ (3×20 mL). The combined organic fractions were then dried over MgSO$_4$, filtered and concentrated in vacuo to afford a crude residue, which was purified using flash column chromatography (15% EtOAc in hexanes) to afford a pure compound.

The following compounds were produced using general procedure B:

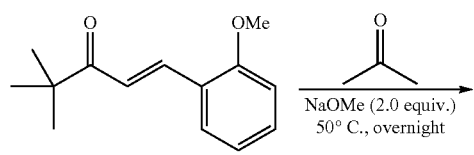

Chemical Formula: C$_{14}$H$_{18}$O$_2$
Molecular Weight: 218.30
S11

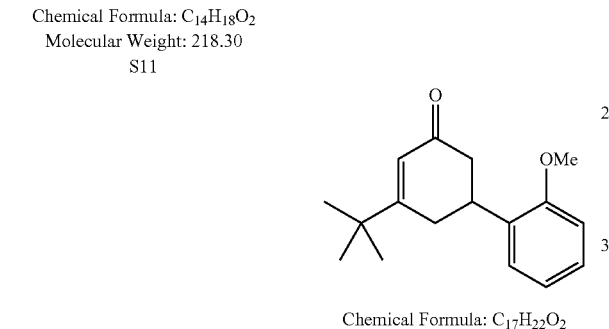

Chemical Formula: C$_{17}$H$_{22}$O$_2$
Molecular Weight: 258.36
S22

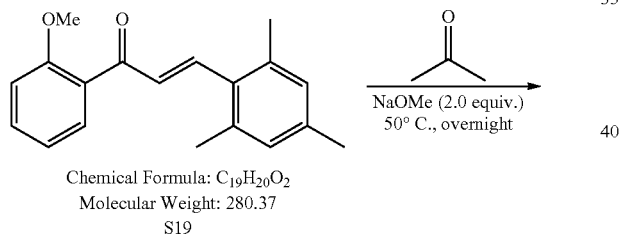

Chemical Formula: C$_{19}$H$_{20}$O$_2$
Molecular Weight: 280.37
S19

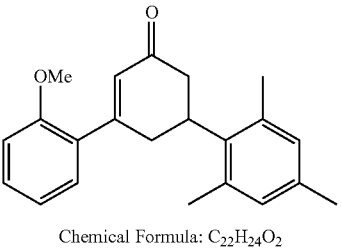

Chemical Formula: C$_{22}$H$_{24}$O$_2$
Molecular Weight: 320.43
S23

General Procedure C

Synthesis of Phenols from Chalcones

Phenols were synthesized using a modified procedure reported by Zhang et al: Qian, J.; Yi, W.; Huang, X.; Miao, Y.; Zhang, J.; Cai, C.; Zhang W. Org. Lett. (2015), 17, 1090-1093. A flame-dried 100-mL high-pressure vessel, equipped with a Teflon coated stir bar was charged with the appropriate chalcone (1 equiv.), ethyl 2-fluoroacetoacetate (1.2 equiv.) cesium carbonate (2 equiv.), and degassed CH$_3$CN (0.25 M with respect to the chalcone). The reaction vessel was capped with a Teflon screw cap, and heated to 130° C. for 3 h. The reaction mixture was then cooled to room temperature, quickly depressurized, capped with a Teflon screw cap and heated to 130° C. for 3 h. Then, the reaction mixture was cooled to room temperature, quenched by the addition of H$_2$O (100-mL) and diluted with EtOAc (50 mL). The phases were then separated and the organic phase was extracted with NaHSO$_4$ (10% by weight aqueous solution, 3×20 mL). The organic fractions were then dried over MgSO$_4$, filtered and concentrated in vacuo to afford a crude residue, which was purified using flash column chromatography (15% EtOAc in hexanes) to afford a pure compound.

The following compounds were also produced using general procedure C:

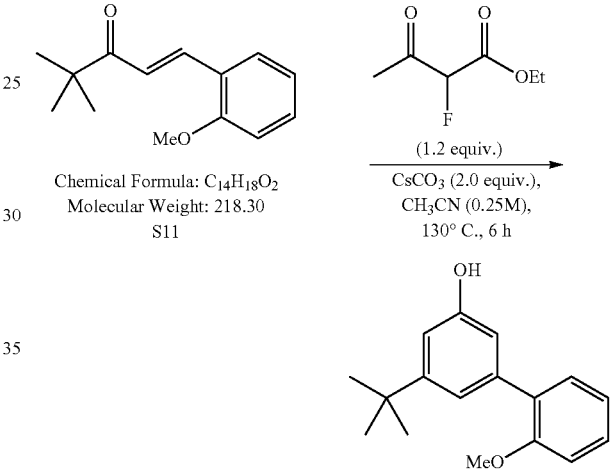

Chemical Formula: C$_{14}$H$_{18}$O$_2$
Molecular Weight: 218.30
S11

Chemical Formula: C$_{17}$H$_{20}$O$_2$
Molecular Weight: 256.35
33

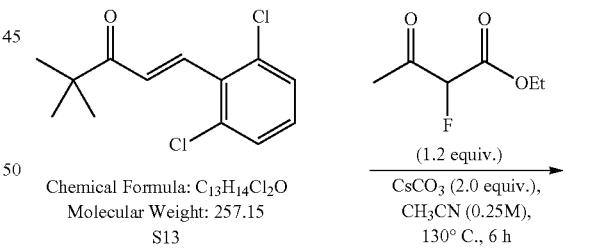

Chemical Formula: C$_{13}$H$_{14}$Cl$_2$O
Molecular Weight: 257.15
S13

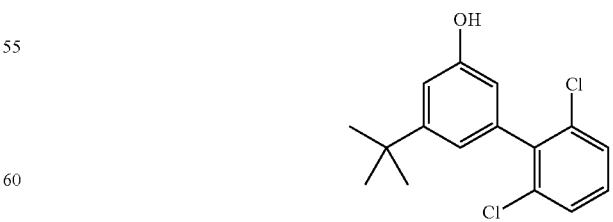

Chemical Formula: C$_{16}$H$_{16}$Cl$_2$O
Molecular Weight: 295.20
19

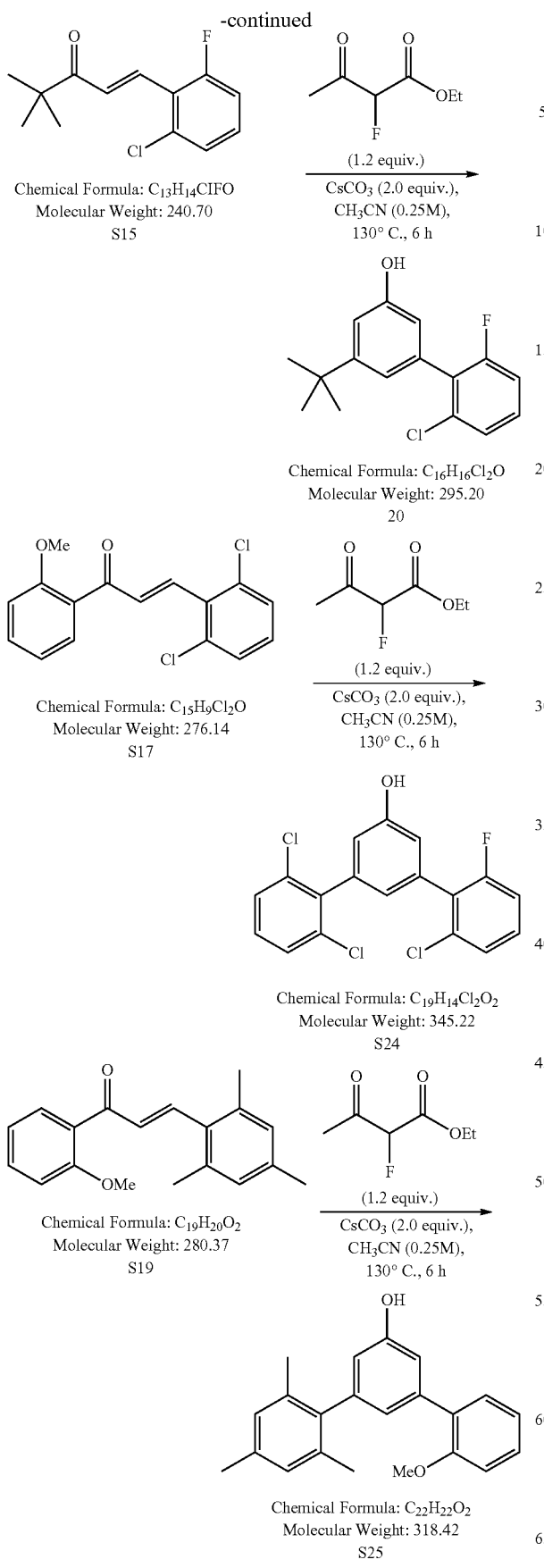

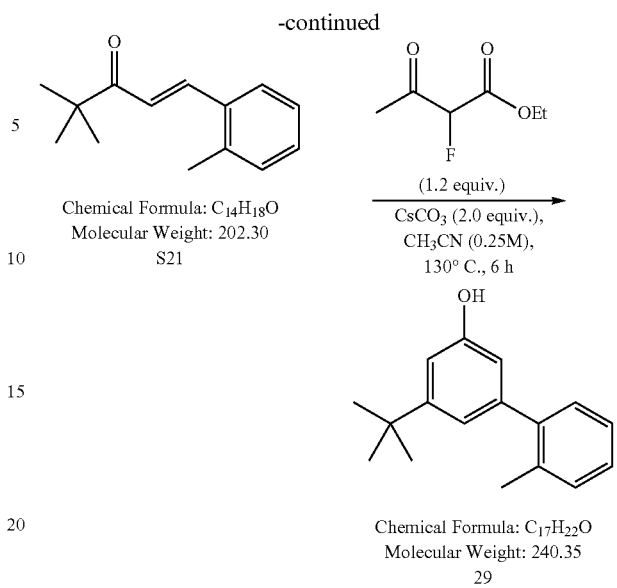

General Procedure D

Synthesis of Phenols from 3,5-Di-Substituted Cyclohexenone

Phenols were Synthesized Using a Modified Procedure Reported by Stahl et al.[1]

A flame-dried 25-mL Radley tube, equipped with a Teflon coated stir bar, was charged with the appropriate cyclohexenone (1 equiv.), $Pd(TFA)_2$ (6 mol %), p-TsOH (24 mol %), 2-(N,N-dimethylamino)pyridine (6 mol %), DMSO (1 mL). The reaction vessel was capped, pressurized with $O_2$ (1 atm) and heated to 80° C. whilst stirring for 24 h. The reaction mixture was depressurized, cooled to room temperature and diluted with distilled $H_2O$ (20 mL) and $CH_2Cl_2$ (30 mL). The phases were then separated and the aqueous phase was extracted with $CH_2Cl_2$ (3×20 mL). The combined organic phases were then dried over $MgSO_4$, filtered and concentrated in vacuo to afford a crude residue, which was purified using flash column chromatography (15% EtOAc in hexanes) to afford a pure compound.

[1] Izawa, Y.; Pun, D.; Stahl, S. S. *Science.* (2011), 333, 201-213

33 can also be synthesized using general procedure D using cyclohexanone S22 (1.0 g, 3.87 mmol, 1 equiv), $Pd(TFA)_2$ (7.7 mg, 0.23 mmol, 6 mol %), p-TsOH (160.0 mg, 0.93 mmol, 24 mol %), 2-(N,N-dimethylamino)pyridine (2.8 mg, 0.23 mmol, 6 mol %) to afford phenol 33 in 90% isolated yield.

S25 can also be synthesized using general procedure D using cyclohexanone S23 (1.0 g, 3.12 mmol, 1 equiv), $Pd(TFA)_2$ (6.2 mg, 0.19 mmol, 6 mol %), p-TsOH (129 mg, 0.75 mmol, 24 mol %), 2-(N,N-dimethylamino)pyridine (2.3 mg, 0.19 mmol, 6 mol %) to afford phenol S25 in 91% isolated yield.

Optimization of Catalytic Aerobic Phenol and Amine Coupling (Table 1)

Amounts Used for Reach Reagent was Summarized in Table S1

A flame-dried, 25-mL Radley tube equipped with a Teflon-coated stir bar and a rubber septum was charged with 3,5-di-tert-butylphenol 1 (1.0 mmol, 1.0 equiv.) and dry, degassed $CH_2Cl_2$ (8 mL). In a separate, flame-dried 5 mL microwave vial, [Cu(CH$_3$CN)$_4$](PF$_6$) (see Table S1) and N,N'-di-tert-butylethylenediamine (see Table S1) were dissolved in dry and degassed CH$_2$Cl$_2$ (2.0 mL) to afford a homogeneous pink solution. This solution was then added to the Radley tube via syringe to afford a final volume of 10 mL and a phenol concentration of 0.1 M. The rubber septum was then rapidly removed and replaced with a Radley cap, which was connected to a tank of O$_2$ and pressurized to 1 atm. Under a constant pressure of O$_2$ (1 atm), the reaction was vented 3 times for 10 s to remove N$_2$. The reaction mixture was then stirred at room temperature for 4 h, depressurized by opening to the atmosphere and benzylamine (see Table S1) was added via a syringe. The reaction vessel was capped with Radley cap, which was connected to a tank of O$_2$, pressurized to 1 atm and stirred for 1-2 h (see Table S1). The reaction was depressurized, quenched by the addition of NaHSO$_4$ (20 mL, 10% by weight aqueous solution), and hexamethylbenzene (0.15 equiv.) was added as an NMR standard was added. The phases were then separated and the aqueous phase was extracted with CH$_2$Cl$_2$ (3×20 mL). The combined organic fractions were then dried over MgSO$_4$, filtered and concentrated in vacuo to afford a red residue which was analyzed directly by $^1$H-NMR.

pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of O$_2$ and pressurized to 1 atm. Under a constant O$_2$ pressure (1 atm), the reaction was vented 3 times for 10 s to eliminate N$_2$. The reaction mixture was then stirred at room temperature for 4 h, depressurized by opening to the atmosphere, and the amine (2 mmol, 2.0 equiv.) was added via a syringe. The reaction mixture was pressurized with O$_2$ (1 atm), stirred at room temperature for 2 h, and then depressurized by opening to the atmosphere. The reaction mixture was then quenched by the addition of NaHSO$_4$ (20 mL, 10% by weight aqueous solution), the phases were separated, and the aqueous phase was extracted with CH$_2$Cl$_2$ (3×20 mL). The combined organic fractions were then dried over MgSO$_4$, filtered and concentrated in vacuo to afford a residue which was analyzed directly by $^1$H-NMR. The crude reaction mixture was then purified using a Biotage Isolera™ One (10% EtOAc in hexanes) to afford the benzoxazole product.

The following compounds were produced using general procedure E:

TABLE S1

Amounts and Reagents used for Table 1

| Entry 1 | CuPF$_6$ | DBED | BnNH$_2$ | Time (h) | Yield of 3 (%)$^a$ |
|---|---|---|---|---|---|
| 1 | 14.9 mg (4 mol %) | 10.78 μL (5 mol %) | 131.1 μL (1.2 equiv) | 1 | 40 (123.0 mg) |
| 2 | 14.9 mg (4 mol %) | 10.78 μL (5 mol %) | 131.1 μL (1.2 equiv) | 2 | 45 (138.3 mg) |
| 3 | 14.9 mg (4 mol %) | 21.56 μL (10 mol %) | 131.1 μL (1.2 equiv) | 2 | 76 (233.6 mg) |
| 4 | 29.8 mg (8 mol %) | 21.56 μL (10 mol %) | 131.1 μL (1.2 equiv) | 2 | 81 (249.0 mg) |
| 5 | 55.9 mg (15 mol %) | 43.12 μL (20 mol %) | 131.1 μL (1.2 equiv) | 2 | 71 (218.3 mg) |
| 6 | 29.8 mg (8 mol %) | 32.3 μL (15 mol %) | 218.4 μL (2.0 equiv) | 2 | 95 (292.0 mg) |
| 7$^b$ | (8 mol %) 745.7 mg | 809.0 μL (15 mol %) | 5.46 mL (2.0 equiv) | 2 | 93$^c$ (7.15 g) |

$^a$Product yields are determined by $^1$H NMR using hexamethylbenzene as internal standard, and calculated based on phenol (1.0 mmol);
$^b$Used 25 mmol (5.16 g) of phenol. Was isolated yields are reported;
$^c$Was isolated yield Scope of Primary Amines:

General Procedure E (Benzoxazoles)

A flame-dried, 25-mL Radley tube, equipped with a Teflon-coated stir bar and a rubber septum, was charged with phenol 1 (1.0 mmol, 1.0 equiv.). The reaction vessel was then purged with a steady stream of N$_2$ for 2 min prior to the addition of dry and degassed CH$_2$Cl$_2$ (8.0 mL). A separate, flame-dried test tube (16×125-mL) was charged with [Cu(CH$_3$CN)$_4$](PF$_6$) (29.8 mg, 0.08 mmol, 0.08 equiv.), N,N'-di-tert-butylethelenediamine (25.8 mg, 32.3 μL, 0.15 mmol, 0.15 equiv.), and CH$_2$Cl$_2$ (2.0 mL) to afford a homogeneous,

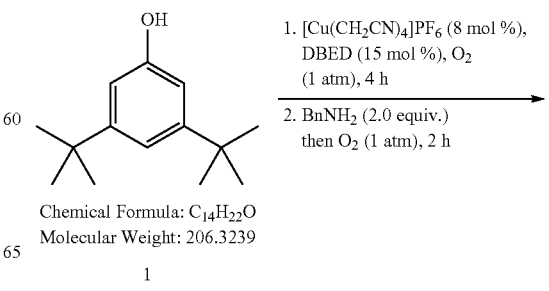

Chemical Formula: C$_{14}$H$_{22}$O
Molecular Weight: 206.3239

1

FIG. 17: Entry 1
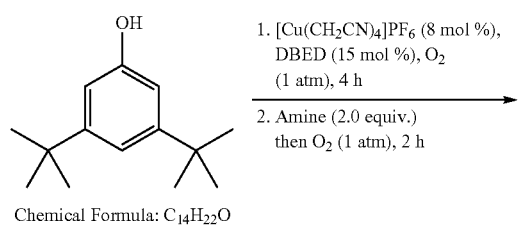
FIG. 17: Entry 2
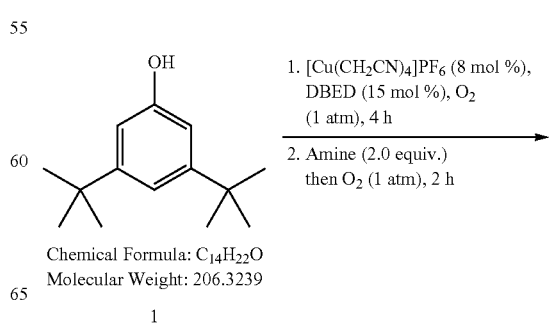
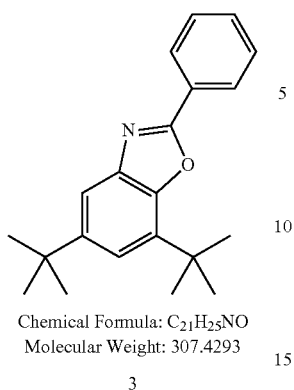
Chemical Formula: C₂₁H₂₅NO
Molecular Weight: 307.4293
3
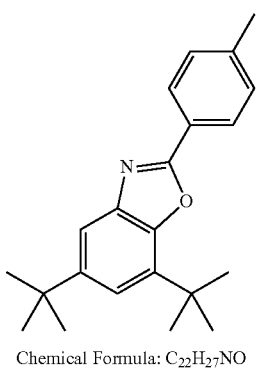
Chemical Formula: C₂₂H₂₇NO
Molecular Weight: 321.46
S26
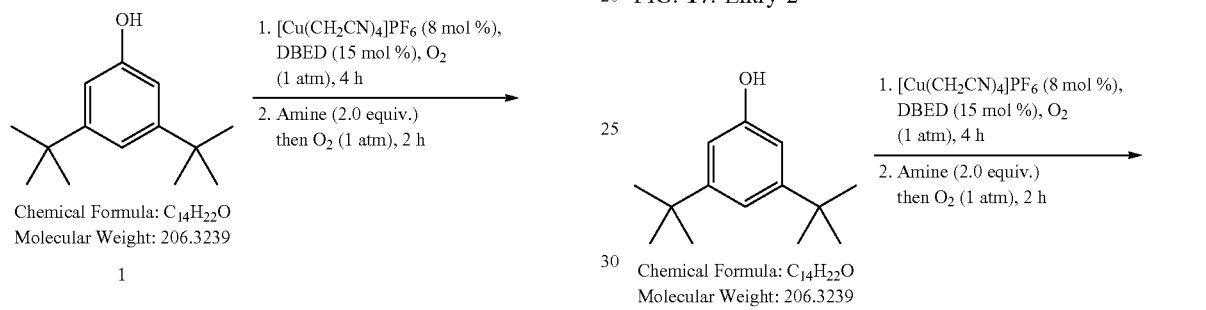
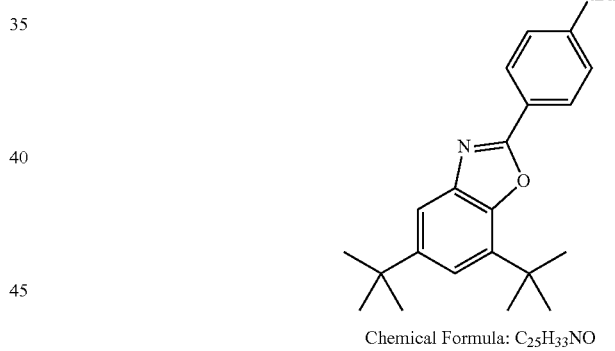
Chemical Formula: C₂₅H₃₃NO
Molecular Weight: 363.5356
S27
FIG. 17: Entry 3

-continued

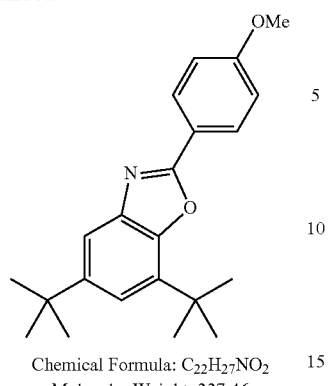

Chemical Formula: C$_{22}$H$_{27}$NO$_2$
Molecular Weight: 337.46

S28

FIG. 17: Entry 4

-continued

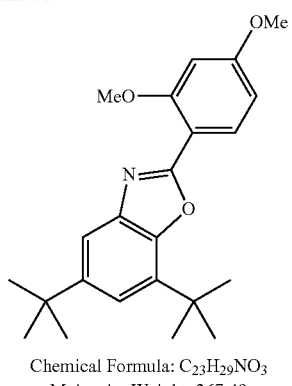

Chemical Formula: C$_{23}$H$_{29}$NO$_3$
Molecular Weight: 367.49

S30

FIG. 17: Entry 6

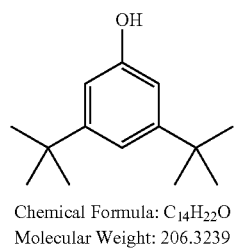

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

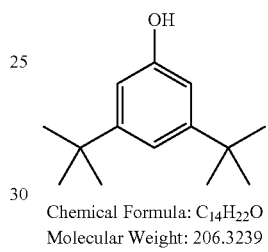

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

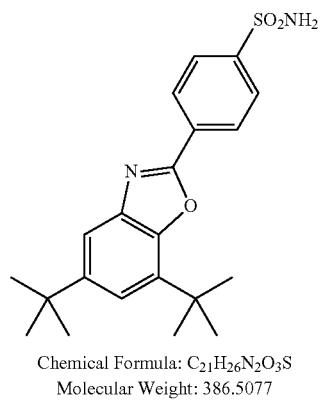

Chemical Formula: C$_{21}$H$_{26}$N$_2$O$_3$S
Molecular Weight: 386.5077

S29

FIG. 17: Entry 5

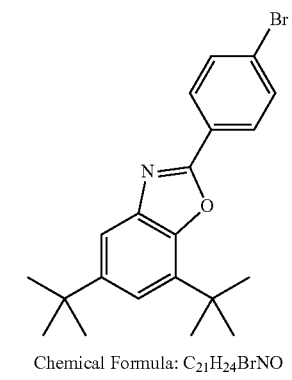

Chemical Formula: C$_{21}$H$_{24}$BrNO
Molecular Weight: 386.3254

S31

FIG. 17: Entry 7

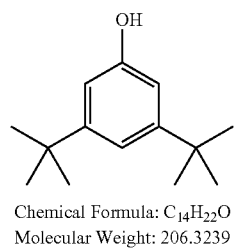

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

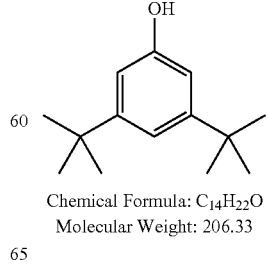

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h -continued

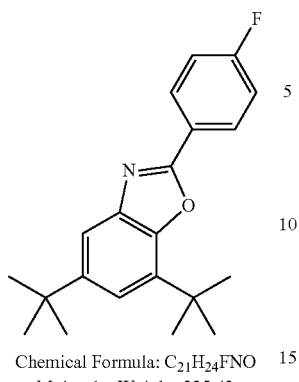

Chemical Formula: C$_{21}$H$_{24}$FNO
Molecular Weight: 325.43

S32

FIG. 17: Entry 8

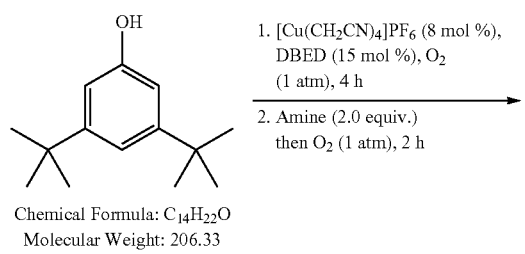

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

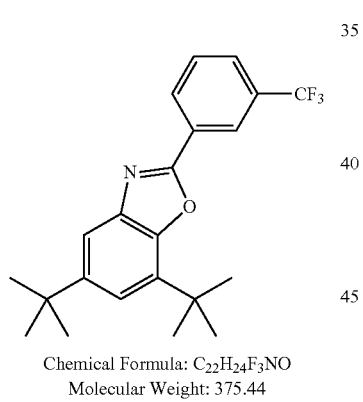

Chemical Formula: C$_{22}$H$_{24}$F$_3$NO
Molecular Weight: 375.44

S33

FIG. 17: Entry 9

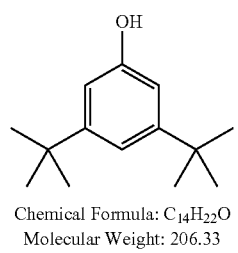

Chemical Formula: C$_{14}$H$_{22}$O
Molecular Weight: 206.33

-continued

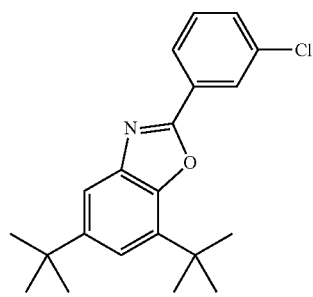

Chemical Formula: C$_{21}$H$_{24}$ClNO
Molecular Weight: 341.88

S34

FIG. 17: Entry 10

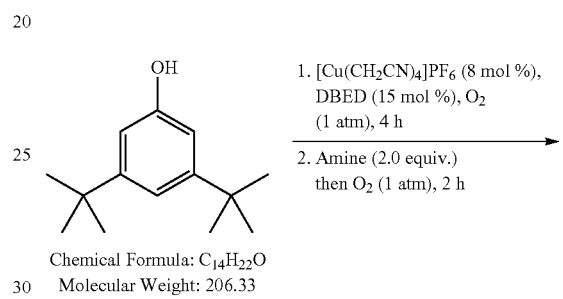

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

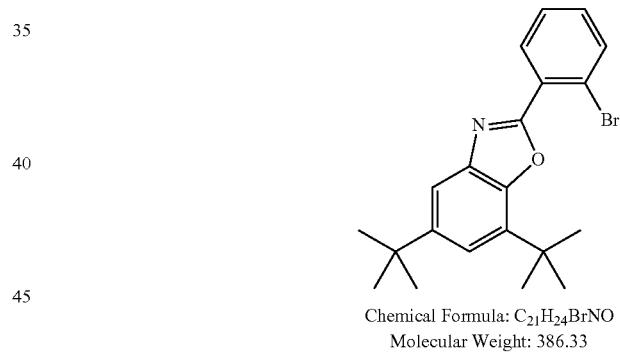

Chemical Formula: C$_{21}$H$_{24}$BrNO
Molecular Weight: 386.33

S35

FIG. 17: Entry 11

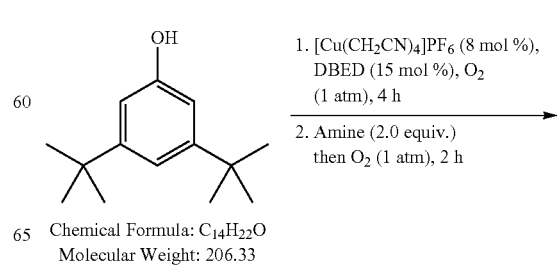

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h -continued

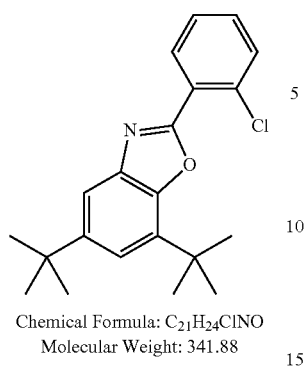

Chemical Formula: C$_{21}$H$_{24}$ClNO
Molecular Weight: 341.88

FIG. 17: Entry 12

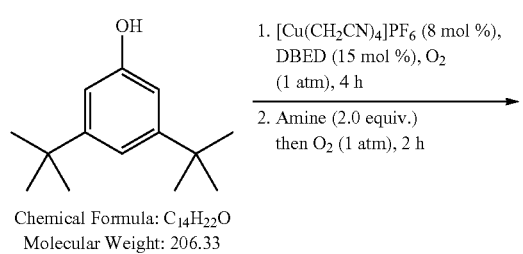

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h FIG. 17: Entry 13

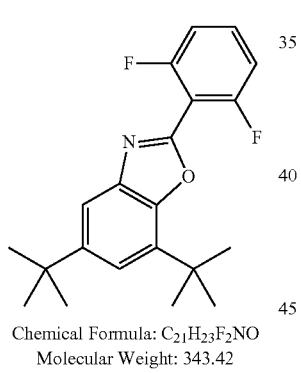

Chemical Formula: C$_{21}$H$_{23}$F$_2$NO
Molecular Weight: 343.42

-continued

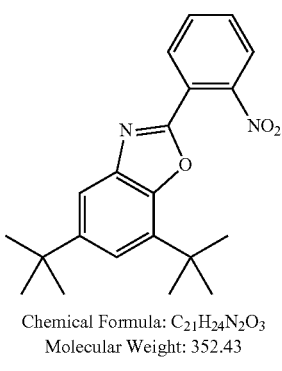

Chemical Formula: C$_{21}$H$_{24}$N$_2$O$_3$
Molecular Weight: 352.43

FIG. 17: Entry 14

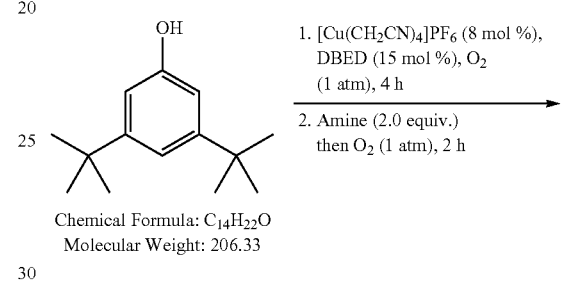

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

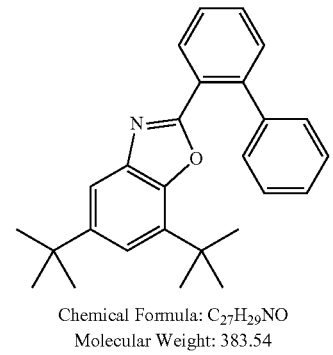

Chemical Formula: C$_{27}$H$_{29}$NO
Molecular Weight: 383.54

FIG. 17: Entry 15

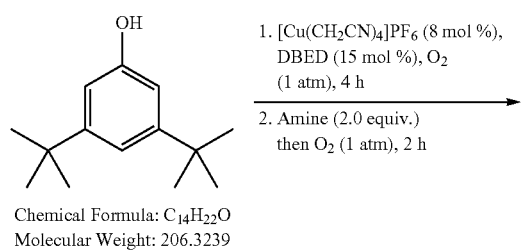

Chemical Formula: C$_{14}$H$_{22}$O
Molecular Weight: 206.3239

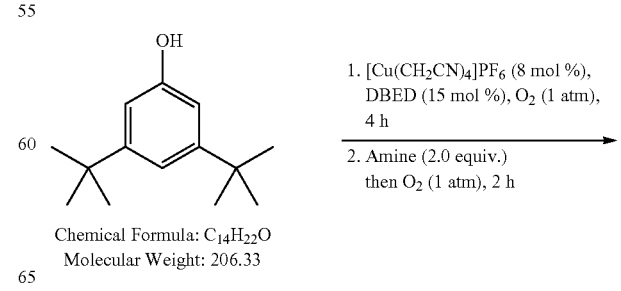

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h -continued

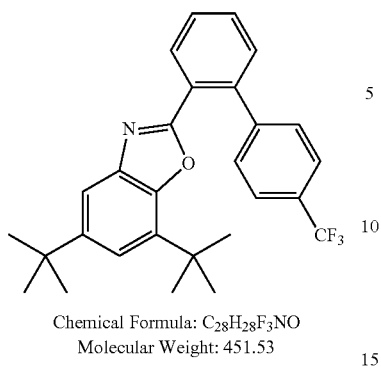

Chemical Formula: C$_{28}$H$_{28}$F$_3$NO
Molecular Weight: 451.53

FIG. 17: Entry 16

-continued

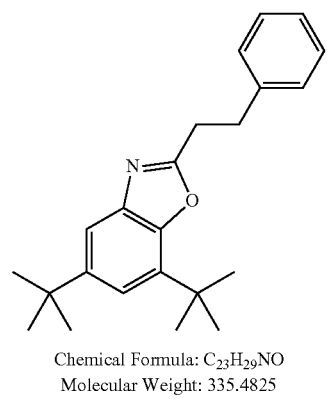

Chemical Formula: C$_{23}$H$_{29}$NO
Molecular Weight: 335.4825

FIG. 17: Entry 18

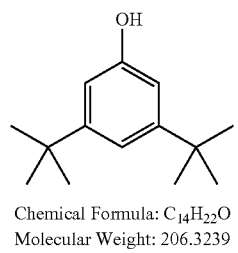

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

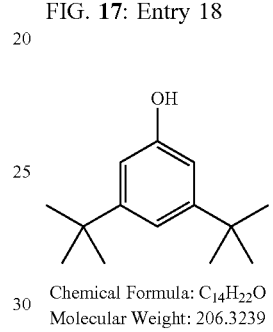

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

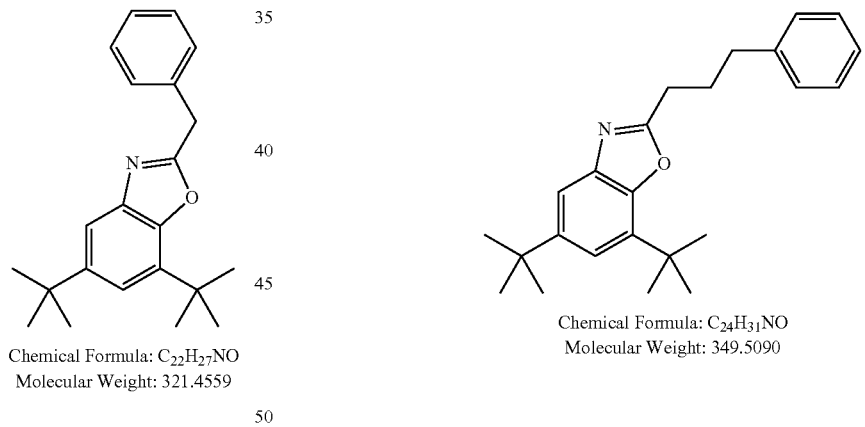

Chemical Formula: C$_{22}$H$_{27}$NO
Molecular Weight: 321.4559

Chemical Formula: C$_{24}$H$_{31}$NO
Molecular Weight: 349.5090

FIG. 17: Entry 17

FIG. 17: Entry 19

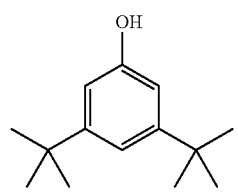

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

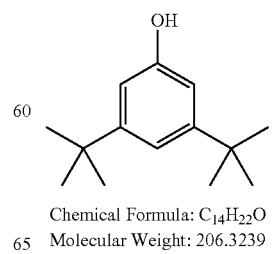

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h -continued

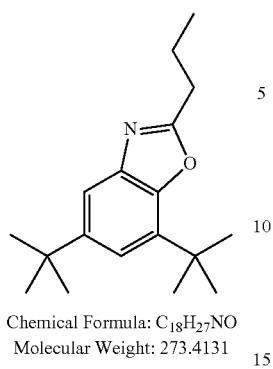

Chemical Formula: C$_{18}$H$_{27}$NO
Molecular Weight: 273.4131

FIG. 17: Entry 20

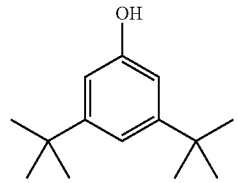

Chemical Formula: C$_{14}$H$_{22}$O
Molecular Weight: 206.3239

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

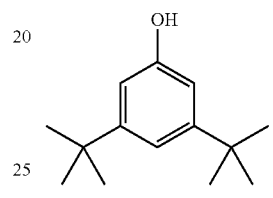

Chemical Formula: C$_{16}$H$_{23}$NO$_2$
Molecular Weight: 261.3593

FIG. 17: Entry 21

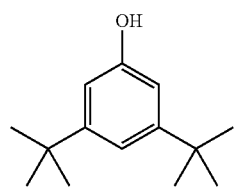

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h -continued

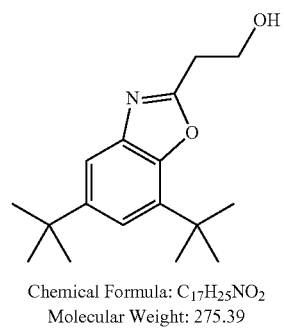

Chemical Formula: C$_{17}$H$_{25}$NO$_2$
Molecular Weight: 275.39

FIG. 17: Entry 22

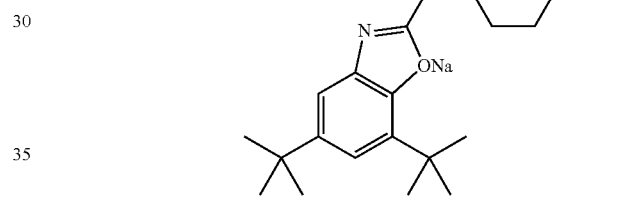

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h Chemical Formula: C$_{20}$H$_{31}$NNaO$_2$
Exact Mass: 340.23
Molecular Weight: 340.46

FIG. 17: Entry 23

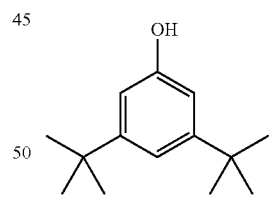

Chemical Formula: C$_{14}$H$_{22}$O
Molecular Weight: 206.33

1. [Cu(CH$_2$CN)$_4$]PF$_6$ (8 mol %), DBED (15 mol %), O$_2$ (1 atm), 4 h
2. Amine (2.0 equiv.) then O$_2$ (1 atm), 2 h

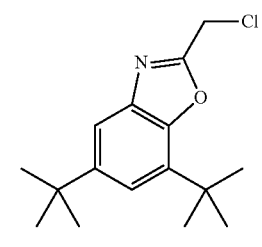

Chemical Formula: C$_{16}$H$_{22}$ClNO
Molecular Weight: 279.81

FIG. 17: Entry 24

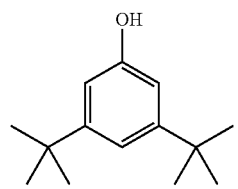

Chemical Formula: C₁₄H₂₂O
Molecular Weight: 206.33

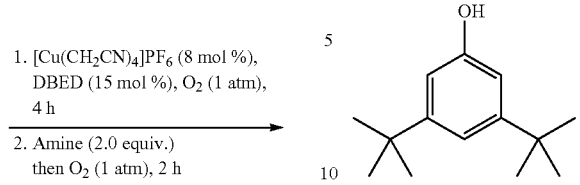

1. [Cu(CH₂CN)₄]PF₆ (8 mol %), DBED (15 mol %), O₂ (1 atm), 4 h
2. Amine (2.0 equiv.) then O₂ (1 atm), 2 h

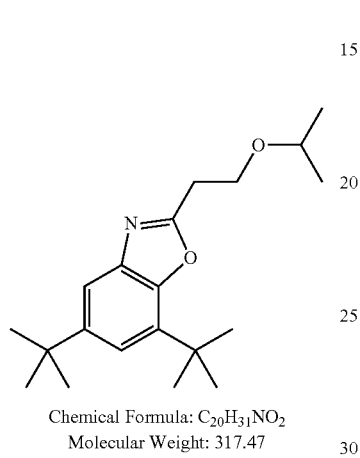

Chemical Formula: C₂₀H₃₁NO₂
Molecular Weight: 317.47

FIG. 17: Entry 25

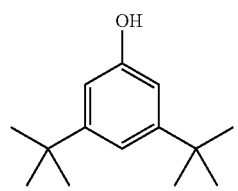

Chemical Formula: C₁₄H₂₂O
Molecular Weight: 206.33

1. [Cu(CH₂CN)₄]PF₆ (8 mol %), DBED (15 mol %), O₂ (1 atm), 4 h
2. Amine (2.0 equiv.) then O₂ (1 atm), 2 h

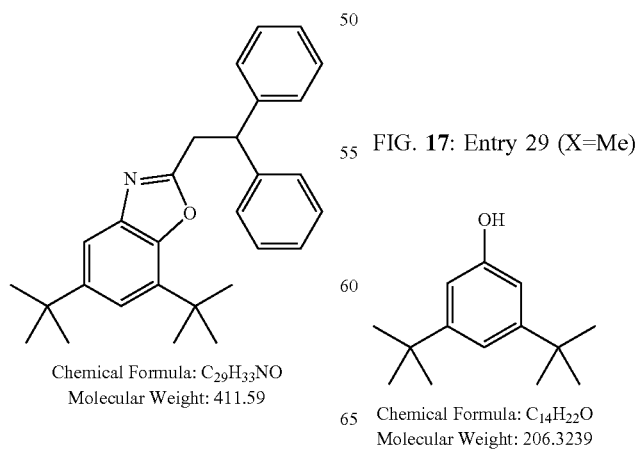

Chemical Formula: C₂₉H₃₃NO
Molecular Weight: 411.59

FIG. 17: Entry 28

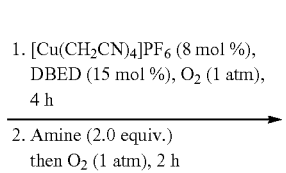

Chemical Formula: C₁₄H₂₂O
Molecular Weight: 206.33

1. [Cu(CH₂CN)₄]PF₆ (8 mol %), DBED (15 mol %), O₂ (1 atm), 4 h
2. Amine (2.0 equiv.) then O₂ (1 atm), 2 h

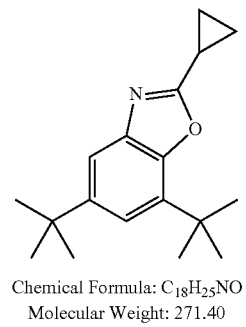

Chemical Formula: C₁₈H₂₅NO
Molecular Weight: 271.40

FIG. 17: Entry 29 (X=H)

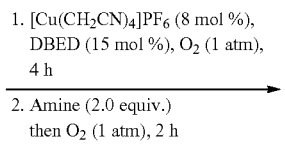

Chemical Formula: C₁₄H₂₂O
Molecular Weight: 206.3239

1. [Cu(CH₂CN)₄]PF₆ (8 mol %), DBED (15 mol %), O₂ (1 atm), 4 h
2. Amine (2.0 equiv.) then O₂ (1 atm), 2 h

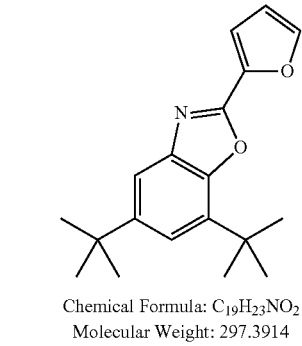

Chemical Formula: C₁₉H₂₃NO₂
Molecular Weight: 297.3914

FIG. 17: Entry 29 (X=Me)

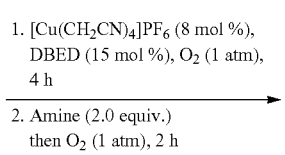

Chemical Formula: C₁₄H₂₂O
Molecular Weight: 206.3239

1. [Cu(CH₂CN)₄]PF₆ (8 mol %), DBED (15 mol %), O₂ (1 atm), 4 h
2. Amine (2.0 equiv.) then O₂ (1 atm), 2 h 75
-continued

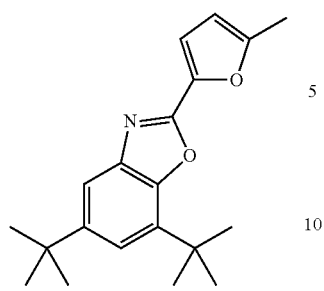

Chemical Formula: C₂₀H₂₅NO₂
Molecular Weight: 311.43

FIG. 17: Entry 30

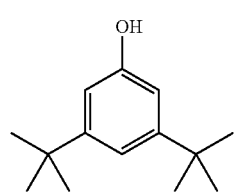

Chemical Formula: C₁₄H₂₂O
Molecular Weight: 206.3239

1. [Cu(CH₂CN)₄]PF₆ (8 mol %),
   DBED (15 mol %), O₂ (1 atm),
   4 h
2. Amine (2.0 equiv.)
   then O₂ (1 atm), 2 h

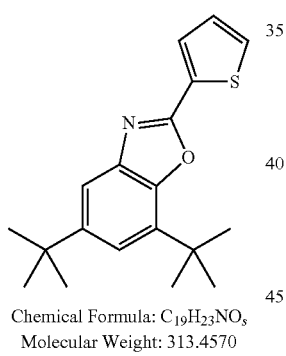

Chemical Formula: C₁₉H₂₃NO₅
Molecular Weight: 313.4570

FIG. 17: Entry 31

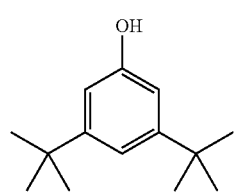

Chemical Formula: C₁₄H₂₂O
Molecular Weight: 206.3239

1. [Cu(CH₂CN)₄]PF₆ (8 mol%),
   DBED (15 mol%), O₂ (1 atm),
   4 h
2. Amine (2.0 equiv.)
   then O₂ (1 atm), 2 h 76
-continued

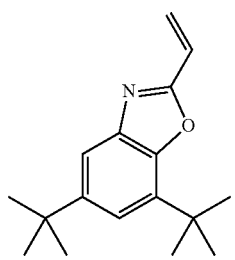

Chemical Formula: C₁₇H₂₃NO
Molecular Weight: 257.3706

FIG. 17: Entry 32

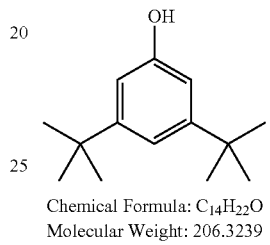

Chemical Formula: C₁₄H₂₂O
Molecular Weight: 206.3239

1. [Cu(CH₂CN)₄]PF₆ (8 mol%),
   DBED (15 mol%), O₂ (1 atm),
   4 h
2. Amine (2.0 equiv.)
   then O₂ (1 atm), 2 h

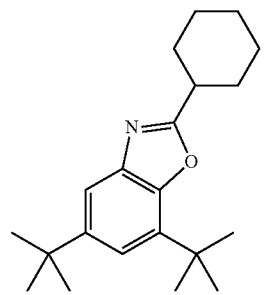

Chemical Formula: C₂₁H₃₁NO
Molecular Weight: 313.4769

FIG. 17: Entry 33

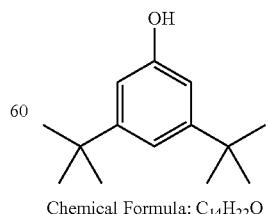

Chemical Formula: C₁₄H₂₂O
Molecular Weight: 206.3239

1. [Cu(CH₂CN)₄]PF₆ (8 mol%),
   DBED (15 mol%), O₂ (1 atm),
   4 h
2. Amine (2.0 equiv.)
   then O₂ (1 atm), 2 h -continued

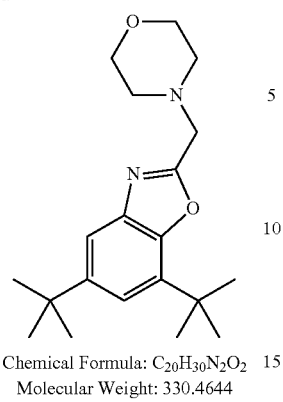

Chemical Formula: C₂₀H₃₀N₂O₂
Molecular Weight: 330.4644

FIG. 17: Entry 34

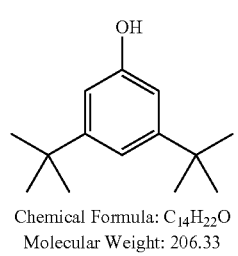

Chemical Formula: C₁₄H₂₂O
Molecular Weight: 206.33

1. [Cu(CH₂CN)₄]PF₆ (8 mol%), DBED (15 mol%), O₂ (1 atm), 4 h
2. Amine (2.0 equiv.) then O₂ (1 atm), 2 h
→

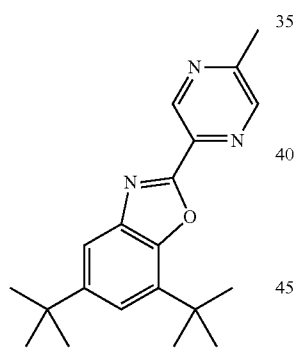

Chemical Formula: C₂₀H₂₅N₃O
Molecular Weight: 323.44

FIG. 17: Entry 35

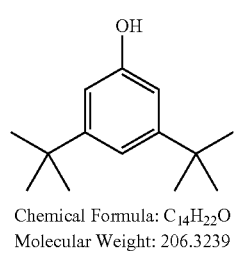

Chemical Formula: C₁₄H₂₂O
Molecular Weight: 206.3239

1. [Cu(CH₂CN)₄]PF₆ (8 mol%), DBED (15 mol%), O₂ (1 atm), 4 h
2. Amine (2.0 equiv.) then O₂ (1 atm), 2 h
→

-continued

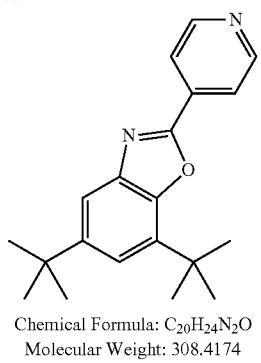

Chemical Formula: C₂₀H₂₄N₂O
Molecular Weight: 308.4174

FIG. 17: Entry 36

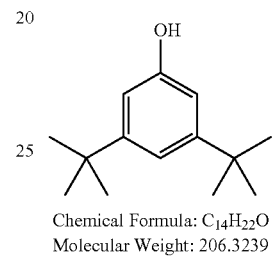

Chemical Formula: C₁₄H₂₂O
Molecular Weight: 206.3239

1. [Cu(CH₂CN)₄]PF₆ (8 mol%), DBED (15 mol%), O₂ (1 atm), 4 h
2. Amine (2.0 equiv.) then O₂ (1 atm), 2 h
→

Chemical Formula: C₂₀H₂₄N₂O
Molecular Weight: 308.4174

FIG. 17: Entry 37

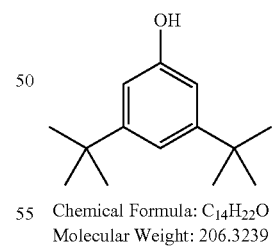

Chemical Formula: C₁₄H₂₂O
Molecular Weight: 206.3239

1. [Cu(CH₂CN)₄]PF₆ (8 mol%), DBED (15 mol%), O₂ (1 atm), 4 h
2. Amine (2.0 equiv.) then O₂ (1 atm), 2 h
→

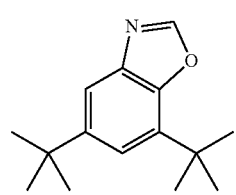

Chemical Formula: C₁₅H₂₁NO
Molecular Weight: 231.3333

General Procedure F (Benzoxazinones)

A flame-dried, 25-mL Radley tube, equipped with a Teflon-coated stir bar and a rubber septum, was charged with phenol (1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with [Cu(CH$_3$CN)$_4$](PF$_6$) (29.8 mg, 0.08 mmol, 0.08 equiv.), N,N'-di-tert-butylethelenediamine (25.8 mg, 32.3 µL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, a solution of amino methyl ester (2 mmol, 2.0 equiv.) in MeOH (5 mL) was added to the reaction mixture via a syringe, heated to 50° C., and stirred for 4 h. The reaction mixture was quenched by the addition of NaHSO$_4$ (20 mL, 10% by weight aqueous solution), phases were separated, and the aqueous phase was extracted with $CH_2Cl_2$ (3×20 mL). The combined organic fractions were then dried over MgSO$_4$, filtered and concentrated in vacuo to afford a residue which was analyzed directly by $^1$H-NMR. The crude reaction mixture was then purified using a Biotage Isolera™ One (10% EtOAc in hexanes) to afford the benzoxazinone product.

The following compounds were produced using general procedure F:

FIG. 18: Entry 1

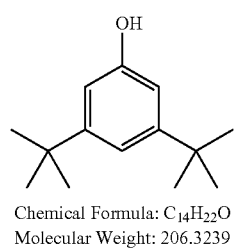

Chemical Formula: C$_{14}$H$_{22}$O
Molecular Weight: 206.3239

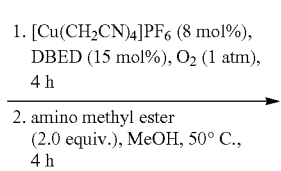

1. [Cu(CH$_2$CN)$_4$]PF$_6$ (8 mol%), DBED (15 mol%), O$_2$ (1 atm), 4 h
2. amino methyl ester (2.0 equiv.), MeOH, 50° C., 4 h

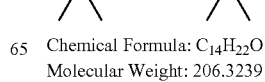

Chemical Formula: C$_{17}$H$_{23}$NO$_2$
Molecular Weight: 273.3700

FIG. 18: Entry 2

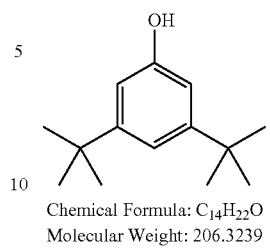

Chemical Formula: C$_{14}$H$_{22}$O
Molecular Weight: 206.3239

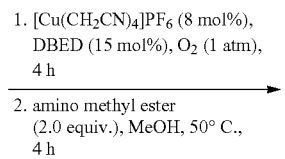

1. [Cu(CH$_2$CN)$_4$]PF$_6$ (8 mol%), DBED (15 mol%), O$_2$ (1 atm), 4 h
2. amino methyl ester (2.0 equiv.), MeOH, 50° C., 4 h

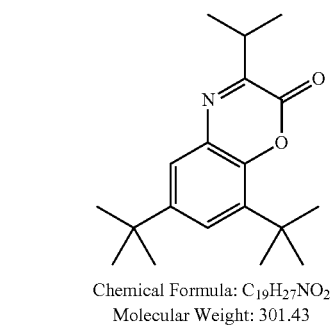

Chemical Formula: C$_{19}$H$_{27}$NO$_2$
Molecular Weight: 301.43

FIG. 18: Entry 3

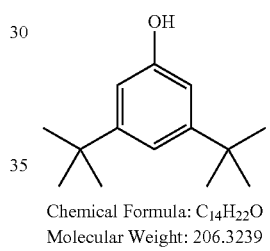

Chemical Formula: C$_{14}$H$_{22}$O
Molecular Weight: 206.3239

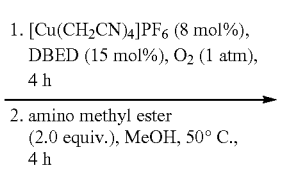

1. [Cu(CH$_2$CN)$_4$]PF$_6$ (8 mol%), DBED (15 mol%), O$_2$ (1 atm), 4 h
2. amino methyl ester (2.0 equiv.), MeOH, 50° C., 4 h

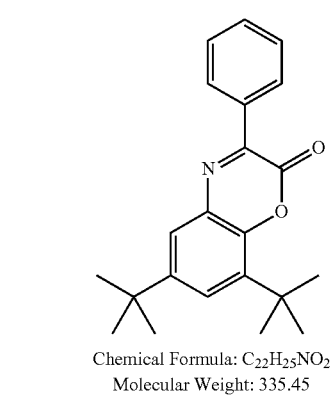

Chemical Formula: C$_{22}$H$_{25}$NO$_2$
Molecular Weight: 335.45

FIG. 18: Entry 4

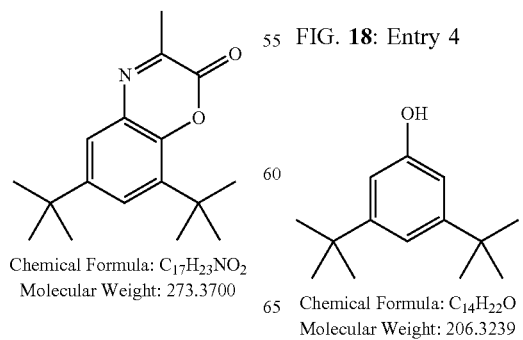

Chemical Formula: C$_{14}$H$_{22}$O
Molecular Weight: 206.3239

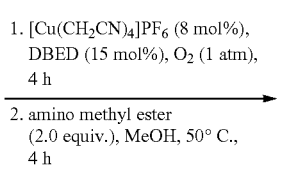

1. [Cu(CH$_2$CN)$_4$]PF$_6$ (8 mol%), DBED (15 mol%), O$_2$ (1 atm), 4 h
2. amino methyl ester (2.0 equiv.), MeOH, 50° C., 4 h -continued

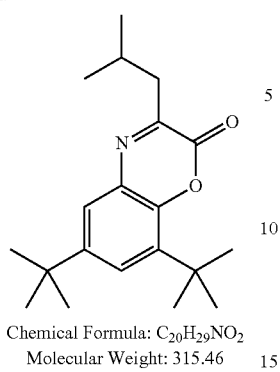

Chemical Formula: C20H29NO2
Molecular Weight: 315.46

-continued

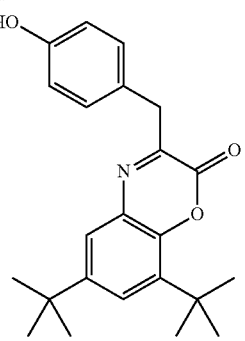

Chemical Formula: C23H27NO3
Molecular Weight: 365.4654

FIG. 18: Entry 5

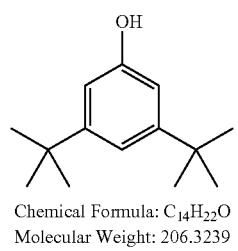

Chemical Formula: C14H22O
Molecular Weight: 206.3239

Figure 18:
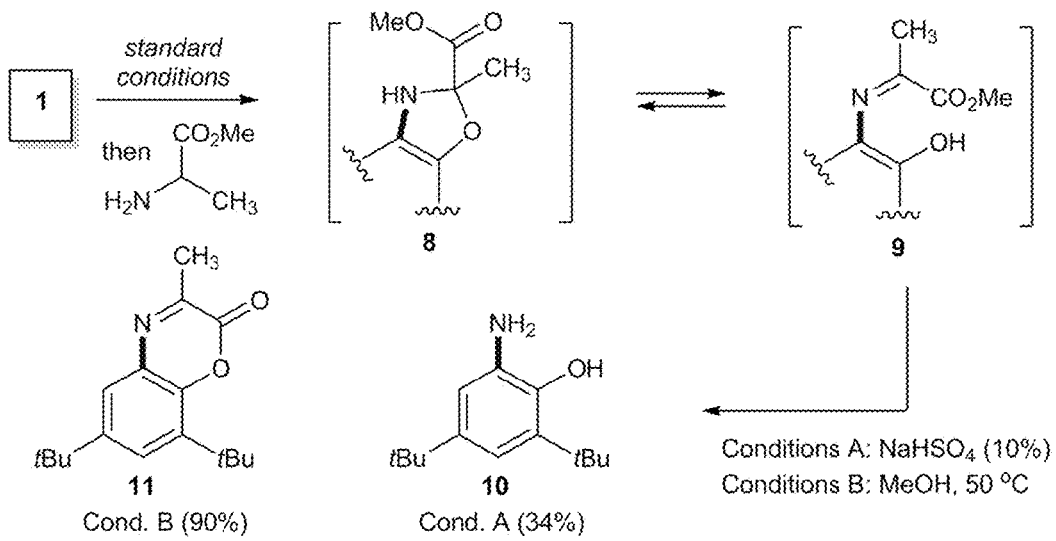
FIG. 18 summarizes the initial studies on the coupling of 1 and alanine methyl ester.

1. [Cu(CH2CN)4]PF6 (8 mol%), DBED (15 mol%), O2 (1 atm), 4 h
2. amino methyl ester (2.0 equiv.), MeOH, 50° C., 4 h FIG. 18: Entry 7

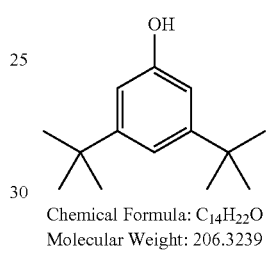

Chemical Formula: C14H22O
Molecular Weight: 206.3239

1. [Cu(CH2CN)4]PF6 (8 mol%), DBED (15 mol%), O2 (1 atm), 4 h
2. amino methyl ester (2.0 equiv.), MeOH, 50° C., 4 h

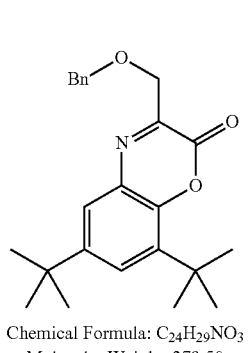

Chemical Formula: C24H29NO3
Molecular Weight: 379.50

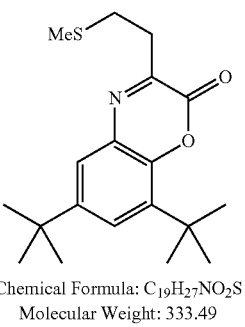

Chemical Formula: C19H27NO2S
Molecular Weight: 333.49

FIG. 18: Entry 6

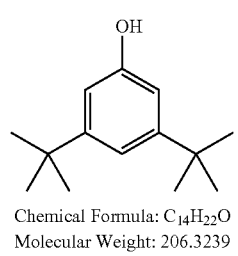

Chemical Formula: C14H22O
Molecular Weight: 206.3239

1. [Cu(CH2CN)4]PF6 (8 mol%), DBED (15 mol%), O2 (1 atm), 4 h
2. amino methyl ester (2.0 equiv.), MeOH, 50° C., 4 h FIG. 18: Entry 8

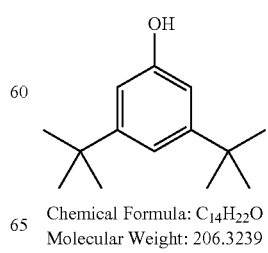

Chemical Formula: C14H22O
Molecular Weight: 206.3239

1. [Cu(CH2CN)4]PF6 (8 mol%), DBED (15 mol%), O2 (1 atm), 4 h
2. amino methyl ester (2.0 equiv.), MeOH, 50° C., 4 h -continued

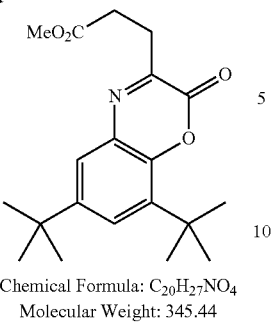

Chemical Formula: $C_{20}H_{27}NO_4$
Molecular Weight: 345.44

General Procedure G (Aminophenol)

A flame-dried, 25-mL Radley tube, equipped with a Teflon-coated stir bar and a rubber septum, was charged with 3,5-di-tert-butylphenol (206.3 mg, 1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with $[Cu(CH_3CN)_4](PF_6)$ (29.8 mg, 0.08 mmol, 0.08 equiv.), N,N'-di-tert-butylethelenediamine (25.8 mg, 32.3 µL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, amine (2.0 mmol, 2.0 equiv.) was added to the reaction mixture via a syringe and the reaction mixture was stirred for 4 h at 50° C. Then, the reaction mixture was cooled to 0° C., followed by the addition of $NaBH_4$ (95.0 mg g, 2.0 mmol, 2.0 equiv.) and MeOH (3 mL). The reaction mixture was warmed to room temperature and stirred for 2 h. Afterwards, the reaction mixture was quenched by the addition of $NaHSO_4$ (20 mL, 10% by weight aqueous solution), phases were separated, and the aqueous phase was extracted with $CH_2Cl_2$ (3×20 mL). The combined organic fractions were then dried over $MgSO_4$, filtered and concentrated in vacuo to afford a residue which was analyzed directly by $^1$H-NMR. The crude reaction mixture was then purified using a Biotage Isolera™ One (15% EtOAc in hexanes) to afford the N,O-fused acetal product in 78% was isolated yield.

The following compounds were produced using general procedure G:

FIG. 20: Entry 16

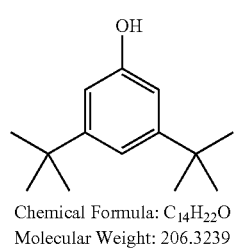

Chemical Formula: $C_{14}H_{22}O$
Molecular Weight: 206.3239

1. $[Cu(CH_2CN_4)]PF_6$ (8 mol%), DBED (15 mol%), $O_2$ (1 atm), rt, 4 h
2. cyclohexylamine (2.0 equiv.), 50° C., 4 h
3. $NaBH_4$ (2.0 equiv.), MeOH (3 mL), 0° C. - rt, 2 h

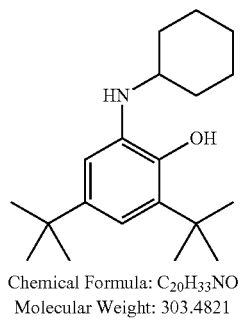

Chemical Formula: $C_{20}H_{33}NO$
Molecular Weight: 303.4821

FIG. 20: Entry 17

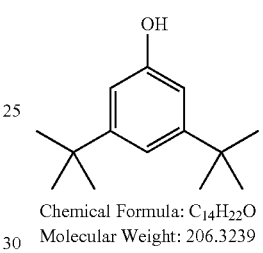

Chemical Formula: $C_{14}H_{22}O$
Molecular Weight: 206.3239

1. $[Cu(CH_2CN_4)]PF_6$ (8 mol%), DBED (15 mol%), $O_2$ (1 atm), rt, 4 h
2. isopropylamine (2.0 equiv.), 50° C., 4 h
3. $NaBH_4$ (2.0 equiv.), MeOH (3 mL), 0° C. - rt, 2 h

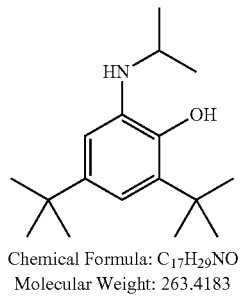

Chemical Formula: $C_{17}H_{29}NO$
Molecular Weight: 263.4183

Scope of Secondary Amine

General Procedure H (Fused N, O-Acetal)

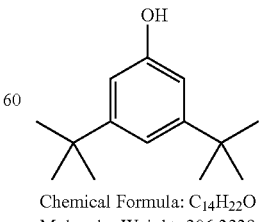

Chemical Formula: $C_{14}H_{22}O$
Molecular Weight: 206.3239

1. $[Cu(CH_2CN_4)]PF_6$ (8 mol%), DBED (15 mol%), $O_2$ (1 atm), 4 h
2. pyrrolidine (2.0 equiv.), rt, 4 h -continued

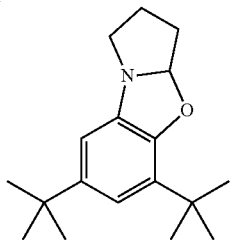

Chemical Formula: $C_{18}H_{27}NO$
Molecular Weight: 273.42

13

A flame-dried, 25-mL Radley tube, equipped with a Teflon-coated stir bar and a rubber septum, was charged with 3,5-di-tert-butylphenol (206.3 mg, 1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with $[Cu(CH_3CN)_4](PF_6)$ (29.8 mg, 0.08 mmol, 0.08 equiv.), N,N'-di-tert-butylethelenediamine (25.8 mg, 32.3 μL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, pyrrolidine (142.2 mg, 164 μL, 2.0 mmol, 2.0 equiv.) was added to the reaction mixture via a syringe and the reaction mixture was stirred for 4 h at room temperature. The reaction mixture was quenched by the addition of $NaHSO_4$ (20 mL, 10% by weight aqueous solution), phases were separated, and the aqueous phase was extracted with $CH_2Cl_2$ (3×20 mL). The combined organic fractions were then dried over $MgSO_4$, filtered and concentrated in vacuo to afford a residue which was analyzed directly by $^1$H-NMR. The crude reaction mixture was then purified using a Biotage Isolera™ One (10% EtOAc in hexanes) to afford the N,O-fused acetal product in 78% isolated yield.

General Procedure I (Saturated Cyclic N-Arylated Amines)

Procedure was analogous to general procedure G. A flame-dried, 25-mL Radley tube, equipped with a Teflon-coated stir bar and a rubber septum, was charged with 3,5-di-tert-butylphenol (206.3 mg, 1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with $[Cu(CH_3CN)_4](PF_6)$ (29.8 mg, 0.08 mmol, 0.08 equiv.), N,N'-di-tert-butylethelenediamine (25.8 mg, 32.3 μL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, amine (2.0 mmol, 2.0 equiv.) was added to the reaction mixture via a syringe and the reaction mixture was stirred for 12 h at 50° C. Then, the reaction mixture was cooled to 0° C., followed by the addition of $NaBH_4$ (95.0 mg g, 2.0 mmol, 2.0 equiv.) and MeOH (3 mL). The reaction mixture was warmed to room temperature and stirred for 2 h. Afterwards, the reaction mixture was quenched by the addition of $NaHSO_4$ (20 mL, 10% by weight aqueous solution), phases were separated, and the aqueous phase was extracted with $CH_2Cl_2$ (3×20 mL). The combined organic fractions were then dried over $MgSO_4$, filtered and concentrated in vacuo to afford a residue which was analyzed directly by $^1$H-NMR. The crude reaction mixture was then purified using a Biotage Isolera™ One (15% EtOAc in hexanes) to afford the N,O-fused acetal product in 78% (213.3 mg, 0.78 mmol) was isolated yield.

The following compounds were produced using general procedure I:

FIG. 20: Entry 15

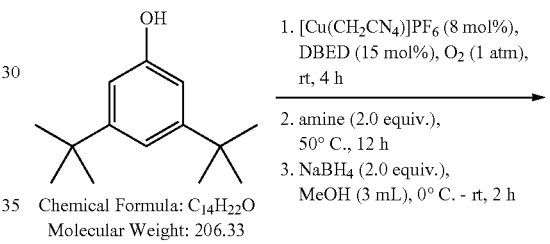

Chemical Formula: $C_{14}H_{22}O$
Molecular Weight: 206.33

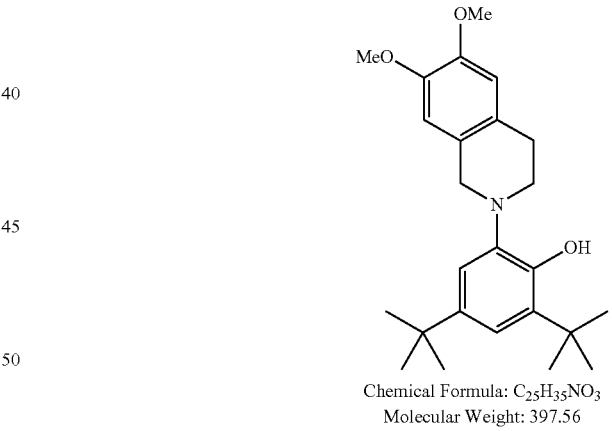

Chemical Formula: $C_{25}H_{35}NO_3$
Molecular Weight: 397.56

FIG. 20: Entry 18

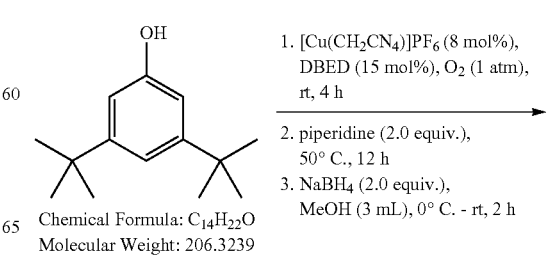

Chemical Formula: $C_{14}H_{22}O$
Molecular Weight: 206.3239

FIG. 20: Entry 19

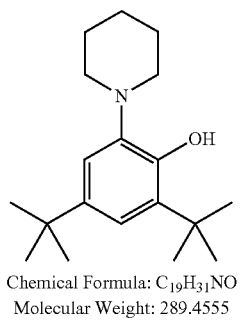

Chemical Formula: C₁₉H₃₁NO
Molecular Weight: 289.4555

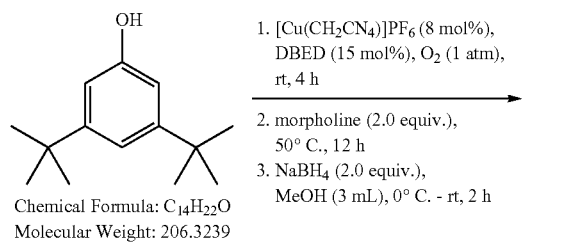

1. [Cu(CH₂CN₄)]PF₆ (8 mol%), DBED (15 mol%), O₂ (1 atm), rt, 4 h
2. morpholine (2.0 equiv.), 50° C., 12 h
3. NaBH₄ (2.0 equiv.), MeOH (3 mL), 0° C. - rt, 2 h Chemical Formula: C₁₄H₂₂O
Molecular Weight: 206.3239

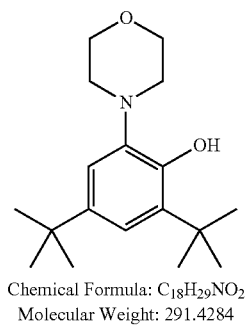

Chemical Formula: C₁₈H₂₉NO₂
Molecular Weight: 291.4284

FIG. 20: Entry 20

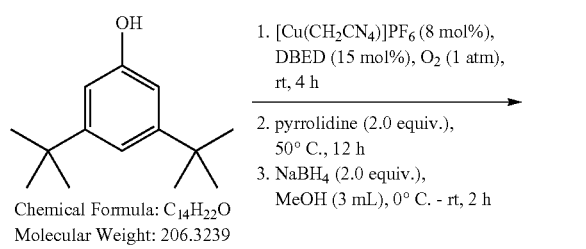

1. [Cu(CH₂CN₄)]PF₆ (8 mol%), DBED (15 mol%), O₂ (1 atm), rt, 4 h
2. pyrrolidine (2.0 equiv.), 50° C., 12 h
3. NaBH₄ (2.0 equiv.), MeOH (3 mL), 0° C. - rt, 2 h Chemical Formula: C₁₄H₂₂O
Molecular Weight: 206.3239

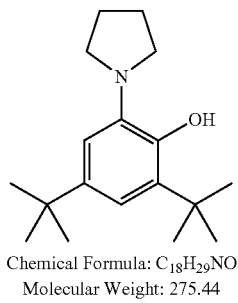

Chemical Formula: C₁₈H₂₉NO
Molecular Weight: 275.44

General Procedure J (2-Substituted N-Aryl Pyrrolidine)

A flame-dried, 25-mL Radley tube, equipped with a Teflon-coated stir bar and a rubber septum, was charged with 3,5-di-tert-butylphenol (206.3 mg, 1.0 mmol, 1.0 equiv.). The reaction vessel was then purged with a steady stream of N₂ for 2 min prior to the addition of dry and degassed CH₂Cl₂ (8.0 mL). A separate, flame-dried test tube (16×125-mL) was charged with [Cu(CH₃CN)₄](PF₆) (29.8 mg, 0.08 mmol, 0.08 equiv.), N,N'-di-tert-butylethelenediamine (25.8 mg, 32.3 μL, 0.15 mmol, 0.15 equiv.), and CH₂Cl₂ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of O₂ and pressurized to 1 atm. Under a constant O₂ pressure (1 atm), the reaction was vented 3 times for 10 s to eliminate N₂. The reaction mixture was then stirred at room temperature for 4 h, depressurized by opening to the atmosphere, and argon gas was bubbled through the reaction mixture for 2 minutes to eliminate O₂. Then, pyrrolidine (142.2 g, 163.5 μL, 162.0 mmol, 2.0 equiv.) was added to the reaction mixture via a syringe and the reaction mixture was stirred at room temperature for 4 h. Then, the reaction mixture was cooled to 0° C., followed by the addition of Grignard reagents (3.0 mmol, 3.0 equiv.). The reaction mixture was warmed to room temperature and stirred for 2 h. Afterwards, the reaction mixture was quenched by the addition of NaHSO₄ (20 mL, 10% by weight aqueous solution), phases were separated, and the aqueous phase was extracted with CH₂Cl₂ (3×20 mL). The combined organic fractions were then dried over MgSO₄, filtered and concentrated in vacuo to afford a residue which was analyzed directly by ¹H-NMR. The crude reaction mixture was then purified using a Biotage Isolera™ One (15% EtOAc in hexanes) to afford the N,O-fused acetal product in 78% was isolated yield.

The following compounds were produced using general procedure J:

FIG. 20: Entry 1

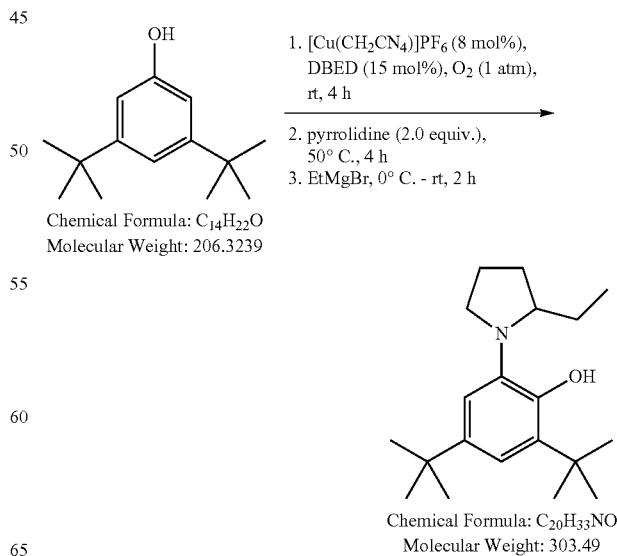

Chemical Formula: C₁₄H₂₂O
Molecular Weight: 206.3239

1. [Cu(CH₂CN₄)]PF₆ (8 mol%), DBED (15 mol%), O₂ (1 atm), rt, 4 h
2. pyrrolidine (2.0 equiv.), 50° C., 4 h
3. EtMgBr, 0° C. - rt, 2 h Chemical Formula: C₂₀H₃₃NO
Molecular Weight: 303.49

FIG. 20: Entry 2

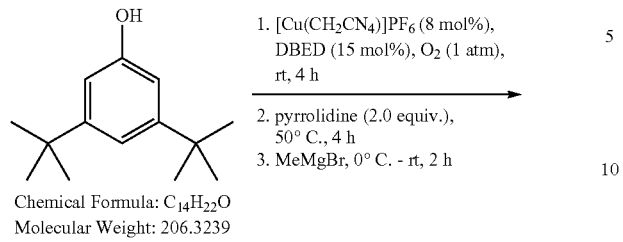

FIG. 20: Entry 3

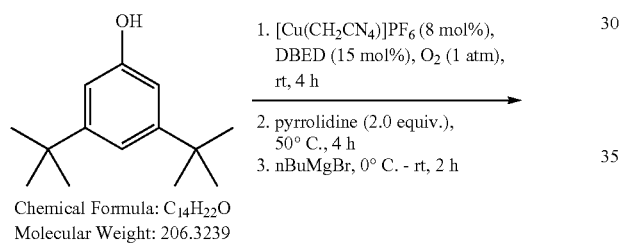

FIG. 20: Entry 4

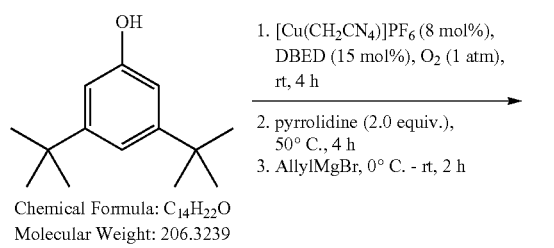

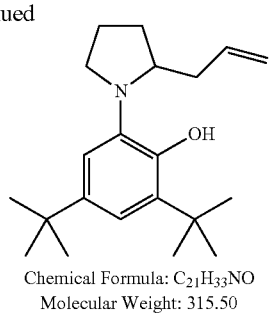

General Procedure K (N-Aryl Pyrrole)

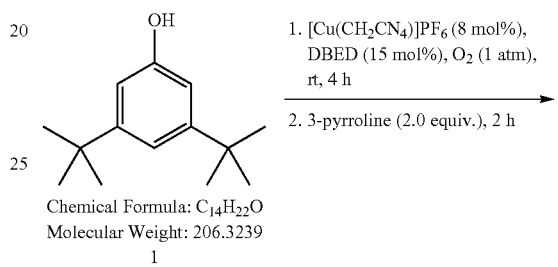

A flame-dried, 25-mL Radley tube, equipped with a Teflon-coated stir bar and a rubber septum, was charged with 3,5-di-tert-butylphenol (206.3 mg, 1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with [Cu(CH$_3$CN)$_4$](PF$_6$) (29.8 mg, 0.08 mmol, 0.08 equiv.), N,N'-di-tert-butylethelenediamine (25.8 mg, 32.3 µL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, 3-pyrroline (138.2 mg, 152 µL, 2.0 mmol, 2.0 equiv.) was added via a syringe and the reaction mixture was stirred at room temperature for 2 h. The reaction mixture was quenched by the addition of NaHSO$_4$ (20 mL, 10% by weight aqueous solution), phases were separated, and the aqueous phase was extracted with CH$_2$Cl$_2$ (3×20 mL). The combined organic fractions were then dried over MgSO$_4$, filtered and concentrated in vacuo to afford a residue which was analyzed directly by $^1$H-NMR. The crude reaction mixture was then purified using a Biotage Isolera™ One (15% EtOAc in hexanes) to afford the N, O-fused acetal product in 89% (241.5 mg, 0.89 mmol) was isolated yield.

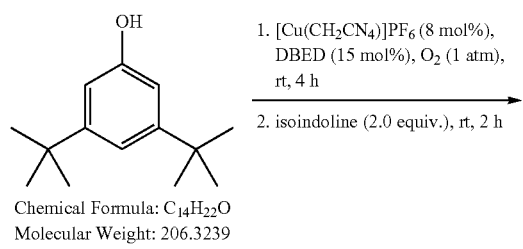

FIG. 20: Entry 8

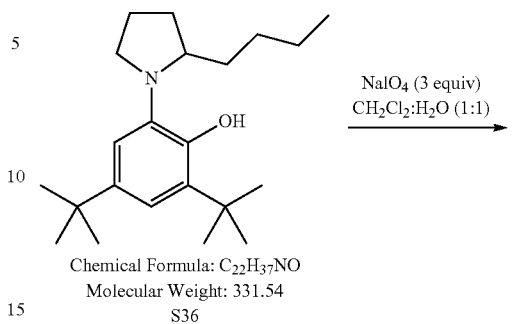

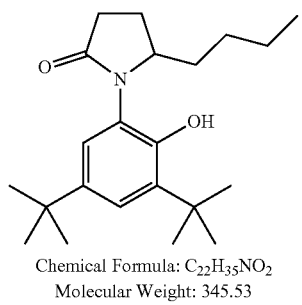

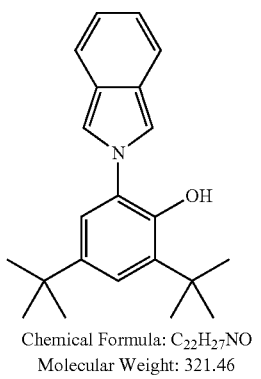

FIG. 20: Entry 9

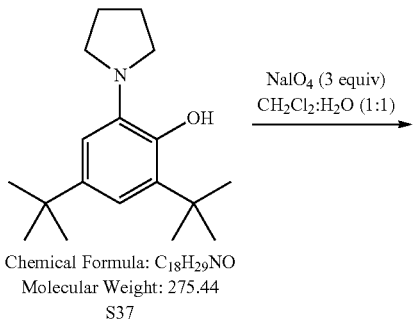

The synthesis was carried out in accordance with procedure stated above to afford the pure product in 51% isolated yield.

Synthesis of Lactam from 2-Substituted N-Aryl Pyrrolidine

A flame-dried 50-mL round-bottomed flask, equipped with a Teflon stir bar, was charged with 2-substituted N-aryl pyrrolidine (1 mmol, 1 equiv.), and degassed CH$_2$Cl$_2$:H$_2$O (1:1, 25-mL). Then, sodium periodate (641.7 mg, 3.0 mmol, 3.0 equiv.) was added to the phenol solution and the reaction was stirred for 4 h. Then, the reaction mixture was quenched by the addition of NaHSO$_4$ (10 mL, 10% by weight aqueous solution), and the phases were separated, and the aqueous phase was washed with CH$_2$Cl$_2$ (3×20 mL). The organic fraction was dried over MgSO$_4$, filtered and concentrated in vacuo to afford a crude residue, which was purified using flash column chromatography (silica gel with 15% EtOAc in hexanes as eluant) to afford a white powder in 95% isolated yield.

The following compounds were produced according to this procedure:

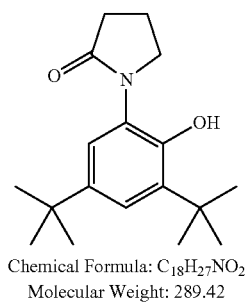

FIG. 20: Entry 10

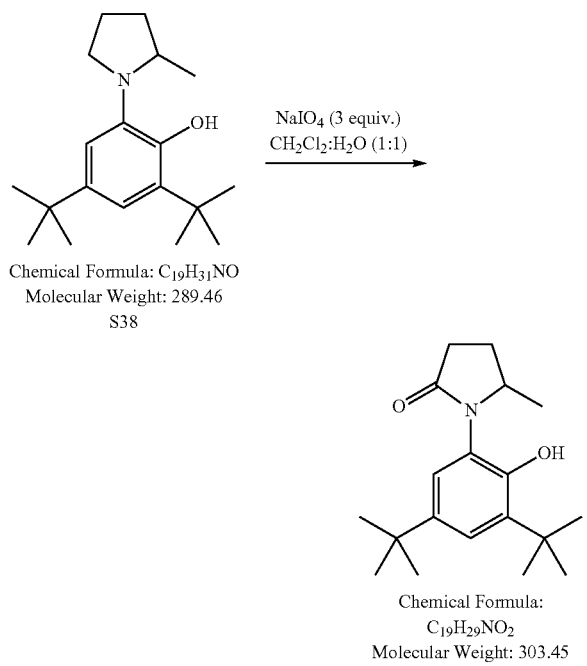

tert-Butyl Deprotection:
Regioselective tert-Butyl Deprotection of Benzoxazoles:

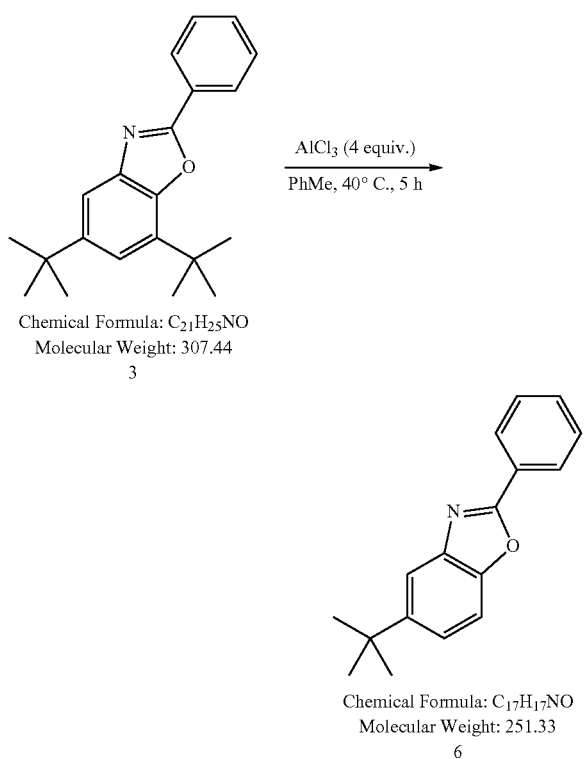

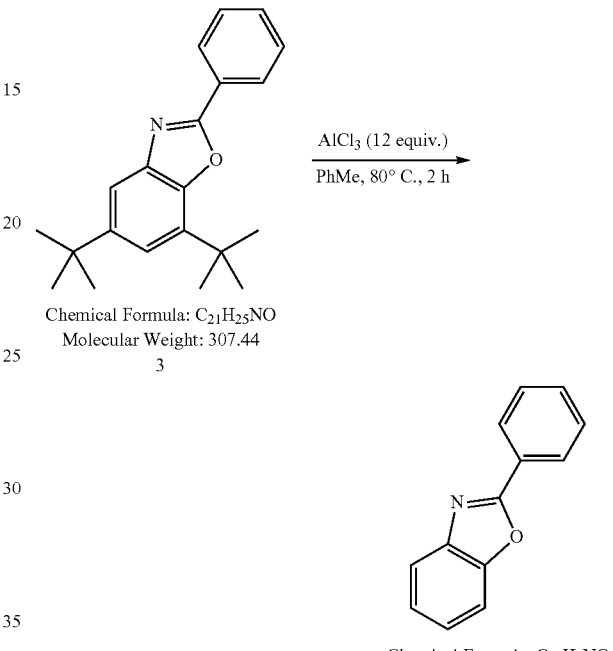

A flame-dried 50-mL pressure vessel, equipped with a Teflon stir bar, was charged with 3 (307.4 mg, 1 mmol, 1 equiv.) and dry, degassed toluene (20 mL). Aluminum trichloride (533.3 mg, 4.0 mmol, 4.0 equiv.) was added to this reaction mixture and the reaction was stirred at 40° C. for 5 h. The reaction mixture was quenched by the addition of distilled $H_2O$ (20 mL), and the phases were separated. The aqueous phase was washed with $CH_2Cl_2$ (3×20 mL). The combined organic fractions was dried over $MgSO_4$, filtered and concentrated in vacuo to afford a crude residue, which was purified using flash column chromatography (silica gel with 10% EtOAc in hexanes as eluant) to afford a white powder in 64% isolated yield.

A flame-dried 50-mL pressure vessel, equipped with a Teflon stir bar, was charged with 3 (307.4 mg, 1 mmol, 1 equiv.) and dry, degassed toluene (40 mL). Aluminum trichloride (1.60 g, 12 mmol, 12 equiv.) was added to this reaction mixture and the reaction was stirred at 80° C. for 2 h. The reaction mixture was quenched by the addition of distilled $H_2O$ (20 mL), and the phases were separated. The aqueous phase was washed with $CH_2Cl_2$ (3×20 mL). The combined organic fractions were dried over $MgSO_4$, filtered and concentrated in vacuo to afford a crude residue, which was purified using flash column chromatography (silica gel with 10% EtOAc in hexanes as eluant) to afford a white powder in 71% isolated yield.

tert-Butyl Deprotection of Aminophenols:

A flame-dried 25-mL round bottom, equipped with a Teflon stir bar, was charged with aminophenol (1 equiv.) and concentrated $H_3PO_4$ (2 mL). The reaction mixture was stirred at 220° C. for 2 h. Then, the reaction was basified with saturated $NaHCO_3$ (20 mL), diluted with EtOAc (25 mL), phases were separated, and the aqueous phase was washed with EtOAc (3×20 mL). The combined organic fractions were dried over $MgSO_4$, filtered and concentrated in vacuo to afford a crude residue. The material was purified using flash column chromatography (silica gel with 15% EtOAc in hexanes as eluant) to afford the pure product.

The following compounds were produced using this procedure:

FIG. 20: Entry 5

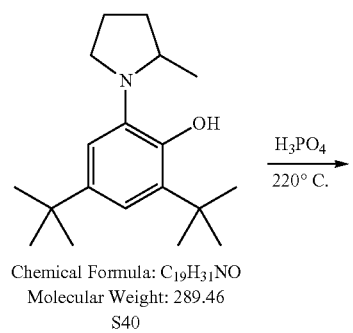

FIG. 20: Entry 6

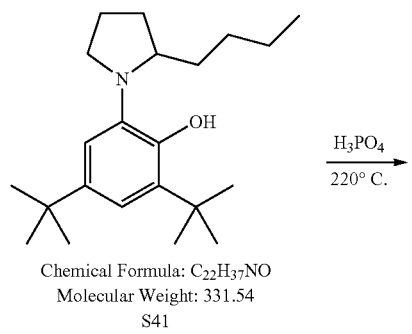

FIG. 20: Entry 7

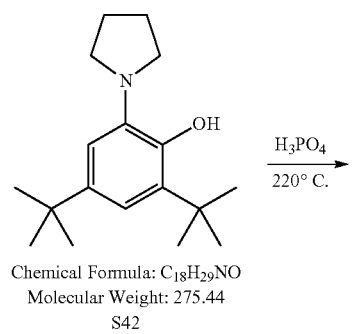

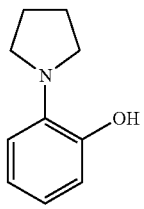

Chemical Formula: $C_{10}H_{13}NO$
Molecular Weight: 163.22 tert-Butyl Deprotection of N-Aryl Lactams:

A flame-dried 25-mL round bottom, equipped with a Teflon stir bar, was charged with N-aryl lactam (1 equiv.) and concentrated $H_3PO_4$ (2 mL). The reaction mixture was stirred at 220° C. for 2 h. Then, the reaction was basified with saturated $NaHCO_3$ (20 mL), diluted with EtOAc (25-mL), phases were separated, and the aqueous phase was washed with EtOAc (3×20 mL). The combined organic fractions were dried over $MgSO_4$, filtered and concentrated in vacuo to afford a crude residue. The material was purified using flash column chromatography (silica gel with 15% EtOAc in hexanes as eluant) to afford the pure product.

The following compounds were produced using this procedure:

FIG. 20: Entry 11

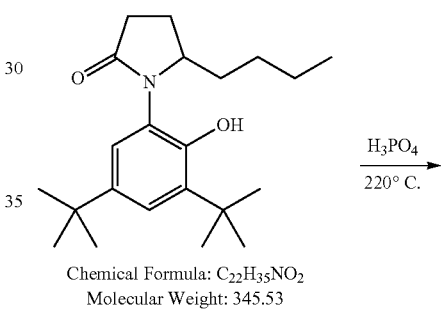

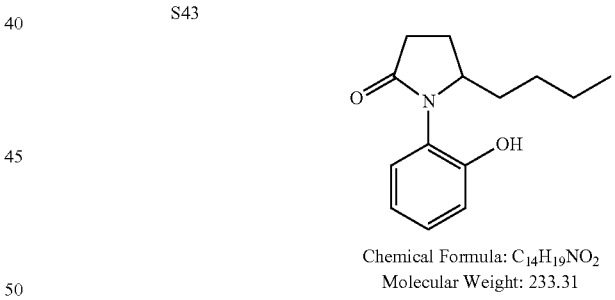

FIG. 20: Entry 12

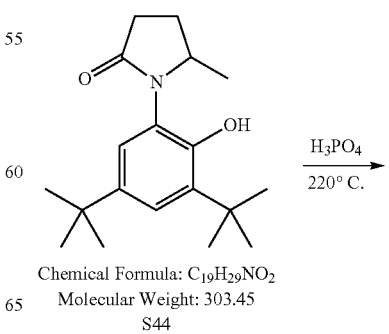

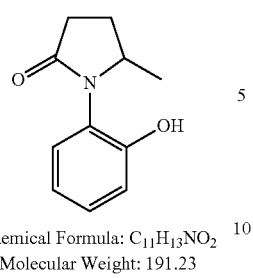

Chemical Formula: C₁₁H₁₃NO₂
Molecular Weight: 191.23

FIG. 20: Entry 12

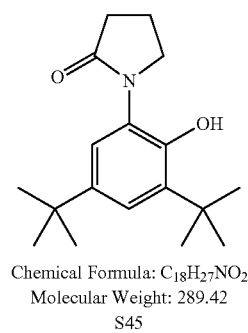

Chemical Formula: C₁₈H₂₇NO₂
Molecular Weight: 289.42
S45

H₃PO₄
220° C.

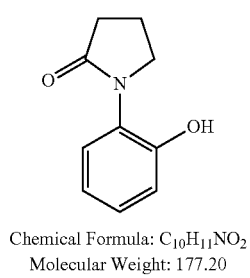

Chemical Formula: C₁₀H₁₁NO₂
Molecular Weight: 177.20

Scope of Mono-Substituted Phenols (FIG. 26):

The following compounds were produced according to general procedure E:

FIG. 26: Entry 1

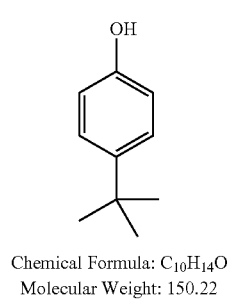

Chemical Formula: C₁₀H₁₄O
Molecular Weight: 150.22

1. [Cu(CH₂CN)₄]PF₆ (8 mol %), DBED (15 mol %), O₂ (1 atm), 4 h
2. BnNH₂ (2.0 equiv.) then O₂ (1 atm), 2 h

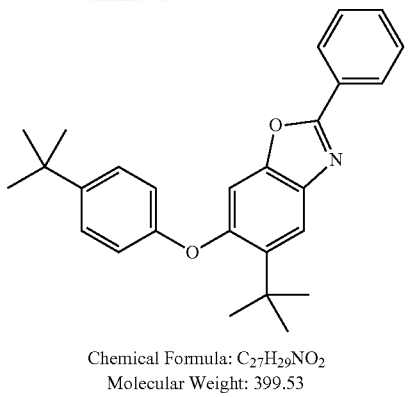

Chemical Formula: C₂₇H₂₉NO₂
Molecular Weight: 399.53

FIG. 26: Entry 2

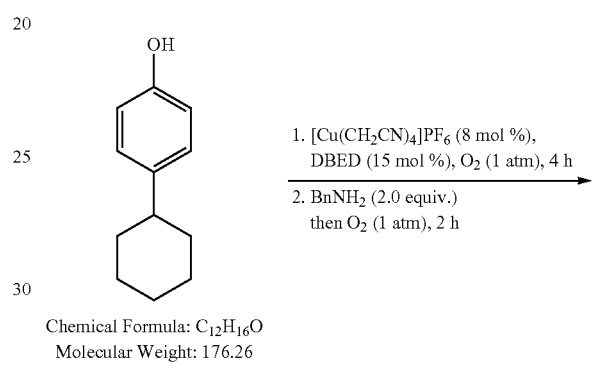

Chemical Formula: C₁₂H₁₆O
Molecular Weight: 176.26

1. [Cu(CH₂CN)₄]PF₆ (8 mol %), DBED (15 mol %), O₂ (1 atm), 4 h
2. BnNH₂ (2.0 equiv.) then O₂ (1 atm), 2 h Chemical Formula: C₃₁H₃₃NO₂
Molecular Weight: 451.5992

FIG. 26: Entry 3

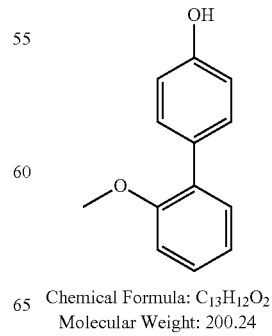

Chemical Formula: C₁₃H₁₂O₂
Molecular Weight: 200.24

1. [Cu(CH₂CN)₄]PF₆ (8 mol %), DBED (15 mol %), O₂ (1 atm), 4 h
2. BnNH₂ (2.0 equiv.) then O₂ (1 atm), 2 h

99
-continued

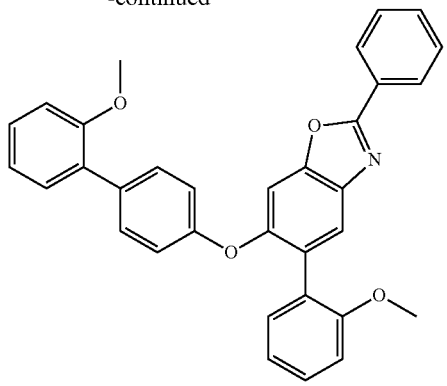

Chemical Formula: C$_{33}$H$_{25}$NO$_{4}$
Molecular Weight: 499.5559

The following compounds were were produced according to general procedure F:

FIG. 26: Entry 4

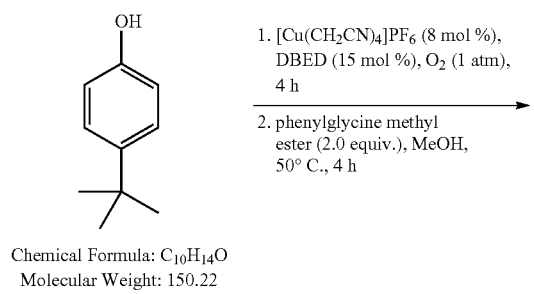

Chemical Formula: C$_{10}$H$_{14}$O
Molecular Weight: 150.22

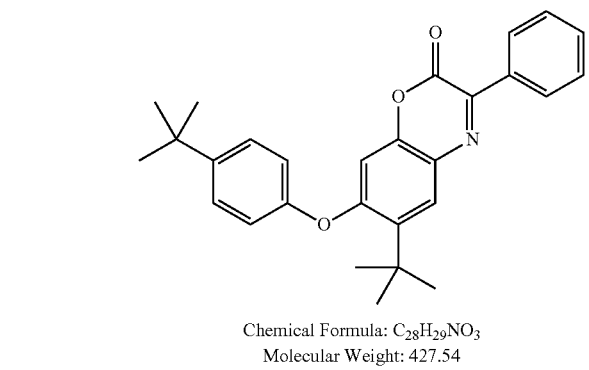

Chemical Formula: C$_{28}$H$_{29}$NO$_{3}$
Molecular Weight: 427.54

FIG. 26: Entry 5

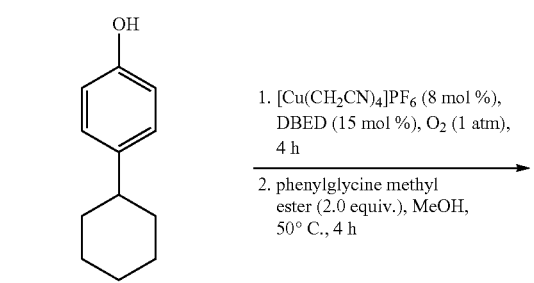

Chemical Formula: C$_{12}$H$_{16}$O
Molecular Weight: 176.26

100
-continued

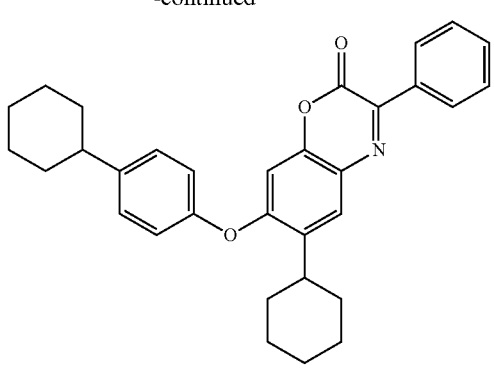

Chemical Formula: C$_{32}$H$_{33}$NO$_{3}$
Molecular Weight: 479.62

FIG. 26: Entry 6

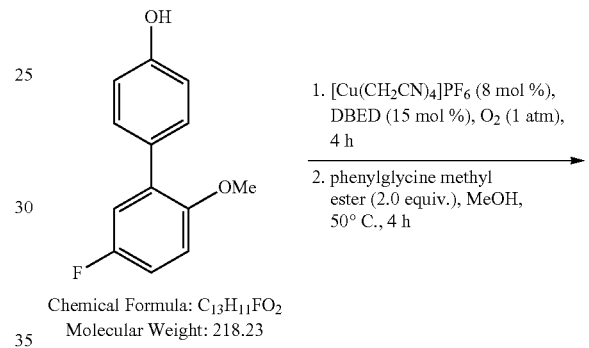

Chemical Formula: C$_{13}$H$_{11}$FO$_{2}$
Molecular Weight: 218.23

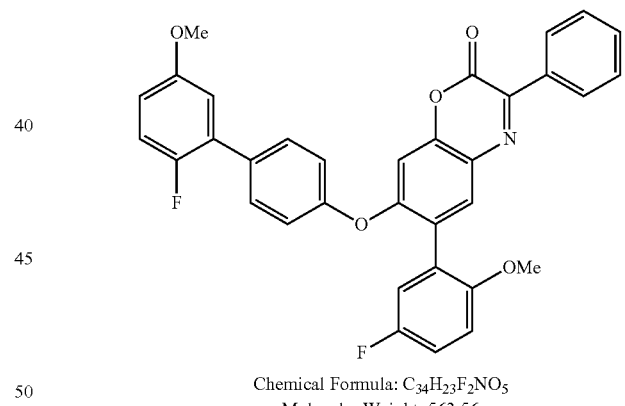

Chemical Formula: C$_{34}$H$_{23}$F$_{2}$NO$_{5}$
Molecular Weight: 563.56

FIG. 26: Entry 13

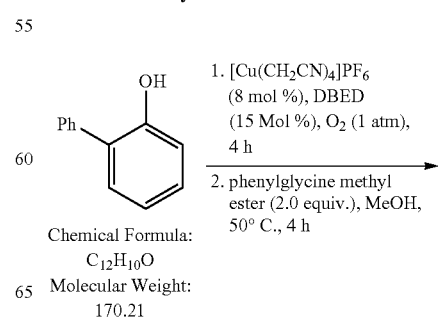

Chemical Formula: C$_{12}$H$_{10}$O
Molecular Weight: 170.21

-continued
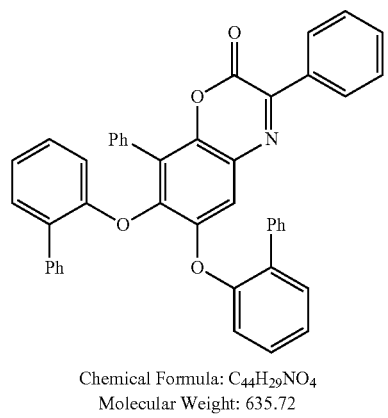
Chemical Formula: C₄₄H₂₉NO₄
Molecular Weight: 635.72
FIG. 26: Entry 14
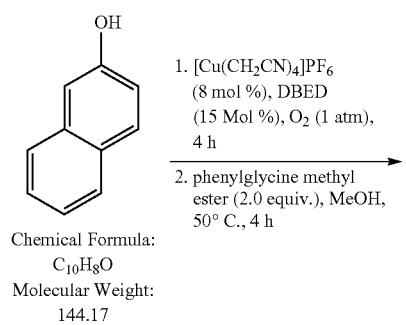
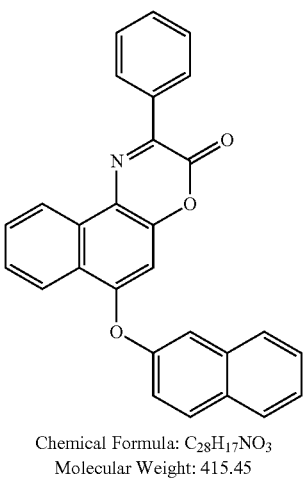
Chemical Formula: C₂₈H₁₇NO₃
Molecular Weight: 415.45
FIG. 26: Entry 7
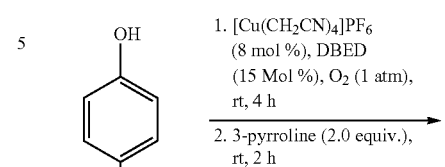
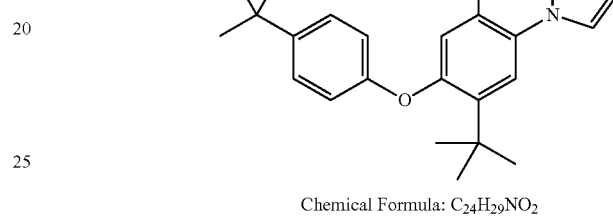
Chemical Formula: C₂₄H₂₉NO₂
Molecular Weight: 363.50
FIG. 26: Entry 8
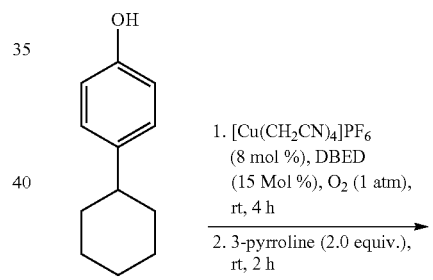
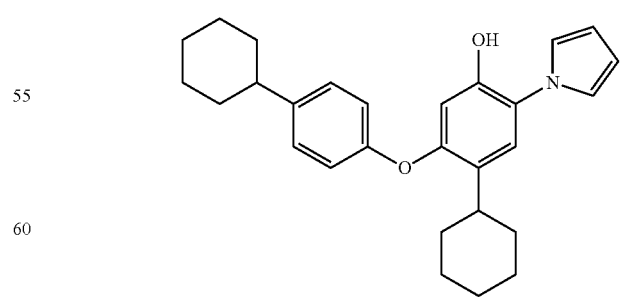
Chemical Formula: C₂₈H₃₃NO₂
Molecular Weight: 415.5671
The following compounds were produced according to general procedure K:

FIG. 26: Entry 9

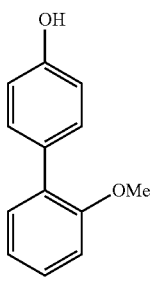

Chemical Formula:
C₁₃H₁₂O
Molecular Weight:
200.2332

1. [Cu(CH₂CN)₄]PF₆
(8 mol %), DBED
(15 Mol %), O₂ (1 atm),
rt, 4 h
2. 3-pyrroline (2.0 equiv.),
rt, 2 h

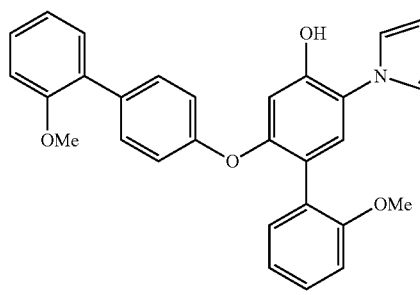

Chemical Formula: C₃₀H₂₅NO₄
Molecular Weight: 463.5238

FIG. 26: Entry 10

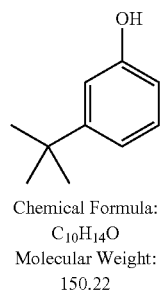

Chemical Formula:
C₁₀H₁₄O
Molecular Weight:
150.22

1. [Cu(CH₂CN)₄]PF₆
(8 mol %), DBED
(15 Mol %), O₂ (1 atm),
rt, 4 h
2. 3-pyrroline (2.0 equiv.),
rt, 2 h

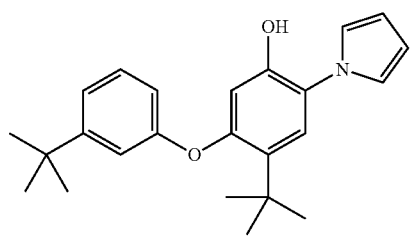

Chemical Formula: C₂₄H₂₉NO₂
Molecular Weight: 363.50

FIG. 26: Entry 11

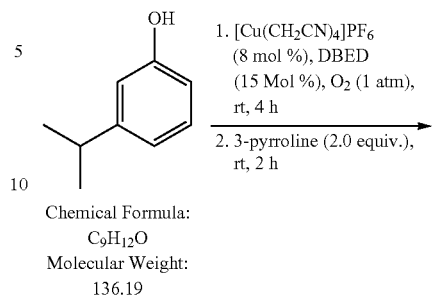

Chemical Formula:
C₉H₁₂O
Molecular Weight:
136.19

1. [Cu(CH₂CN)₄]PF₆
(8 mol %), DBED
(15 Mol %), O₂ (1 atm),
rt, 4 h
2. 3-pyrroline (2.0 equiv.),
rt, 2 h

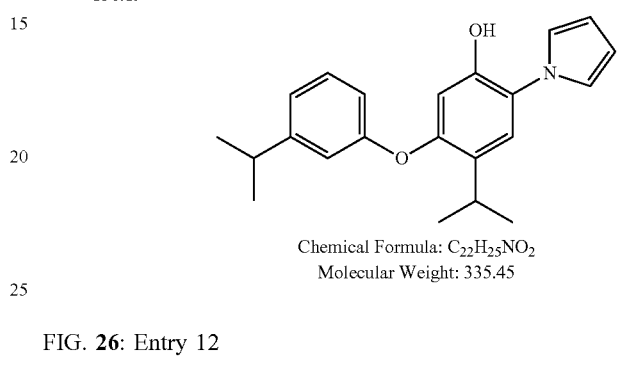

Chemical Formula: C₂₂H₂₅NO₂
Molecular Weight: 335.45

FIG. 26: Entry 12

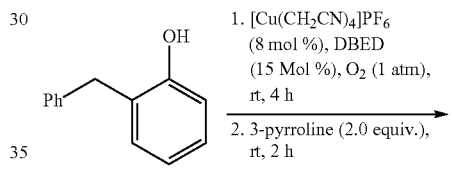

Chemical Formula:
C₁₃H₁₂O
Molecular Weight:
184.24

1. [Cu(CH₂CN)₄]PF₆
(8 mol %), DBED
(15 Mol %), O₂ (1 atm),
rt, 4 h
2. 3-pyrroline (2.0 equiv.),
rt, 2 h

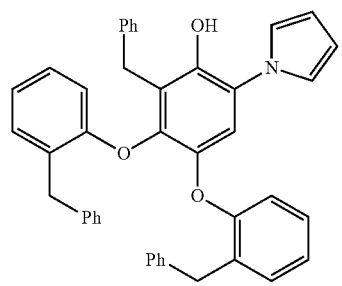

Chemical Formula: C₄₃H₃₅NO₃
Molecular Weight: 613.76

FIG. 26: Entry 15

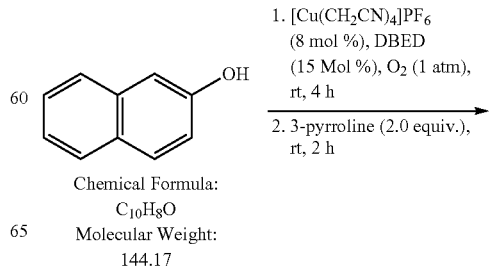

Chemical Formula:
C₁₀H₈O
Molecular Weight:
144.17

1. [Cu(CH₂CN)₄]PF₆
(8 mol %), DBED
(15 Mol %), O₂ (1 atm),
rt, 4 h
2. 3-pyrroline (2.0 equiv.),
rt, 2 h

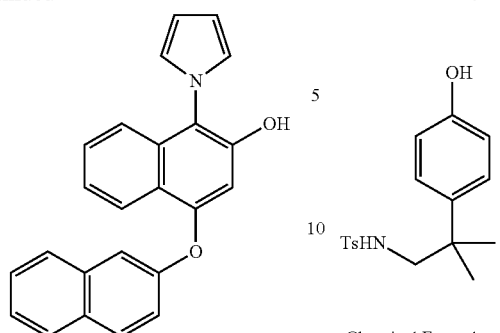

Chemical Formula: C₂₄H₁₇NO₂
Molecular Weight: 351.41

Multi C—H Functionalization:

The following compounds were also produced according to general procedure E:

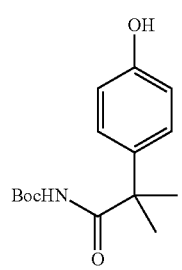

Chemical Formula: C₁₅H₂₁NO₄
Molecular Weight: 279.34
38

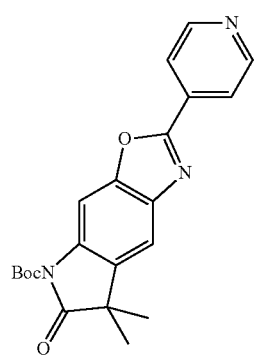

Chemical Formula: C₂₁H₂₁N₃O₄
Molecular Weight: 379.42
39

FIG. 28: Entry 1a

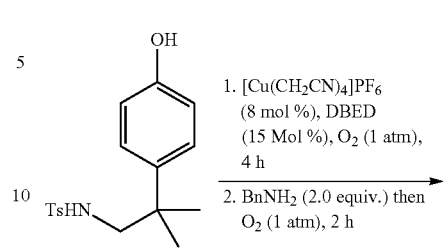

Chemical Formula: C₁₇H₂₁NO₃S
Molecular Weight: 319.4185
S46

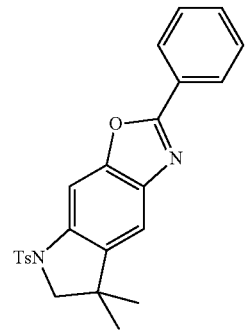

Chemical Formula: C₂₄H₂₂N₂O₃S
Molecular Weight: 418.51

FIG. 28: Entry 2a

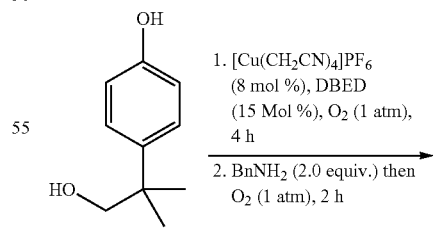

Chemical Formula: C₁₀H₁₄O₂
Molecular Weight: 166.2170
S47

-continued

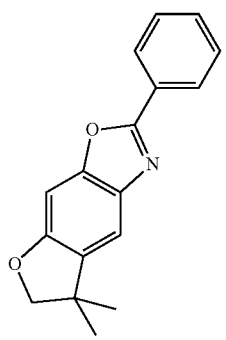

Chemical Formula: C₁₇H₁₅NO₂
Molecular Weight: 265.3065

FIG. 28: Entry 3a

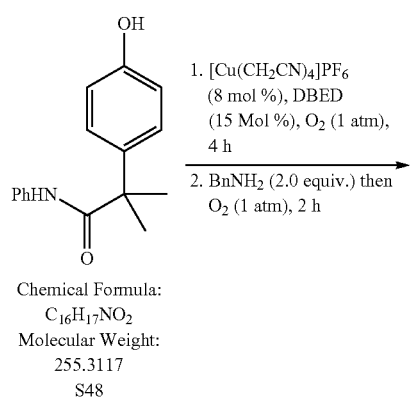

Chemical Formula: C₁₆H₁₇NO₂
Molecular Weight: 255.3117
S48

FIG. 28: Entry 3a'

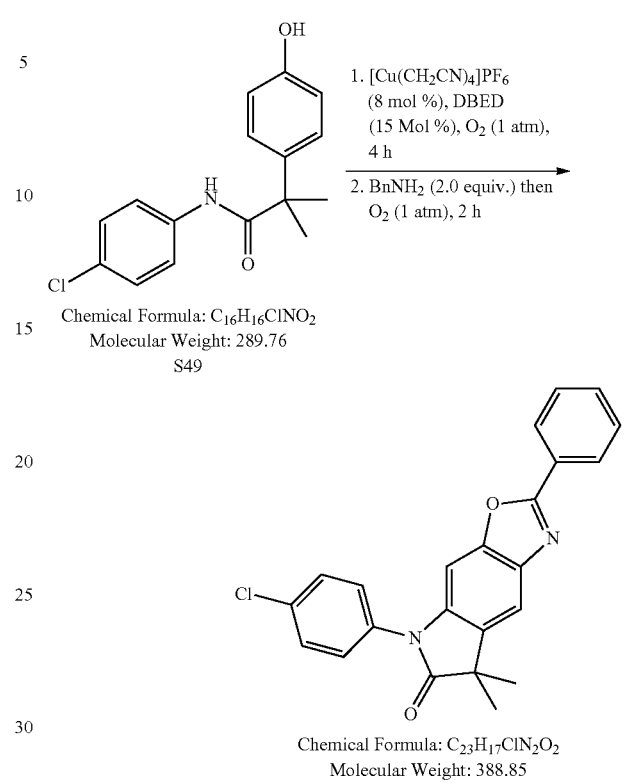

Chemical Formula: C₁₆H₁₆ClNO₂
Molecular Weight: 289.76
S49

Chemical Formula: C₂₃H₁₇ClN₂O₂
Molecular Weight: 388.85

The following compounds were produced according to general procedure F:
FIG. 28: Entry 1b

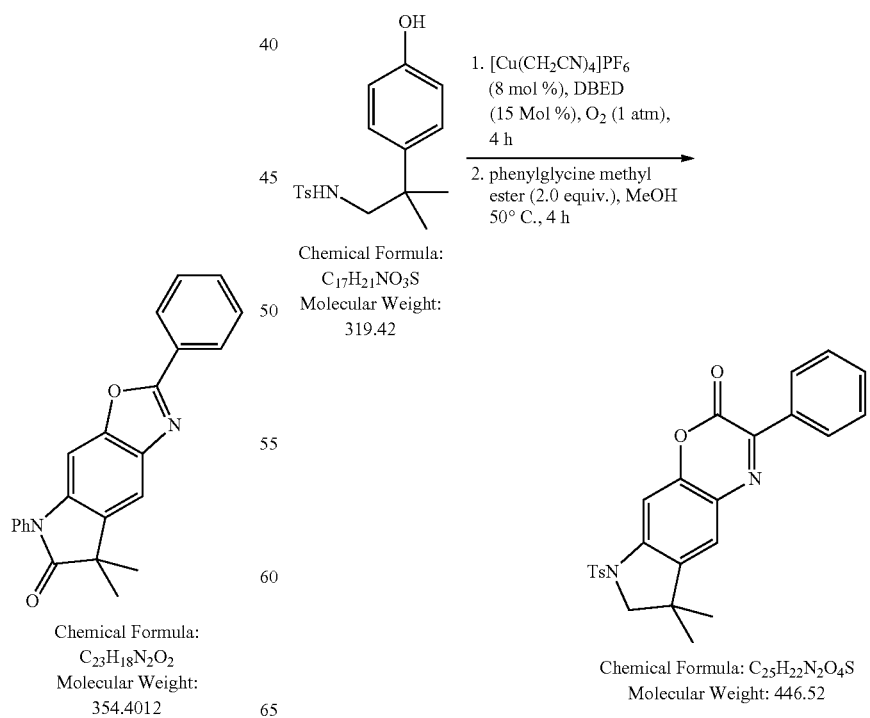

Chemical Formula: C₁₇H₂₁NO₃S
Molecular Weight: 319.42

Chemical Formula: C₂₃H₁₈N₂O₂
Molecular Weight: 354.4012

Chemical Formula: C₂₅H₂₂N₂O₄S
Molecular Weight: 446.52

FIG. 28: Entry 2b

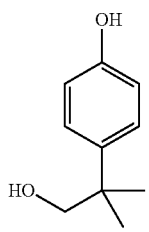

Chemical Formula: $C_{10}H_{14}O_2$
Molecular Weight: 166.2170

1. [Cu(CH$_2$CN)$_4$]PF$_6$(8 mol%), DBED (15 mol%), O$_2$(1 atm), 4 h
2. phenylglycine methyl ester (2.0 equiv.), MeOH, 50° C., 4 h

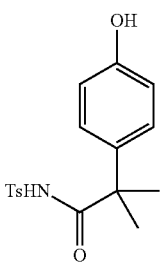

Chemical Formula: $C_{18}H_{15}NO_3$
Molecular Weight: 293.3166

FIG. 28: Entry 3b

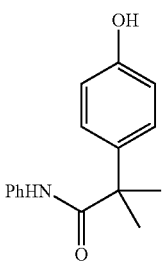

Chemical Formula: $C_{16}H_{17}NO_2$
Molecular Weight: 255.32

1. [Cu(CH$_2$CN)$_4$]PF$_6$(8 mol%), DBED (15 mol%), O$_2$(1 atm), 4 h
2. phenylglycine methyl ester (2.0 equiv.), MeOH, 50° C., 4 h

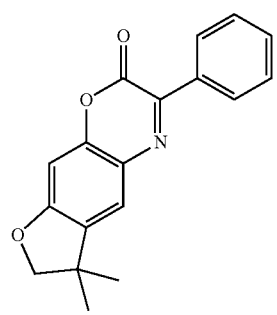

Chemical Formula: $C_{24}H_{18}N_2O_3$
Molecular Weight: 382.42

FIG. 28: Entry 1c

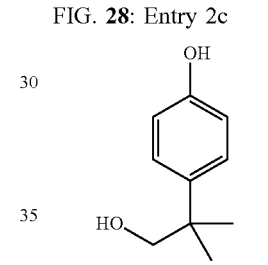

Chemical Formula: $C_{17}H_{21}NO_3S$
Molecular Weight: 319.42

1. [Cu(CH$_2$CN)$_4$]PF$_6$(8 mol%), DBED (15 mol%), O$_2$(1 atm), rt, 4 h
2. 3-pyrroline (2.0 equiv.), rt, 2 h

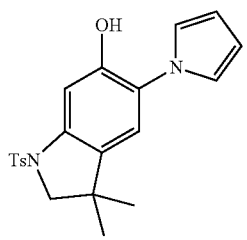

Chemical Formula: $C_{21}H_{22}N_2O_3S$
Molecular Weight: 382.48

FIG. 28: Entry 2c

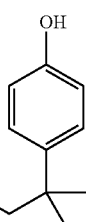

Chemical Formula: $C_{10}H_{14}O_2$
Molecular Weight: 166.22

1. [Cu(CH$_2$CN)$_4$]PF$_6$(8 mol%), DBED (15 mol%), O$_2$(1 atm), rt, 4 h
2. 3-pyrroline (2.0 equiv.), rt, 2 h

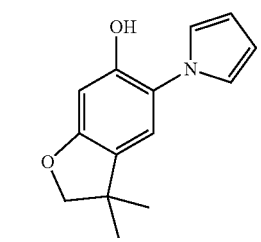

Chemical Formula: $C_{14}H_{15}NO_2$
Molecular Weight: 299.28

FIG. 28: Entry 3c

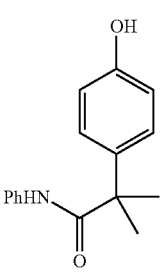

Chemical Formula: $C_{16}H_{17}NO_2$
Molecular Weight: 255.32

1. [Cu(CH$_2$CN)$_4$]PF$_6$(8 mol%), DBED (15 mol%), O$_2$(1 atm), rt, 4 h
2. 3-pyrroline (2.0 equiv.), rt, 2 h The following compounds were produced according to general procedure K:

-continued

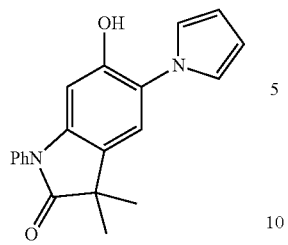

Chemical Formula: $C_{20}H_{18}N_2O_2$
Molecular Weight: 318.38

The following compounds were produced according to general procedure I:

FIG. 28: Entry 1d

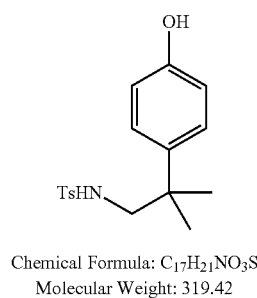

Chemical Formula: $C_{17}H_{21}NO_3S$
Molecular Weight: 319.42

1. [Cu(CH$_2$CN)$_4$]PF$_6$(8 mol%), DBED (15 mol%), O$_2$(1 atm), rt, 4 h
2. pyrrolidine (2.0 equiv.), 50° C., 4 h
3. NaBH$_4$ (2.0 equiv.), MeOH (3 mL), 0° C. - rt, 2 h

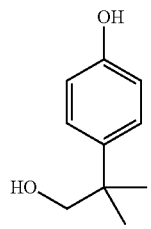

Chemical Formula: $C_{21}H_{26}N_2O_3S$
Molecular Weight: 386.51

FIG. 28: Entry 2d

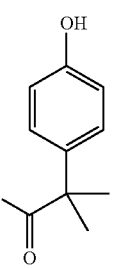

Chemical Formula: $C_{10}H_{14}O_2$
Molecular Weight: 166.2170

1. [Cu(CH$_2$CN)$_4$]PF$_6$(8 mol%), DBED (15 mol%), O$_2$(1 atm), rt, 4 h
2. pyrrolidine (2.0 equiv.), 50° C., 4 h
3. NaBH$_4$ (2.0 equiv.), MeOH (3 mL), 0° C. - rt, 2 h -continued

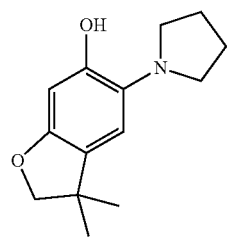

Chemical Formula: $C_{14}H_{19}NO_2$
Molecular Weight: 233.31

FIG. 28: Entry 3d

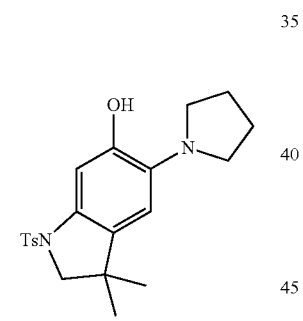

Chemical Formula: $C_{16}H_{17}NO_2$
Molecular Weight: 255.3117

1. [Cu(CH$_2$CN)$_4$]PF$_6$(8 mol%), DBED (15 mol%), O$_2$(1 atm), rt, 4 h
2. pyrrolidine (2.0 equiv.), 50° C., 4 h
3. NaBH$_4$ (2.0 equiv.), MeOH (3 mL), 0° C. - rt, 2 h

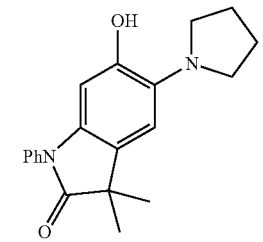

Chemical Formula: $C_{20}H_{22}N_2O_2$
Molecular Weight: 322.4009

Scope of Phenol (Di-Substituted Phenols):

The following compounds were produced according to general procedure E:

FIG. 23: Entry 1

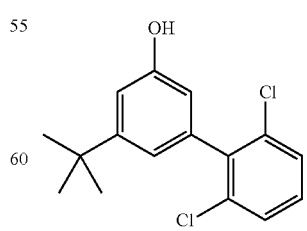

Chemical Formula: $C_{16}H_{16}Cl_2O$
Molecular Weight: 295.20

1. [Cu(CH$_2$CN)$_4$]PF$_6$(8 mol%), DBED (15 mol%), O$_2$(1 atm), 4 h
2. BnNH$_2$(2.0 equiv.) then O$_2$(1 atm), 2 h -continued

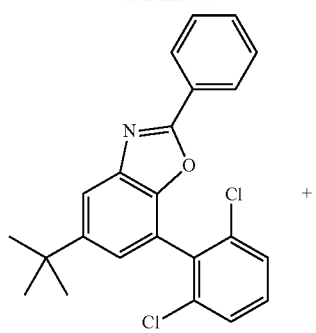

Chemical Formula: C$_{23}$H$_{19}$Cl$_2$NO
Molecular Weight: 396.31
27

+

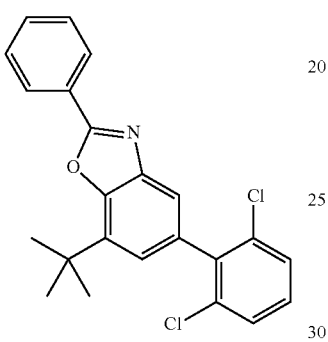

Chemical Formula: C$_{23}$H$_{19}$Cl$_2$NO
Molecular Weight: 396.31
25

FIG. 23: Entry 2

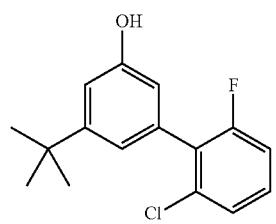

Chemical Formula: C$_{16}$H$_{16}$ClFO
Molecular Weight: 278.75
20

1. [Cu(CH$_2$CN)$_4$]PF$_6$(8 mol%), DBED (15 mol%), O$_2$(1 atm), 4 h
2. BnNH$_2$(2.0 equiv.) then O$_2$(1 atm), 2 h
→

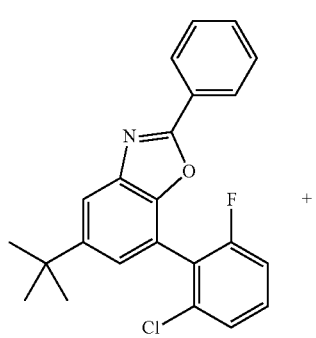

Chemical Formula: C$_{23}$H$_{19}$ClFNO
Molecular Weight: 379.86
28

-continued

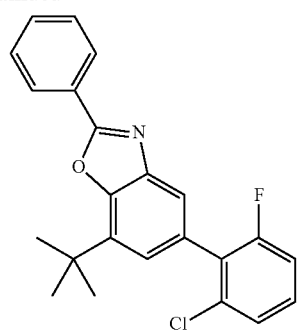

Chemical Formula: C$_{23}$H$_{19}$ClFNO
Molecular Weight: 379.86
26

FIG. 23: Entry 3

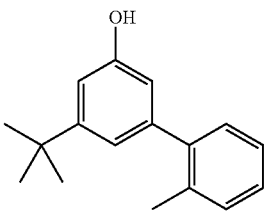

Chemical Formula: C$_{17}$H$_{20}$O
Molecular Weight: 240.35

1. [Cu(CH$_2$CN)$_4$]PF$_6$(8 mol%), DBED (15 mol%), O$_2$(1 atm), 4 h
2. BnNH$_2$(2.0 equiv.) then O$_2$(1 atm), 2 h
→

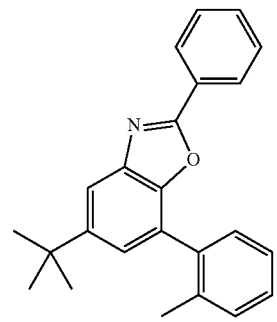

Chemical Formula: C$_{24}$H$_{23}$NO
Molecular Weight: 341.45

The following compounds were produced according to general procedure K:

FIG. 23: Entry 4

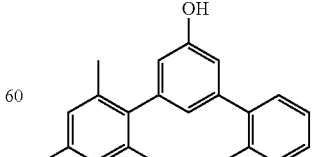

Chemical Formula: C$_{22}$H$_{22}$O$_2$
Molecular Weight: 318.42

1. [Cu(CH$_2$CN)$_4$]PF$_6$(8 mol%), DBED (15 mol%), O$_2$(1 atm), rt, 4 h
2. 3-pyrroline (2.0 equiv.) rt, 2 h
→

115
-continued

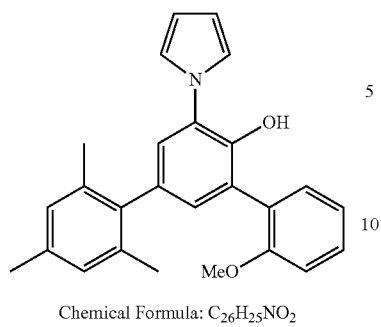

Chemical Formula: C$_{26}$H$_{25}$NO$_2$
Molecular Weight: 383.49

FIG. 23: Entry 5

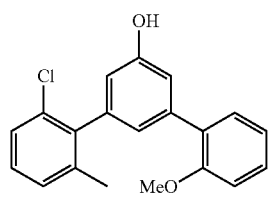

Chemical Formula: C$_{19}$H$_{14}$Cl$_2$O$_2$
Molecular Weight: 345.22

1. [Cu(CH$_2$CN)$_4$]PF$_6$(8 mol%), DBED (15 mol%), O$_2$(1 atm), rt, 4 h
2. 3-pyrroline (2.0 equiv.) rt, 2 h

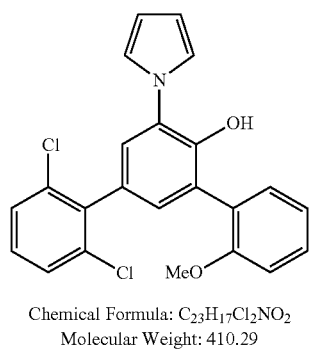

Chemical Formula: C$_{23}$H$_{17}$Cl$_2$NO$_2$
Molecular Weight: 410.29

FIG. 23: Entry 6

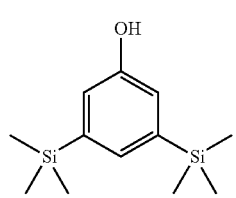

Chemical Formula: C$_{12}$H$_{22}$OSi$_2$
Molecular Weight: 238.48

1. [Cu(CH$_2$CN)$_4$]PF$_6$(8 mol%), DBED (15 mol%), O$_2$(1 atm), rt, 4 h
2. 3-pyrroline (2.0 equiv.) rt, 2 h 116
-continued

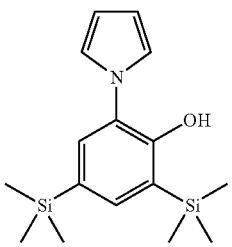

Chemical Formula: C$_{16}$H$_{25}$NOSi$_2$
Molecular Weight: 303.55

FIG. 23: Entry 7

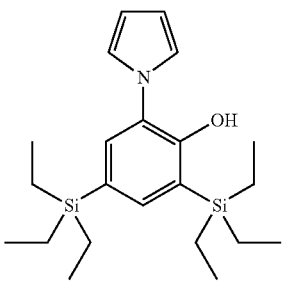

Chemical Formula: C$_{18}$H$_{34}$OSi$_2$
Molecular Weight: 322.64

1. [Cu(CH$_2$CN)$_4$]PF$_6$(8 mol%), DBED (15 mol%), O$_2$(1 atm), rt, 4 h
2. 3-pyrroline (2.0 equiv.) rt, 2 h Chemical Formula: C$_{22}$H$_{37}$NOSi$_2$
Molecular Weight: 387.71

FIG. 23: Entry 8

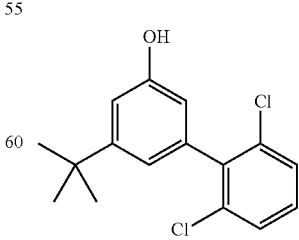

Chemical Formula: C$_{16}$H$_{16}$Cl$_2$O
Molecular Weight: 295.20

1. [Cu(CH$_2$CN)$_4$]PF$_6$ (8 mol %), DBED (15 mol %), O$_2$ (1 atm), rt, 4 h
2. 3-pyrroline (2.0 equiv.), rt, 2 h

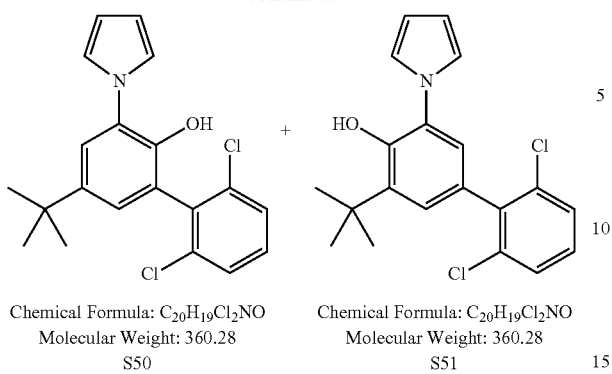

Chemical Formula: C20H19Cl2NO
Molecular Weight: 360.28
S50

Chemical Formula: C20H19Cl2NO
Molecular Weight: 360.28
S51

FIG. 23: Entry 9

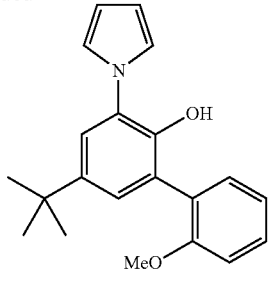

Chemical Formula: C21H23NO2
Molecular Weight: 321.42

The following compounds were produced according to general procedure F:
FIG. 23: Entry 11

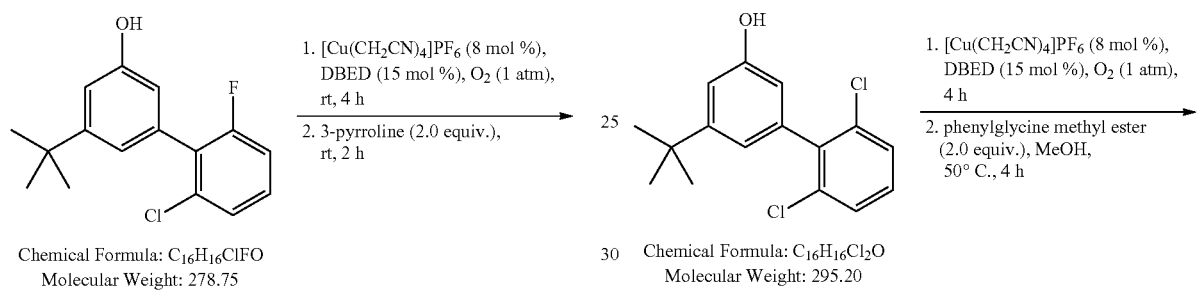

Chemical Formula: C16H16ClFO
Molecular Weight: 278.75

1. [Cu(CH2CN)4]PF6 (8 mol %), DBED (15 mol %), O2 (1 atm), rt, 4 h
2. 3-pyrroline (2.0 equiv.), rt, 2 h Chemical Formula: C16H16Cl2O
Molecular Weight: 295.20

1. [Cu(CH2CN)4]PF6 (8 mol %), DBED (15 mol %), O2 (1 atm), 4 h
2. phenylglycine methyl ester (2.0 equiv.), MeOH, 50° C., 4 h

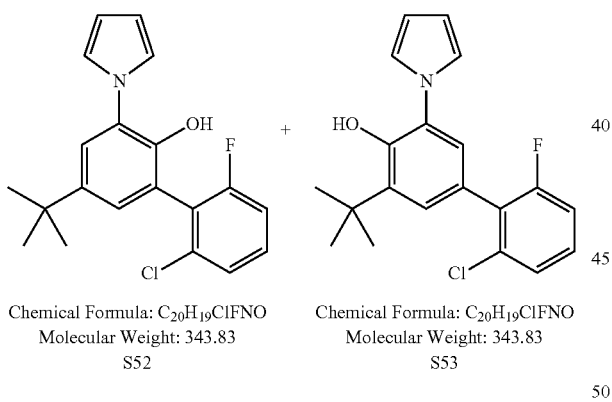

Chemical Formula: C20H19ClFNO
Molecular Weight: 343.83
S52

Chemical Formula: C20H19ClFNO
Molecular Weight: 343.83
S53

FIG. 23: Entry 10

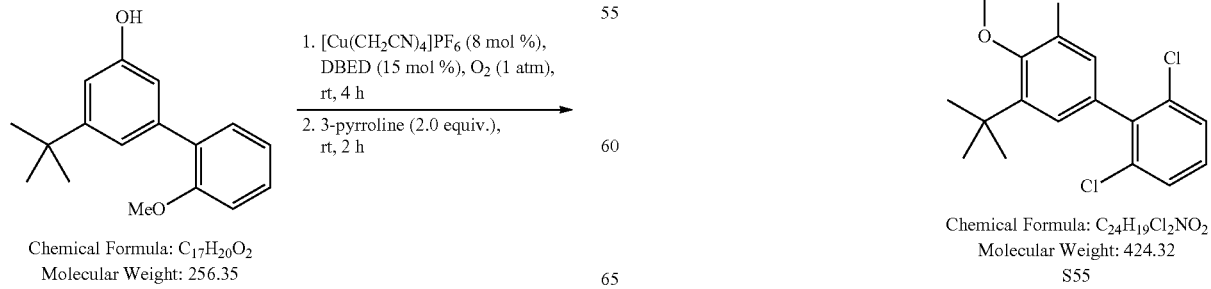

Chemical Formula: C17H20O2
Molecular Weight: 256.35

1. [Cu(CH2CN)4]PF6 (8 mol %), DBED (15 mol %), O2 (1 atm), rt, 4 h
2. 3-pyrroline (2.0 equiv.), rt, 2 h Chemical Formula: C24H19Cl2NO2
Molecular Weight: 424.32
S54

Chemical Formula: C24H19Cl2NO2
Molecular Weight: 424.32
S55

FIG. 23: Entry 12

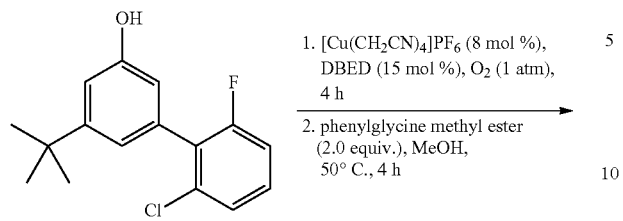

Chemical Formula: C$_{16}$H$_{16}$ClFO
Molecular Weight: 278.75

1. [Cu(CH$_2$CN)$_4$]PF$_6$ (8 mol %), DBED (15 mol %), O$_2$ (1 atm), 4 h
2. phenylglycine methyl ester (2.0 equiv.), MeOH, 50° C., 4 h

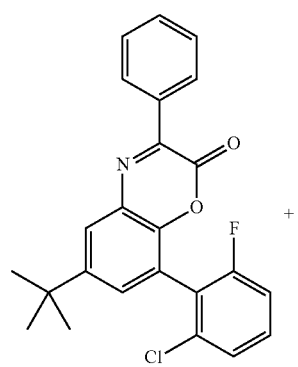

Chemical Formula: C$_{24}$H$_{19}$ClFNO$_2$
Molecular Weight: 407.87
S56

+

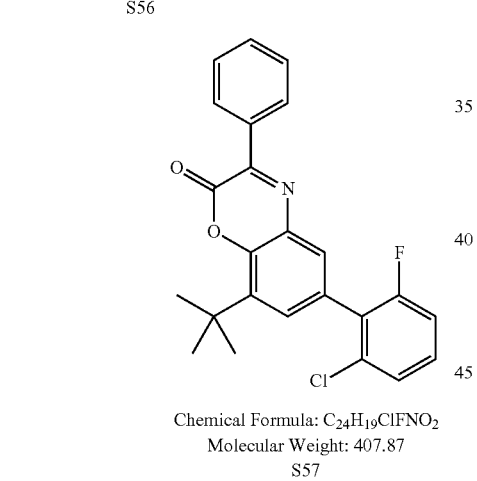

Chemical Formula: C$_{24}$H$_{19}$ClFNO$_2$
Molecular Weight: 407.87
S57

FIG. 23: Entry 13

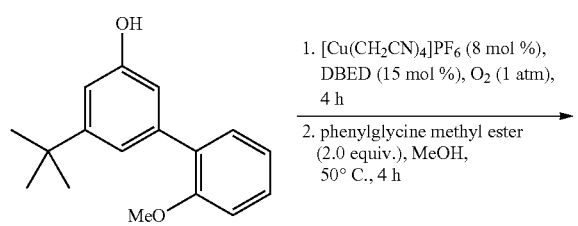

Chemical Formula: C$_{17}$H$_{20}$O$_2$
Molecular Weight: 256.35

1. [Cu(CH$_2$CN)$_4$]PF$_6$ (8 mol %), DBED (15 mol %), O$_2$ (1 atm), 4 h
2. phenylglycine methyl ester (2.0 equiv.), MeOH, 50° C., 4 h -continued

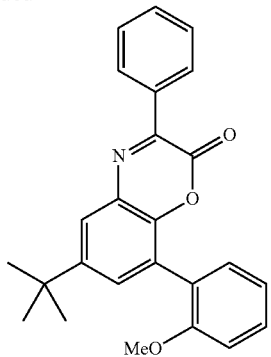

Chemical Formula: C$_{25}$H$_{23}$NO$_3$
Molecular Weight: 385.46

FIG. 23: Entry 14

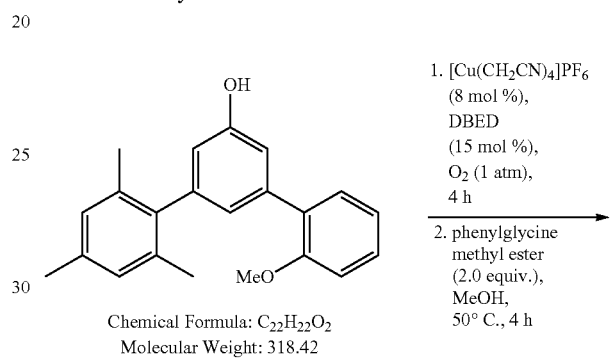

Chemical Formula: C$_{22}$H$_{22}$O$_2$
Molecular Weight: 318.42

1. [Cu(CH$_2$CN)$_4$]PF$_6$ (8 mol %), DBED (15 mol %), O$_2$ (1 atm), 4 h
2. phenylglycine methyl ester (2.0 equiv.), MeOH, 50° C., 4 h

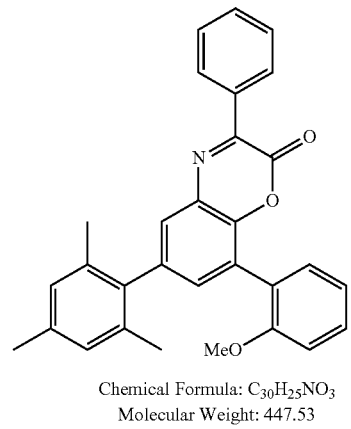

Chemical Formula: C$_{30}$H$_{25}$NO$_3$
Molecular Weight: 447.53

The following compounds were produced according to general procedure E:

FIG. 23: Entry 15

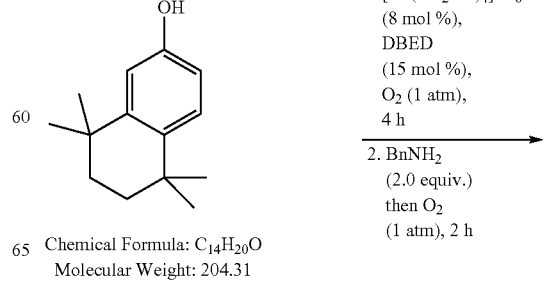

Chemical Formula: C$_{14}$H$_{20}$O
Molecular Weight: 204.31

1. [Cu(CH$_2$CN)$_4$]PF$_6$ (8 mol %), DBED (15 mol %), O$_2$ (1 atm), 4 h
2. BnNH$_2$ (2.0 equiv.) then O$_2$ (1 atm), 2 h -continued

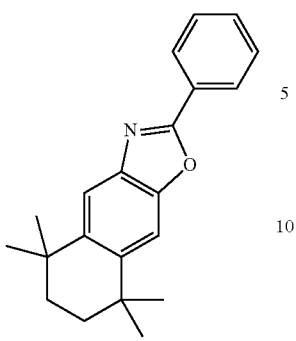

Chemical Formula: $C_{21}H_{23}NO$
Molecular Weight: 305.42

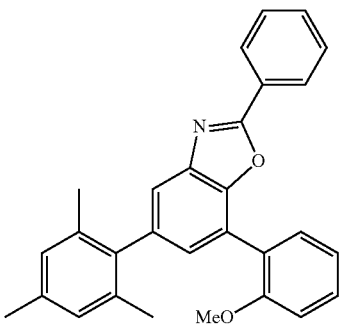

Chemical Formula: $C_{29}H_{25}NO_2$
Molecular Weight: 419.52
S60

Scheme 9a

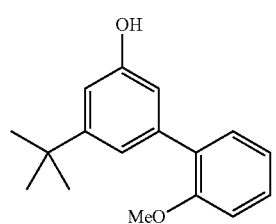

Chemical Formula: $C_{17}H_{20}O_2$
Molecular Weight: 256.35

1. [Cu(CH$_2$CN)$_4$]PF$_6$ (8 mol %), DBED (15 mol %), O$_2$ (1 atm), 4 h
2. BnNH$_2$ (2.0 equiv.) then O$_2$ (1 atm), 2 h
→

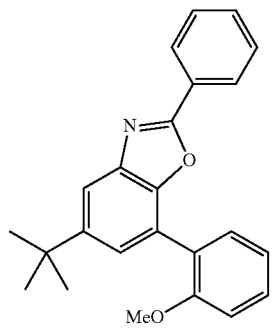

Chemical Formula: $C_{24}H_{23}NO_2$
Molecular Weight: 357.45
S58

+

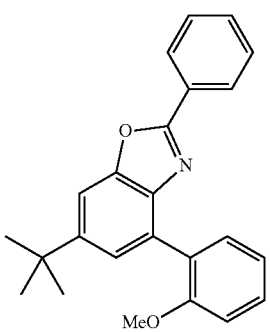

Chemical Formula: $C_{24}H_{23}NO_2$
Molecular Weight: 357.45
S59

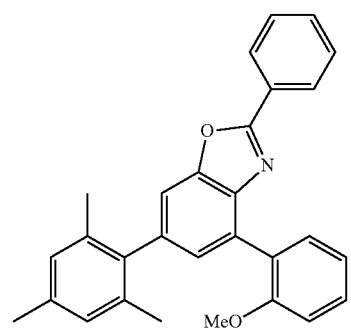

Chemical Formula: $C_{29}H_{25}NO_2$
Molecular Weight: 419.52
S61

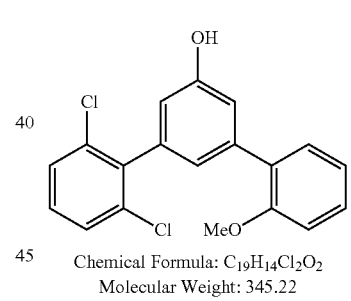

Chemical Formula: $C_{19}H_{14}Cl_2O_2$
Molecular Weight: 345.22

1. [Cu(CH$_2$CN)$_4$]PF$_6$ (8 mol %), DBED (15 mol %), O$_2$ (1 atm), 4 h
2. BnNH$_2$ (2.0 equiv.) then O$_2$ (1 atm), 2 h
→

Scheme 9b

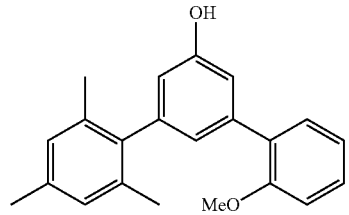

Chemical Formula: $C_{22}H_{22}O_2$
Molecular Weight: 318.42

1. [Cu(CH$_2$CN)$_4$]PF$_6$ (8 mol %), DBED (15 mol %), O$_2$ (1 atm), 4 h
2. BnNH$_2$ (2.0 equiv.) then O$_2$ (1 atm), 2 h
→

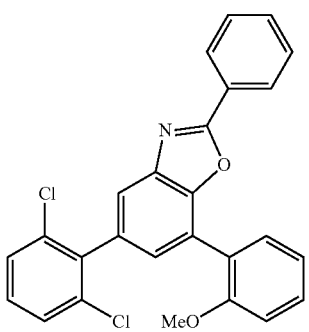

Chemical Formula: $C_{26}H_{17}Cl_2NO_2$
Molecular Weight: 446.33
S62

+

-continued

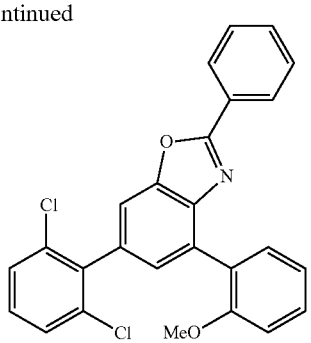

Chemical Formula: C₂₆H₁₇Cl₂NO₂
Molecular Weight: 446.33
S63

Confirmation of Regiochemistry:

3,5-Di-Substituted Phenols

As can be seen in FIG. 24: (a) 3,5-Di-Substituted phenols, 19 and 20, afford two regio-wasomeric quinones resulting in two benzoxazoles; and (b) 29 produces one quinone intermediate and produces one benzoxazole wasomer.

General Procedure L (Ortho-Oxygenation)

A flame-dried, 25-mL Radley tube, equipped with a Teflon-coated stir bar and a rubber septum, was charged with phenol (1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with [Cu(CH₃CN)₄](PF₆) (29.8 mg, 0.08 mmol, 0.08 equiv.), N,N'-di-tert-butylethelenediamine (25.8 mg, 32.3 μL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, quenched by the addition of NaHSO₄ (20 mL, 10% by weight aqueous solution), phases were separated, and the aqueous phase was extracted with $CH_2Cl_2$ (3×20 mL). The combined organic fractions were then dried over MgSO₄, filtered and concentrated in vacuo to afford a residue which was analyzed directly by ¹H-NMR. The crude reaction mixture was then purified using a Biotage Isolera™ One (15% EtOAc in hexanes) to afford the quinone product.

The following compounds were produced according to general procedure L:

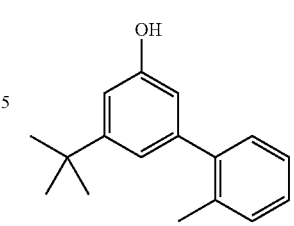

Chemical Formula: C₁₇H₂₀O
Molecular Weight: 240.35

[Cu(CH₂CN)₄]PF₆ (8 mol%),
DBED (15 mol%), O₂ (1 atm),
rt, 4 h

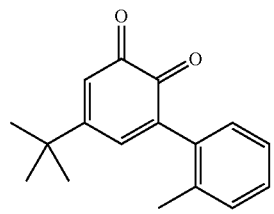

Chemical Formula: C₁₇H₁₈O₂
Molecular Weight: 254.33

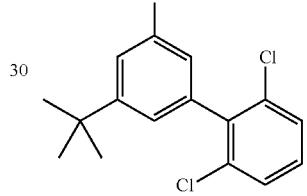

Chemical Formula: C₁₆H₁₆Cl₂O
Molecular Weight: 295.20

[Cu(CH₂CN)₄]PF₆ (8 mol%),
DBED (15 mol%), O₂ (1 atm),
rt, 4 h

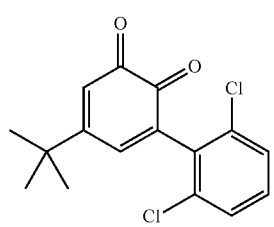

Chemical Formula: C₁₆H₁₄Cl₂O₂
Molecular Weight: 309.19

+

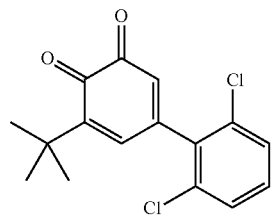

Chemical Formula: C₁₆H₁₄Cl₂O₂
Molecular Weight: 309.19

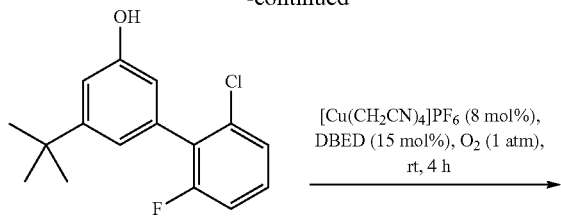

Chemical Formula: C₁₆H₁₆ClFO
Molecular Weight: 278.75

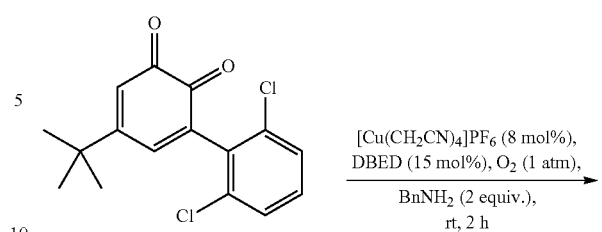

Chemical Formula: C₁₆H₁₄Cl₂O₂
Molecular Weight: 309.19

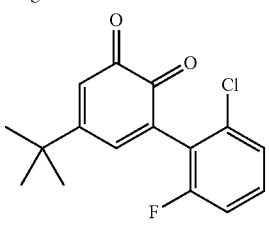

Chemical Formula: C₁₆H₁₄ClFO₂
Molecular Weight: 292.73

+

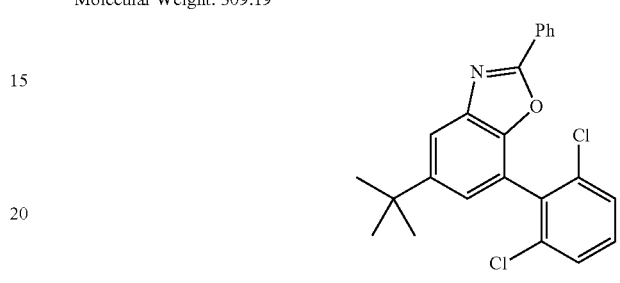

Chemical Formula: C₂₃H₁₉Cl₂NO
Molecular Weight: 396.31

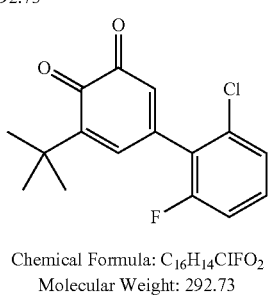

Chemical Formula: C₁₆H₁₄ClFO₂
Molecular Weight: 292.73

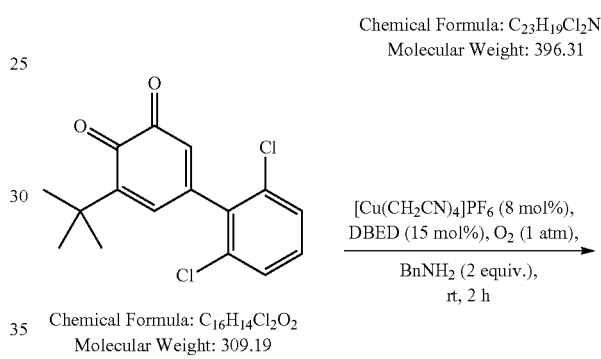

Chemical Formula: C₁₆H₁₄Cl₂O₂
Molecular Weight: 309.19

General Procedure M (Ortho-Quinone to Benzoxazole)

A flame-dried, 25-mL Radley tube, equipped with a Teflon-coated stir bar and a rubber septum, was charged with quinone (1.0 mmol, 1.0 equiv.), [Cu(CH₃CN)₄](PF₆) (29.8 mg, 0.08 mmol, 0.08 equiv.), and CH₂Cl₂ (10 mL). The reaction vessel was then purged with a steady stream of N₂ for 2 min prior to the addition of N,N'-di-tert-butylethelenediamine (25.8 mg, 32.3 µL, 0.15 mmol, 0.15 equiv.) and benzylamine (214.3 mg, 2.0 mmol, 2.0 equiv.). The rubber septum was then rapidly removed and replaced with a Radley cap, which was connected to a tank of I₂ and pressurized to 1 atm. Under a constant O₂ pressure (1 atm), the reaction was vented 3 times for 10 s to eliminate N₂. The reaction mixture was then stirred at room temperature for 2 h, depressurized by opening to the atmosphere, quenched by the addition of NaHSO₄ (20 mL, 10% by weight aqueous solution), phases were separated, and the aqueous phase was extracted with CH₂Cl₂ (3×20 mL). The combined organic fractions were then dried over MgSO₄, filtered and concentrated in vacuo to afford a residue which was analyzed directly by ¹H-NMR. The crude reaction mixture was then purified using a Biotage Isolera™ One (15% EtOAc in hexanes) to afford the benzoxazole product.

The following compounds were produced according to general procedure M:

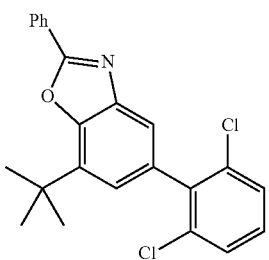

Chemical Formula: C₂₃H₁₉Cl₂NO
Molecular Weight: 396.31

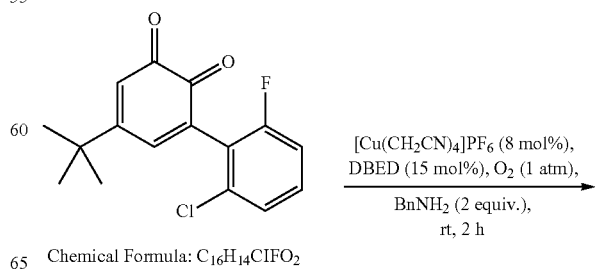

Chemical Formula: C₁₆H₁₄ClFO₂
Molecular Weight: 292.73

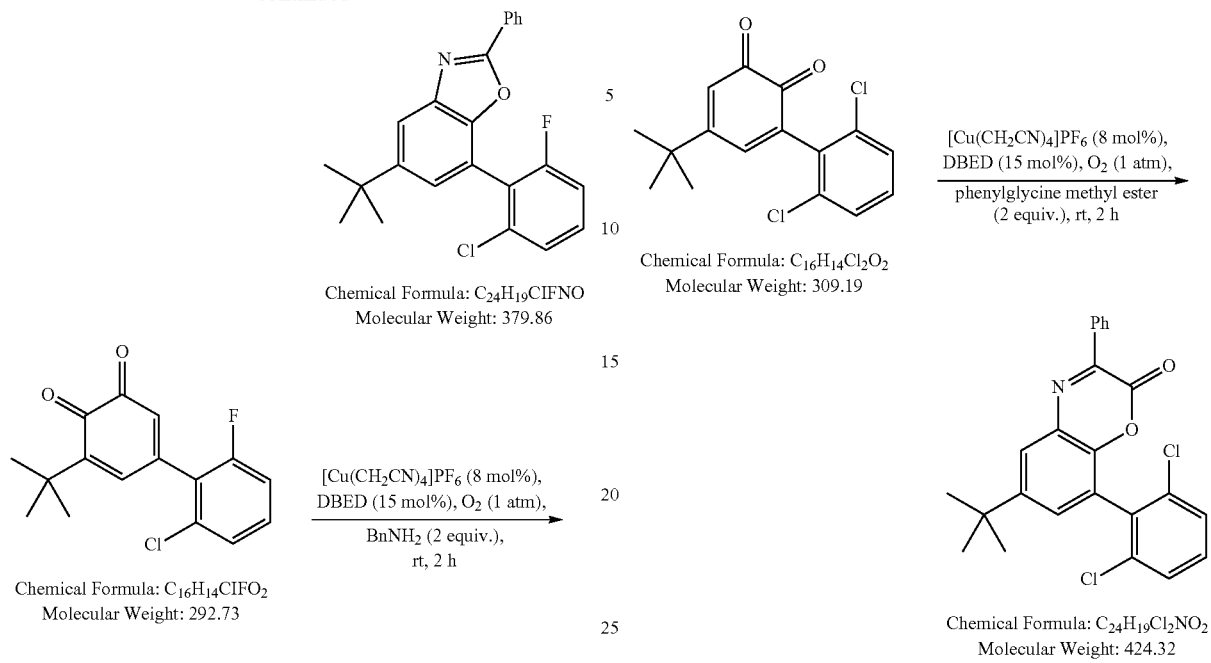

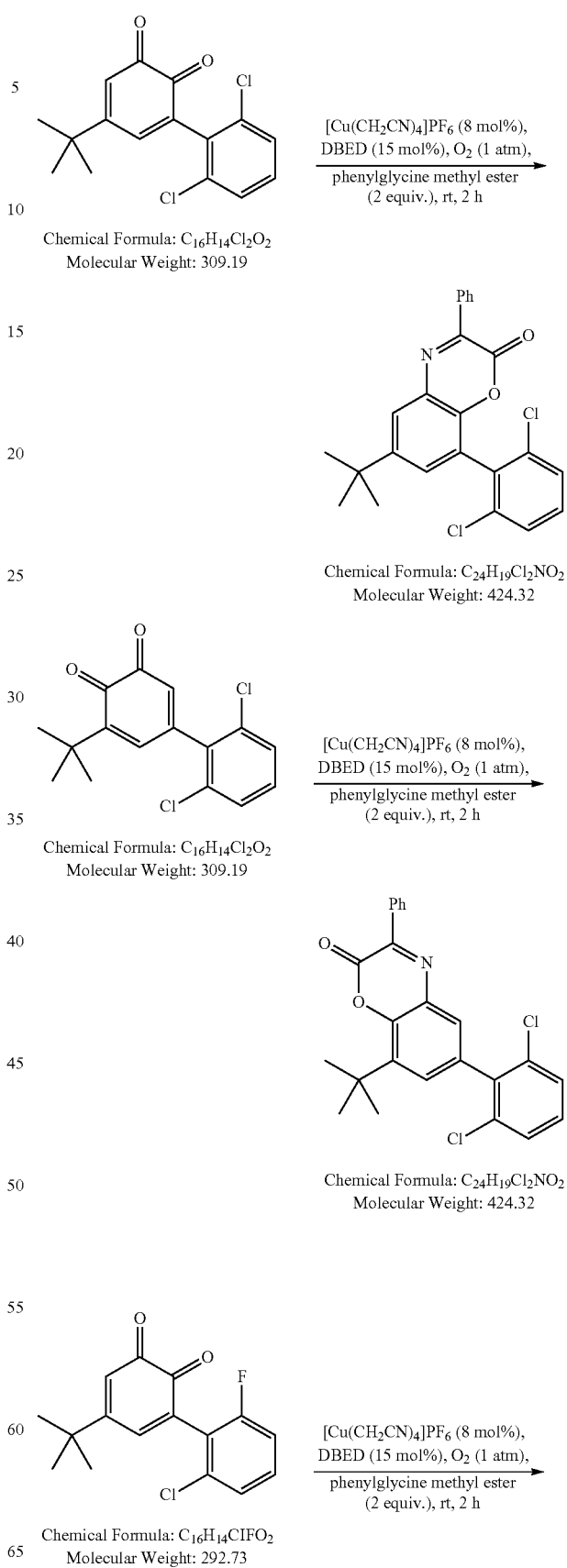

General Procedure N (Ortho-Quinone to Benzoxazinone)

A flame-dried, 25-mL round bottom flask, equipped with a Teflon-coated stir bar and a rubber septum, was charged with the quinone (1.0 mmol, 1.0 equiv.), phenylglycine methyl ester (330.4 g, 2.0 mmol, 2.0 equiv.), and $CH_2Cl_2$:MeOH (1:1, v/v, 10 mL). The reaction vessel was capped, and was purged with a steady stream of $N_2$ for 2 min to eliminate $O_2$. The reaction mixture was then stirred 50° C. for 4 h, quenched by the addition of $NaHSO_4$ (20 mL, 10% by weight aqueous solution), phases were separated, and the aqueous phase was extracted with $CH_2Cl_2$ (3×20 mL). The combined organic fractions were then dried over $MgSO_4$, filtered and concentrated in vacuo to afford a residue which was analyzed directly by $^1$H-NMR. The crude reaction mixture was then purified using a Biotage Isolera™ One (10% EtOAc in hexanes) to afford the benzoxazinone product.

The following compounds were produced according to general procedure N:

-continued

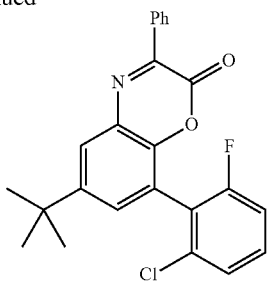

Chemical Formula: C$_{24}$H$_{19}$ClFNO$_2$
Molecular Weight: 407.87

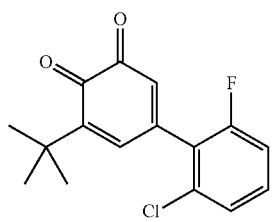

Chemical Formula: C$_{16}$H$_{14}$ClFO$_2$
Molecular Weight: 292.73

[Cu(CH$_2$CN)$_4$]PF$_6$ (8 mol%),
DBED (15 mol%), O$_2$ (1 atm),
phenylglycine methyl ester
(2 equiv.), rt, 2 h
→

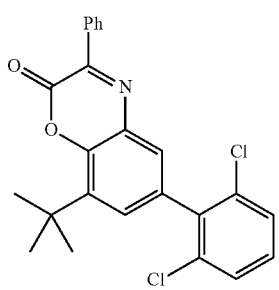

Chemical Formula: C$_{24}$H$_{19}$Cl$_2$NO$_2$
Molecular Weight: 424.32

Intramolecular Cyclization to Benzoxazole

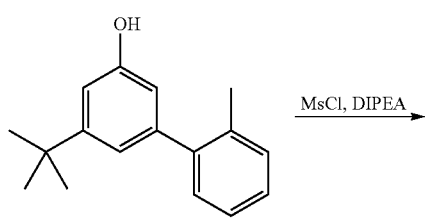

Chemical Formula: C$_{17}$H$_{20}$O
Molecular Weight: 240.35

MsCl, DIPEA →

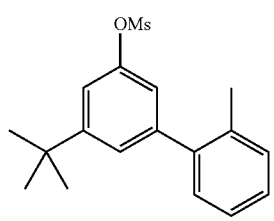

Chemical Formula: C$_{18}$H$_{22}$O$_3$S
Molecular Weight: 318.43

A flame-dried 50-mL round bottom flask, equipped with a Teflon coated stir bar, was charged with phenol 29 (240.4 mg, 1 mmol, 1.0 equiv.) and CH$_2$CL$_2$ (20 mL). Using a syringe, methanesulfonyl chloride (116 μL, 171.8 mg, 1.5 mmol, 1.5 equiv.) and N,N-diwasopropylethylamine (350 μL, 258.0 mg, 2.0 mmol, 2.0 equiv.) were added, and the reaction mixture was stirred overnight at room temperature. Then, the reaction mixture was quenched by the addition of distilled H$_2$O (20 mL), and diluted with EtOAc (100-mL). Then, the phases were separated and the organic phase was washed with brine (3×50-mL). The organic fraction was dried over MgSO$_4$, filtered and concentrated in vacuo to afford a crude residue, which was purified using flash column chromatography (silica gel with 15% EtOAc in hexanes as eluant) to afford a white powder in 99% isolated yield.

Chemical Formula: C$_{18}$H$_{22}$O$_3$S
Molecular Weight: 318.43

Pd(OAc)$_2$ (1 mol %),
tBuBrettPhos (2.2 mol %),
Cs$_2$CO$_3$ (1.4 equiv.),
benzamide (1.4 equiv.),
H$_2$O (8 mo %),
110° C., 12 h
→

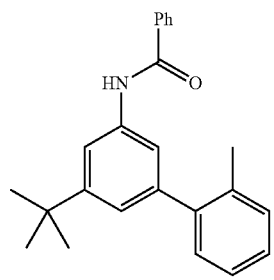

Chemical Formula: C$_{24}$H$_{25}$NO
Molecular Weight: 343.47

SXX was synthesized using a modified procedure reported by Buchwald et al.: Dooleweerdt, K.; Fors, B. P.; Buchwald, S. L. Org. Lett. (2010), 12, 2350-2353. A flame-dried 25-mL pressure vessel, equipped with a Teflon coated stir bar, was charged with mesylate (318.4 mg, 1.0 mmol, 1 equiv.), Pd(OAc)$_2$ (2.2 mg, 0.01 mmol, 1.0 mol %), tBu-BrettPhos (10.7 mg, 0.022 mmol, 2.2 mol %), Cs$_2$CO$_3$ (456.1 mg, 1.4 mmol, 1.4 equiv.), benzamide (170.0 mg, 1.4 mmol, 1.4 equiv.) distilled H$_2$O (2.0 μL, 0.08 mmol, 8 mol %) and tert-butanol (15 mL). The reaction mixture was sealed and stirred overnight at 110° C. Then, the reaction mixture was quenched by the addition of distilled H$_2$O (20 mL), and diluted with EtOAc (100-mL). Then, the phases were separated and the organic phase was washed with brine (3×50-mL). The organic fraction was dried over MgSO$_4$, filtered and concentrated in vacuo to afford a crude residue, which was purified using flash column chromatography (silica gel with 20% EtOAc in hexanes as eluant) to afford a white powder in 75% isolated yield.

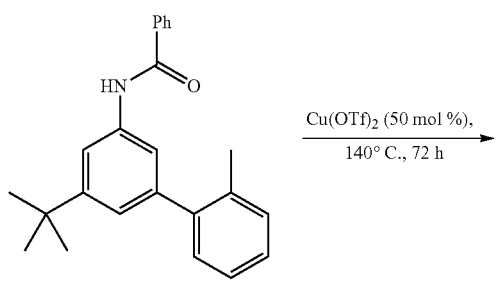

Chemical Formula: C$_{24}$H$_{25}$NO
Molecular Weight: 343.47

Cu(OTf)$_2$ (50 mol %),
140° C., 72 h

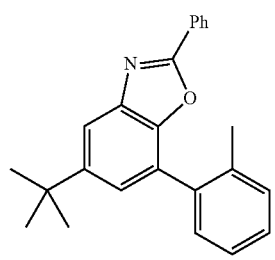

Chemical Formula: C$_{24}$H$_{23}$NO
Molecular Weight: 341.45

Phenols were synthesized using a modified procedure reported by Nagasawa et al.: Ueda, S.; Nagasawa, H. Angew. Chem. Int. Ed. (2008), 129, 6511-6513 A flame-dried 25-mL Radley tube, equipped with a Teflon coated stir bar, was charged with 32 (100 mg, 0.29 mmol, 1 equiv.), Cu(OTf)$_2$ (52.6 mg, 0.3 mmol, 50 mol %), o-xylene (1.0 mL). The reaction vessel was capped, pressurized with O$_2$ (1 atm) and heated to 140° C. whilst stirring for 3 days (72 h). The reaction mixture was depressurized, cooled to room temperature and diluted with distilled H$_2$O (20 mL) and CH$_2$Cl$_2$ (30 mL). The phases were then separated and the aqueous phase was extracted with CH$_2$Cl$_2$ (3×20 mL). The combined organic fractions were then dried over MgSO$_4$, filtered and concentrated in vacuo to afford a crude residue, which was purified using flash column chromatography (5% EtOAc in hexanes) to afford SXX (61.6 mg, 0.18 mmol) compound in 62% yield.

3,5-Di-Substituted Phenols with Ortho-Methoxyphenyl Substituent

Substrates with ortho-methoxy phenyl substituent produce a single ortho-quinone intermediate, but generates two regioisomeric benzoxazoles. This suggest that the amine condenses with both carbonyl moiety, but shows preference with the least hindered carbonyl.

See FIG. 1: Confirmation of regiochemwastry for phenols with 3-(ortho-methoxy) phenyl substituent Ortho-Oxygenation

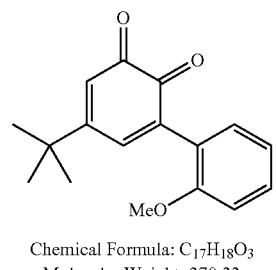

Chemical Formula: C$_{17}$H$_{18}$O$_3$
Molecular Weight: 270.33

The synthesis was carried out in accordance with general procedure L using 33 (256.3 mg, 1.0 mmol, 1.0 equiv) to afford the pure product in 78% isolated yield.

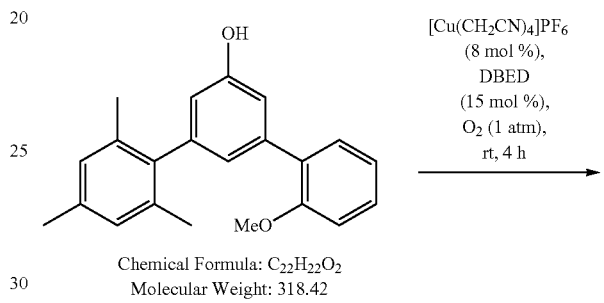

Chemical Formula: C$_{22}$H$_{22}$O$_2$
Molecular Weight: 318.42

[Cu(CH$_2$CN)$_4$]PF$_6$
(8 mol %),
DBED
(15 mol %),
O$_2$ (1 atm),
rt, 4 h

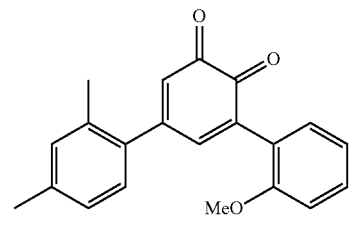

Chemical Formula: C$_{22}$H$_{20}$O$_3$
Molecular Weight: 332.40

The synthesis was carried out in accordance with general procedure L using S25 (318.4 mg, 1.0 mmol, 1.0 equiv) to afford the pure product in 92% isolated yield.

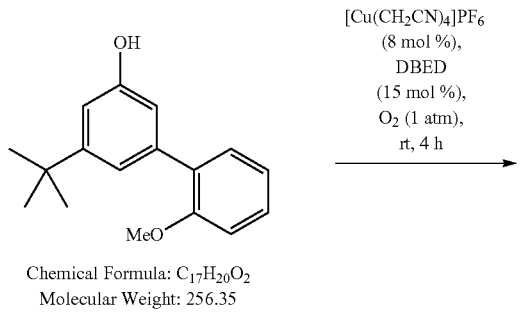

Chemical Formula: C$_{17}$H$_{20}$O$_2$
Molecular Weight: 256.35

[Cu(CH$_2$CN)$_4$]PF$_6$
(8 mol %),
DBED
(15 mol %),
O$_2$ (1 atm),
rt, 4 h

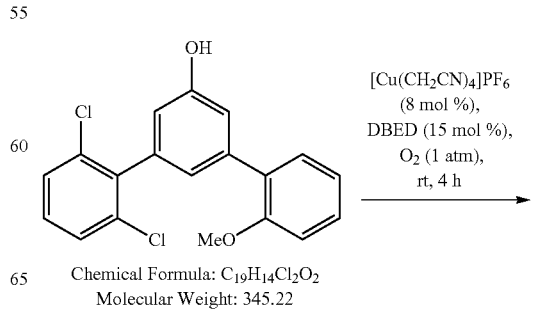

Chemical Formula: C$_{19}$H$_{14}$Cl$_2$O$_2$
Molecular Weight: 345.22

[Cu(CH$_2$CN)$_4$]PF$_6$
(8 mol %),
DBED (15 mol %),
O$_2$ (1 atm),
rt, 4 h

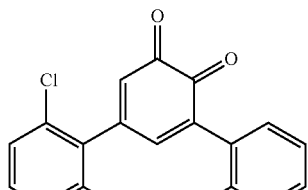

Chemical Formula: C₁₉H₁₂Cl₂O₃
Molecular Weight: 359.20

The synthesis was carried out in accordance with general procedure L using S24 (345.2 mg, 1.0 mmol, 1.0 equiv) to afford the pure product in 81% isolated yield.

Ortho-Quinone to Benzoxazole

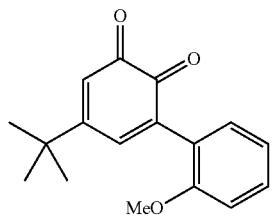

Chemical Formula: C₁₇H₁₈O₃
Molecular Weight: 270.33

[Cu(CH₂CN)₄]PF₆ (8 mol %), DBED (15 mol %), O₂ (1 atm), BnNH₂ (2 equiv.), rt, 2 h

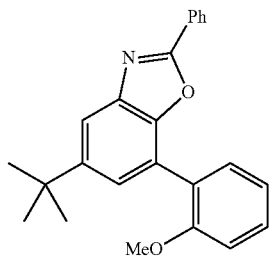

Chemical Formula: C₂₄H₂₃NO₂
Molecular Weight: 357.45

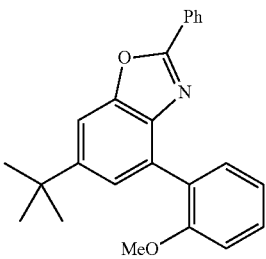

Chemical Formula: C₂₄H₂₃NO₂
Molecular Weight: 357.45

The synthesis was carried out in accordance with general procedure N using 33 (270.3 mg, 1.0 mmol, 1.0 equiv) to afford a mixture of 34 and 35 (60:40) in 92% isolated yield.

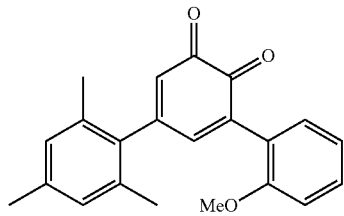

Chemical Formula: C₂₂H₂₀O₃
Molecular Weight: 332.40
S61

[Cu(CH₂CN)₄]PF₆ (8 mol %), DBED (15 mol %), O₂ (1 atm), BnNH₂ (2 equiv.), rt, 2 h

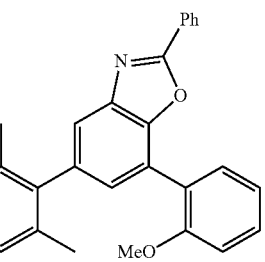

Chemical Formula: C₂₉H₂₅NO₂
Molecular Weight: 419.52
S62

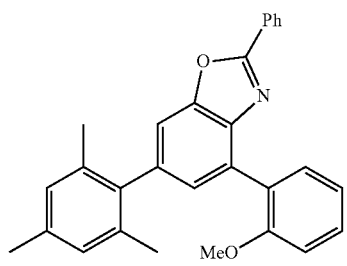

Chemical Formula: C₂₉H₂₅NO₂
Molecular Weight: 419.52
S63

The synthesis was carried out in accordance with general procedure M using S61 (332.4 mg, 1.0 mmol, 1.0 equiv) to afford a mixture of S62 and S63 (60:40) in 88% isolated yield.

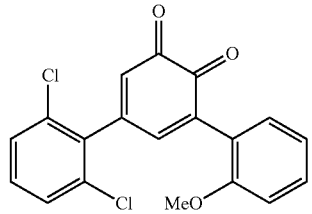

Chemical Formula: C₁₉H₁₂Cl₂O₃
Molecular Weight: 359.20
S64

[Cu(CH₂CN)₄]PF₆ (8 mol %), DBED (15 mol %), O₂ (1 atm), BnNH₂ (2 equiv.), rt, 2 h

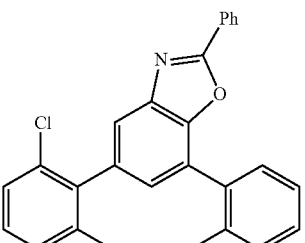

Chemical Formula: C₂₆H₁₇Cl₂NO₂
Molecular Weight: 446.33
S65

-continued

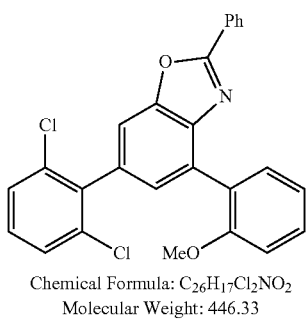

Chemical Formula: C$_{26}$H$_{17}$Cl$_2$NO$_2$
Molecular Weight: 446.33
S66

The synthesis was carried out in accordance with general procedure S64 using S24 (359.2 mg, 1.0 mmol, 1.0 equiv) to afford a mixture of S65 and S66 (60:40) in 89% isolated yield.

Intramolecular Cyclization

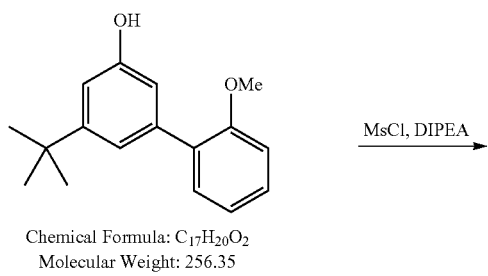

Chemical Formula: C$_{17}$H$_{20}$O$_2$
Molecular Weight: 256.35

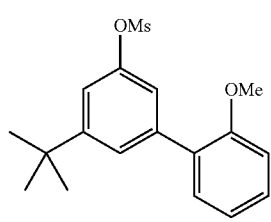

Chemical Formula: C$_{18}$H$_{22}$O$_4$S
Molecular Weight: 334.43

A flame-dried 50-mL round bottom flask, equipped with a Teflon coated stir bar, was charged with phenol 33 (256.4 mg, 1.0 mmol, 1 equiv.) and CH$_2$CL$_2$ (20 mL). Using a syringe, methanesulfonyl chloride (116 µL, 171.8 g, 1.5 mmol, 1.5 equiv.) and N,N-diwasopropylethylamine (350 µL, 258.5 mg, 2.0 mmol, 2.0 equiv.) were added, and the reaction mixture was stirred overnight at room temperature. Then, the reaction mixture was quenched by the addition of distilled H$_2$O (20 mL), and diluted with EtOAc (100-m L). Then, the phases were separated and the organic phase was washed with brine (3×50-mL). The organic fraction was dried over MgSO$_4$, filtered and concentrated in vacuo to afford a crude residue, which was purified using flash column chromatography (silica gel with 20% EtOAc in hexanes as eluant) to afford a white powder in 99% isolated yield.

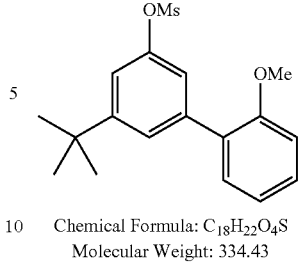

Chemical Formula: C$_{18}$H$_{22}$O$_4$S
Molecular Weight: 334.43

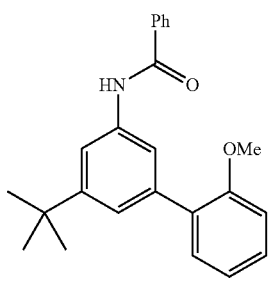

Pd(OAc)$_2$ (1 mol %),
tBuBrettPhos (2.2 mol %),
Cs$_2$CO$_3$ (1.4 equiv.),
benzamide (1.4 equiv.),
H$_2$O (8 mo %), 110° C.,
12 h Chemical Formula: C$_{24}$H$_{25}$NO$_2$
Molecular Weight: 359.47

SXX was synthesized using a modified procedure reported by Buchwald et al.: Dooleweerdt, K.; Fors, B. P.; Buchwald, S. L. Org. Lett. (2010), 12, 2350-2353. A flame-dried 25-mL pressure vessel, equipped with a Teflon coated stir bar, was charged with mesylate (256.4 mg, 1.0 mmol, 1 equiv.), Pd(OAc)$_2$ (2.2 mg, 0.01 mmol, 1.0 mol %), tBu-BrettPhos (10.7 mg, 0.022 mmol, 2.2 mol %), Cs$_2$CO$_3$ (456.1 mg, 1.4 mmol, 1.4 equiv.), benzamide (170.0 mg, 1.4 mmol, 1.4 equiv.) distilled H$_2$O (2.0 µL, 0.08 mmol, 8 mol %) and tert-butanol (15 mL). The reaction mixture was sealed and stirred overnight at 110° C. Then, the reaction mixture was quenched by the addition of distilled H$_2$O (20 mL), and diluted with EtOAc (100-mL). Then, the phases were separated and the organic phase was washed with brine (3×50-mL). The organic fraction was dried over MgSO$_4$, filtered and concentrated in vacuo to afford a crude residue, which was purified using flash column chromatography (silica gel with 20% EtOAc in hexanes as eluant) to afford a white powder in 71% isolated yield.

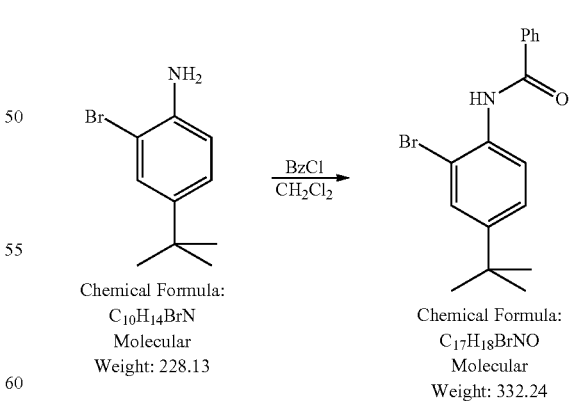

Chemical Formula:
C$_{10}$H$_{14}$BrN
Molecular Weight: 228.13

Chemical Formula:
C$_{17}$H$_{18}$BrNO
Molecular Weight: 332.24

2-bromo-4-tert-butylaniline S67 was synthesized according to literature procedure: Chi, Y., Clifford, J. N.; Chou, P.-T. et al. Angew. Chem. Int. Ed. (2014), 53, 178-183.

A flame-dried 50-mL pressure vessel, equipped with a Teflon stir bar, was charged with aniline S67 (2.0 g, 8.77 mmol, 1 equiv.) and CH$_2$Cl$_2$ (50-mL). The reaction mixture was cooled to 0° C., followed by the dropwise addition of benzoyl chloride (1.48 g, 10.5 mmol, 1.2 equiv.), and the resulting reaction mixture was stirred at room temperature for 12 h. The reaction mixture was quenched by the addition of distilled H$_2$O (100-mL), and the phases were separated. The aqueous phase was washed with CH$_2$Cl$_2$ (3×50-mL). The combined organic fractions were dried over MgSO$_4$, filtered and concentrated in vacuo to afford a crude residue, which was purified using flash column chromatography (silica gel with 15% EtOAc in hexanes as eluant) to afford a white powder in 99% isolated yield.

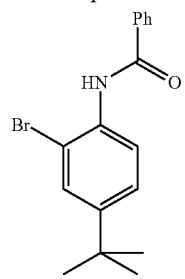

Chemical Formula: C$_{17}$H$_{18}$BrNO
Molecular Weight: 332.24

(Ph$_3$P)$_2$PdCl$_2$ (10 mo %),
MeCN:H$_2$O (1:1),
o-tolueneboronic acid
(1.5 equiv),
K$_2$CO$_3$ (2 equiv.),
100° C., 12 h

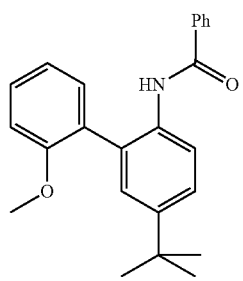

Chemical Formula: C$_{24}$H$_{25}$NO$_2$
Molecular Weight: 359.47

A flame-dried 50-mL pressure vessel, equipped with a Teflon stir bar, was charged with anilide (1.0 g, 3.0 mmol, 1 equiv.), (Ph$_3$P)$_2$PdCl$_2$ (211.3 mg, 0.3 mmol, 10 mol %), o-tolueneboronic acid (613.8 mg, 4.51 mmol, 1.5 equiv.), K$_2$CO$_3$ (2 equiv.), and degassed MeCN:H$_2$O (50-mL). The reaction mixture was capped, and stirred at 100° C. for 12 h. Then, the reaction was quenched with H$_2$O (20 mL), diluted with EtOAc (50-mL), phases were separated, and the aqueous phase was washed with EtOAc (3×50-mL). The combined organic fractions were dried over MgSO$_4$, filtered and concentrated in vacuo to afford a crude residue, which was purified using flash column chromatography (silica gel with 10% EtOAc in hexanes as eluant) to afford a white powder in 80% isolated yield.

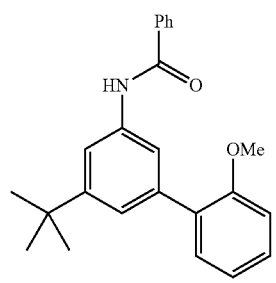

Chemical Formula: C$_{24}$H$_{25}$NO$_2$
Molecular Weight: 359.47

Cu(OTf)$_2$ (50 mol %),
140° C., 72 h

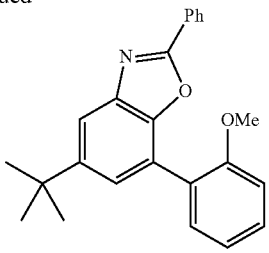

Chemical Formula: C$_{24}$H$_{23}$NO$_2$
Molecular Weight: 357.45

Phenols were synthesized using a modified procedure reported by Nagasawa et al.: Ueda, S.; Nagasawa, H. Angew. Chem. Int. Ed. (2008), 129, 6511-6513. A flame-dried 25-mL Radley tube, equipped with a Teflon coated stir bar, was charged with 36 (50 mg, 0.14 mmol, 1 equiv.), Cu(OTf)$_2$ (25 mg, 0.070 mmol, 50 mol %), o-xylene (0.5 mL). The reaction vessel was capped, pressurized with O$_2$ (1 atm) and heated to 140° C. whilst stirring for 3 days (72 h). The reaction mixture was depressurized, cooled to room temperature and diluted with distilled H$_2$O (20 mL) and CH$_2$Cl$_2$ (30 mL). The phases were then separated and the aqueous phase was extracted with CH$_2$Cl$_2$ (3×20 mL). The combined organic fractions were then dried over MgSO$_4$, filtered and concentrated in vacuo to afford a crude residue, which was purified using flash column chromatography (5% EtOAc in hexanes) to afford SXX compound in 51% yield.

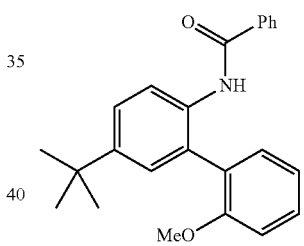

Chemical Formula: C$_{24}$H$_{25}$NO$_2$
Molecular Weight: 359.47

Cu(OTf)$_2$ (50 mol %),
140° C., 72 h

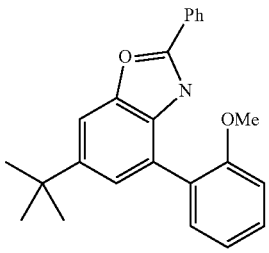

Chemical Formula: C$_{24}$H$_{23}$NO$_2$
Molecular Weight: 357.45

Phenols were synthesized using a modified procedure reported by Nagasawa et al: Ueda, S.; Nagasawa, H. Angew. Chem. Int. Ed. (2008), 129, 6511-6513. A flame-dried 25-mL Radley tube, equipped with a Teflon coated stir bar, was charged with 37 (100 mg, 0.28 mmol, 1 equiv.), Cu(OTf)$_2$ (50.3 mg, 0.14 mmol, 50 mol %), o-xylene (0.5 mL). The reaction vessel was capped, pressurized with O$_2$ (1 atm) and heated to 140° C. whilst stirring for 3 days (72 h). The reaction mixture was depressurized, cooled to room temperature and diluted with distilled H$_2$O (20 mL) and $CH_2Cl_2$ (30 mL). The phases were then separated and the aqueous phase was extracted with $CH_2Cl_2$ (3×20 mL). The combined organic fractions were then dried over $MgSO_4$, filtered and concentrated in vacuo to afford a crude residue, which was purified using flash column chromatography (5% EtOAc in hexanes) to afford SXX compound in 77% yield.

Supporting Information Regarding Example 3

General Experimental

Chemicals and solvents were purchased from Sigma Aldrich, Alfa Aesar, Strem Chemicals or TCI. Solvents were dried and purified using a PureSolv MD 7 (from Innovative Technology) or MB SPS 800 (from MBraun). All phenol and amine substrates were purified prior to use: liquids were distilled using a Hickman apparatus immediately prior to use and solids were recrystallized. N,N'-di-tert-butylethylenedimaine (DBED) were distilled over $CaH_2$ under $N_2$. [Cu(MeCN)$_4$](PF$_6$) was purchased from Sigma Aldrich or Strem. Unless otherwise noted, reactions were performed in flame-dried glassware under a positive pressure of $N_2$ using standard synthetic organic, inert atmosphere techniques. All oxidation reactions were set-up in flame-dried, 25-mL Radley tubes with a Teflon-coated stir bar under a nitrogen atmosphere (Praxair, $N_2$ pre-purified). The reaction vessels were then connected to a cylinder of $O_2$ (Praxair), purged three times with $O_2$ and then pressurized to +1.0 atm (see experimental section for details).

Proton and carbon nuclear magnetic resonance ($^1$H NMR and $^{13}$C NMR) spectra were acquired using Varian Inova 400 MHz, Varian Mercury 300 MHz spectrometers, Bruker 400 MHz, and Bruker 500 MHz. Chemical shifts (δ) are reported in parts per million (ppm) and are calibrated to the residual solvent peak. Coupling constants (J) are reported in Hz. Multiplicities are reported using the following abbreviations: s=singlet; d=doublet; t=triplet; q=quartet; m=multiplet (range of multiplet was given). Carbon nuclear magnetic resonance ($^{13}$C NMR) spectra were acquired using Varian Inova 100 MHz and Varian Mercury 75 MHz spectrometers. Chemical shifts (δ) are reported in parts per million (ppm) and are calibrated to the residual solvent peak. High resolution mass spectra (HRMS) were recorded using a Bruker maXis Impact TOF mass spectrometer. Fourier-transform infrared (FT-IR) spectra were recorded on a Perkin-Elmer FT-IR ATR spectrometer.

Analytical thin-layer chromatography was performed on pre-coated 250 □m layer thickness silica gel 60 $F_{254}$ plates (EMD Chemicals Inc.). Visualization was performed by ultraviolet light and/or by staining with potassium permanganate or iodine. Purifications by column chromatography were performed using either a Biotage Isolera™ One (Snap Ultra, particle size 25 μm, 230-400 mesh), or standard column chromatography using silica gel (40-63 μm, 230-400 mesh).
Synthesis of Phenolic Synthesis of Phenolic Substrates

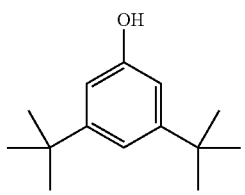

S1

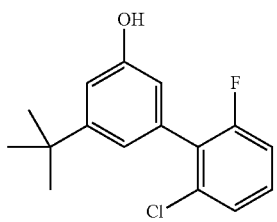

S2

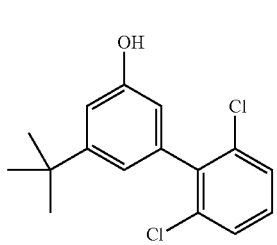

S3

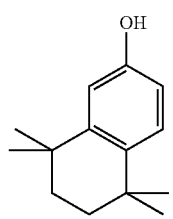

S4

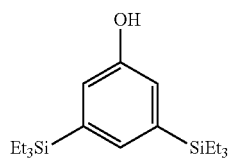

S5

Phenolic substrates (S1-S5) were synthesized according to procedures outlined in manuscript entitled, "A General Platform for the Synthesis of 1,2-Oxy-Amino Arenes by a Bio-Inspired Coupling of Phenols and Amines" K. V. N. Esguerra, W. Xu, and J. P. Lumb.

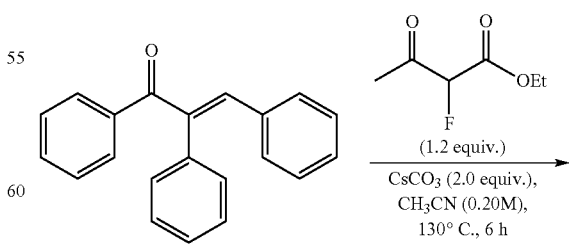

Chemical Formula: $C_{21}H_{16}O$
Molecular Weight: 284.36
S6

141
-continued

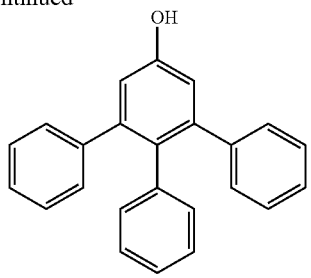

Chemical Formula: C$_{24}$H$_{18}$O
Molecular Weight: 322.41
S7

S6 was synthesized according to literature procedure: Lu, S. M.; Bolm, C. Angew. Chem. Int. Ed. (2008), 47, 8920-8923

A flame-dried 100-mL high-pressure vessel, equipped with a Teflon coated stir bar was charged with the appropriate S6 (2.0 g, 7.03 mmol, 1 equiv.), ethyl 2-fluoroacetoacetate (1.53 g, 8.44 mmol, 1.2 equiv.) cesium carbonate (4.58 g, 14.06 mmol, 2 equiv.), and degassed CH$_3$CN (35 mL, 0.2 M with respect to the chalcone). The reaction vessel was capped with a Teflon screw cap, and heated to 130° C. for 3 h. The reaction mixture was then cooled to room temperature, quickly depressurized, capped with a Teflon screw cap and heated to 130° C. for 3 h. Then, the reaction mixture was cooled to room temperature, quenched by the addition of H$_2$O (100 mL) and diluted with EtOAc (50 mL). The phases were then separated and the organic phase was extracted with NaHSO$_4$ (10% by weight aqueous solution, 3×20 mL). The organic fractions were then dried over MgSO$_4$, filtered and concentrated in vacuo to afford a crude residue, which was purified using flash column chromatography (15% EtOAc in hexanes) to afford a S7 in 71% isolated yield.

$^1$H NMR (500 MHz, CDCl$_3$): δ=7.15-7.13 (m, 7H), 7.07-7.05 (m, 5H), 6.96 (m, 3H), 6.93 (d, 2H), 5.24 (brs, 1H) ppm. $^{13}$C NMR (125 MHz, CDCl$_3$): δ=154.2, 143.5, 141.6, 139.2, 132.2, 131.9, 129.8, 127.5, 127.1, 126.3, 125.6, 116.3 ppm. Analytical data matches that reported in the literature: Li, C.; Zheng, Y; Zhang, H.; Feng, J.; Zhang, Y; Wang, J. Angew. Chem. Int. Ed. (2010), 49, 6413-6417.

Synthesis of Push-Pull Azophenols

General Procedure A

A flame-dried, 25-mL Radley tube, equipped with a Teflon-coated stir bar and a rubber septum, was charged with phenol (1.0 mmol, 1.0 equiv.). The reaction vessel was then purged with a steady stream of N$_2$ for 2 min prior to the addition of dry and degassed CH$_2$Cl$_2$ (8.0 mL). A separate, flame-dried test tube (16×125-mL) was charged with [Cu(CH$_3$CN)$_4$](PF$_6$) (29.8 mg, 0.08 mmol, 0.08 equiv.), N,N'-di-tert-butylethelenediamine (25.8 mg, 32.3 μL, 0.15 mmol, 0.15 equiv.), and CH$_2$Cl$_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of O$_2$ and pressurized to 1 atm. Under a constant O$_2$ pressure (1 atm), the reaction was vented 3 times for 10 s to eliminate N$_2$. The reaction mixture was then stirred at room temperature for 4 h, depressurized by opening to the atmosphere, and argon gas was bubbled through the reaction mixture for 2 minutes to eliminate O$_2$. Then, a solution of hydrazine or hydrazide (2 mmol, 2.0 equiv.) in MeOH (5 mL) was added to the reaction mixture via a syringe, and stirred for 4 h. The reaction mixture was quenched by the addition of NaHSO$_4$ (20 mL, 10% by weight aqueous solution), phases were separated, and the aqueous phase was extracted with CH$_2$Cl$_2$ (3×20 mL). The combined organic fractions were then dried over MgSO$_4$, filtered and concentrated in vacuo to afford a residue which was analyzed directly by $^1$H-NMR. The crude reaction mixture was then purified using a Biotage Isolera™ One (15% EtOAc in hexanes) to afford the azophenol product.

FIG. 31: Entry 1—Large Scale Synthesis:

A flame-dried, 500-mL Radley round-bottom flask, equipped with a Teflon-coated stir bar and a rubber septum, 3,5-di-tert-butylphenol (4.13 g, 20.0 mmol, 1.0 equiv.). The reaction vessel was then purged with a steady stream of N$_2$ for 5 min prior to the addition of dry and degassed CH$_2$Cl$_2$ (180 mL). A separate, flame-dried 25-mL round-bottom flask was charged with [Cu(CH$_3$CN)$_4$](PF$_6$) (570.0 mg, 1.60 mmol, 0.08 equiv.), N,N'-di-tert-butylethelenediamine (517.4 mg, 0.65 mL, 3.0 mmol, 0.15 equiv.), and CH$_2$Cl$_2$ (20 mL) to afford a homogeneous, pink solution. This solution was then added to the Radley tube via syringe to afford a final volume of 200 mL and a concentration of 0.1 M with respect to the phenol. The rubber septum was then rapidly removed and replaced with a Radley cap, which was connected to a tank of O$_2$ and pressurized to 1 atm. Under a constant O$_2$ pressure (1 atm), the reaction was vented 3 times for 10 s to eliminate N$_2$. The reaction mixture was then stirred at room temperature for 4 h, depressurized by opening to the atmosphere, and argon gas was bubbled through the reaction mixture for 2 minutes to eliminate O$_2$. Then, a solution of 2,4-dinitrophenylhydrazine (7.93 g, 40.0 mmol, 2.0 equiv.) in MeOH (50 mL) was added to the reaction mixture via a syringe, and stirred overnight. The reaction mixture was quenched by the addition of NaHSO$_4$ (100 mL, 10% by weight aqueous solution), phases were separated, and the aqueous phase was extracted with CH$_2$Cl$_2$ (3×100 mL). The combined organic fractions were then dried over MgSO$_4$, filtered and concentrated in vacuo to afford a residue which was analyzed directly by $^1$H-NMR. The crude reaction mixture was then purified using a Biotage Isolera™ One (15% EtOAc in hexanes) to afford S8 in 87% isolated yield.

Synthesis of Diazobenzoquinone

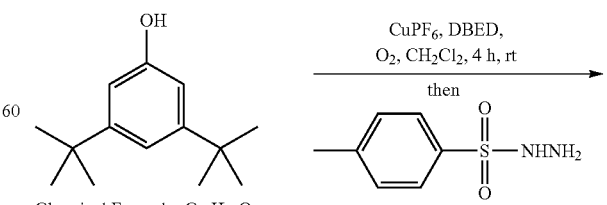

Chemical Formula: C$_{14}$H$_{22}$O$_2$
Molecular Weight: 206.33
S1

-continued

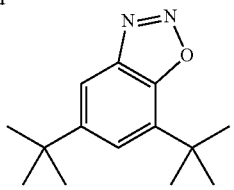

Chemical Formula: $C_{14}H_{20}N_2O$
Molecular Weight: 232.33
S35

A flame-dried, 25-mL Radley tube, equipped with a Teflon-coated stir bar and a rubber septum, was charged with 3,5-di-tert-butylphenol (206.32 mg, 1.0 mmol, 1.0 equiv.). The reaction vessel was then purged with a steady stream of $N_2$ for 2 min prior to the addition of dry and degassed $CH_2Cl_2$ (8.0 mL). A separate, flame-dried test tube (16×125-mL) was charged with $[Cu(CH_3CN)_4](PF_6)$ (29.8 mg, 0.08 mmol, 0.08 equiv.), N,N'-di-tert-butylethelenediamine (25.8 mg, 32.3 µL, 0.15 mmol, 0.15 equiv.), and $CH_2Cl_2$ (2.0 mL) to afford a homogeneous, pink solution. This solution was then added to the Radley tube via syringe to afford a final volume of 10.0 mL and a concentration of 0.1 M with respect to the phenol. The rubber septum was then rapidly removed and replaced with a Radley cap, which was connected to a tank of $O_2$ and pressurized to 1 atm. Under a constant $O_2$ pressure (1 atm), the reaction was vented 3 times for 10 s to eliminate $N_2$. The reaction mixture was then stirred at room temperature for 4 h, depressurized by opening to the atmosphere, and argon gas was bubbled through the reaction mixture for 2 minutes to eliminate $O_2$. Then, a solution of para-toluenesulfonyl hydrazide (372.4 mg, 2.0 mmol, 2.0 equiv.) in MeOH (5 mL) was added to the reaction mixture via a syringe, and stirred for 4 h. The reaction mixture was quenched by the addition of $NaHSO_4$ (20 mL, 10% by weight aqueous solution), phases were separated, and the aqueous phase was extracted with $CH_2Cl_2$ (3×20 mL). The combined organic fractions were then dried over $MgSO_4$, filtered and concentrated in vacuo to afford a residue which was analyzed directly by $^1$H-NMR. The crude reaction mixture was then purified using a Biotage Isolera™ One (15% EtOAc in hexanes) to afford the diazobenzoquinone S35 in 83% isolated yield.

Synthesis of Azophenol from Diazobenzoquinone
(General Procedure B)

A flame-dried 50-mL round-bottom flask, equipped with a Teflon stir bar, was charged with S35 (232.3 mg, 1.0 mmol, 1 equiv.). Then, the reaction vessel was purged with a steady stream of $N_2$ for 2 min prior to the addition of dry and degassed $CH_2Cl_2$ (20 mL). The reaction mixture was cooled to −78° C. using an acetone/dry ice bath. Grignard reagent (1.2 mmol, 1.2 equiv.) was added to this reaction mixture via a syringe and the reaction was stirred at −78° C. for 1 h. Then, the reaction mixture was allowed to warm to room temperature and was stirred at this temperature overnight. The reaction mixture was quenched by the addition of distilled $H_2O$ (50 mL), and the phases were separated. The aqueous phase was washed with $CH_2Cl_2$ (3×20 mL). The combined organic fractions were dried over $MgSO_4$, filtered and concentrated in vacuo to afford a crude residue, which was purified using flash column chromatography (silica gel with 15% EtOAc in hexanes as eluant) to afford a red residue.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Abdel-Magid, A. F.; Carson, K. G.; Harris, B. D.; Maryanoff, C. A.; Shah, R. D., J. Org. Chem. 1996, 61 (11), 3849-3862

Alla, S. K., Kumar, R. K., Sadhu, P. & Punniyamurthy, T. Iodobenzene Catalyzed C—H Amination of N-Substituted Amidines Using m-Chloroperbenzoic Acid. Org. Lett. 15, 1334-1337, (2013).

Allen, L. J., Cabrera, P. J., Lee, M. & Sanford, M. S. N-Acyloxyphthalimides as Nitrogen Radical Precursors in the Visible Light Photocatalyzed Room Temperature C—H Amination of Arenes and Heteroarenes. J. Am. Chem. Soc. 136, 5607-5610, (2014).

Bafana, A.; Devi, S. S.; Chakrabarti, T., Environmental Reviews 2011, 19 (NA), 350-371.

Bassoli, A.; Borgonovo, G.; Busnelli, G.; Morini, G., Eur. J. Org. Chem. 2006, 2006 (7), 1656-1663.

Bruckner, R., Substitution Reactions on Aromatic Compounds. In Advanced Organic Chemistry, Bruckner, R., Ed. Academic Press: San Diego, 2002; pp 169-219

Campbell, A. N. & Stahl, S. S. Overcoming the "Oxidant Problem": Strategies to Use O(2) as the Oxidant in Organometallic C—H Oxidation Reactions Catalyzed by Pd (and Cu). Acc. Chem. Res. 45, 851-863, (2012).

Campiani, G.; Morelli, E.; Fabbrini, M.; Nacci, V.; Greco, G.; Novellino, E.; Ramunno, A.; Maga, G.; Spadari, S.; Caliendo, G.; Bergamini, A.; Faggioli, E.; Uccella, I.; Bolacchi, F.; Marini, S.; Coletta, M.; Nacca, A.; Caccia, S., J. Med. Chem. 1999, 42 (21), 4462-4470

Çanakçi, D.; Tunçel, M.; Mart, H.; Serin, S., Polym. Int. 2007, 56 (12), 1537-1543.

Chen, Q.-A.; Chen, M.-W.; Yu, C.-B.; Shi, L.; Wang, D.-S.; Yang, Y.; Zhou, Y.-G., J. Am. Chem. Soc. 2011, 133 (41), 16432-16435.

Chen, X.; Ji, F.; Zhao, Y.; Liu, Y.; Zhou, Y.; Chen, T.; Yin, S.-F. Adv. Synth. Catal. (2015), 327, 2924-2930.

Chen, Z.; Zeng, H.; Girard, S. A.; Wang, F.; Chen, N.; Li, C.-J., Angew. Chem. Int. Ed. 2015, 54 (48), 14487-14491.

Cheng, Y.-F.; Rong, H.-J.; Yi, C.-B.; Yao, J.-J.; Qu, J. Org. Lett. (2015), 17, 4758-4761.

Chi, Y., Clifford, J. N.; Chou, P.-T. et al. Angew. Chem. Int. Ed. (2014), 53, 178-183.

Chintareddy, V. R.; Wadhwa, K.; Verkade, J. G. J. Org. Chem. (2009), 74, 8118-8132.

Chiranjeevi, B.; Vinayak, B.; Parsharamulu, T.; PhaniBabu, V. S.; Jagadeesh, B.; Sridhar, B.; Chandrasekharam, M., Eur. J. Org. Chem. 2014, 2014 (35), 7839-7849.

Cho, S. H., Yoon, J. & Chang, S. Intramolecular Oxidative C—N Bond Formation for the Synthesis of Carbazoles: Comparison of Reactivity between the Copper-Catalyzed and Metal-Free Conditions. J. Am. Chem. Soc. 133, 5996-6005, (2011).

Cho, S. H.; Kim, J. Y.; Kwak, J.; Chang, S., Chem. Soc. Rev. 2011, 40 (10), 5068-5083

Cho, S. H.; Yoon, J.; Chang, S., J. Am. Chem. Soc. 2011, 133 (15), 5996-6005

Corey, E. J.; Achiwa, K., J. Am. Chem. Soc. 1969, 91 (6), 1429-1432.
Daugulis, O., Do, H.-Q. & Shabashov, D. Palladium- and Copper-Catalyzed Arylation of Carbon-Hydrogen Bonds. Acc. Chem. Res. 42, 1074-1086, (2009).
Davies, H. M. L.; Long, M. S., Angew. Chem. Int. Ed. 2005, 44 (23), 3518-3520
Davies, H. M. L.; Manning, J. R., Nature 2008, 451 (7177), 417-424
Deibl, N.; Ament, K.; Kempe, R., J. Am. Chem. Soc. 2015, 137 (40), 12804-12807
Deligeorgiev, T.; Zaneva, D.; Kalcheva, V.; Simov, D., Dyes and Pigments 1993, 23 (2), 85-90.
Dey, K. Schiff-bases and their uses. J. Sci. Ind. Res. 33, 76-100 (1974).
Dick, A. R.; Sanford, M. S., Tetrahedron 2006, 62 (11), 2439-2463
Don, M. J.; Shen, C. C.; Lin, Y. L.; Syu, W. J.; Ding, Y. H.; Sun, C. M., J. Nat. Prod. 2005, 68 (7), 1066-70
Dooleweerdt, K.; Fors, B. P.; Buchwald, S. L. Org. Lett. (2010), 12, 2350-2353.
Easmon, J.; Pürstinger, G.; Thies, K.-S.; Heinisch, G.; Hofmann, J., J. Med. Chem. 2006, 49 (21), 6343-6350.
Emerson, W. S. in Organic Reactions (John Wiley & Sons, Inc., 2004).
Erkkila, A., Majander, I. & Pihko, P. M. Iminium catalysis. Chem. Rev. 107, 5416-5470, (2007).
Esguerra, K. V. N.; Fall, Y.; Lumb, J.-P., Angew. Chem. Int. Ed. 2014, 53 (23), 5877-5881.
Esguerra, K. V. N.; Fall, Y.; Petitjean, L.; Lumb, J.-P., J. Am. Chem. Soc. 2014, 136 (21), 7662-7668.
Evano, G., Blanchard, N. & Toumi, M. Chem. Rev. 108, 3054 (2008).
Fache, F., Schulz, E., Tommasino, M. L. & Lemaire, M. Nitrogen-Containing Ligands for Asymmetric Homogeneous and Heterogeneous Catalysis. Chem. Rev. 100, 2159-2232, (2000).
Fier, P. S. & Hartwig, J. F. Synthesis and Late-Stage Functionalization of Complex Molecules through C—H Fluorination and Nucleophilic Aromatic Substitution. J. Am. Chem. Soc. 136, 10139-10147, (2014).
Finkbeiner, P., Kloeckner, U. & Nachtsheim, B. J. OH-Directed Alkynylation of 2-Vinylphenols with Ethynyl Benziodoxolones: A Fast Access to Terminal 1,3-Enynes. Angew. Chem. Int. Ed., doi:10.1002/anie.201412148 (2015).
Finley, K. T., Quinones as synthones. In The Quinonoid Compounds (1988), John Wiley & Sons, Inc.: 2010; pp 537-717
Finley, K. T., The addition and substitution chemistry of quinones. In Quinonoid Compounds (1974), John Wiley & Sons, Ltd.: 2010; pp 877-1144.
Fishwick, C. W. G.; Jones, D. W., ortho-Quinonoid compounds. In The Quinonoid Compounds (1988), John Wiley & Sons, Inc.: 2010; pp 403-453
Foo, K., Sella, E., Thomé, I., Eastgate, M. D. & Baran, P. S. A Mild, Ferrocene-Catalyzed C—H Imidation of (Hetero) Arenes. J. Am. Chem. Soc. 136, 5279-5282, (2014).
Gao, T.; Sun, P., J. Org. Chem. 2014, 79 (20), 9888-9893
Garcia-Amorós, J.; Velasco, D., Beilstein J. Org. Chem. 2012, 8, 1003-1017.
Garcia-Amorós, J.; Velasco, D., Tautomerizable Azophenol Dyes: Cornerstones for Advanced Light-Responsive Materials. In Tautomerism, Wiley-VCH Verlag GmbH & Co. KGaA: 2016; pp 253-272.
Gembus, V.; Poisson, T., Oudeyer, S., Marsais, F. & Levacher, V. Preparation of β-Lactams by Mannich-Type Addition of Ethyl(trimethylsilyl)acetate (ETSA) to N-(2-Hydroxyphenyl)aldimine Sodium Salts. Synlett 2009, 2437-2440, (2009).
Girard, S. A., Huang, H., Zhou, F., Deng, G.-J. & Li, C.-J. Catalytic dehydrogenative aromatization: an alternative route to functionalized arenes. Organic Chemistry Frontiers 2, 279-287, (2015).
Govindachari, T. R. Chinnasamy, P., Rajeswari, S., Chandrasekaran, S., Premila, M. S., Natarajan, S., Nagarajan, K. & Pai, B. R. Some recent work on Schiff-Bases, imines and iminium slats in synthetic heterocyclic chemistry-a review. Heterocycles 22, 585-655 (1984).
Grimsdale, A. C., Leok Chan, K., Martin, R. E., Jokisz, P. G. & Holmes, A. B. Synthesis of Light-Emitting Conjugated Polymers for Applications in Electroluminescent Devices. Chem. Rev. 109, 897-1091, (2009).
Grobler, J. A.; Dornadula, G.; Rice, M. R.; Simcoe, A. L.; Hazuda, D. J.; Miller, M. D., J. Biol. Chem. 2007, 282 (11), 8005-10.
Hansen, T. V.; Skattebøl, L., Tetrahedron Lett. 2005, 46 (19), 3357-3358.
Hartwig, J. F. Carbon-heteroatom bond formation catalysed by organometallic complexes. Nature 455, 314-322 (2008).
Hernández-Molina, R. & Mederos, A. in Comprehensive Coordination Chemistry II (ed Jon A. McCleverty Thomas J. Meyer) 411-446 (Pergamon, 2003).
Herrmann, A. Dynamic mixtures and combinatorial libraries: imines as probes for molecular evolution at the interface between chemistry and biology. Org. Bio. Chem. 7, 3195-3204, (2009).
Hili, R. & Yudin, A. K. Making carbon-nitrogen bonds in biological and chemical synthesis. Nat Chem Biol 2, 284-287 (2006).
Hong, W. P., Iosub, A. V. & Stahl, S. S. Pd-Catalyzed Semmler-Wolff Reactions for the Conversion of Substituted Cyclohexenone Oximes to Primary Anilines. J. Am. Chem. Soc. 135, 13664-13667, (2013).
Horton, D. A., Bourne, G. T. & Smythe, M. L. The Combinatorial Synthesis of Bicyclic Privileged Structures or Privileged Substructures. Chem. Rev. 103, 893-930, (2003).
Huang, C.; Ghavtadze, N.; Chattopadhyay, B.; Gevorgyan, V., J. Am. Chem. Soc. 2011, 133 (44), 17630-17633
Iida, K.; Miura, T.; Ando, J.; Saito, S., Org. Lett. 2013, 15 (7), 1436-1439
Izawa, Y.; Pun, D.; Stahl, S. S. Science. (2011), 333, 201-213.
Jagadeesh, R. V.; Natte, K.; Junge, H. & Beller, M. Nitrogen-Doped Graphene-Activated Iron-Oxide-Based Nanocatalysts for Selective Transfer Hydrogenation of Nitroarenes. ACS Catalysis 5, 1526-1529, (2015).
Jawale, D. V.; Gravel, E.; Shah, N.; Dauvois, V.; Li, H.; Namboothiri, I. N. N.; Doris, E., Chemistry—A European Journal 2015, 21 (19), 7039-7042
Jiang, L. & Buchwald, S. L. in Metal-Catalyzed Cross-Coupling Reactions 699-760 (Wiley-VCH Verlag GmbH, 2008).
Jiang, T.-S.; Wang, G.-W., J. Org. Chem. 2012, 77 (21), 9504-9509
Johnson, T. W.; Corey, E. J., J. Am. Chem. Soc. 2001, 123 (19), 4475-4479.
Jordan-Hore, J. A.; Johansson, C. C. C.; Gulias, M.; Beck, E. M.; Gaunt, M. J., J. Am. Chem. Soc. 2008, 130 (48), 16184-16186

Kelly, M et al. Preparation of heterocyclic anticancer agents and uses thereof. U.S. Patent 2008/0280891 A1, Nov. 13, 2008.

Kim, H. J., Kim, J., Cho, S. H. & Chang, S. Intermolecular Oxidative C—N Bond Formation under Metal-Free Conditions: Control of Chemoselectivity between Aryl sp2 and Benzylic sp3 C—H Bond Imidation. *J. Am. Chem. Soc.* 133, 16382-16385, (2011).

Kogan, V. A.; Lyubchenko, S. N.; Shcherbakov, I. N.; Ionov, A. M.; Tkachev, V. V.; Shilov, G. V.; Aldoshin, S. M. Russ. J. Coord. Chem. (2005), 31, 533-540.

Kremer, C. B. *J. Am. Chem. Soc.* 61, 1321 (1939).

Kumar, R., Ermolat'ev, D. S. & Van der Eycken, E. V. Synthesis of Differentially Substituted 2-Aminoimidazolidines via a Microwave-Assisted Tandem Staudinger/Aza-Wittig Cyclization. *J. Org. Chem.* 78, 5737-5743, (2013).

Laliberte, D.; Maris, T.; Wuest, J. D. J. Org. Chem. (2004), 69, 1776-1787.

Largeron, M.; Chiaroni, A.; Fleury, M.-B., Chemistry—A European Journal 2008, 14 (3), 996-1003

Largeron, M.; Fleury, M.-B., Angew. Chem. Int. Ed. 2012, 51 (22), 5409-5412

Largeron, M.; Fleury, M.-B., Chemistry—A European Journal 2015, 21 (9), 3815-3820

Layer, R. W. The Chemistry of Imines. Chem. Rev. 63, 489-510, (1963).

Leaver, I. H.; Milligan, B., Dyes and Pigments 1984, 5 (2), 109-144.

Lee, D. H.; Lee, K. H.; Hong, J.-I., Org. Lett. 2001, 3 (1), 5-8.

Ley, S. V. & Thomas, A. W. Modern Synthetic Methods for Copper-Mediated C(aryl)-O, C(aryl)-N, and C(aryl)-S Bond Formation. *Angew. Chem. Int. Ed.* 42, 5400-5449, (2003).

Li, C.; Zheng, Y.; Zhang, H.; Feng, J.; Zhang, Y.; Wang, J. Angew. Chem. Int. Ed. (2010), 49, 6413-6417.

Louillat, M.-L. & Patureau, F. W. Oxidative C—H amination reactions. *Chem. Soc. Rev.* 43, 901-910, (2014).

Louillat, M.-L. & Patureau, F. W. Toward Polynuclear Ru—Cu Catalytic Dehydrogenative C—N Bond Formation, on the Reactivity of Carbazoles. *Org. Lett.* 15, 164-167, (2013).

Louillat-Habermeyer, M.-L.; Jin, R.; Patureau, F. W., Angew. Chem. Int. Ed. 2015, 54 (13), 4102-4104.

Lu, S. M.; Bolm, C. Angew. Chem. Int. Ed. (2008), 47, 8920-8923.

Luo, G.; Mattson, G. K.; Bruce, M. A.; Wong, H.; Murphy, B. J.; Longhi, D.; Antal-Zimanyi, I.; Poindexter, G. S., Bioorg. Med. Chem. Lett. 2004, 14 (24), 5975-5978

Magdziak, D., Rodriguez, A. A., Van De Water, R. W. & Pettus, T. R. R. Regioselective oxidation of phenols to o-quinones with o-iodoxybenzoic acid (IBX). *Org. Lett* 4, 285-288, (2002).

Magdziak, D.; Rodriguez, A. A.; Van De Water, R. W.; Pettus, T. R. R., Org. Lett. 2002, 4 (2), 285-288

Majhi, B.; Kundu, D.; Ahammed, S.; Ranu, B. C., Chemistry—A European Journal 2014, 20 (32), 9862-9866.

McCoy, G.; Day, A. R., J. Am. Chem. Soc. 1943, 65 (10), 1956-1959.

McGrath, N. A., Brichacek, M. & Njardarson, J. T. A Graphical Journey of Innovative Organic Architectures That Have Improved Our Lives. *J. Chem. Educ.* 87, 1348-1349, (2010).

McLaughlin, M., Palucki, M. & Davies, I. W. Efficient Access to Azaindoles and Indoles. *Org. Lett* 8, 3307-3310, (2006).

Mei, T.-S., Kou, L., Ma, S., Engle, K. M. & Yu, J.-Q. Heterocycle Formation via Palladium-Catalyzed C—H Functionalization. *Synthesis* 44, 1778-1791, (2012).

Mei, T.-S., Leow, D., Xiao, H., Laforteza, B. N. & Yu, J.-Q. Synthesis of Indolines via Pd(II)-Catalyzed Amination of C—H Bonds Using PhI(OAc)2 as the Bystanding Oxidant. *Org. Lett.* 15, 3058-3061, (2013).

Mei, T.-S., Wang, X. & Yu, J.-Q. Pd(II)-Catalyzed Amination of C—H Bonds Using Single-Electron or Two-electron Oxidants. *J. Am. Chem. Soc.* 131, 10806-10807, (2009).

Mei, T.-S.; Wang, X.; Yu, J.-Q., J. Am. Chem. Soc. 2009, 131 (31), 10806-10807; (f) Wang, S.; Ni, Z.;

Huang, X.; Wang, J.; Pan, Y., Org. Lett. 2014, 16 (21), 5648-5651

Meyer, C. D., Joiner, C. S. & Stoddart, J. F. Template-directed synthesis employing reversible imine bond formation. *Chem. Soc. Rev.* 36, 1705-1723, (2007).

Michlik, S.; Kempe, R., Nat Chem 2013, 5 (2), 140-144

Mirica, L. M. et al. Tyrosinase reactivity in a model complex: an alternative hydroxylation mechanism. *Science* 308, 1890-1892, (2005).

Miyabe, H.; Yamaoka, Y.; Takemoto, Y., J. Org. Chem. 2006, 71 (5), 2099-2106.

Montgomery, J. H. *Agrochemicals desk reference*. (CRC Press, 2010).

Moon, J.-K.; Kim, J.-H.; Shibamoto, T., J. Agric. Food. Chem. 2010, 58 (23), 12357-12365.

Moriarty, R. M. & Om, P. in *Organic Reactions* (John Wiley & Sons, Inc., 2004).

Morofuji, T., Shimizu, A. & Yoshida, J.-i. Direct C—N Coupling of Imidazoles with Aromatic and Benzylic Compounds via Electrooxidative C—H Functionalization. *J. Am. Chem. Soc.* 136, 4496-4499, (2014).

Morofuji, T., Shimizu, A. & Yoshida, J.-i. Electrochemical C—H Amination: Synthesis of Aromatic Primary Amines via N-Arylpyridinium Ions. *J. Am. Chem. Soc.* 135, 5000-5003, (2013).

Morofuji, T., Shimizu, A. & Yoshida, J.-i. Electrochemical Intramolecular C—H Amination: Synthesis of Benzoxazoles and Benzothiazoles. *Chemistry—A European Journal* 21, 3211-3214, (2015).

Mukaiyama, T. Explorations into new reaction chemistry. *Angew. Chem. Int. Ed.* 43, 5590-5614, (2004).

Murakami, Y.; Yoshimoto, N.; Fujieda, N.; Ohkubo, K.; Hasegawa, T.; Kano, K.; Fukuzumi, S.; Itoh, S., J. Org. Chem. 2007, 72 (9), 3369-3380

Mure, M., Acc. Chem. Res. 2004, 37 (2), 131-139

Mure, M.; Klinman, J. P., J. Am. Chem. Soc. 1995, 117 (34), 8707-8718

Nakamura, M.; Hamasaki, T.; Tokitou, M.; Baba, M.; Hashimoto, Y.; Aoyama, H. Bioorg. Med. Chem. (2009), 17, 4740-4746.

Nicolaides, D. N., Gautam, D. R., Litinas, K. E., Hadjipavlou-Litina, D. J. & Kontogiorgis, C. A. Synthesis and biological evaluation of benzo[7,8]chromeno[5,6-b][1,4]oxazin-3-ones. *Journal of Heterocyclic Chemistry* 41, 605-611, (2004).

Nun, P., Martinez, J. & Lamaty, F. Microwave-Assisted Neat Procedure for the Petasis Reaction. *Synthesis* 2010, 2063-2068, (2010).

Op't Holt, B. T. et al. Reaction coordinate of a functional model of tyrosinase: spectroscopic and computational characterization. *J. Am. Chem. Soc.* 131, 6421-6438, (2009).

Ostrem, J. M.; Peters, U.; Sos, M. L.; Wells, J. A.; Shokat, K. M., Nature 2013, 503 (7477), 548-551

Ovenden, S. P. B.; Nielson, J. L.; Liptrot, C. H.; Willis, R. H.; Tapiolas, D. M.; Wright, A. D.; Motti, C. A., J. Nat. Prod. 2010, 74 (1), 65-68.

Qian, J.; Yi, W.; Huang, X.; Miao, Y.; Zhang, J.; Cai, C.; Zhang W. Org. Lett. (2015), 17, 1090-1093.

Qin, Y.; Zhang, L.; Lv, J.; Luo, S.; Cheng, J.-P., Org. Lett. 2015, 17 (6), 1469-1472.

Ramsden, C. A. Heterocycle-Forming Reactions of 1,2-Benzoquinones. Adv. Heterocycl. Chem. 100, 1-51, (2010).

Rath, R. K.; Nethaji, M.; Chakravarty, A. R., J. Organomet. Chem. 2001, 633 (1-2), 79-84.

Ren, P.; Salihu, I.; Scopelliti, R.; Hu, X., Org. Lett. 2012, 14 (7), 1748-1751.

Riley, P. A.; Ramsden, C. A.; Land, E. J., Biological Chemistry of o-Quinones. In Melanins and Melanosomes, Wiley-VCH Verlag GmbH & Co. KGaA: 2011; pp 63-86

Rodriguez, A. D.; Ramirez, C.; Rodriguez, II; Gonzalez, E., Org. Lett. 1999, 1 (3), 527-30; (e) Davidson, J. P.; Corey, E. J., J. Am. Chem. Soc. 2003, 125 (44), 13486-13489

Rueping, M.; Antonchick, A. P.; Theissmann, T., Angew. Chem. Int. Ed. 2006, 45 (40), 6751-6755.

Ruiz-Castillo, P., Blackmond, D. G. & Buchwald, S. L. Rational Ligand Design for the Arylation of Hindered Primary Amines Guided by Reaction Progress Kinetic Analysis. J. Am. Chem. Soc. 137, 3085-3092, (2015).

Said, G.; Grippon, S.; Kirkpatrick, P., Nat Rev Drug Discov 2012, 11 (3), 185-6.

Salehzadeh, H.; Nematollahi, D.; Hesari, H. Greem Chem. (2013), 15, 2441-2446.

Sandhu, J. S. & Sain, B. Some Recent Advances in the Chemistry of Imines, in Particular Cycloaddition Reactions. Heterocycles 26, 777-818 (1987).

Sapountzis, I. & Knochel, P. A New General Preparation of Polyfunctional Diarylamines by the Addition of Functionalized Arylmagnesium Compounds to Nitroarenes. J. Am. Chem. Soc. 124, 9390-9391, (2002).

Sato, S.; Kajiura, T.; Noguchi, M.; Takehana, K.; Kobayashi, T.; Tsuji, T., J Antibiot (Tokyo) 2001, 54 (1), 102-4

Seth, K.; Garg, S. K.; Kumar, R.; Purohit, P.; Meena, V. S.; Goyal, R.; Banerjee, U. C.; Chakraborti, A. K., ACS Med. Chem. Lett. 2014, 5 (5), 512-516.

Seth, K.; Nautiyal, M.; Purohit, P.; Parikh, N.; Chakraborti, A. K., Chem. Commun. 2015, 51 (1), 191-194.

Seth, K.; Purohit, P.; Chakraborti, A. K., Org. Lett. 2014, 16 (9), 2334-2337.

Shabashov, D. & Daugulis, O. Auxiliary-Assisted Palladium-Catalyzed Arylation and Alkylation of sp2 and sp3 Carbon-Hydrogen Bonds. J. Am. Chem. Soc. 132, 3965-3972, (2010).

Smith, M. B. & March, J. March's Advanced Organic Chemistry: Reactions, mechanisms, and structure. (2001).

Smith, M. B.; March, J., March's Advanced Organic Chemistry: Reactions, Mechanisms and Structure, 5th Ed., Wiley: New York. 2001; pp 1552-1554.

Sparling B. A.; Moslin, R. M.; Jamwason, T. F. Org. Lett. (2008), 10, 1291-1294.

Sprott, K. T.; Corey, E. J., Org. Lett. 2003, 5 (14), 2465-2467.

Srimani, D.; Ben-David, Y.; Milstein, D., Angew. Chem. Int. Ed. 2013, 52 (14), 4012-4015

Sun, K.; Li, Y.; Xiong, T.; Zhang, J.; Zhang, Q., J. Am. Chem. Soc. 2011, 133 (6), 1694-1697

Surry, D. S. & Buchwald, S. L. Chem. Sci. 2, 27 (2011).

Tajbakhsh, M.; Hosseinzadeh, R.; Alinezhad, H.; Ghahari, S.; Heydari, A.; Khaksar, S., Synthesis 2011, 2011 (03), 490-496

Takamatsu, K.; Hirano, K.; Satoh, T.; Miura, M., J. Org. Chem. 2015, 80 (6), 3242-3249.

Tanaka, R.; Viehmann, P.; Hecht, M. Organometallics. (2012), 31, 4216-4220.

Taylor, E. C.; Katz, A. H.; Alvarado, S. I.; McKillop, A., J. Org. Chem. 1986, 51 (9), 1607-1609

Thansandote, P. & Lautens, M. Construction of Nitrogen-Containing Heterocycles by C—H Bond Functionalization. Chemistry—A European Journal 15, 5874-5883, (2009).

Thirunavukkarasu, V. S.; Kozhushkov, S. I.; Ackermann, L., Chem. Commun. 2014, 50 (1), 29-39

Tsang, W. C. P., Munday, R. H., Brasche, G., Zheng, N. & Buchwald, S. L. Palladium-Catalyzed Method for the Synthesis of Carbazoles via Tandem C—H Functionalization and C—N Bond Formation. J. Org. Chem. 73, 7603-7610, (2008).

Tsang, W. C. P., Zheng, N. & Buchwald, S. L. Combined C—H Functionalization/C—N Bond Formation Route to Carbazoles. J. Am. Chem. Soc. 127, 14560-14561, (2005).

Tully, D. C.; Liu, H.; Alper, P. B.; Chatterjee, A. K.; Epple, R.; Roberts, M. J.; Williams, J. A.; Nguyen, K. T.; Woodmansee, D. H.; Tumanut, C.; Li, J.; Spraggon, G.; Chang, J.; Tuntland, T.; Harris, J. L.; Karanewsky, D. S., Bioorg. Med. Chem. Lett. 2006, 16 (7), 1975-1980.

Ueda, S.; Nagasawa, H., Angew. Chem. 2008, 120 (34), 6511-6513.

Ueki, M.; Ueno, K.; Miyadoh, S.; Abe, K.; Shibata, K.; Taniguchi, M.; Oi, S., J Antibiot (Tokyo) 1993, 46 (7), 1089-94

Uyanik, M., Mutsuga, T. & Ishihara, K. IBS-Catalyzed Regioselective Oxidation of Phenols to 1,2-Quinones with Oxone®. Molecules 17, 8604-8616 (2012).

Venkateswarlu, V.; Kumar, K. A. A.; Balgotra, S.; Reddy, G. L.; Srinivas, M.; Vishwakarma, R. A.; Sawant, S. D., Chemistry—A European Journal 2014, 20 (22), 6641-6645

Vickers, C. J., Mei, T.-S. & Yu, J.-Q. Pd(II)-Catalyzed o-C—H Acetoxylation of Phenylalanine and Ephedrine Derivatives with MeCOOOtBu/Ac2O. Org. Lett 12, 2511-2513, (2010).

Vinsova, J. et al. Bioorg. Med. Chem. (2006), 14, 5850-5865.

Wang, C.; Chen L.; Huo, H.; Shen, X.; Harms, K.; Gong, L.; Meggers, E. Chem. Sci. (2015), 6, 1094-1100.

Wang, Y.; Wu, C.; Nie, S.; Xu, D.; Yu, M.; Yao, X. Tetrahedron Lett. (2015), 56, 6827-6832.

Wasa, M.; Yu, J.-Q., J. Am. Chem. Soc. 2008, 130 (43), 14058-14059

Weinstein, A. B. & Stahl, S. S. Palladium catalyzed aryl C—H amination with O2via in situ formation of peroxide-based oxidant(s) from dioxane. Catalysis Science & Technology 4, 4301-4307, (2014).

Weissermel, K. & Arpe, H.-J. in Industrial Organic Chemistry 337-385 (Wiley-VCH Verlag GmbH, 2008).

Wendlandt, A. E. & Stahl, S. S. Bioinspired Aerobic Oxidation of Secondary Amines and Nitrogen Heterocycles with a Bifunctional Quinone Catalyst. J. Am. Chem. Soc. 136, 506-512, (2013).

Wendlandt, A. E. & Stahl, S. S. Modular o-Quinone Catalyst System for Dehydrogenation of Tetrahydroquinolines under Ambient Conditions. J. Am. Chem. Soc. 136, 11910-11913, (2014).

Wendlandt, A. E., Suess, A. M. & Stahl, S. S. Copper-catalyzed aerobic oxidative C—H functionalizations: trends and mechanistic insights. Angew. Chem. Int. Ed. 50, 11062-11087, (2011).

Wendlandt, A. E.; Stahl, S. S., J. Am. Chem. Soc. 2014, 136 (1), 506-512
Wendlandt, A. E.; Stahl, S. S., J. Am. Chem. Soc. 2014, 136 (34), 11910-11913
Wendlandt, A. E.; Stahl, S. S., Org. Lett. 2012, 14 (11), 2850-2853
Woo Bae, J.; Hwan Lee, S.; Jin Cho, Y.; Min Yoon, C., J. Chem. Soc., Perkin Trans. 1 2000, (2), 145-146.
Wu, X.; See, J. W. T.; Xu, K.; Hirao, H.; Roger, J.; Hierso, J.-C.; Zhou, J., Angew. Chem. 2014, 126 (49), 13791-13795.
Yan, S.; Ye, L.; Liu, M.; Chen, J.; Ding, J.; Gao, W.; Huang, X.; Wu, H., RSC Adv. 2014, 4 (32), 16705-16709
Yan, X.; Yang, X.; Xi, C., Catal. Sci. Tech, 2014, 4 (12), 4169-4177.
Yang, X.; Shan, G.; Rao, Y., Org. Lett. 2013, 15 (10), 2334-2337
Yoshida, S.; Shiokawa, S.; Kawano, K.-i.; Ito, T.; Murakami, H.; Suzuki, H.; Sato, Y., J. Med. Chem. 2005, 48 (22), 7075-7079.
Yoshino, J.; Furuta, A.; Kambe, T.; Itoi, H.; Kano, N.; Kawashima, T.; Ito, Y.; Asashima, M., Chemistry—A European Journal 2010, 16 (17), 5026-5035.
Yuan, H.; Yoo, W.-J.; Miyamura, H.; Kobayashi, S., J. Am. Chem. Soc. 2012, 134 (34), 13970-13973
Zalatan, D. & Bois, J. D. in C—H Activation Vol. 292 *Topics in Current Chemistry* (eds Jin-Quan Yu & Zhangjie Shi) Ch. 19, 347-378 (Springer Berlin Heidelberg, 2010).
Zhang, Z.-J.; Quan, X.-J.; Ren, Z.-H.; Wang, Y.-Y.; Guan, Z.-H., Org. Lett. 2014, 16 (12), 3292-3295
Zhu, D. et al. Ligand-Promoted ortho-C—H Amination with Pd Catalysts. *Angew. Chem. Int. Ed.* 54, 2497-2500, (2015).

The invention claimed is:

1. A method for producing an arene with an aromatic C—N bond ortho to an aromatic C—O bond from a hydroxy arene comprising said aromatic C—O bond, the method comprising the following steps:

a. ortho-oxygenating a hydroxy arene of Formula (I) to produce an ortho-quinone of Formula (II):

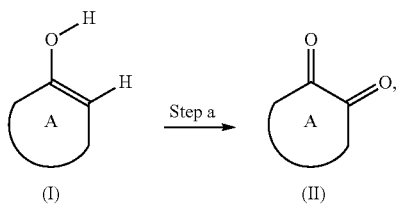

b. condensating the ortho-quinone of Formula (II) with a nitrogen nucleophile of Formula (IIIa):

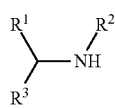

or (IIIb):

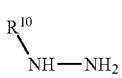

to generate a compound of Formula (IVa) or (IVb), respectively:

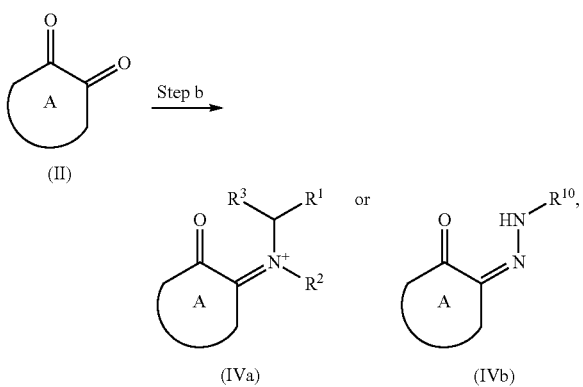

and c. allowing 1,5-hydrogen atom shift of the compound of Formula (IVa) or (IVb), thereby producing arenes with a C—N bond ortho to a C—O bond of Formula (Va) and (Vb), respectively:

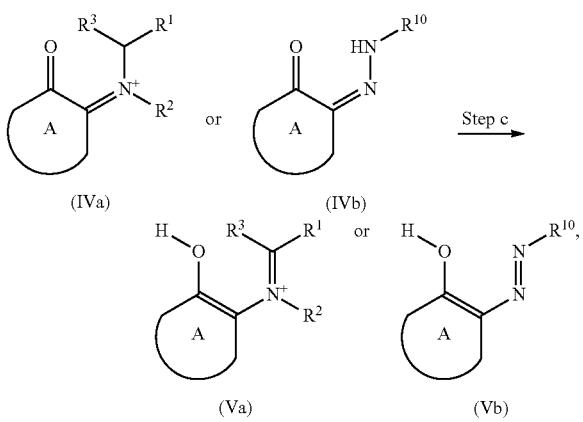

wherein $R^1$, $R^2$, and $R^3$ each independently represent:
  a hydrogen atom,
  alkyl unsubstituted or substituted with one or more one or more substituents selected from the group consisting of:
    aryl unsubstituted or substituted with one or more hydroxy,
    hydroxy,
    alkoxy unsubstituted or substituted with one or more aryl,
    aminoalkyl or aminodialkyl,
    alkoxy carbonyl,
    alkylthio,
    heterocycloalkyl, and
    halogen atom,
  cycloalkyl,
  alkenyl,
  hydroxyl,
  —C(═O)—O—$R^{20}$, wherein $R^{20}$ is an aliphatic or aromatic group, unsubstituted or substituted, or
  aryl or heteroaryl unsubstituted or substituted with one or more one or more substituents selected from the group consisting of:

alkyl unsubstituted or substituted with one or more halogen atoms,
alkoxy,
aryl unsubstituted or substituted with one or more alkyl, the alkyl being unsubstituted or substituted with one or more halogen atoms,
nitro,
sulfonamine, and
halogen atom; or
$R^1$ and $R^3$ together with the carbon atom to which they are attached form a ring; or
$R^1$ and $R^2$ together with the carbon and nitrogen atoms to which they are attached form a ring, that:
is saturated or unsaturated;
is unsubstituted or substituted with one or more hydroxy;
optionally comprises, in addition to the nitrogen atom to which $R^2$ is attached, one or more additional heteroatom; and
is optionally fused with an aromatic ring that is unsubstituted or substituted with one or more alkyloxy,
wherein $R^{10}$ represents:
aryl substituted with one or more substituents selected from the group consisting of:
—$NO_2$,
—$SO_2$,
halogen atom, and
perfluorinated alkyl,
heteroaryl unsubstituted or substituted with one or more:
—$NO_2$,
—$SO_2$,
halogen atom, and
perfluorinated alkyl, or
—C(=O)—$R^{11}$, wherein $R^{11}$ represents:
aryl or heteroaryl unsubstituted or substituted with one or more aryl, or
alkyloxy
with the proviso that nitrogen nucleophile is Formula (IIIb) is not

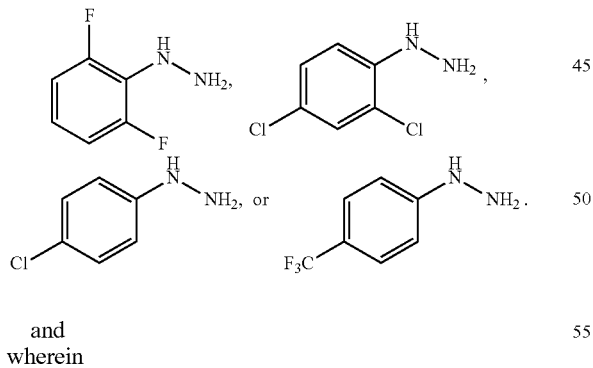

and
wherein

denotes an unsubstituted or substituted arene, an arene being an aromatic hydrocarbon with its carbon atoms arranged into one or more rings, the ring(s) presenting alternating double and single bonds between the ring atoms, and wherein one or more of the carbon ring atoms may be replaced by a heteroatom, the arene being optionally fused with an optionally substituted cycloalkyl.

2. The method of claim 1, wherein the nitrogen nucleophile is of Formula (IIIa).

3. The method of claim 2, wherein $R^2$ represents a hydrogen atom.

4. The method of claim 3, wherein $R^3$ represents a hydrogen atom and wherein the compound of Formula (Va) spontaneously forms an oxazole arene of Formula (VI):

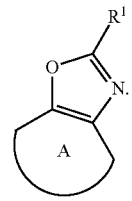

5. The method of claim 3, wherein $R^3$ does not represent a hydrogen atom.

6. The method of claim 5, further comprising hydrolysis to produce an ortho-amino-hydroxy arene of Formula (X):

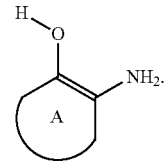

7. The method of claim 5, further comprising reaction with an organometallic reagent of formula $R^4$-M, wherein M is a metal and $R^4$ is alkyl, alkenyl, aryl, O—$R^{30}$, or N($R^{30}$)$_2$, wherein is $R^{30}$ is H, or an aliphatic or aromatic group, to yield an α,α,α-trisubstituted compound of Formula (XI):

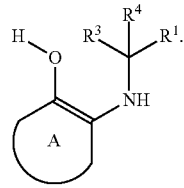

8. The method of claim 5, wherein $R^3$ represents —C(=O)—O—$R^{20}$, wherein $R^{20}$ is an aliphatic or aromatic group, unsubstituted or substituted, and the method further comprises lactonization to produce an oxazinone arene of Formula (IX):

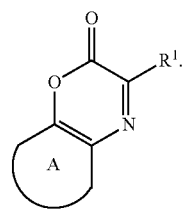

9. The method of claim 8, wherein R¹ in the oxazinone arene of Formula (IX) comprises a hydroxy arene and steps a) to c) followed by lactonization are repeated multiple times to produce a heterocyclic polymer.

10. The method of claim 2, wherein R³ represents a hydrogen atom and R¹ and R² together with the carbon and nitrogen atoms to which they are attached form said ring that:
   is saturated or unsaturated;
   is unsubstituted or substituted with one or more hydroxy;
   optionally comprises, in addition to the nitrogen atom to which R² is attached, one or more additional heteroatom; and
   is optionally fused with an aromatic ring that is unsubstituted or substituted with one or more alkyloxy.

11. The method of claim 10, wherein said ring is pyrrolidine, piperazine, morpholine, indoline, iso-indoline, tetrahydroisoquinoline, piperidine, 2,5-dihydropyrrole, dihydropyrrolidine, dihydroindoline, or dihydroisoindoline or one of their substituted derivatives.

12. The method of claim 10, further comprising quenching the reaction mixture to produce a dihydrooxazole arene of Formula (XII):

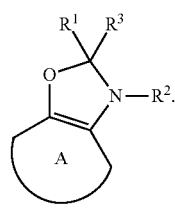

13. The method of claim 12, further comprising reducing the dihydrooxazole arene of Formula (XII) to yield to yield an ortho-amino-hydroxy arene of Formula (XIII):

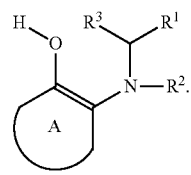

14. The method of claim 13, further comprising reacting with an aryl boronic acid to yield a compound of Formula (XV):

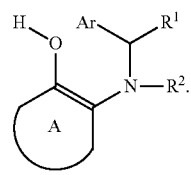

15. The method of claim 2, wherein arene A is benzene unsubstituted or substituted by one or more substituents selected from the group consisting of:
   alkyl unsubstituted or substituted with one or more:
      aryl,
      sulfoamidoaryl unsubstituted or substituted with one or more alkyl,
      hydroxy, and/or
      aryl carbamoyl,
   cycloalkyl,
   alkenyl, and
   aryl unsubstituted or substituted with one or more:
      alkyl,
      alkyloxy,
      halogen atom,
      trialkylsilyl, and/or
      halogen atoms.

16. The method of claim 1, wherein the nitrogen nucleophile is of Formula (IIIb).

17. The method of claim 16, wherein the nitrogen nucleophile of Formula (IIIb) is

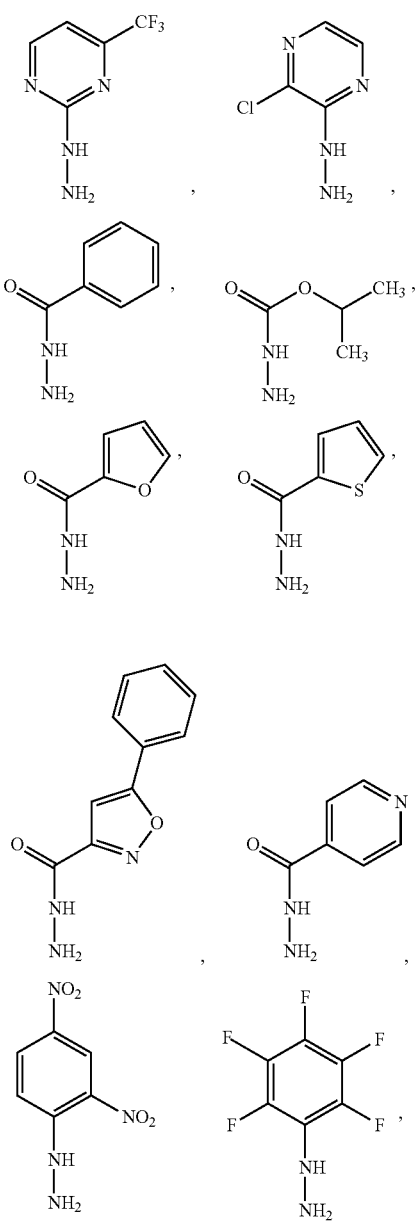

-continued

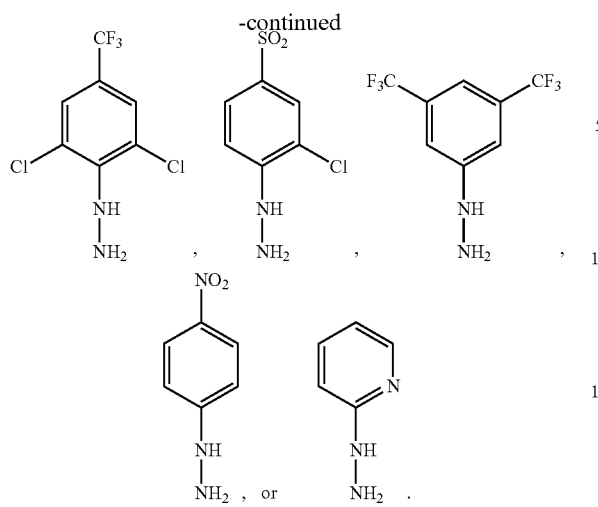

18. The method of claim 16, wherein arene A is benzene unsubstituted or substituted by one or more substituents selected from the group consisting of:
    $NO_2$,
    alkyl,
    trialkylsilyl, and/or
    aryl substituted with one or more alkyl and/or halogen atoms,
    wherein arene A is optionally fused with a cycloalkyl, the cycloalkyl being optionally substituted with one or more alkyl.

19. The method of claim 1, wherein step a) comprises reacting the hydroxy arene of Formula (I) in a reaction mixture with a solvent with $[Cu(CH_3CN)_4]PH_6$ and N,N'-di-tert-butyl-ethylene diamine at about room temperature in the presence of $O_2$.

20. The method of claim 19, wherein step b) comprises mixing the nitrogen nucleophile of Formula (IIIa) or (IIIb) in the reaction mixture.

* * * * *